US012409046B2

(12) United States Patent
Peterman et al.

(10) Patent No.: US 12,409,046 B2
(45) Date of Patent: Sep. 9, 2025

(54) TOTAL SPINAL JOINT SYSTEMS WITH MOTION MODERATORS

(71) Applicant: 3SPINE, INC, Chattanooga, TN (US)

(72) Inventors: Marc M Peterman, Duxbury, MA (US); Steven C Humphreys, Chattanooga, TN (US); Scott Hodges, Soldatna, AK (US)

(73) Assignee: 3SPINE, Inc., Chattanooga, TN (US)

( * ) Notice: Subject to any disclaimer, the term of this patent is extended or adjusted under 35 U.S.C. 154(b) by 148 days.

(21) Appl. No.: 18/232,685

(22) Filed: Aug. 10, 2023

(65) Prior Publication Data

US 2024/0041612 A1 Feb. 8, 2024

Related U.S. Application Data

(63) Continuation of application No. PCT/US2023/018341, filed on Apr. 12, 2023.

(60) Provisional application No. 63/330,033, filed on Apr. 12, 2022, provisional application No. 63/345,560, filed on May 25, 2022, provisional application No. 63/375,379, filed on Sep. 12, 2022.

(51) Int. Cl.
*A61F 2/44* (2006.01)
*A61F 2/30* (2006.01)

(52) U.S. Cl.
CPC ........ *A61F 2/4425* (2013.01); *A61F 2/30734* (2013.01); *A61F 2/30749* (2013.01); *A61F 2002/30957* (2013.01); *A61F 2310/00029* (2013.01); *A61F 2310/00059* (2013.01); *A61F 2310/00101* (2013.01)

(58) Field of Classification Search
CPC .......... A61F 2/44; A61F 2/442; A61F 2/4425; A61F 2002/443; A61F 2002/4435
USPC ............................................ 623/17.11–17.16
See application file for complete search history.

(56) References Cited

U.S. PATENT DOCUMENTS

| | | |
|---|---|---|
| 3,320,951 A | 5/1967 | Wittebol |
| 3,510,883 A | 5/1970 | Cathcart, III |
| 3,740,769 A | 6/1973 | Haboush |
| 3,903,549 A | 9/1975 | Deyerle |
| 4,309,777 A | 1/1982 | Patil |
| 4,349,921 A | 9/1982 | Kuntz |
| 4,470,158 A | 9/1984 | Pappas et al. |

(Continued)

FOREIGN PATENT DOCUMENTS

| | | |
|---|---|---|
| CA | 2552361 A1 | 8/2005 |
| CH | 624573 A5 | 8/1981 |

(Continued)

OTHER PUBLICATIONS

TH. Marnay—Lumbar Intervertebral Arthroplasty—Jun.-Sep. 1991, 15 pages, Kennedy Clinic, U.S.A.

(Continued)

*Primary Examiner* — Eduardo C Robert
*Assistant Examiner* — Christina Negrellirodriguez
(74) *Attorney, Agent, or Firm* — BRAINSPARK ASSOCIATES, LLC

(57) ABSTRACT

Disclosed are devices, system and methods for spinal implants to be deployed into an intervertebral space between adjacent vertebrae to replace the function of the intervertebral disc and the facets, while restoring stability, flexibility, coronal alignment/balance, sagittal alignment/balance and proper biomechanical motion.

20 Claims, 50 Drawing Sheets

(56) References Cited

U.S. PATENT DOCUMENTS

| | | |
|---|---|---|
| 4,550,450 A | 11/1985 | Kinnett |
| 4,622,959 A | 11/1986 | Marcus |
| 4,653,487 A | 3/1987 | Maale |
| 4,681,589 A | 7/1987 | Tronzo |
| 4,697,582 A | 10/1987 | William |
| 4,697,586 A | 10/1987 | Gazale |
| 4,702,930 A | 10/1987 | Heide et al. |
| 4,743,262 A | 5/1988 | Tronzo |
| 4,759,766 A | 7/1988 | Buettner-Janz et al. |
| 4,759,769 A | 7/1988 | Hedman et al. |
| 4,805,607 A | 2/1989 | Engelhardt et al. |
| 4,836,196 A | 6/1989 | Park et al. |
| 4,874,389 A | 10/1989 | Downey |
| 4,875,474 A | 10/1989 | Border |
| 4,892,545 A | 1/1990 | Day et al. |
| 4,932,975 A | 6/1990 | Main et al. |
| 4,946,378 A | 8/1990 | Hirayama |
| 4,997,432 A | 3/1991 | Keller |
| 5,004,476 A | 4/1991 | Cook |
| 5,037,438 A | 8/1991 | Davidson |
| 5,062,850 A | 11/1991 | MacMillan et al. |
| 5,071,437 A | 12/1991 | Steffee |
| 5,092,866 A | 3/1992 | Breard |
| 5,108,442 A | 4/1992 | Smith |
| 5,122,130 A | 6/1992 | Keller |
| 5,258,031 A | 11/1993 | Salib et al. |
| 5,271,737 A | 12/1993 | Baldwin et al. |
| 5,282,863 A | 2/1994 | Burton |
| 5,282,868 A | 2/1994 | Bahler |
| 5,290,312 A | 3/1994 | Kojimoto et al. |
| 5,314,477 A | 5/1994 | Marnay |
| 5,344,458 A | 9/1994 | Bonutti |
| 5,387,213 A | 2/1995 | Breard et al. |
| 5,401,269 A | 3/1995 | Buttner-Janz et al. |
| 5,415,661 A | 5/1995 | Holmes |
| 5,423,825 A | 6/1995 | Levine |
| 5,425,773 A | 6/1995 | Boyd et al. |
| 5,443,513 A | 8/1995 | Moumene et al. |
| 5,443,515 A | 8/1995 | Cohen et al. |
| 5,507,816 A | 4/1996 | Bullivant |
| 5,509,934 A | 4/1996 | Cohen |
| 5,534,029 A | 7/1996 | Shima |
| 5,534,030 A | 7/1996 | Navarro et al. |
| 5,554,191 A | 9/1996 | Lahille et al. |
| 5,554,194 A | 9/1996 | Sanders |
| 5,556,431 A | 9/1996 | Buttner-Janz |
| 5,562,660 A | 10/1996 | Grob |
| 5,562,737 A | 10/1996 | Graf |
| 5,562,738 A | 10/1996 | Boyd et al. |
| 5,571,109 A | 11/1996 | Bertangnoli |
| 5,571,190 A | 11/1996 | Ulrich et al. |
| 5,591,235 A | 1/1997 | Kuslich |
| 5,607,425 A | 3/1997 | Rogozinski |
| 5,609,638 A | 3/1997 | Price et al. |
| 5,658,347 A | 8/1997 | Sarkisian et al. |
| 5,672,175 A | 9/1997 | Martin |
| 5,674,294 A | 10/1997 | Bainville |
| 5,674,296 A | 10/1997 | Bryan et al. |
| 5,676,701 A | 10/1997 | Yuan et al. |
| 5,683,465 A | 11/1997 | Shinn et al. |
| 5,702,450 A | 12/1997 | Bisserie |
| 5,702,469 A | 12/1997 | Whipple et al. |
| 5,728,098 A | 3/1998 | Sherman et al. |
| 5,752,957 A | 5/1998 | Ralph et al. |
| 5,755,811 A | 5/1998 | Tanamal et al. |
| 5,772,661 A | 6/1998 | Michelson |
| 5,800,547 A | 9/1998 | Shafer et al. |
| 5,824,093 A | 10/1998 | Ray et al. |
| 5,824,094 A | 10/1998 | Serhan et al. |
| 5,888,222 A | 3/1999 | Coates et al. |
| 5,895,428 A | 4/1999 | Berry |
| 5,899,941 A | 5/1999 | Nishijima et al. |
| RE36,221 E | 6/1999 | Breard et al. |
| 5,928,284 A | 7/1999 | Mehdizadeh |
| 5,961,516 A | 10/1999 | Graf |
| 6,010,502 A | 1/2000 | Bagby |
| 6,019,792 A | 2/2000 | Cauthen |
| 6,039,763 A | 3/2000 | Shelokov |
| 6,042,582 A | 3/2000 | Ray |
| RE36,758 E | 6/2000 | Fitz |
| 6,096,080 A | 8/2000 | Nicholson et al. |
| 6,102,954 A | 8/2000 | Albrektsson et al. |
| 6,106,557 A | 8/2000 | Robioneck et al. |
| 6,113,637 A | 9/2000 | Gill et al. |
| 6,113,638 A | 9/2000 | Williams et al. |
| 6,132,464 A | 10/2000 | Martin |
| 6,146,421 A | 11/2000 | Gordon et al. |
| 6,156,067 A | 12/2000 | Bryan et al. |
| 6,159,211 A | 12/2000 | Boriani et al. |
| 6,159,214 A | 12/2000 | Michelson |
| 6,159,244 A | 12/2000 | Suddaby |
| 6,174,311 B1 | 1/2001 | Branch et al. |
| 6,179,874 B1 | 1/2001 | Cauthen |
| 6,179,875 B1 | 1/2001 | Strempel |
| 6,190,414 B1 | 2/2001 | Young et al. |
| 6,193,757 B1 | 2/2001 | Foley et al. |
| 6,200,322 B1 | 3/2001 | Branch et al. |
| 6,224,599 B1 | 5/2001 | Baynham et al. |
| 6,224,607 B1 | 5/2001 | Michelson |
| 6,228,118 B1 | 5/2001 | Gordon |
| 6,231,609 B1 | 5/2001 | Mehdizadeh |
| 6,235,059 B1 | 5/2001 | Benezech et al. |
| 6,238,396 B1 | 5/2001 | Lombardo |
| 6,251,112 B1 | 6/2001 | Jackson |
| 6,251,140 B1 | 6/2001 | Marino et al. |
| 6,264,655 B1 | 7/2001 | Pisharodi |
| 6,277,122 B1 | 8/2001 | McGahan et al. |
| 6,325,827 B1 | 12/2001 | Lin |
| 6,368,350 B1 | 4/2002 | Erickson et al. |
| 6,368,353 B1 | 4/2002 | Arcand |
| 6,375,681 B1 | 4/2002 | Truscott |
| 6,387,130 B1 | 5/2002 | Stone et al. |
| 6,402,750 B1 | 6/2002 | Atkinson et al. |
| 6,402,785 B1 | 6/2002 | Zdeblick et al. |
| 6,409,766 B1 | 6/2002 | Brett |
| 6,413,278 B1 | 7/2002 | Marchosky |
| 6,419,703 B1 | 7/2002 | Fallin et al. |
| 6,419,705 B1 | 7/2002 | Erickson |
| 6,432,140 B1 | 8/2002 | Lin |
| 6,440,139 B2 | 8/2002 | Michelson |
| 6,440,168 B1 | 8/2002 | Cauthen |
| 6,454,807 B1 | 9/2002 | Jackson |
| 6,471,724 B2 | 10/2002 | Zdeblick et al. |
| 6,514,260 B1 | 2/2003 | Zdeblick et al. |
| 6,517,580 B1 | 2/2003 | Ramadan et al. |
| 6,524,312 B2 | 2/2003 | Landry et al. |
| 6,527,804 B1 | 3/2003 | Gauchet et al. |
| 6,540,747 B1 | 4/2003 | Marino |
| 6,540,785 B1 | 4/2003 | Gill et al. |
| 6,562,074 B2 | 5/2003 | Gerbec et al. |
| 6,565,571 B1 | 5/2003 | Jackowski et al. |
| 6,565,574 B2 | 5/2003 | Michelson |
| 6,565,605 B2 | 5/2003 | Goble et al. |
| 6,572,653 B1 | 6/2003 | Simonson |
| 6,579,319 B2 | 6/2003 | Goble et al. |
| 6,582,466 B1 | 6/2003 | Gauchet |
| 6,582,468 B1 | 6/2003 | Gauchet |
| 6,589,247 B2 | 7/2003 | McGahan et al. |
| 6,599,291 B1 | 7/2003 | Foley et al. |
| 6,607,557 B1 | 8/2003 | Brosnahan et al. |
| 6,610,065 B1 | 8/2003 | Branch et al. |
| 6,610,091 B1 | 8/2003 | Reiley |
| 6,610,093 B1 | 8/2003 | Pisharodi |
| 6,641,582 B1 | 11/2003 | Hanson et al. |
| 6,641,614 B1 | 11/2003 | Wagner et al. |
| 6,648,895 B2 | 11/2003 | Burkus et al. |
| 6,669,729 B2 | 12/2003 | Chin |
| 6,679,915 B1 | 1/2004 | Cauthen |
| 6,685,742 B1 | 2/2004 | Jackson |
| 6,692,495 B1 | 2/2004 | Zacouto |
| 6,699,247 B2 | 3/2004 | Zucherman et al. |
| 6,709,458 B2 | 3/2004 | Michelson |
| 6,733,532 B1 | 5/2004 | Gauchet et al. |
| 6,740,118 B2 | 5/2004 | Eisermann et al. |

(56) References Cited

U.S. PATENT DOCUMENTS

| | | | |
|---|---|---|---|
| 6,743,255 B2 | 6/2004 | Ferree |
| 6,749,635 B1 | 6/2004 | Bryan |
| 6,780,186 B2 | 8/2004 | Errrico et al. |
| 6,805,714 B2 | 10/2004 | Sutcliffe |
| 6,811,567 B2 | 11/2004 | Reily |
| 6,908,484 B2 | 6/2005 | Zubok et al. |
| 6,936,071 B1 | 8/2005 | Marnay et al. |
| 6,949,123 B2 | 9/2005 | Reily |
| 6,958,077 B2 | 10/2005 | Suddaby |
| 6,966,929 B2 | 11/2005 | Mitchell |
| 6,984,245 B2 | 1/2006 | McGahan et al. |
| 6,984,246 B2 | 1/2006 | Huang |
| 6,986,772 B2 | 1/2006 | Michelson |
| 6,994,727 B2 | 2/2006 | Khandkar et al. |
| 7,044,971 B2 | 5/2006 | Suddaby |
| 7,052,515 B2 | 5/2006 | Simonson |
| 7,066,960 B1 | 6/2006 | Dickman |
| 7,070,598 B2 | 7/2006 | Lim et al. |
| 7,074,240 B2 | 7/2006 | Pisharodi |
| 7,083,649 B2 | 8/2006 | Zucherman et al. |
| 7,083,650 B2 | 8/2006 | Moskowitz et al. |
| 7,090,698 B2 | 8/2006 | Goble et al. |
| 7,128,761 B2 | 10/2006 | Kuras et al. |
| 7,137,985 B2 | 11/2006 | Jahng |
| 7,147,665 B1 | 12/2006 | Bryan et al. |
| 7,794,480 B2 * | 9/2010 | Gordon ............... A61B 17/7037 606/257 |
| 8,372,150 B2 * | 2/2013 | Humphreys .......... A61F 2/4425 623/17.15 |
| 8,888,852 B2 * | 11/2014 | Humphreys .......... A61F 2/4405 623/17.15 |
| 2001/0005796 A1 | 6/2001 | Zdeblick et al. |
| 2001/0010021 A1 | 7/2001 | Boyd et al. |
| 2001/0016773 A1 | 8/2001 | Serhan et al. |
| 2001/0016774 A1 | 8/2001 | Bresina et al. |
| 2001/0032020 A1 | 10/2001 | Besselink |
| 2001/0034553 A1 | 10/2001 | Michelson |
| 2001/0047207 A1 | 11/2001 | Michelson |
| 2001/0049560 A1 | 12/2001 | Paul et al. |
| 2002/0045943 A1 | 4/2002 | Uk |
| 2002/0049394 A1 | 4/2002 | Roy et al. |
| 2002/0049497 A1 | 4/2002 | Mason |
| 2002/0052656 A1 | 5/2002 | Michelson |
| 2002/0068976 A1 | 6/2002 | Jackson |
| 2002/0068977 A1 | 6/2002 | Jackson |
| 2002/0077702 A1 | 6/2002 | Castro |
| 2002/0095154 A1 | 7/2002 | Atkinson et al. |
| 2002/0095155 A1 | 7/2002 | Michelson |
| 2002/0099444 A1 | 7/2002 | Boyd et al. |
| 2002/0107572 A1 | 8/2002 | Foley et al. |
| 2002/0116065 A1 | 8/2002 | Jackson |
| 2002/0123806 A1 | 9/2002 | Reiley |
| 2002/0128712 A1 | 9/2002 | Michelson |
| 2002/0128713 A1 | 9/2002 | Ferree |
| 2002/0133155 A1 | 9/2002 | Ferree |
| 2002/0138143 A1 | 9/2002 | Grooms et al. |
| 2002/0138146 A1 | 9/2002 | Jackson |
| 2002/0143399 A1 | 10/2002 | Sutcliffe |
| 2002/0151895 A1 | 10/2002 | Soboleski et al. |
| 2002/0151976 A1 | 10/2002 | Foley et al. |
| 2002/0156528 A1 | 10/2002 | Gau |
| 2002/0161366 A1 | 10/2002 | Robie et al. |
| 2002/0169508 A1 | 11/2002 | Songer et al. |
| 2002/0183756 A1 | 12/2002 | Michelson |
| 2003/0004572 A1 | 1/2003 | Goble et al. |
| 2003/0004575 A1 | 1/2003 | Erickson |
| 2003/0009226 A1 | 1/2003 | Graf |
| 2003/0028250 A1 | 2/2003 | Reiley et al. |
| 2003/0040797 A1 | 2/2003 | Fallin et al. |
| 2003/0045939 A1 | 3/2003 | Casutt |
| 2003/0055427 A1 | 3/2003 | Graf |
| 2003/0074068 A1 | 4/2003 | Errico et al. |
| 2003/0078666 A1 | 4/2003 | Ralph et al. |
| 2003/0100949 A1 | 5/2003 | Michelson |
| 2003/0120348 A1 | 6/2003 | Brosnahan et al. |
| 2003/0135278 A1 | 7/2003 | Eckman |
| 2003/0139812 A1 | 7/2003 | Garcia et al. |
| 2003/0139813 A1 | 7/2003 | Messerli et al. |
| 2003/0153984 A1 | 8/2003 | Khandkar |
| 2003/0171813 A1 | 9/2003 | Kiester |
| 2003/0176923 A1 | 9/2003 | Keller et al. |
| 2003/0191532 A1 | 10/2003 | Goble et al. |
| 2003/0199981 A1 | 10/2003 | Ferree |
| 2003/0199982 A1 | 10/2003 | Bryan |
| 2003/0204259 A1 | 10/2003 | Goble et al. |
| 2003/0204260 A1 | 10/2003 | Ferree |
| 2003/0204261 A1 | 10/2003 | Eisermann et al. |
| 2003/0204271 A1 | 10/2003 | Grinberg et al. |
| 2003/0208273 A1 | 11/2003 | Eisermann et al. |
| 2003/0233146 A1 | 12/2003 | Gringberg et al. |
| 2004/0002712 A1 | 1/2004 | Grinberg et al. |
| 2004/0002761 A1 | 1/2004 | Rogers et al. |
| 2004/0002762 A1 | 1/2004 | Hawkins |
| 2004/0006391 A1 | 1/2004 | Reiley |
| 2004/0024462 A1 | 2/2004 | Ferree et al. |
| 2004/0030390 A1 | 2/2004 | Ferree |
| 2004/0030391 A1 | 2/2004 | Ferree |
| 2004/0034430 A1 | 2/2004 | Falahee |
| 2004/0039385 A1 | 2/2004 | Mazda et al. |
| 2004/0039448 A1 | 2/2004 | Pisharodi |
| 2004/0049190 A1 | 3/2004 | Biedermann et al. |
| 2004/0049272 A1 | 3/2004 | Reiley |
| 2004/0049273 A1 | 3/2004 | Reiley |
| 2004/0049274 A1 | 3/2004 | Reiley |
| 2004/0049275 A1 | 3/2004 | Reiley |
| 2004/0049276 A1 | 3/2004 | Reiley |
| 2004/0049277 A1 | 3/2004 | Reiley |
| 2004/0049278 A1 | 3/2004 | Reiley |
| 2004/0049279 A1 | 3/2004 | Sevrain |
| 2004/0049281 A1 | 3/2004 | Reiley |
| 2004/0068318 A1 | 4/2004 | Coates et al. |
| 2004/0073311 A1 | 4/2004 | Ferree |
| 2004/0097931 A1 | 5/2004 | Mitchell |
| 2004/0098131 A1 | 5/2004 | Bryan et al. |
| 2004/0102848 A1 | 5/2004 | Michelson |
| 2004/0111161 A1 | 6/2004 | Trieu |
| 2004/0126407 A1 | 7/2004 | Falahee |
| 2004/0127991 A1 | 7/2004 | Ferree |
| 2004/0133281 A1 | 7/2004 | Khandkar et al. |
| 2004/0138749 A1 | 7/2004 | Zucherman et al. |
| 2004/0143270 A1 | 7/2004 | Zucherman et al. |
| 2004/0143332 A1 | 7/2004 | Krueger et al. |
| 2004/0162562 A1 | 8/2004 | Martz |
| 2004/0162618 A1 | 8/2004 | Mujwid et al. |
| 2004/0176764 A1 | 9/2004 | Dant |
| 2004/0176845 A1 | 9/2004 | Zubok et al. |
| 2004/0176850 A1 | 9/2004 | Zubok et al. |
| 2004/0181284 A1 | 9/2004 | Simonson |
| 2004/0181285 A1 | 9/2004 | Simonson |
| 2004/0186570 A1 | 9/2004 | Rapp |
| 2004/0186576 A1 | 9/2004 | Biscup et al. |
| 2004/0186577 A1 | 9/2004 | Ferree |
| 2004/0193272 A1 | 9/2004 | Zubok et al. |
| 2004/0220567 A1 | 11/2004 | Eisermann et al. |
| 2004/0220670 A1 | 11/2004 | Eisermann et al. |
| 2004/0220672 A1 | 11/2004 | Shadduck |
| 2004/0225370 A1 | 11/2004 | Cruchet |
| 2004/0230307 A1 | 11/2004 | Eisermann |
| 2004/0243240 A1 | 12/2004 | Beaurain et al. |
| 2004/0243241 A1 | 12/2004 | Istephanous et al. |
| 2004/0249461 A1 | 12/2004 | Ferree |
| 2004/0249462 A1 | 12/2004 | Huang |
| 2004/0254643 A1 | 12/2004 | Jackson |
| 2005/0027359 A1 | 2/2005 | Mashburn |
| 2005/0033432 A1 | 2/2005 | Gordon et al. |
| 2005/0033439 A1 | 2/2005 | Gordon et al. |
| 2005/0043800 A1 | 2/2005 | Paul et al. |
| 2005/0043802 A1 | 2/2005 | Eisermann et al. |
| 2005/0055099 A1 | 3/2005 | Ku |
| 2005/0071008 A1 | 3/2005 | Kirschman |
| 2005/0075644 A1 | 4/2005 | DiPoto et al. |
| 2005/0080488 A1 | 4/2005 | Schultz |
| 2005/0113916 A1 | 5/2005 | Branch, Jr. |
| 2005/0113920 A1 | 5/2005 | Foley et al. |

(56) References Cited

U.S. PATENT DOCUMENTS

| | | |
|---|---|---|
| 2005/0119747 A1 | 6/2005 | Fabris Monterumici et al. |
| 2005/0119753 A1 | 6/2005 | McGahan et al. |
| 2005/0131540 A1 | 6/2005 | Trieu |
| 2005/0143820 A1 | 6/2005 | Zucherman et al. |
| 2005/0149189 A1 | 7/2005 | Mokhtar et al. |
| 2005/0149196 A1 | 7/2005 | Zucherman et al. |
| 2005/0154461 A1 | 7/2005 | Humphreys et al. |
| 2005/0154462 A1 | 7/2005 | Zucherman et al. |
| 2005/0154464 A1 | 7/2005 | Humphreys et al. |
| 2005/0154465 A1 | 7/2005 | Hodges et al. |
| 2005/0154466 A1 | 7/2005 | Humphreys et al. |
| 2005/0154467 A1 | 7/2005 | Peterman et al. |
| 2005/0159818 A1 | 7/2005 | Blain |
| 2005/0165407 A1 | 7/2005 | Diaz |
| 2005/0165484 A1 | 7/2005 | Ferree |
| 2005/0171608 A1 | 8/2005 | Peterman et al. |
| 2005/0171609 A1 | 8/2005 | Humphreys et al. |
| 2005/0171610 A1 | 8/2005 | Humphreys et al. |
| 2005/0187625 A1 | 8/2005 | Wolek et al. |
| 2005/0192671 A1 | 9/2005 | Bao et al. |
| 2005/0197702 A1 | 9/2005 | Coppes et al. |
| 2005/0209698 A1 | 9/2005 | Gordon et al. |
| 2005/0216081 A1 | 9/2005 | Taylor |
| 2005/0228500 A1 | 10/2005 | Kim et al. |
| 2005/0234551 A1 | 10/2005 | Fallin et al. |
| 2005/0234555 A1 | 10/2005 | Sutton et al. |
| 2005/0240270 A1 | 10/2005 | Zubock et al. |
| 2005/0251261 A1 | 11/2005 | Peterman |
| 2005/0256578 A1 | 11/2005 | Blatt et al. |
| 2005/0261773 A1 | 11/2005 | Ferree |
| 2005/0261774 A1 | 11/2005 | Trieu |
| 2005/0267581 A1 | 12/2005 | Marnay et al. |
| 2005/0273178 A1 | 12/2005 | Boyan et al. |
| 2005/0277930 A1 | 12/2005 | Parsons |
| 2005/0277938 A1 | 12/2005 | Parsons |
| 2005/0283237 A1 | 12/2005 | Zucherman et al. |
| 2005/0283242 A1 | 12/2005 | Zucherman et al. |
| 2006/0004448 A1 | 1/2006 | Casey |
| 2006/0009849 A1 | 1/2006 | Reiley |
| 2006/0025862 A1 | 2/2006 | Villiers et al. |
| 2006/0036325 A1 | 2/2006 | Paul et al. |
| 2006/0064170 A1 | 3/2006 | Smith et al. |
| 2006/0069437 A1 | 3/2006 | Weber |
| 2006/0069438 A1 | 3/2006 | Zucherman et al. |
| 2006/0069440 A1 | 3/2006 | Zucherman et al. |
| 2006/0085076 A1 | 4/2006 | Krishna et al. |
| 2006/0089717 A1 | 4/2006 | Krishna et al. |
| 2006/0095133 A1 | 5/2006 | Eisermann et al. |
| 2006/0106459 A1 | 5/2006 | Truckai et al. |
| 2006/0116768 A1 | 6/2006 | Krueger et al. |
| 2006/0129160 A1 | 6/2006 | Mingyan |
| 2006/0142860 A1 | 6/2006 | Navarro et al. |
| 2006/0178744 A1 | 8/2006 | De Villiers et al. |
| 2006/0178745 A1 | 8/2006 | Bartish, Jr. et al. |
| 2006/0241769 A1 | 10/2006 | Gordon et al. |
| 2006/0241771 A1 | 10/2006 | Gordon et al. |
| 2006/0247650 A1 | 11/2006 | Yerby et al. |
| 2006/0247769 A1 | 11/2006 | Molz et al. |
| 2007/0050033 A1 | 3/2007 | Reo et al. |
| 2007/0050037 A1 | 3/2007 | Snell et al. |
| 2007/0055378 A1 | 3/2007 | Ankney et al. |
| 2007/0270972 A1 | 11/2007 | Gordon |
| 2008/0300685 A1* | 12/2008 | Carls .................... A61F 2/4405 606/151 |
| 2011/0028600 A1 | 2/2011 | Rufner |
| 2014/0100658 A1 | 4/2014 | Schmura et al. |
| 2021/0322178 A1 | 10/2021 | Peterman et al. |

FOREIGN PATENT DOCUMENTS

| | | |
|---|---|---|
| CN | 1713866 A | 12/2005 |
| CN | 1917832 A | 2/2007 |
| CN | 1976651 A | 6/2007 |
| CN | 1925799 B | 10/2010 |
| CN | 101969888 A | 2/2011 |
| CN | 102049782 A | 5/2011 |
| CN | 102049785 A | 5/2011 |
| CN | 103293057 A | 9/2013 |
| CN | 103908359 A | 7/2014 |
| CN | 105877878 A | 8/2016 |
| CN | 106236329 A | 12/2016 |
| CN | 107982582 A | 5/2018 |
| CN | 111973324 A | 11/2020 |
| DE | 2804936 A1 | 8/1979 |
| DE | 3023353 A1 | 4/1983 |
| DE | 0277282 A1 | 10/1998 |
| DE | 20017962 U1 | 1/2001 |
| DE | 10135771 A1 | 2/2003 |
| DE | 202004015198 U1 | 11/2004 |
| EP | 0042271 A1 | 9/1984 |
| EP | 0640326 A1 | 3/1995 |
| EP | 0677277 A2 | 10/1995 |
| EP | 0716840 A2 | 6/1996 |
| EP | 0953317 A1 | 11/1999 |
| EP | 1281361 A1 | 2/2003 |
| EP | 0820731 B1 | 5/2003 |
| EP | 0886506 B1 | 4/2005 |
| EP | 1685811 A | 8/2006 |
| EP | 1685811 A1 | 8/2006 |
| EP | 1711134 A1 | 10/2006 |
| EP | 1711137 A2 | 10/2006 |
| EP | 1711141 B1 | 10/2006 |
| EP | 2247266 B1 | 3/2013 |
| EP | 2793759 A1 | 8/2015 |
| EP | 2890314 A4 | 7/2016 |
| EP | 3357459 A1 | 8/2018 |
| EP | 3463202 A4 | 10/2019 |
| FR | 2676911 A1 | 12/1992 |
| FR | 2724108 A1 | 9/1994 |
| FR | 2718635 A1 | 10/1995 |
| FR | 2742653 A1 | 12/1995 |
| FR | 2723841 A1 | 3/1996 |
| FR | 2799638 A1 | 4/2001 |
| FR | 3075032 A1 | 6/2019 |
| JP | 63145650 A | 6/1988 |
| JP | 2261446 A | 10/1990 |
| JP | 10501705 A | 2/1998 |
| JP | 10286262 A | 10/1998 |
| JP | 2001511392 A | 8/2001 |
| JP | 2002512079 A | 4/2002 |
| JP | 2002521090 A | 7/2002 |
| JP | 2002528223 A | 9/2002 |
| JP | 2002532142 A | 10/2002 |
| JP | 2003512090 A | 4/2003 |
| JP | 2003515381 A | 5/2003 |
| JP | 2003518978 A | 6/2003 |
| JP | 2004514498 A | 5/2004 |
| JP | 2004167254 A | 6/2004 |
| JP | 2005503861 A | 2/2005 |
| JP | 2005515002 A | 5/2005 |
| JP | 2005526550 A | 9/2005 |
| JP | 2006500078 A | 1/2006 |
| JP | 2006502274 A | 1/2006 |
| JP | 2019517372 A | 6/2019 |
| WO | 1993010725 A2 | 6/1993 |
| WO | 1996000049 A1 | 1/1996 |
| WO | 1997035529 A1 | 10/1997 |
| WO | 1998014142 A1 | 4/1998 |
| WO | 1999008627 A1 | 2/1999 |
| WO | 1999053871 A1 | 10/1999 |
| WO | 2000004851 A1 | 2/2000 |
| WO | 2000041654 A2 | 7/2000 |
| WO | 2000069351 A1 | 11/2000 |
| WO | 2001039678 A1 | 6/2001 |
| WO | 2001045576 A1 | 6/2001 |
| WO | 2002011650 A2 | 2/2002 |
| WO | 2002043603 A1 | 6/2002 |
| WO | 2002047586 A1 | 6/2002 |
| WO | 2003026522 A2 | 4/2003 |
| WO | 2003041618 A2 | 5/2003 |
| WO | 2003045262 A2 | 6/2003 |
| WO | 2003059212 A1 | 7/2003 |
| WO | 2003084449 A1 | 10/2003 |

(56) References Cited

FOREIGN PATENT DOCUMENTS

| WO | 2003101350 | A1 | 4/2004 |
|---|---|---|---|
| WO | 2004034935 | A1 | 4/2004 |
| WO | 2004041131 | A2 | 5/2004 |
| WO | 2004098465 | A1 | 11/2004 |
| WO | 2005011522 | A2 | 2/2005 |
| WO | 2005025431 | A | 3/2005 |
| WO | 2005070354 | A2 | 4/2005 |
| WO | 2005067824 | A1 | 7/2005 |
| WO | 2005070278 | A2 | 8/2005 |
| WO | 2005070349 | A1 | 8/2005 |
| WO | 2005070350 | A | 8/2005 |
| WO | 2005070350 | A2 | 8/2005 |
| WO | 2005070352 | A2 | 8/2005 |
| WO | 2005070353 | A1 | 8/2005 |
| WO | 2005077304 | A1 | 8/2005 |
| WO | 2005094736 | A1 | 10/2005 |
| WO | 2005112835 | A2 | 12/2005 |
| WO | 2005117725 | A2 | 12/2005 |
| WO | 2006063354 | A1 | 6/2006 |
| WO | 2007028098 | A2 | 3/2007 |
| WO | 2007087477 | A | 8/2007 |
| WO | 2007124467 | A | 11/2007 |

OTHER PUBLICATIONS

TH. Marnay—L'Arthoplatie Intervertebral Lombaire—Jun.-Sep. 1991, 9 pages, Kennedy Clinic, FRANCE.
Ab Swanson, et al.—The Journal of Bone and Joint Surgery, Unicompartmental and Biocompartmental Arthroplasty of the Knee with a Finned Metal Tibial-Plateau Implant, Oct. 1985, 9 pages, J Bone Joint Surg Am. 1985;67:1175-1182, Needham, MA.
David S. Hungerford, M.D., Kenneth A. Krackow, M.D., Robert V. Kenna—Total Knee Arthroplasty: A Comprehensive Approach, 1984, 20 pages, Publisher Williams and Wilkins, Baltimore, MD.
David S. Hungerford, M.D., and Robert V. Kenna—Preliminary Experience with a Total Knee Prosthesis with Pourous Coating Used Without Cement, Jun. 1983, 13 pages, J.B.Lippincott, Co., No. 176, U.S.A.
T. Hooligan, A.D. Steffe, J.D. Black, A.S. Greenwald—Total Lumbar Intervertebral Disc Replacement: Testing of a New Articulating Spacer in Human Cadaver Spines, Feb. 21-23, 1978, 1 page, Cleveland Clinic Foundation, 24th Annual ORS, Dallas, TX.
Jeanette E. Ahrens, PHD, Alexis P Shelokov, MD, Jeffrey L. Carver, BS—Normal Joint Mobility is Maintained with an Artificial Disc Prosthesis, 1999, Texas Health Research Institute, Plano, Texas.
Zimmer—The Journal of Bone and Joint Surgery, Jul. 1970, 2 pages, American Volume, vol. 52-A, No. 5, Boston, MA.
Viscoglioski Bro., LLC, Spine Arthroplasty: Market Potential & Technology Update, Spine Industry Analysis Series, Nov. 2001, 202 pages, U.S.A.
A.H. Crenshaw—Campbell's Operative Orthopedics, 1987, 11 pages, Seventh Edition, vol. 2, The C.V. Mosby Company, 1987.
Zimmer—The Journal of Bone and Joint Surgery, Sep. 1971, 2 pages, American Volume, vol. 53-A, No. 6, Boston, MA.
International Search Authority, United States Patent & Trademark Office, International Search Report and Written Opinion for PCT Appl. No. PCT/US2023/018341, Aug. 29, 2023, pp. 1-22.
International Search Authority, European Patent Office, International Search Report and Written Opinion for PCT Appl. No. PCT/US2008/065504, Dec. 1, 2009, 1-11 pgs.
Australian Patent Office, Patent Examination Report No. 1 for Pat. Appl. 2008259888, dated Sep. 28, 2012, 1-4 pgs.
European Patent Office, European Search Report for Pat. Appl. No. 18787514.1, Dec. 23, 2020, pp. 1-8.
International Search Authority, United States Patent & Trademark Office, International Search Report and Written Opinion for PCT Appl. No. PCT/US2018/028028, Jun. 13, 2018, pp. 1-8.
PCT—International Searching Authority, International Search Report and Written Opinion of the International Searching Authority for Application No. PCT/US2005/000585, Jun. 8, 2005, 12 pages.
PCT—International Searching Authority, International Search Report and Written Opinion of the International Searching Authority for Application No. PCT/US2005/000704, Aug. 23, 2005, 17 pages.
PCT—International Searching Authority, International Search Report and Written Opinion of the International Searching Authority for Application No. PCT/US2005/000656, Aug. 23, 2005, 12 pages.
PCT—International Searching Authority, International Search Report and Written Opinion of the International Searching Authority for PCT/US2007/060491, Apr. 25, 2007, 8 pages.
PCT—International Searching Authority, International Search Report and Written Opinion of the International Searching Authority for PCT/US2005/000706, Sep. 13, 2005, 19 pages.
PCT—International Searching Authority, International Search Report and Written Opinion of the International Searching Authority for Application No. PCT/US2005/000586, Dec. 16, 2005, 17 pages.
PCT—European Patent Office, International Search Report and International Preliminary Examination Report for PCT/US2001/024791, Jun. 20, 2002, 8 pages.
PCT—International Searching Authority, International Search Report and Written Opinion of the International Searching Authority for PCT/US2005/000705, Jun. 6, 2005, 17 pages.
PCT—International Searching Authority, International Search Report and Written Opinion of the International Searching Authority for PCT/US2005/000648, Jun. 6, 2005, 12 pages.

\* cited by examiner

| Level (n = 1054) | Transverse pedicle width (mm) Mean ± SD | Transverse pedicle angle (°) Mean ± SD | Sagittal pedicle angle (°) Mean ± SD | Sagittal pedicle diameter (mm) Mean ± SD | Screw path length (mm) Mean ± SD |
|---|---|---|---|---|---|
| D9 (n = 126) | 5.4 ± 0.70 | 4.3 ± 1.62 | 12.1 ± 0.80[a] | 11.6 ± 0.70 | 40.7 ± 2.40 |
| D10 (n = 122) | 5.8 ± 0.84 | 4.5 ± 1.59 | 11.8 ± 0.64[a] | 12.3 ± 0.84 | 40.0 ± 2.06 |
| D11 (n = 116) | 6.4 ± 0.86 | 4.1 ± 1.74 | 11.7 ± 0.16[a] | 11.7 ± 0.86 | 35.9 ± 2.05 |
| D12 (n = 106) | 6.9 ± 0.97 | 4.4 ± 2.22 | 9.9 ± 0.19[a] | 10.8 ± 0.97 | 35.8 ± 2.10 |
| L1 (n = 102) | 7.2 ± 0.87 | 8.5 ± 1.71 | 6.3 ± 0.47[b] | 10.2 ± 0.62 | 41.9 ± 2.18 |
| L2 (n = 112) | 7.6 ± 0.89 | 9.6 ± 1.24 | 7.6 ± 0.22[b] | 10.6 ± 0.76 | 43.7 ± 1.75 |
| L3 (n = 124) | 8.4 ± 1.06 | 11.2 ± 1.77 | 5.4 ± 0.36[b] | 10.2 ± 0.66 | 45.0 ± 1.74 |
| L4 (n = 122) | 10.1 ± 1.18 | 13.9 ± 1.86 | 4.2 ± 1.20[b] | 11.6 ± 0.78 | 46.7 ± 1.72 |
| L5 (n = 124) | 13 ± 1.48 | 30.2 ± 3.16 | 2 ± 0.82[a] | 16.3 ± 1.52 | 47.4 ± 5.05 |

[a] Caudal direction
[b] Cranial direction

FIG. 4C

| Level | n | Transverse Pedicle Width (mm) | | | n | Transverse pedicle angle (degrees) | | |
| --- | --- | --- | --- | --- | --- | --- | --- | --- |
| | | Mean | Range | Median | | Mean | Range | Median |
| T1 concave | 11 | 5.3±0.9 | 3.8-6.5 | 5.7 | 11 | 33.2±4.8 | 26.8-42.5 | 32.6 |
| T1 convex | 12 | 4.8±0.9 | 3.5-5.9 | 4.9 | 12 | 35±5 | 27.6-42.6 | 34.9 |
| T2 concave | 16 | 4.5±1.4 | 1.9-7.1 | 5 | 16 | 25.2±6.6 | 17.2-40.1 | 24.8 |
| T2 convex | 16 | 3.9±1.2 | 1.7-6.4 | 3.8 | 16 | 26.6±7.2 | 17.4-42.8 | 25.6 |
| T3 concave | 17 | 4±1.1* | 1.9-5.6 | 3.9 | 17 | 19.8±6.3 | 9.7-32.3 | 18.2 |
| T3 convex | 17 | 2.4±1.3 | 0.9-4.6 | 2.2 | 17 | 19.3±6.8 | 11.3-38.3 | 17.2 |
| T4 concave | 17 | 2.9±0.8* | 1.3-4.1 | 3.1 | 17 | 16.1±3.9 | 7.8-23.4 | 16.7 |
| T4 convex | 17 | 1.8±0.7 | 0.5-3.4 | 1.6 | 17 | 15.1±4.1 | 8.1-23.6 | 14.6 |
| T5 concave | 17 | 2.8±0.7* | 1.6-4.1 | 2.8 | 17 | 15±3.7 | 8.6-25.1 | 14.7 |
| T5 convex | 17 | 1.8±0.9 | 0.8-3.7 | 1.8 | 17 | 15.2±5 | 11-33 | 13.9 |
| T6 concave | 17 | 2.4±0.8 | 0.9-3.7 | 2.6 | 17 | 14.9±3.3 | 10.6-22.1 | 14.6 |
| T6 convex | 17 | 2.4±1 | 1.2-4.4 | 2.2 | 17 | 14.1±2.9 | 8.4-19.6 | 14.3 |
| T7 concave | 17 | 2.1±0.6* | 1-3.2 | 2.1 | 17 | 14.7±2.8* | 9.4-20 | 14.5 |
| T7 convex | 17 | 2.7±0.9 | 1.5-4.2 | 2.8 | 17 | 12.8±2.1 | 9.4-16.1 | 12.8 |
| T8 concave | 17 | 2.2±0.6* | 0.8-2.9 | 2.4 | 17 | 14±3.4 | 9-24.4 | 13.2 |
| T8 convex | 17 | 3.1±0.8 | 1.3-4 | 3.5 | 17 | 12.9±2.8 | 8.3-19.5 | 13.5 |
| T9 concave | 17 | 2.9±1.1 | 1.1-5 | 2.7 | 17 | 14.5±2.9 | 10.9-21.1 | 14.3 |
| T9 convex | 17 | 3±0.9 | 0.9-4.4 | 3.2 | 17 | 13.8±2.9 | 10.3-21.4 | 13 |
| T10 concave | 17 | 3.7±1.3 | 1.7-6.7 | 3.7 | 17 | 13±2.4 | 9.7-20.4 | 12.6 |
| T10 convex | 17 | 3.4±1 | 1.1-5.2 | 3 | 17 | 13.9±2.8 | 836-22.8 | 13.8 |
| T11 concave | 17 | 4.5±1.2 | 2.7-6.6 | 4.5 | 17 | 11.9±2.5 | 7.6-15.6 | 11.7 |
| T11 convex | 17 | 4±1.4 | 2-6.9 | 3.7 | 17 | 13.3±3.3 | 8-22.6 | 13.1 |
| T12 convex | 17 | 4.8±1.9 | 2.2-7.8 | 4.4 | 17 | 12.7±2.9 | 7.8-17.7 | 13.1 |
| L1 concave | 17 | 4.9±1.6 | 1.6-7.9 | 5.4 | 17 | 13.2±3.3* | 7.8-18.8 | 12.2 |
| L1 convex | 17 | 4.3±1.6 | 1.8-7.5 | 4.3 | 17 | 16±3.5 | 7.9-23.7 | 15.8 |
| L2 concave | 17 | 4.4±1.3 | 1.9-7.1 | 4.1 | 17 | 14.9±3.6 | 8.6-22.2 | 15.5 |
| L2 convex | 17 | 4.1±1.8 | 1-7.4 | 3.9 | 17 | 15.6±2.9 | 11.1-21.7 | 15.3 |
| L3 concave | 15 | 5.5±1.4 | 3.4-8.2 | 6 | 15 | 16.4±3.5 | 11.5-24.2 | 15.1 |
| L3 convex | 15 | 5.5±2.3 | 2.8-10.2 | 5.1 | 15 | 15.6±3.3 | 9.6-19.7 | 16.2 |
| L4 concave | 13 | 7.9±2.1 | 5.2-11.2 | 7.6 | 13 | 20.2±5.2 | 13.1-31.7 | 18.7 |
| L4 convex | 13 | 7.6±2.1 | 4.9-10.5 | 7.6 | 13 | 19.3±4 | 14.5-28.2 | 18 |
| L5 concave | 10 | 9.8±2.8 | 5.5-14.8 | 9.4 | 10 | 27.9±5.3 | 18.3-34.8 | 28.7 |
| L5 convex | 10 | 9.9±1.8 | 5.6-12.6 | 9.9 | 10 | 29.2±5.5 | 17.6-37.9 | 29.2 |

FIG. 4D

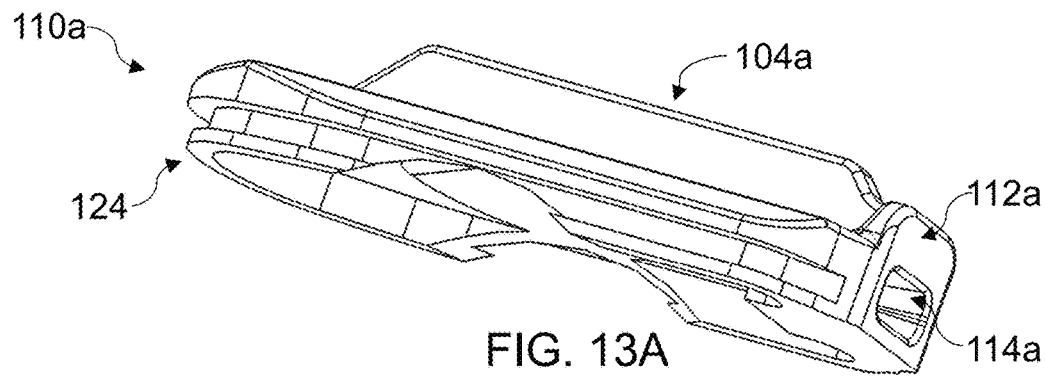
FIG. 13A
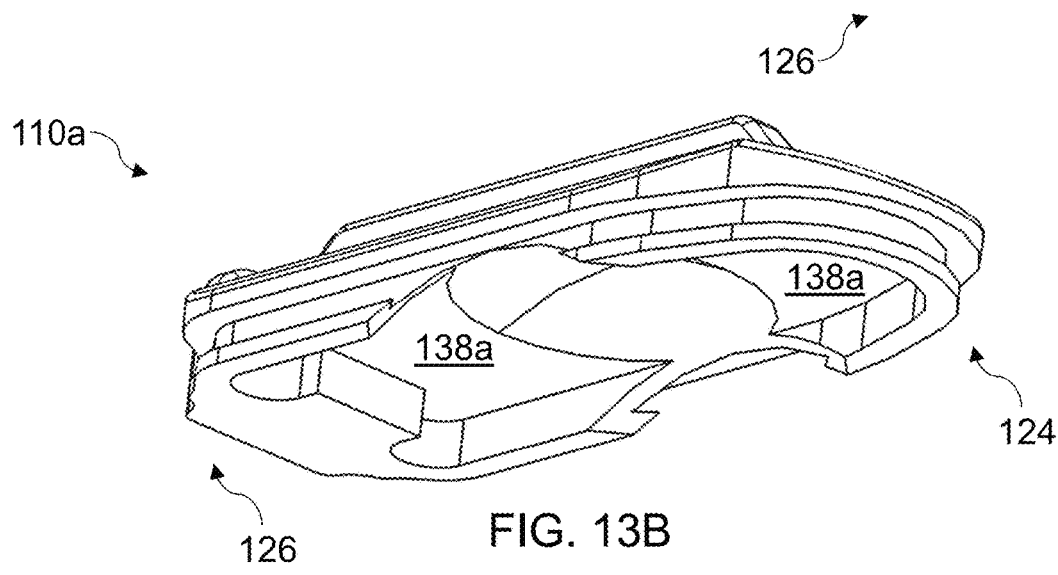
FIG. 13B
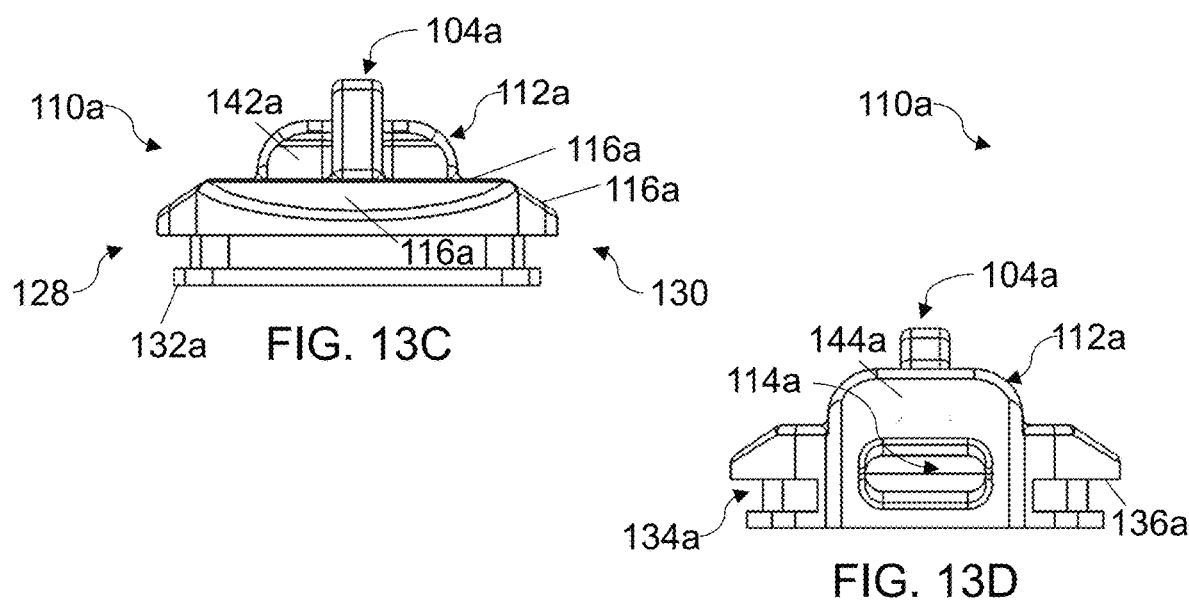
FIG. 13C
FIG. 13D

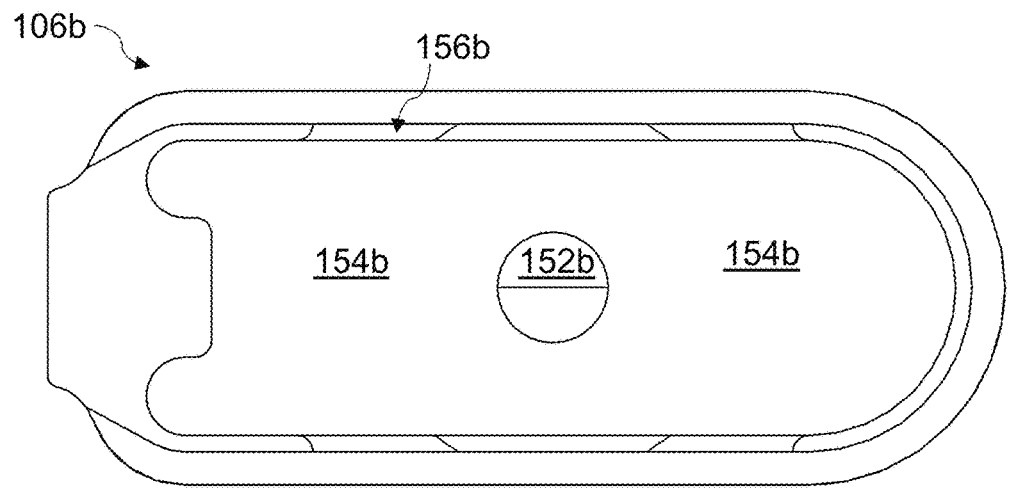
FIG. 15K
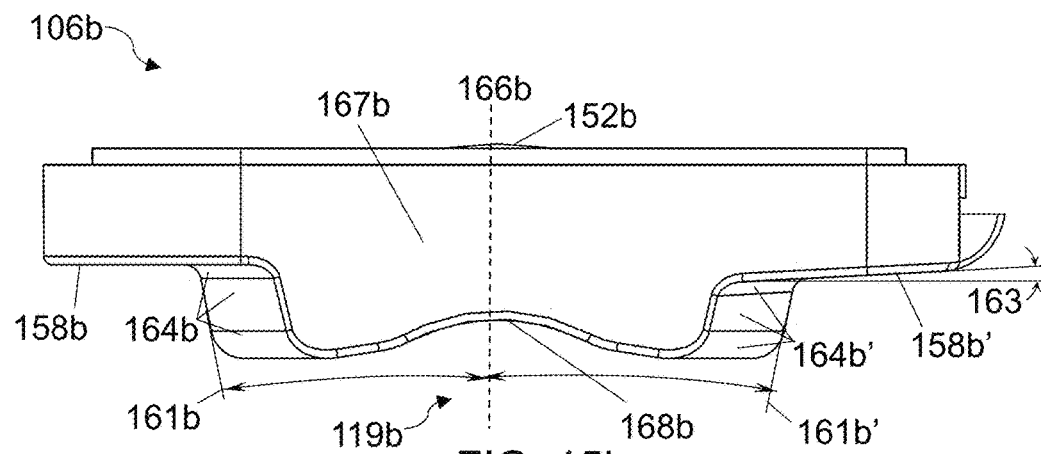
FIG. 15L
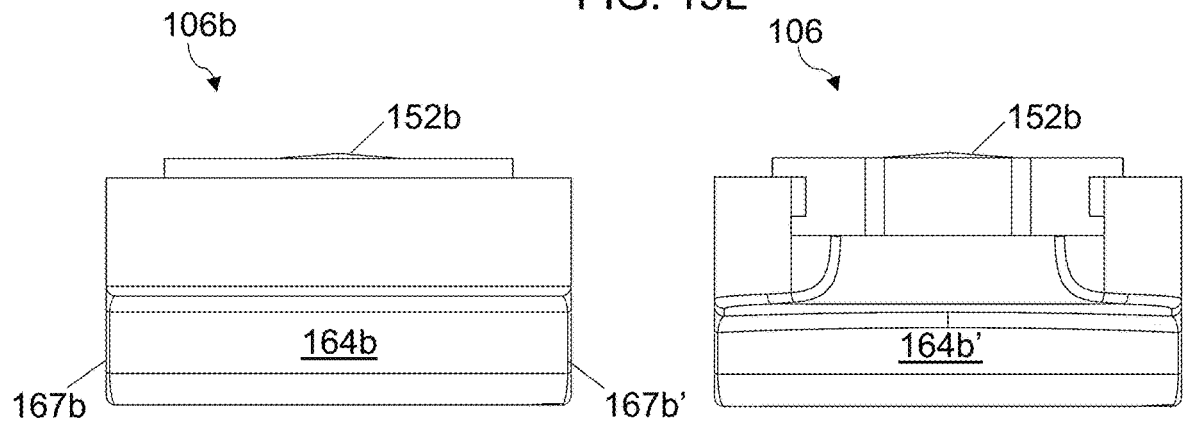
FIG. 15M
FIG. 15N

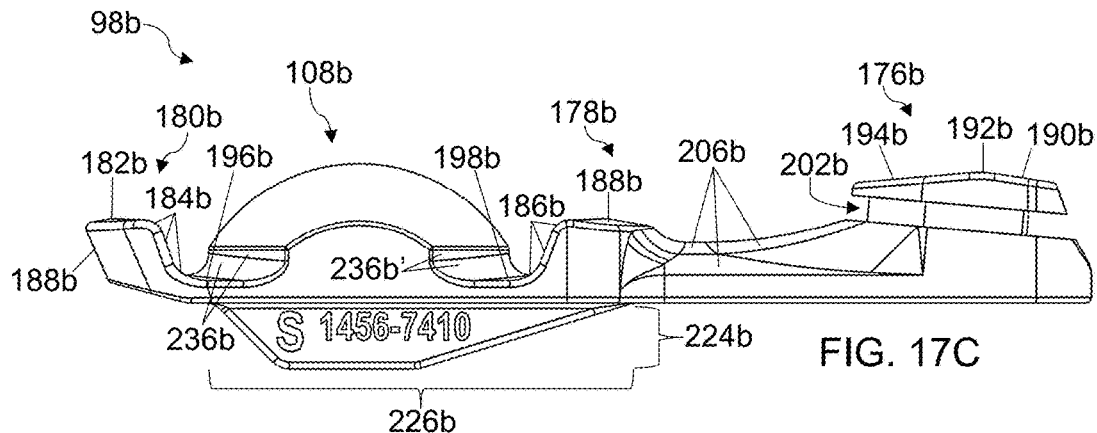
FIG. 17C
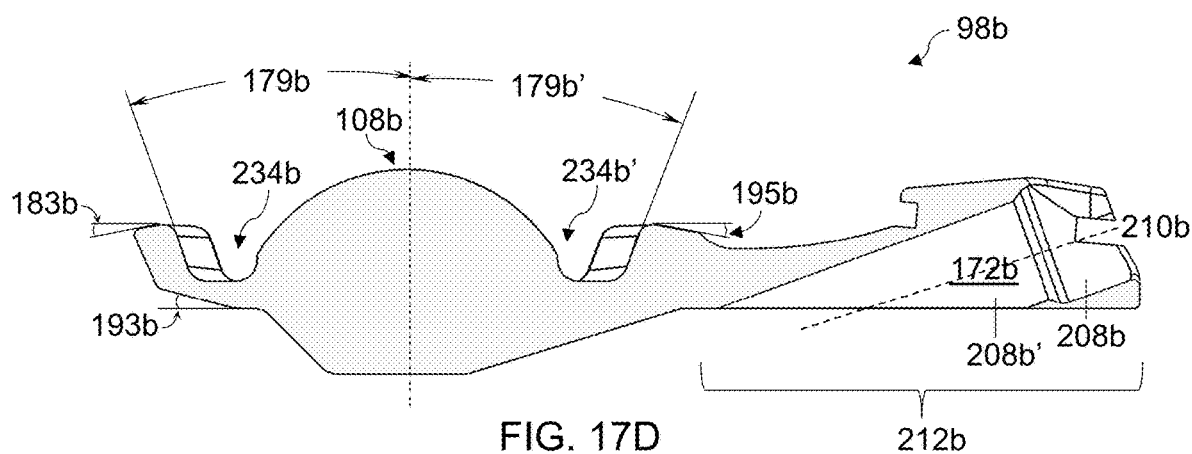
FIG. 17D
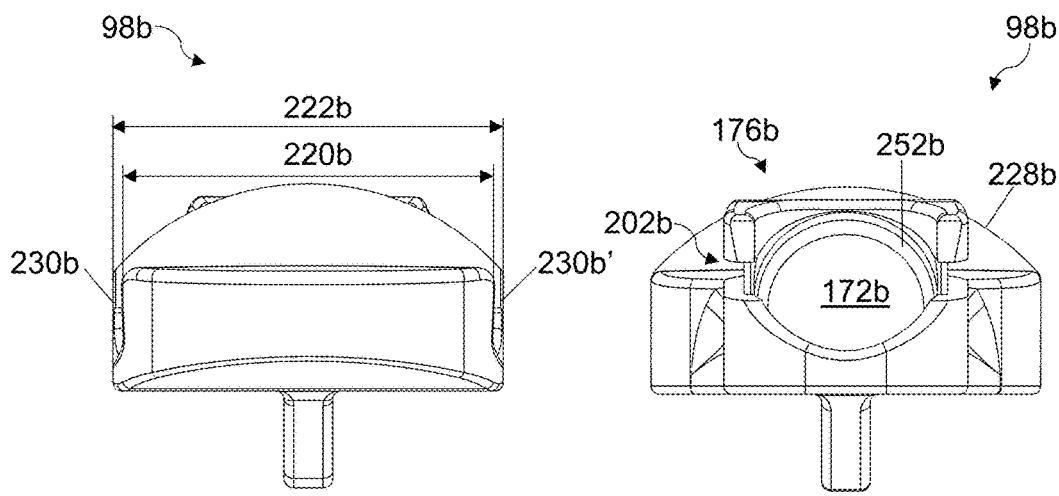
FIG. 17E
FIG. 17F

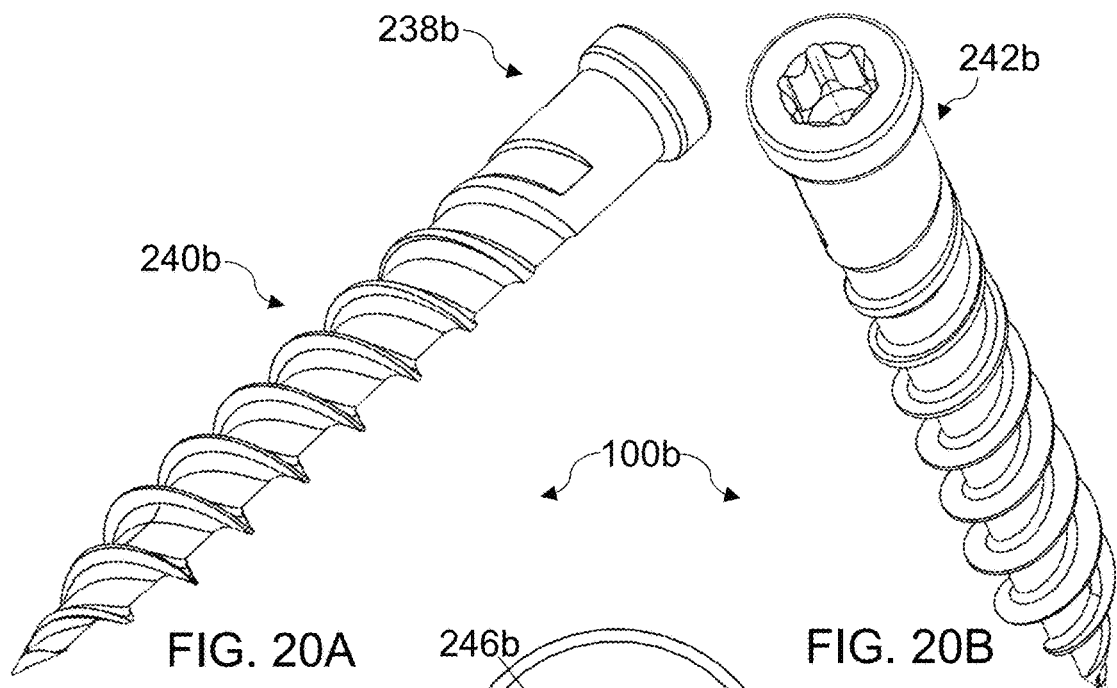
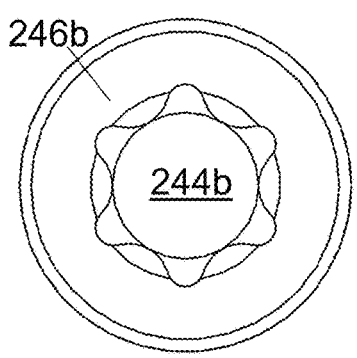
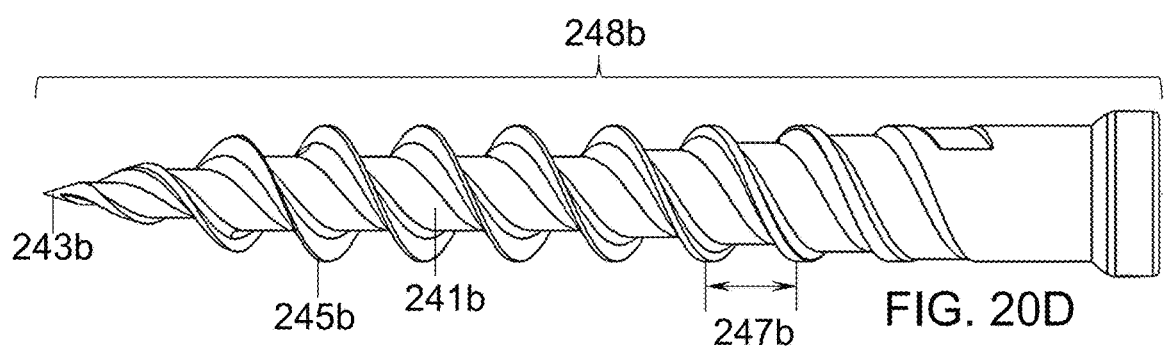
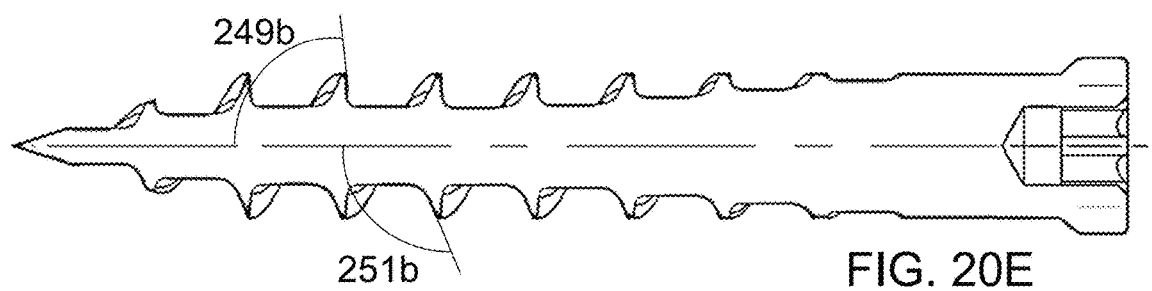

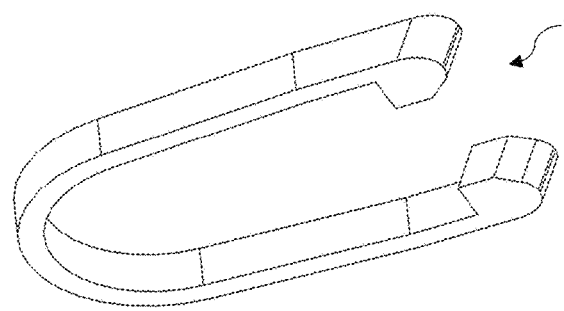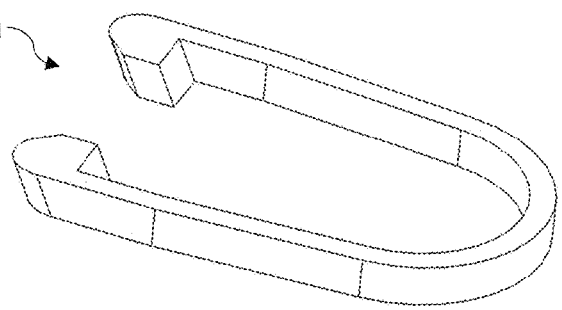
FIG. 21A  FIG. 21B
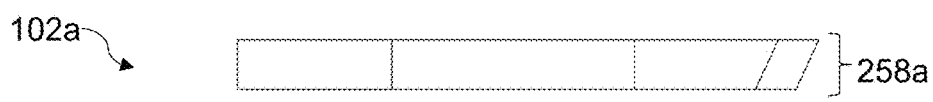
FIG. 21C
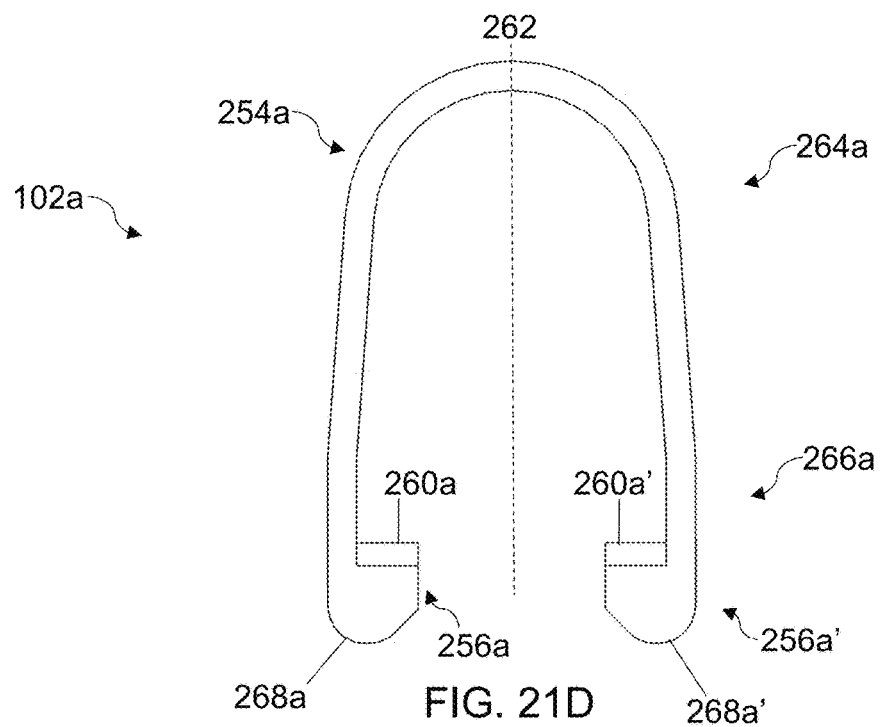
FIG. 21D

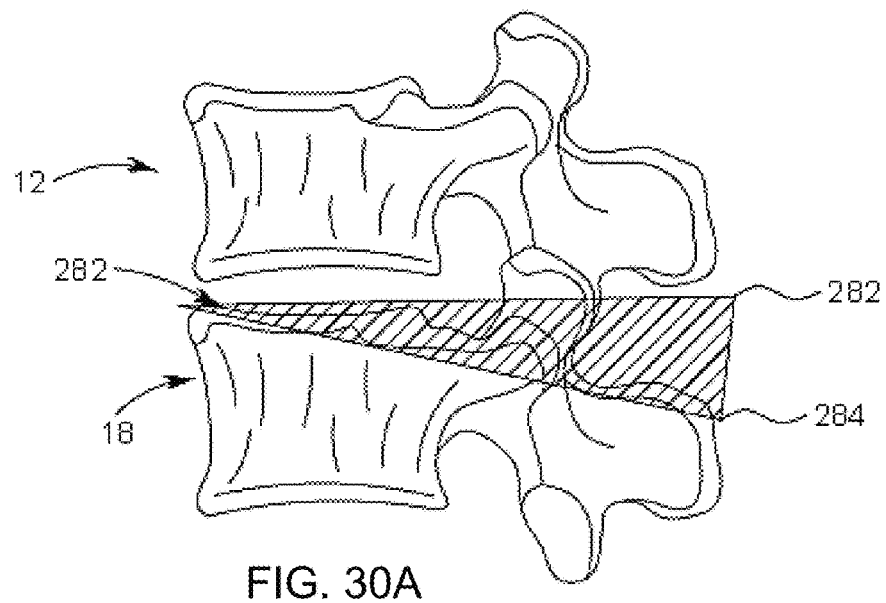
FIG. 30A
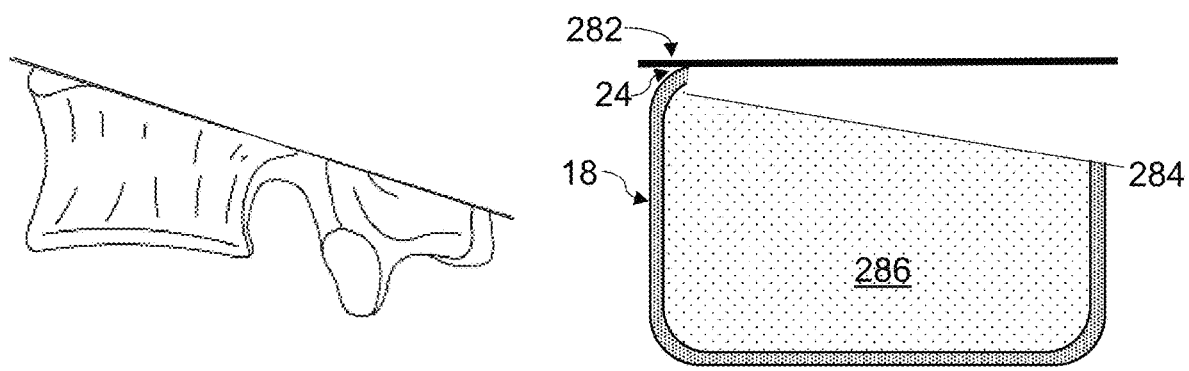
FIG. 30B
FIG. 30C
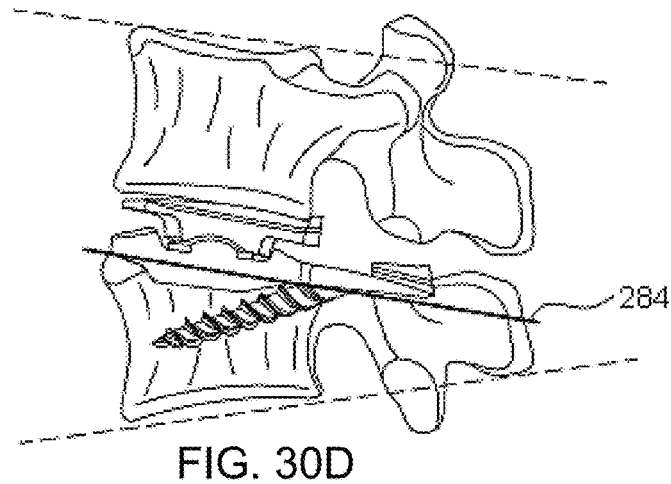
FIG. 30D

TOTAL SPINAL JOINT SYSTEMS WITH MOTION MODERATORS

CROSS-REFERENCE TO RELATED APPLICATIONS

This application is a continuation application of PCT Application No. PCT/US2023/018341 entitled "Total Spinal Joint Replacement Spinal Implant System," filed on Apr. 12, 2023, which claims the benefit of U.S. Provisional Application No. 63/330,033 entitled "Total Joint Replacement Spinal Implant System" filed Apr. 12, 2022; U.S. Provisional Application No. 63/345,560 entitled "Total Spinal Joint Replacement Methods & Instrumentation," filed May 25, 2022; and U.S. Provisional Application No. 63/375,379 entitled "Surgical Instrumentation for Total Spinal Joint Replacement," filed on Sep. 12, 2022, the disclosures of which are incorporated by reference herein in their entireties.

TECHNICAL FIELD

The improved intervertebral spinal implant system generally relates to at least one system for insertion into an intervertebral space between adjacent vertebrae of a human spine, to provide and/or restore range of motion, stability, flexibility, coronal alignment/balance, sagittal alignment/balance and proper biomechanical motion. More specifically, the improved intervertebral spinal implant system may include at least two systems for insertion into an intervertebral space and/or may be inserted into multi-level intervertebral spaces.

BACKGROUND OF THE INVENTION

At times, the source of a patient's back pain may not be clear. Among possible causes for such pain are disease, degradation and/or injury to the vertebra and/or discs of the spine, as well as to various ancillary structures such as the lamina and/or associated facet joints. While spinal fusion and/or disc arthroplasty procedures have been successful in treating spinal joints to reduce pain, such treatments are often limited in their efficacy. Such fusion surgeries often fuse or immobilize portions or a patient's spine and are often unable to address and/or correct severe spinal deformities, return or restore patients sagittal or coronal alignment, as well as maintain columnar stability without affecting adjacent vertebral segments.

However, in the past decade, there has been an emerging option of dynamic stabilization as an alternative to fusion. Dynamic stabilization was designed to ameliorate the instability while maintaining segmental motility, thus reducing or eliminating the potential for adjacent segment disease. Unfortunately, the current interbody dynamic stabilization devices have many disadvantages, including: (1) increased wear debris that initiates inflammatory responses; (2) does not preserve, support or stabilize the posterior bony spinal elements (e.g., facets); (3) increased improper placements or less than ideal position, which can affect the expected range of motion and cause an increase of load to the facets; (4) improper alignment of the spine, including but not limited to undesired increased segmental lordosis; (5) increased migration; (6) requires preservation of endplate; and (7) must come equipped with various degrees of angulation to accommodate an individual's lumbar lordosis.

BRIEF SUMMARY OF THE INVENTION

Therefore, an improved motion preserving spinal implant system and/or an intervertebral spinal implant system is needed to function as a total spinal joint replacement or total joint replacement rather than just a dynamic stabilization device. The spinal implant system functions as a total joint replacement because it replaces at least two structures in the spine—the intervertebral disc and facets—in a single medical procedure, while restoring or optimizing freedom of movement (e.g., the dynamic or motion feature of the spinal implant). Furthermore, the spinal implant may further restore or optimize the biomechanics of one or more spinal segments, redistribute loads throughout the vertebral bodies (e.g., improve load sharing characteristics or features) to facilitate stabilization and/or support, and restore or optimize spinal curvature and balance via adjusting the sagittal and/or coronal orientation.

In one embodiment, a dynamic spinal implant system comprising: a first spinal implant system, the first spinal implant system comprises a first length, a first inferior element and a first superior element; the first superior element comprises a socket; the first inferior element comprises a ball component, the ball component of the first inferior component engages with the socket component of the first superior component to allow the first superior element to move relative to the first inferior element; and a second spinal implant system, the second spinal implant system comprises a second length, a second inferior element and a second superior element; the second superior element comprises a socket; the second inferior element comprises a ball component, the ball component of the second inferior component engages with the socket component of the second superior component to allow the second superior element to move relative to the second inferior element; the first spinal implant system disposed between a first vertebra and a second vertebra at a first orientation, at least a portion of the first spinal implant is disposed, extends or contacts within each of the three columns of the spine; the second spinal implant system disposed between the first vertebra and the second vertebra at a second orientation, at least a portion of the second spinal implant extends or contacts within each of the three columns of the spine.

In another embodiment, a dynamic spinal implant system comprising: a first spinal implant system, the first spinal implant system comprises a first length, a first inferior element and a first superior element; the first superior element comprises a socket; the first inferior element comprises a ball component, the ball component of the first inferior component engages with the socket component of the first superior component to allow the first superior element to move relative to the first inferior element; and a second spinal implant system, the second spinal implant system comprises a second length, a second inferior element and a second superior element; the second superior element comprises a socket; the second inferior element comprises a ball component, the ball component of the second inferior component engages with the socket component of the second superior component to allow the second superior element to move relative to the second inferior element; the first spinal implant system positioned at a first toe-in angle between an upper vertebra and a lower vertebra; the second spinal implant system positioned at a second toe-in angle between the upper vertebra and lower vertebra.

In another embodiment, a multi-level dynamic spinal implant system comprising: a first spinal implant system, the first spinal implant system comprises a first length, a first inferior element and a first superior element; the first superior element comprises a socket; the first inferior element comprises a ball component, the ball component of the first inferior component engages with the socket component of the first superior component to allow the first superior element to move relative to the first inferior element; and a second spinal implant system, the second spinal implant system comprises a second length, a second inferior element and a second superior element; the second superior element comprises a socket; the second inferior element comprises a ball component, the ball component of the second inferior component engages with the socket component of the second superior component to allow the second superior element to move relative to the second inferior element; the first spinal implant system positioned into a first vertebral level and a first toe-in angle; the second spinal implant system positioned into a second vertebral level and a second toe-in angle.

In another embodiment, a multi-level dynamic spinal implant system comprising: a first pair of spinal implant systems, each of the first pair of spinal implant systems comprises a first length, a first inferior element and a first superior element; the first superior element comprises a socket; the first inferior element comprises a ball component, the ball component of the first inferior component engages with the socket component of the first superior component to allow the first superior element to move relative to the first inferior element; and a second pair of spinal implant systems, each of the second pair of spinal implant systems comprises a second length, a second inferior element and a second superior element; the second superior element comprises a socket; the second inferior element comprises a ball component, the ball component of the second inferior component engages with the socket component of the second superior component to allow the second superior element to move relative to the second inferior element; each of the first pair of spinal implant systems positioned into a first vertebral level at a first pair of toe-in angles; each of the second pair of spinal implant systems positioned into a second vertebral level at a second pair of toe-in angles.

In another embodiment, a dynamic spinal implant system comprising: a first spinal implant system, the first spinal implant system comprises a first length, a first inferior element and a first superior element; the first superior element comprises a socket; the first inferior element comprises a ball component, the ball component of the first inferior component engages with the socket component of the first superior component to allow the first superior element to move relative to the first inferior element; and a second spinal implant system, the second spinal implant system comprises a second length, a second inferior element and a second superior element; the second superior element comprises a socket; the second inferior element comprises a ball component, the ball component of the second inferior component engages with the socket component of the second superior component to allow the second superior element to move relative to the second inferior element; the first spinal implant system positioned at a first orientation between a first vertebra and a second vertebra; the second spinal implant system positioned at a second orientation between the first vertebra and the second vertebra.

In another embodiment, a dynamic spinal implant system comprising: a first spinal implant system, the first spinal implant system comprises a first length, a first inferior element and a first superior element; the first superior element comprises a socket; the first inferior element comprises a ball component, the ball component of the first inferior component engages with the socket component of the first superior component to allow the first superior element to move relative to the first inferior element; and a second spinal implant system, the second spinal implant system comprises a second length, a second inferior element and a second superior element; the second superior element comprises a socket; the second inferior element comprises a ball component, the ball component of the second inferior component engages with the socket component of the second superior component to allow the second superior element to move relative to the second inferior element; the first spinal implant system positioned at a first toe-in angle and a first orientation between a first vertebra and a second vertebra; the second spinal implant system positioned at a second toe-in angle and a second orientation between the first vertebra and the second vertebra.

In another embodiment, a motion preserving spinal implant comprising: an upper element, the upper element comprises a base and a first articulating component, the base including a material, at least a portion of the first articulating component coupled to the base, the first articulating component comprising a material and a socket; a lower element, the lower element comprises a base, a second articulating component, and a bridge, the base comprising a first stop and a second stop, the second articulating component is disposed between the first stop and the second stop, the second articulating component comprises a ball, the ball is sized and configured to be disposed within the socket of the first articulating component of the upper element, the bridge extends away from a posterior surface of the base, the bridge comprising a screw housing, the screw housing including a threaded through hole, the through-hole positioned in an oblique orientation; the ball of the second articulating component reciprocally engages with the socket of the first articulating component to allow a multi-axial rotation and/or translation of the upper element relative to the lower element; and a fixation screw, the fixation screw comprising a screw body and a screw head, the fixation screw disposed within the threaded through-hole, the screw head is positioned below or equal to a posterior surface of the screw housing. The motion preserving spinal implant further comprises a retaining clip, the retaining clip is disposed onto the screw housing, at least a portion of the retaining clip extends and contacts a portion of the fixation screw to prevent migration of the fixation screw.

BRIEF DESCRIPTION OF THE SEVERAL VIEWS OF THE DRAWINGS

FIGS. 4C-4D illustrates tables with various pedicle morphological measurements in different spine regions;

FIGS. 13A-13G depict various plan views of one embodiment of a base of the superior element of FIGS. 10A-10F;

FIGS. 15H-15N depict various plan views of an alternate embodiment of a superior articulating component;

FIGS. 17A-17F depict various plan views of an alternate embodiment of an inferior element of the spinal implant of FIGS. 8A-8D;

FIGS. 20A-20E depicts various plan views of an alternate embodiment of a fixation screw;

FIGS. 21A-21D depicts various plan views of one embodiment of a retention clip;

FIGS. 30A-30D illustrates a sagittal view and cross-sectional view of one embodiment of the non-parallel orientation angles or orientation planes in the sagittal view cut into the vertebral body to create additional lordosis for correcting sagittal imbalance;

DETAILED DESCRIPTION OF THE INVENTION

The human spine is a complex mechanical structure including alternating bony vertebrae and fibrocartilaginous discs that are connected by strong ligaments and supported by musculature that extends from the skull to the pelvis and provides axial support to the body. Accordingly, the human spine is a highly flexible structure capable of a high degree of curvature and twist in nearly every direction, such as flexion and extension in sagittal plane, left lateral flexion and right lateral flexion in the frontal plane and left and right rotation in transverse plane. However, genetic or developmental irregularities, trauma, chronic stress, and degenerative wear can result in spinal pathologies for which surgical intervention may be necessary.

Due to the many disadvantages of fusion surgery, there is a need for a more effective and versatile total joint replacement spinal implant system that functions as a successful alternative to fusion rather than the standard available dynamic stabilization devices. The disclosed total joint replacement systems described herein are improved dynamic or motion preserving spinal implants that can restore biomechanical function, restore spino-pelvic balance, and stabilize the spine without the loss of spinal integrity and mobility. Surgical correction of the spino-pelvic balance is needed to lead a better quality of life for patients.

The total joint replacement system is a dynamic spinal implant which replaces the function of the disc and the facet joints by comprising a unique design with motion preservation and load sharing features that allow the implant to extend within two or more columns and/or all three columns of the spine. Furthermore, the total joint replacement system can accomplish the above with using one design in different sizes and without requiring the availability of different designs with degrees of lordotic angulations for lordotic correction. This is counterintuitive to the traditional spinal implants—traditional spinal implants typically require different sized and/or shaped designs with varying degrees of lordotic angulations to help align or optimize the spinal curvatures of a patient.

This specification describes novel systems and devices to treat spinal degenerative diseases. Aspects of the present invention will be described regarding the treatment of vertebral bodies at the different levels of the spine, including cervical, thoracic and lumbar levels. It should be appreciated, however, that various aspects of the invention may not limited in their application to spinal injuries and/or degeneration. The systems and methods may be applicable to the treatment of degeneration in diverse bone types or bone joints, as well as in other anatomical locations, including the elbow, neck, knee, shoulder, and/or hip. However, to understand unique features of the improved dynamic spinal implant, further explanation of the spinal morphology is necessary.

Spinal Morphology

Figure 1A:
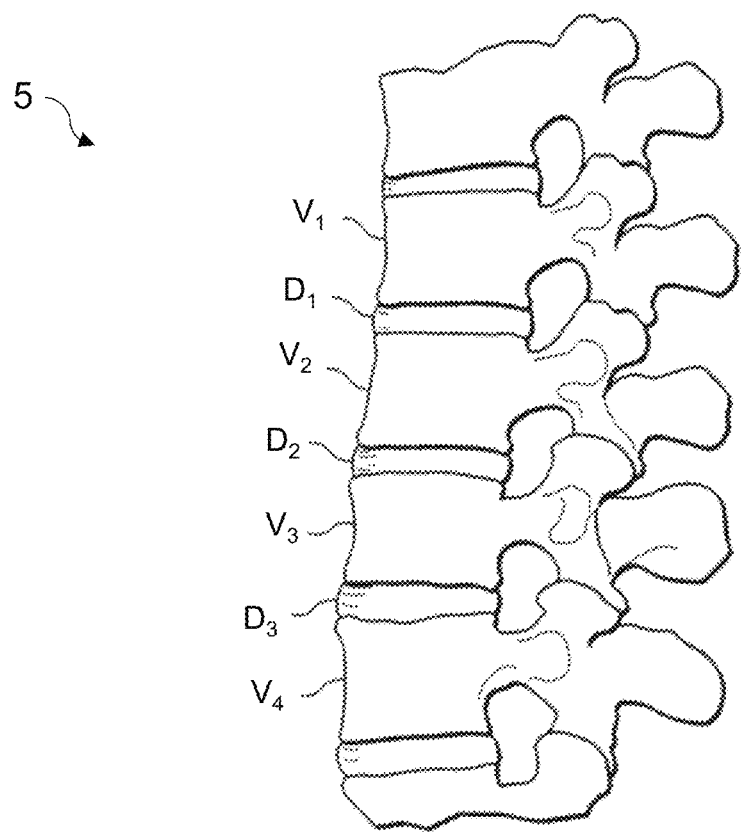
FIGS. 1A-1B depict a sagittal view of one embodiment of one or more spinal functional units or segments.

Referring to FIG. 1A, a sagittal view of a healthy vertebral column 5 is shown, illustrating a sequence of vertebrae V1, V2, V3, V4 separated by natural intervertebral discs D1, D2, D3, respectively. Although the illustration generally depicts a lumbar section of a spinal column, it is understood that the devices, systems, and methods of this disclosure may also be applied to all regions of the vertebral column, including thoracic and cervical regions.

Figure 1B:
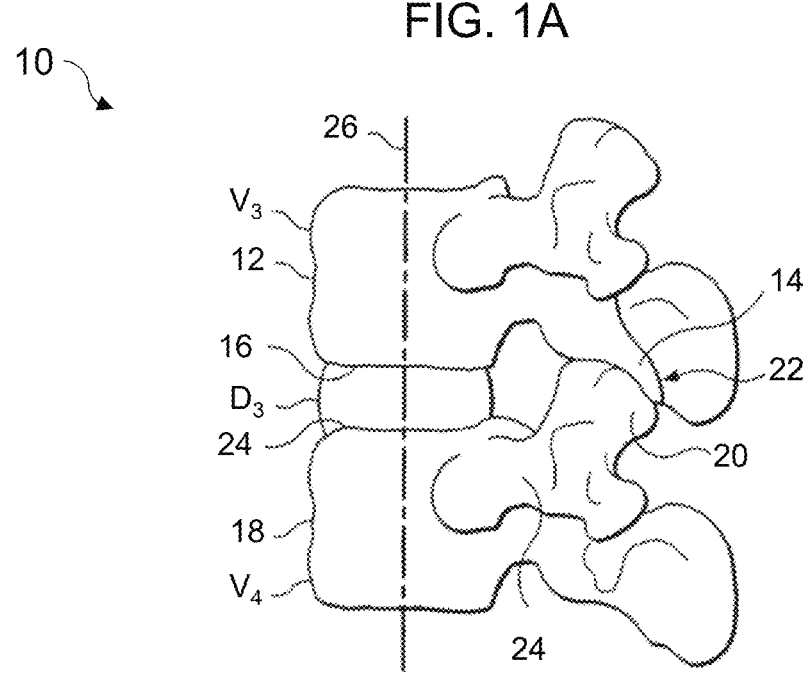

Referring to FIG. 1B, in any given vertebral joint, functional spinal unit or spinal segment 10 of the vertebral column 5 includes the adjacent vertebrae V3, V4 which the intervertebral disc D3 is disposed in between. More specifically, the top vertebra V3 may be referred to as the superior vertebra or the upper vertebra and the bottom vertebra V4 may be referred to as the inferior vertebra or the lower vertebra. The top vertebra V3 includes a generally cylindrical vertebral body portion 12, an inferior articular process 14, and an inferior facing endplate 16. The vertebra V4 includes a generally cylindrical vertebral body portion 18 (which is a weight bearing area), a superior articular process 20, and a superior facing endplate 24. For reference purposes, a longitudinal axis 26 extends through the centers of the cylindrical vertebral body portions 12, 18. A pedicle 24 extends between the inferior vertebral body 18 and superior articular process 20.

Figure 2A:
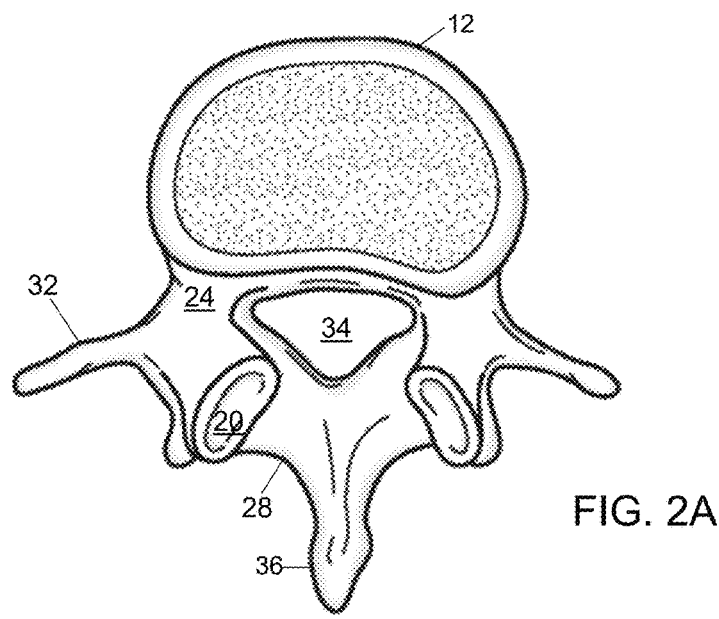
FIGS. 2A-2C depict various anatomical views of one embodiment of a vertebral body.
Figure 2B:
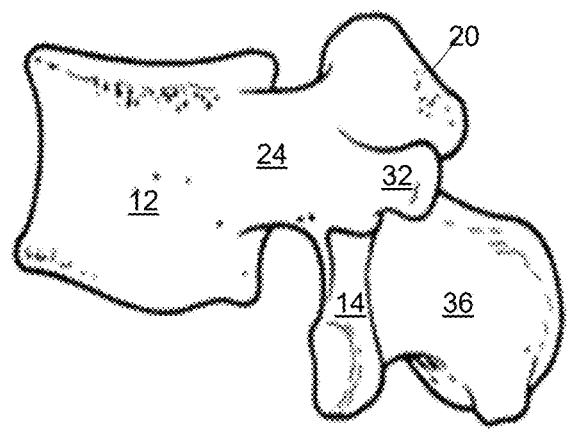
Figure 2C:
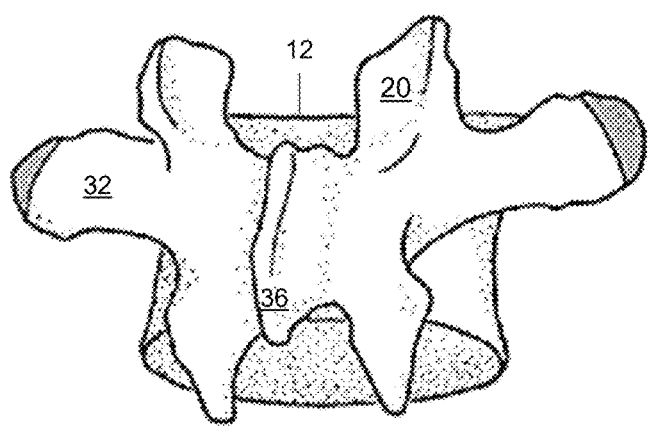

FIGS. 2A-2C depicts different plane views of a portion of a vertebra V3, V4. On the vertebra V3, V4 there are seven processes projecting from the vertebra body portion 12, 18. There is one spinous process 36, two transverse processes 32, four articular processes 14, 20 and a spinal canal 34. The two transverse processes 32, one on each side of the vertebral body portion 12, 18 project laterally from either side at the point where the lamina 28 joins the pedicle 24, between the superior 20 and inferior 14 articular processes. The lamina 28 covers the spinal canal, which is the large hole in the center of the vertebra that the spinal nerves pass. The spinous process 36 extends from the lamina 28 and projects centrally. The spinous process 36 serves to attach muscles and ligaments. The inferior articular process 14 and the superior articular process 20 form a facet or zygapophyseal joint 22. The facet joint 22 has a fluid filled capsule and cartilage to provide articulating surfaces for the articular processes 16, 20 and help restrict the range of motion.

Figure 3A:
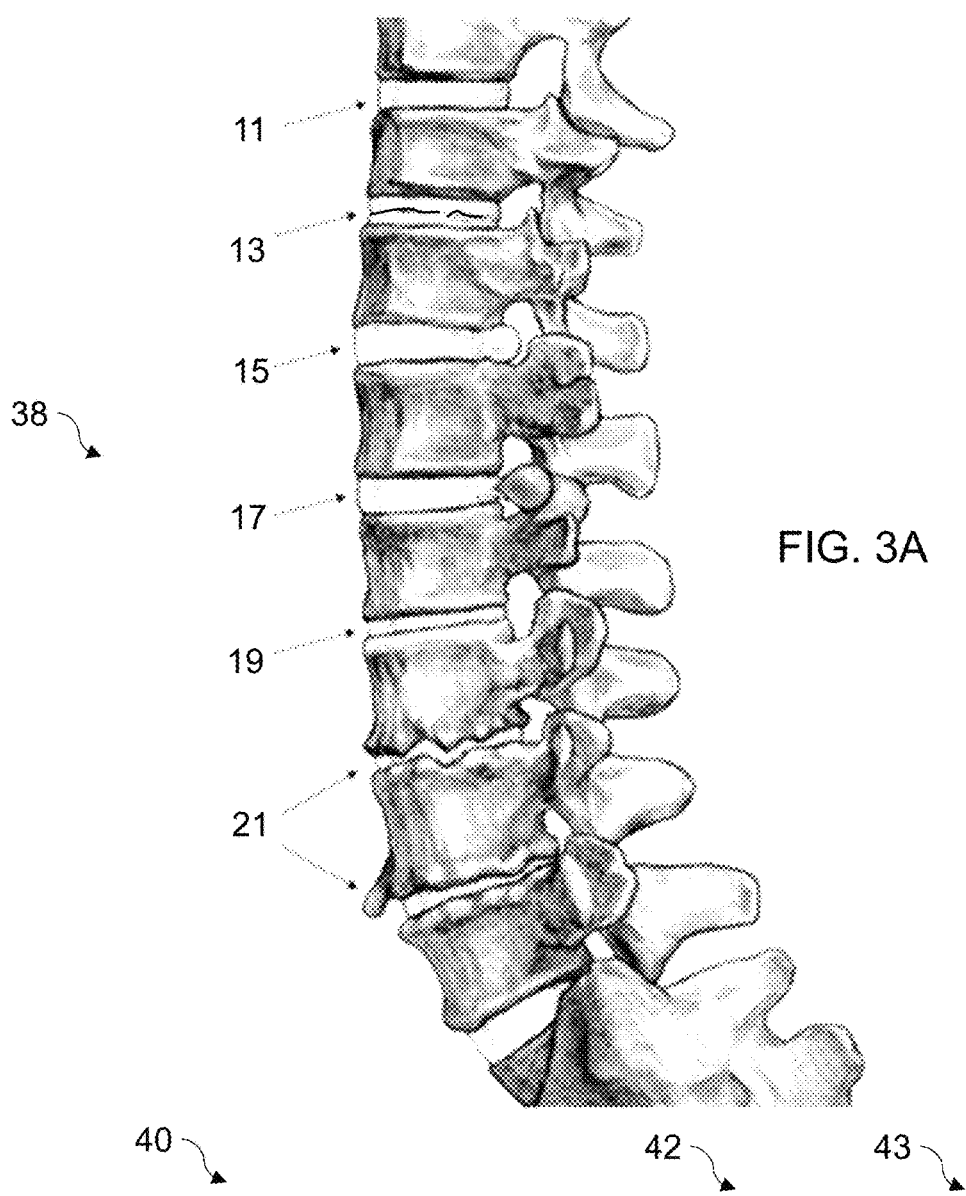
FIG. 3A depicts a sagittal view of a various spine segments with different types of degenerated discs.
Figure 3B:
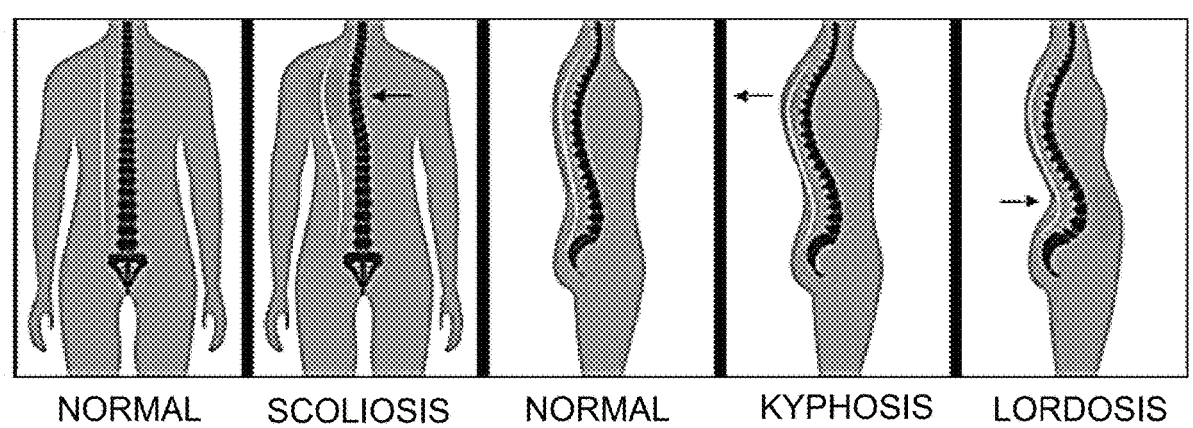
FIG. 3B depict an anterior and sagittal view of one embodiment of a scoliotic and lordotic spine.

Both the disc D1 and the facet joint 26 permit motion between adjacent bone surfaces, allowing the total vertebral joint, functional spinal unit or spinal segment 10 to comprise translational motion, the translational motion includes a normal range of flexion/extension, lateral bending, and axial or transverse rotational motion. As the disc D1 and/or the facet joint 26 deteriorate due to aging, injury, disease, or other factors, all or portions of the disc, the facet joint, and/or the articular processes 16, 22 leading to disc and/or facet degeneration. FIG. 3A depicts a spinal column with different types of degenerated discs 38 that may lead to changes of certain properties of the normal disc 11, including a degenerated disc 13, a bulging disc 15, herniated discs 17, thinning discs 19, or contain osteophytes 21. Such degeneration can adversely affect the structural integrity of the spine and contribute to scoliosis 40, kyphosis 42 and/or lordosis 43 as shown in FIG. 3B. Scoliosis, lordosis and kyphosis 40, 42, 43 are curves that are exaggerated or abnormal to the spine's natural curvatures (e.g., natural lordotic or kyphotic curves) leading to pain, deformity and/or neurologic dysfunction. More specifically, scoliosis is abnormal or exaggerated curvature in the coronal plane, and lordosis is abnormal or exaggerated curvature in the sagittal plane. Any exaggeration or abnormalities of the curves in the sagittal plane or coronal plane, results in sagittal imbalance or coronal imbalance. If the degeneration and/or curve abnormalities significantly or severely affect the patient, a surgeon may opt for surgical repairs (e.g., fusion) that attempt to stabilize the spine, even where such surgical intervention might alter a single level or group of levels to less desirable and/or non-desirable curves. Unfortunately, current fusion procedures may further cause hyperlordosis or hyperkyphosis, which causes the adjacent segments or vertebral joints to compensate with either increased lordosis 43 or kyphosis 42, respectively (e.g., adjacent segment disease). Therefore, understanding the vertebral anatomy and variation between patients to gauge the optimal placement, orientation and the return to normal spino-pelvic balance can improve the surgeon's precision while performing the surgery and achieve more optimal results for the patient.

Figure 4A:
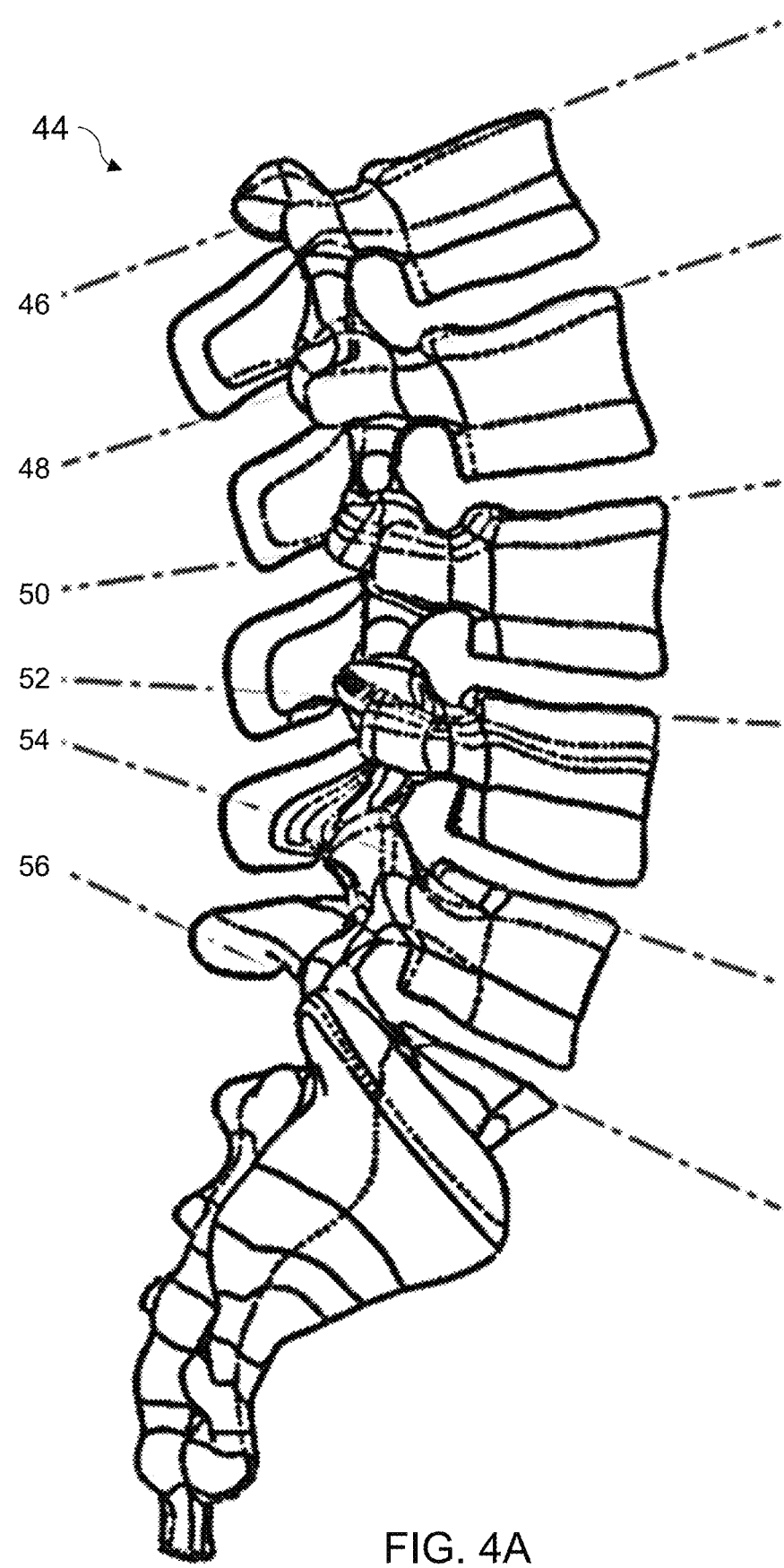
FIG. 4A depicts a sagittal view of a portion of a spine with natural lordotic spine orientations in multiple spinal segments.

FIG. 4A depicts a lateral or sagittal view of an exemplary lower lumbar region 44, with typical lumbar lordotic angular variance across one or more spinal segments 10 indicated by dotted lines. The spine's natural lordotic and kyphotic curvatures and its angular variance are designed for even distribution of weight and flexibility of movement. These natural curves work in harmony to keep the body's center of gravity aligned over the hips and pelvis. The article "*Lumbar Lordosis: A Study of Angle Values And Of Vertebral Bodies And Intervertebral Discs Role*" by Fonseca Damasceno et al., published in Acta Orthopedica Brasileira, pgs. 193-198 (2006), discloses natural or normal lordotic angles of a person's spine at each lumbar spinal level within the lumbar region. The L1 46 normally has a typical lumbar lordosis angular range of 14 degrees to −9 degrees (46: 14°/−9°); L2 48 has a typical angular range of 7 degrees to −8 degrees (48: 7°/−8°), L3 50 has a typical angular range of 14 degrees to −9 degrees (50: 14°/−9°), L4 52 has a typical angular range of 4 degrees to −14 degrees (52: 4°/−14°) and L5 54 has a typical lumbar angular range of 0 degrees to −19 degrees (54: 0°:−19°) and/or the S1 56 has a typical angular range of −5 degrees to −30 degrees. Thus, maintaining a mechanical balance within the sagittal plane and coronal plane by returning the patient or person to their natural lordotic or kyphotic curvatures would help facilitate equilibrium of the spine and body with minimum energy expenditure or reduction of stresses to other regions of the spine. It is desirable to restore the spine to adequate or optimal lordosis or kyphosis as a primary surgical strategy to prevent adjacent segment disease and/or changes of load on different structures within the spine.

Figure 4B:
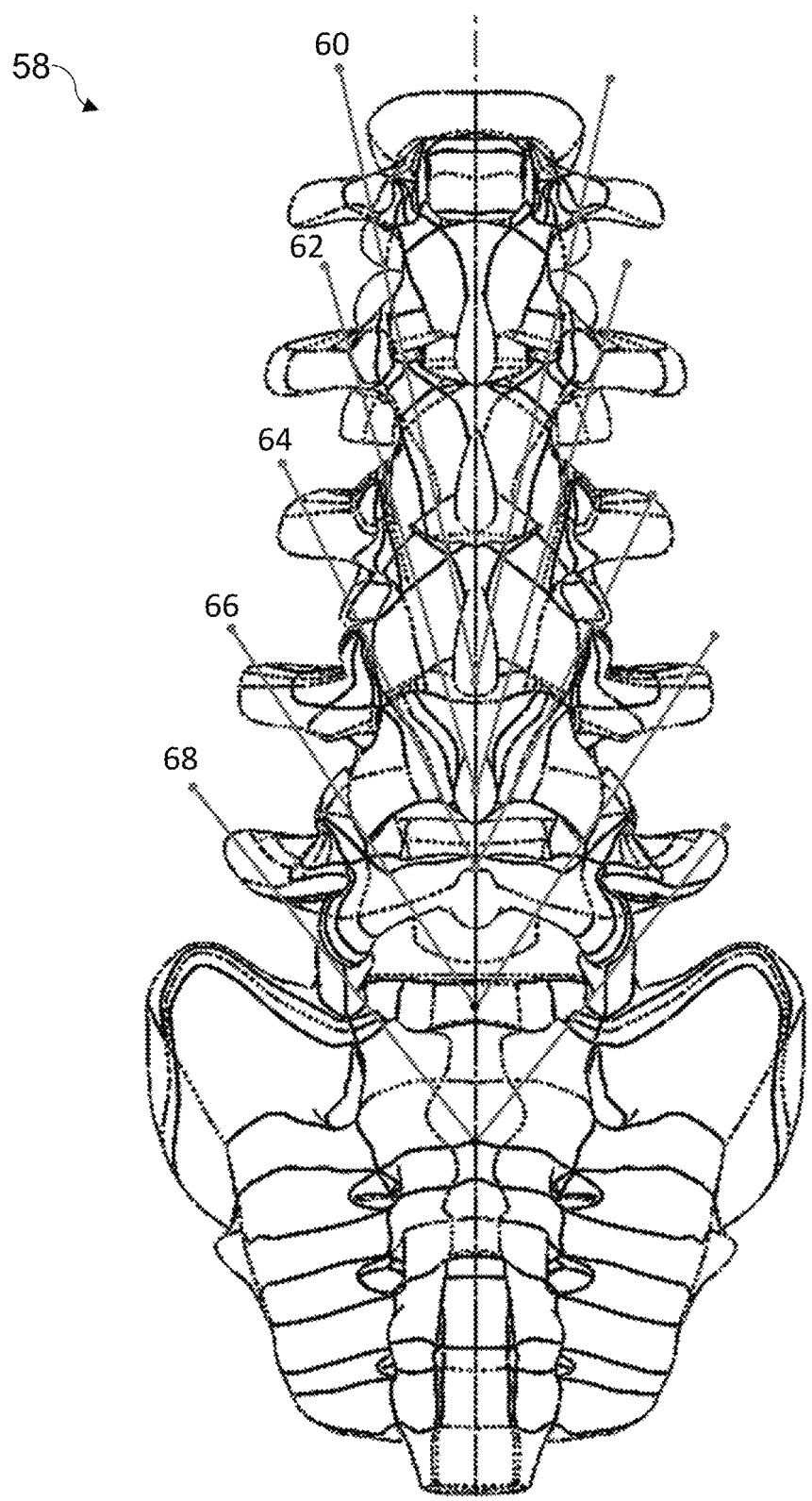
FIG. 4B depicts a posterior view of multiple spinal segments within the lumbar region illustrating the natural transverse pedicle angles on right and left sides.

FIG. 4B depicts an anterior-posterior (A/P) view of the lumbar spinal region 58 of FIG. 4, showing typical facet joint angles or transverse pedicle angles (TPA) 60, 62, 64, 66, 68 for each lower spinal vertebral joint, body, level or segment. The calculation of the TPA may help assist spinal implant and/or fixation screw trajectory, positioning and/or orientation onto one or more vertebral bodies in spinal region. The transverse pedicle angles (TPA) 60, 62, 64, 66, 68, the transverse pedicle width 72, the transverse sagittal pedicle angle 82 and the transverse pedicle height or diameter 80, may vary between each vertebral spinal segment or each vertebral functional spinal unit in the different regions of the spine as disclosed in "*Thoracic and Lumbar Vertebrae Morphology in Lenke Type 1 Female Adolescent Idiopathic Scoliosis Patients*" by Xiobang Hu, MD, PhD et al, *Int. J. Spine Surg.* (2014) 8:30; "*Morphometry of the Lower Thoracic and Lumbar Pedicles and its Relevance in Pedicle Fixation*, "S. P. Mohanty et al., Musculoskeletal Surgery (2018) 102:299-305; "*A Comparison of Lumbar Transverse Pedicle Angles between Ethnic Groups: A Retrospective Review*," by Robert Stockton et al., BMC Musculoskeletal Disorders (2019) 20:114; and Hu et al., *Thoracic and Lumbar Vertebrae Morphology in Lenke Type 1 Female Adolescent Idiopathic Scoliosis Patients*, Int'l Journal of Spine Surg. (January 2014), all of which are herein incorporated by reference in their entireties. The understanding of the anatomic and morphological relationship of the pedicles and vertebral bodies may help reduce pedicle screw and spinal implant malposition, as well as increase strength, stiffness and support of the spinal implant relative to vertebral body to decrease postoperative complications and pain sensation. FIG. 4C-4D displays tables disclosed in S. P. Mohanty et al. and Hu et al. with varying TPA values at each lower lumbar level and/or spine region.

Figure 5A:
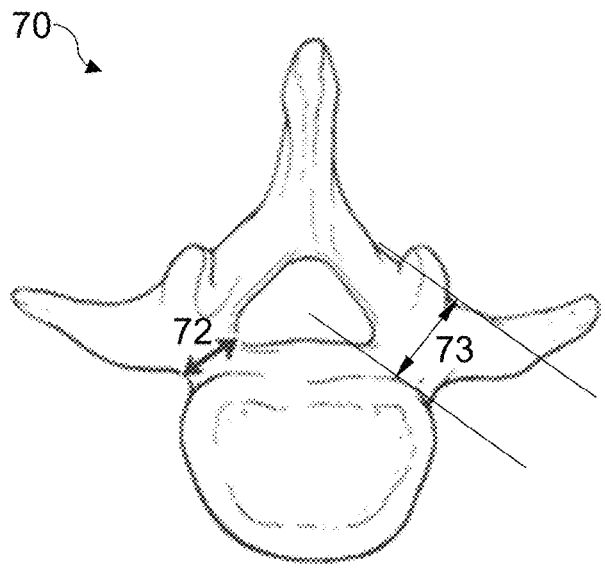
FIGS. 5A-5C depicts multiple anatomical views of a vertebral body within the lumbar region illustrating the natural transverse pedicle angles and other anatomical dimensions.
Figure 5B:
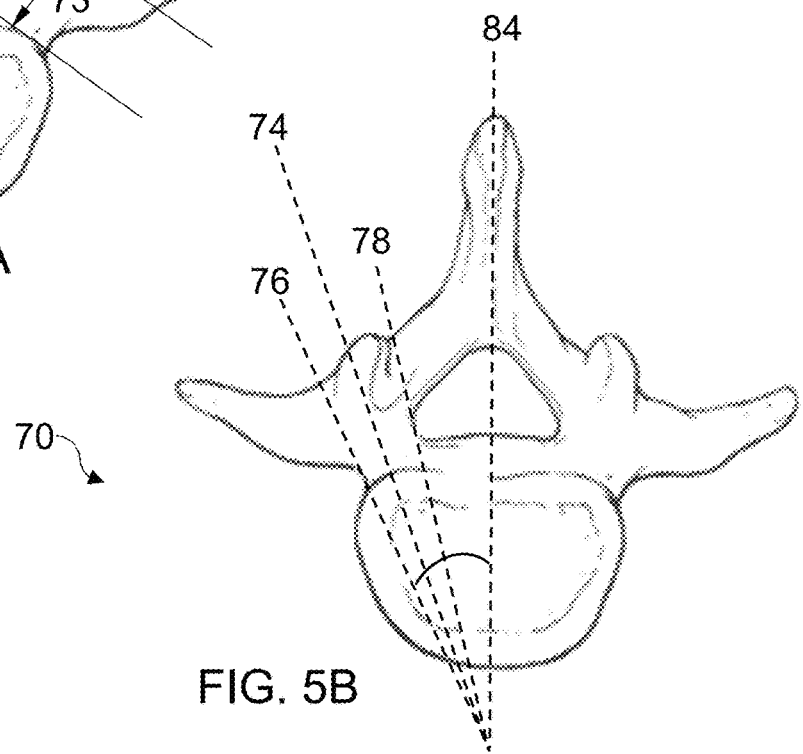
Figure 5C:
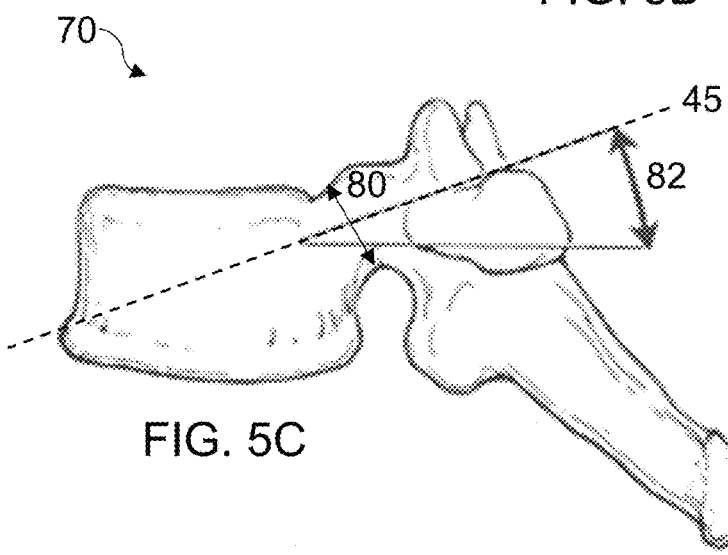

FIGS. 5A-5C depict a superior and sagittal view of a vertebral body 70 to illustrate one embodiment of a transverse pedicle angle 60, 62, 64, 66, 68 (in the posterior view) and the transverse pedicle angle 74, 76, 78 (in the anterior view), transverse pedicle height 80, transverse pedicle width 72 and transverse sagittal pedicle angle 82. In varying embodiments, the spinal implant 94a, 94b may be inserted at a specific toe-in angle and/or different orientations at a single spinal segment and/or at two or more spinal segments. The toe-in angle and/or orientations may match or substantially match the transverse pedicle angle 60, 62, 64, 66, 68. The toe-in angle and/or orientations may match or substantially match the transverse pedicle angle 60, 62, 64, 66, 68 to further allow the fixation screw 100a, 100b trajectory into the pedicle to follow along or be coaxial with the central axis 45 of the pedicle in the sagittal plane. The toe-in angles and/or orientations may be different or variable according to the vertebral level.

As shown in FIG. 5A, vertebral body 70 highlights the transverse pedicle width 72 or pedicle width 72 and pedicle length 73. The pedicle width 72 and pedicle length 73 is different at each vertebral level and each region (cervical, thoracic and lumbar). For example, the transverse pedicle width 72 in the thoracic region (T1 to T12) may comprise a pedicle width 72 range of 1 mm to 10 mm, and/or a median pedicle width 72 range of 1.5 to 6 mm. Alternatively, the transverse pedicle width 72 in the lumbar region (L1 to L5) may comprise a pedicle width 72 range of 1 mm to 15 mm with a median pedicle width of 3 mm to 10 mm. The pedicle length 73 in the lumbar region (L1 to L5) may comprise a 3 mm to 30 mm; the pedicle length 73 may comprise a width of 3 mm to 25 mm; the pedicle length 73 may comprise a of 3 mm to 20 mm; and/or the pedicle length 73 may comprise a pedicle length of 3 mm to 15 mm. The pedicle length 73 may comprise a mean length of 5 mm to 10 mm.

In one embodiment, at least a portion of the spinal implant 94a, 94b matches or substantially matches the transverse pedicle width 72. In another embodiment, the bridge width 214a, 214b of the bridge 174a, 174b of the spinal implant 94a, 94b matches or substantially matches the transverse pedicle width 72. Also, the fixation screw 100a, 100b comprises an outer diameter that may be less or substantially less than the pedicle width 72 and/or the pedicle height 80. In another embodiment, at least a portion of the spinal implant 94a, 94b matches or substantially matches the pedicle length 73. In another embodiment, the bridge length 212a, 212b of the bridge 174a, 174b of the spinal implant 94a, 94b matches or substantially matches the pedicle length 73.

FIG. 5B highlights various acceptable pedicle angles 74, 76, 78 within a vertebral body 70. The transverse pedicle angle or the pedicle angle 78 is defined as the angle between the pedicle axis and a vertebral midline axis 84 as measured in the transverse plane. A vertebral body 70 further comprises an average or exemplary pedicle angle 78 that changes at each vertebral level and each region (cervical, thoracic and lumbar regions). For example, the transverse pedicle angle 78 in the thoracic region (T1 to T12) may comprise a pedicle angle 78 range of 5 degrees to 45 degrees, and/or a median pedicle angle 78 range of 10 degrees to 40 degrees. Alternatively, the transverse pedicle angle 78 in the lumbar region (L1 to L5) may comprise a pedicle angle 78 of 6 degrees to 40 degrees with a median pedicle angle 78 of 10 degrees to 35 degrees. However, the transverse pedicle angles 74, 76, 78 may further comprise a buffer zone, which includes angles that deviate from the average or exemplary pedicle angle 78, but may be maintained within the pedicle width 72. These buffer pedicle angles 76, 78, include any angle that are between the pedicle width borders (left and right borders). More specifically, the transverse pedicle angle 78 at the S1 level comprises a pedicle angle 78 range from 20 degrees to 40 degrees; at the L5 level comprises a pedicle angle 78 from 10 degrees to 35 degrees, at the L4 level comprises a pedicle angle 78 from 10 degrees to 25 degrees; at the L4 level comprises a pedicle angle 78 from 5 degrees to 25 degrees; at the L2 level comprises a pedicle angle 78 from 5 degrees to 20 degrees; and/or at the L1 level comprises a pedicle angle from zero degrees to 15 degrees.

In one embodiment, at least one spinal implant 94a, 94b is positioned onto a vertebral body matching or substantially matching the transverse pedicle angle 74, 76, 78. In another embodiment, a first spinal implant 94a is positioned onto a vertebral body matching or substantially matching a first transverse pedicle angle 74, 76, 78 in a first spinal region and a second spinal implant 94b is positioned onto the vertebral body matching or substantially matching a second transverse pedicle angle 74, 76, 78 in a second spinal region. The first transverse pedicle angle may be the same or different than the first transverse pedicle angle. The first spinal region may be the same or different than the second spinal region.

FIG. 5C highlights various sagittal pedicle angles 82 and the pedicle height or diameter 80 within a vertebral body 70. As previously disclosed herein, the vertebral body 70 further comprises an average or exemplary pedicle height or diameter 80 and a sagittal pedicle angle 82 that changes at each vertebral level and each region (cervical, thoracic and lumbar regions). For example, the pedicle height 80 in the thoracic region (T1 to T12) may comprise a pedicle height 80 range of 5 mm to 20 mm. Alternatively, the pedicle height 80 in the lumbar region (L1 to L5) may comprise a pedicle height 80 of 10 mm to 16 mm degrees. Moreover, the sagittal pedicle angle 82 in the thoracic region (T1 to T12) may comprise a sagittal pedicle angle 82 of 7 degrees to 25 degrees. Alternatively, the sagittal pedicle angle 8, in the lumbar region (L1 to L5) may comprise a sagittal pedicle angle 82 of 1 degree to 10 degrees. In one embodiment, the fixation screw or pedicle screw 100a, 100b may comprise an axis or trajectory, the axis or the trajectory may be positioned to match or substantially match the sagittal pedicle angle 82.

Figure 6A:
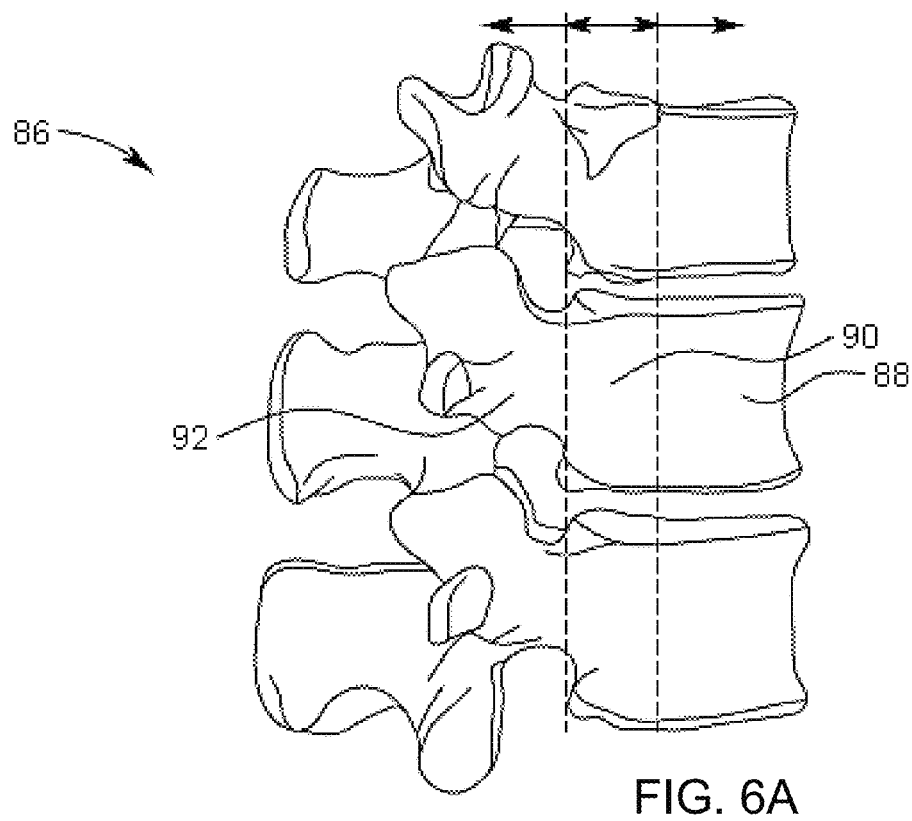
FIGS. 6A-6B depicts a sagittal and superior view of one or more vertebral segments highlighting the three supporting columns.
Figure 6B:
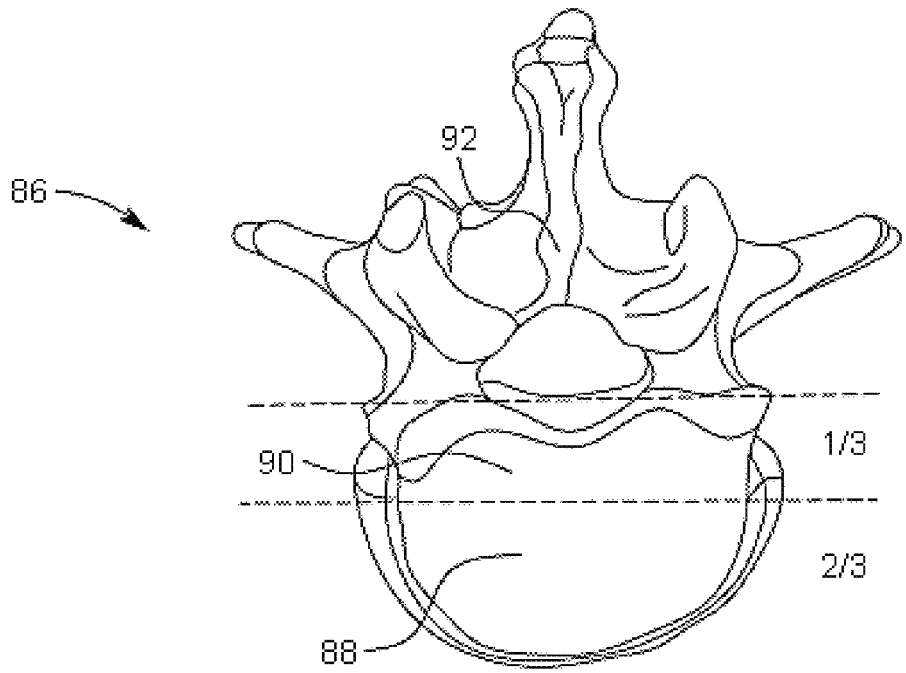

FIG. 6A-6B depicts one embodiment of the "three-columns" of the spine 86. The three-column spine 86 concept divides a vertebral body and/or spinal segment into three parts, including an anterior column 88, a middle column 90, and a posterior column 92 as disclosed by Denis, Ferguson et al. and/or Su. Each column 88, 90, 92 has a different contribution to stability of the spine and to damage one or more of these columns 88, 90, 92 may affect stability of a patient differently. Furthermore, at least two of the columns 88, 90, 92 typically should remain intact to have spinal stability and maintain structural integrity. Spinal stability is the ability of the spine under physiologic loads to limit patterns of displacement so as not to damage or irritate the spinal cord and nerve roots and, in addition, so as to prevent incapacitating deformity or pain due to structural changes; instability (acute or chronic) refers to excessive displacement of the spine that would result in neurologic deficit, deformity, or pain. When two of the three columns 88, 90, 92 are disrupted, it will allow abnormal segmental motion and various complications. Typically, surgical management to correct any instabilities of the spine from degenerative diseases involve fusion. Fusion may include discectomy, decompression, and removal of facet joints, which affects two or more columns of the spine, thus affecting the stability of the spine. The surgeon must immobilize one or more vertebral segments with a variety of different instrumentation in the columns 88, 90, 92 to recover or restore the stability of the vertebrae. However, the spinal implant 94a, 94b can provide this stability across the 3 columns of the spine 88, 90, 92 without further complex instrumentation. In one embodiment, it is desirable to have one or more spinal implants 94a, 94b disposed along at least two of the three columns 88, 90, 92 to maintain stability. In various embodiments, at least a portion of a spinal implant 94a, 94b can be disposed within each of the three spinal columns 88, 90, 92.

Total Joint Replacement Spinal Implant

FIGS. 7A-7H, 8A-8D and 9A-9B depict various views of embodiments of a total joint replacement spinal implant 94a, 94b. The total joint replacement spinal implant 94a, 94b may also be referred to as a dynamic spinal implant 94a, 94b. The terms "dynamic intervertebral spinal implant" or "dynamic spinal implant" as used herein generally refer to an artificial intervertebral implant and/or a motion preserving and stabilization implant that provides for relative movement between adjacent vertebral bodies and further provides some level of control of the motion between the vertebrae, including the motion of flexion/extension, lateral bending and/or axial rotation. The spinal implant 94a, 94b is biomechanically designed to incorporate motion preservation features that desirably allow the implant to perform as a total disc replacement device and a total facet replacement device, because the device can mimic the functions of both the facet joint and the intravertebral disc. The spinal implant 94a, 94b can be used for the treatment of single or multi-level degenerative disease in the different spinal regions, the spinal regions including cervical, thoracic and/or lumbar.

The spinal implant embodiments 94a, 94b comprise a superior element or component 96a, 96b, an inferior element or component 98a, 98b, and a fixation screw 100a, 100b. The spinal implant 94a, 94b may further comprise a clip or retaining clip 102a, 102b, an upper keel 104a, 104b and a lower keel 104a', 104b'. The superior element or upper element 96a, 96b comprises a superior, upper or first articulating element 106a, 106b. The inferior element or lower element 98a, 98b comprises an inferior, lower or second articulating element or component 108a, 108b. The inferior articulating element 108a, 108b engages with the superior articulating component 106a, 106b to allow the superior element 96a, 96b to move relative to the first inferior element 98a, 98b in a controlled manner. This motion may include at least one of flexion, extension, axial rotation, left lateral flexion and right lateral flexion.

FIGS. 10A-10F, 10H-10L, 11A-11E and 12A-12C depict several different views of different embodiments of an upper or superior element 96a, 96b. The superior element 96a, 96b comprises a superior base 110a, 110b and a superior articulating component 106a, 106b. The articulating component 106a, 106b may be coupled to the base 110a, 110b as a multi-piece assembly. Coupling may include adhesives, screws, quick release mechanisms, compression or friction coupling, ultrasonic welding, insert molding, compression molding and/or over molding. Alternatively, the articulating component 106a, 106b may be fixed with the base 110a, 110b as a one-piece component. Once the articulating component 106a, 106b is coupled to the base 110a, 110b of the superior element, the perimeter edges of the articulating component 106a, 106b should optionally be flush with the perimeter edges of the base or superior base 110a, 110b. Alternatively, the perimeter edges of the articulating component 106a, 106ba may not be flush with the perimeter edges of the base or superior base 110a, 110b. The superior element or upper element 96a 96b further comprises a superior, upper or first articulating element 106a, 106b, the superior articulating element or component 106a, 106b comprising a socket 119a, 119b.

Figure 10A:
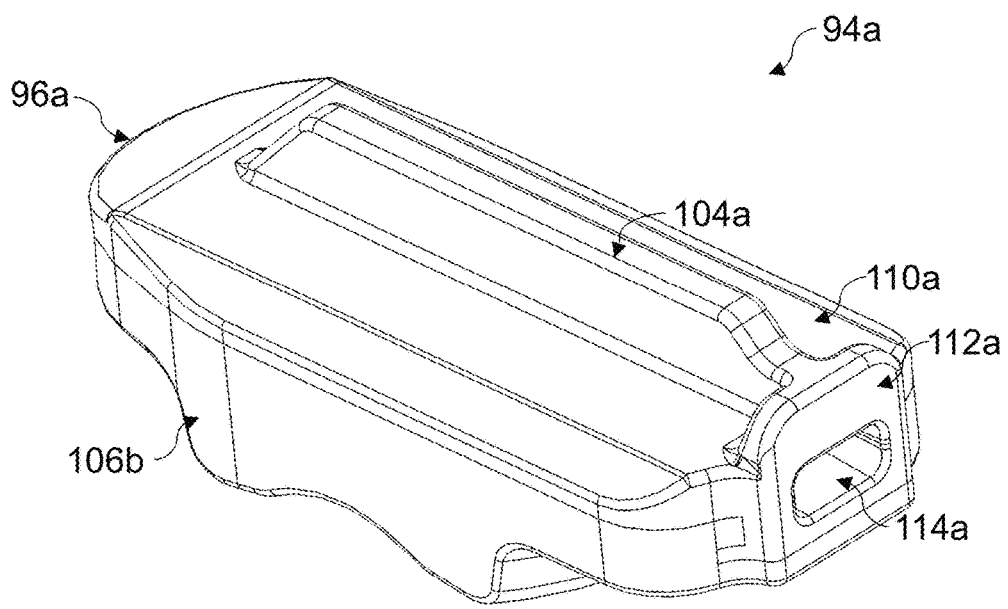
FIGS. 10A-10F depicts various plan views of one embodiment of a superior element of the dynamic spinal implant of FIGS. 7A-7H.
Figure 10B:
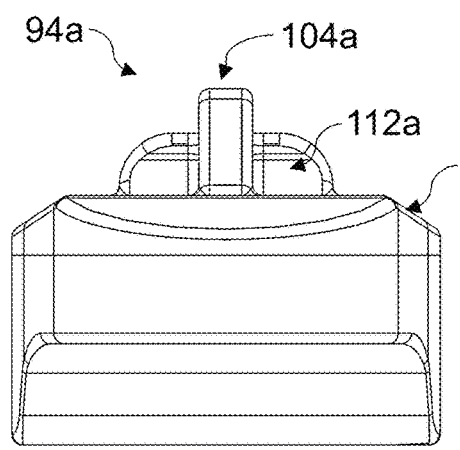
Figure 10C:
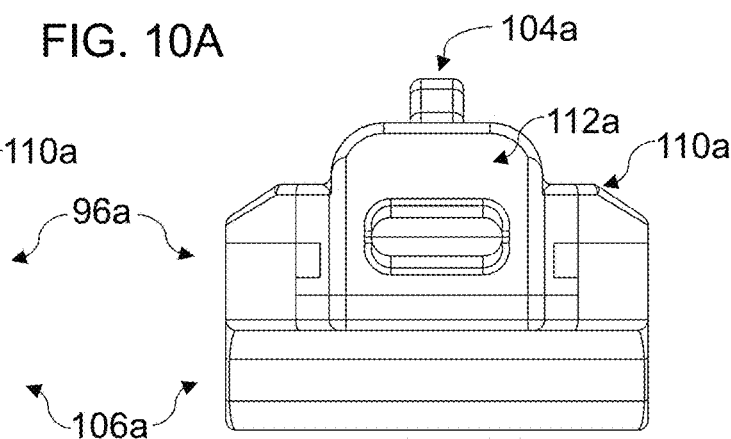
Figure 10D:
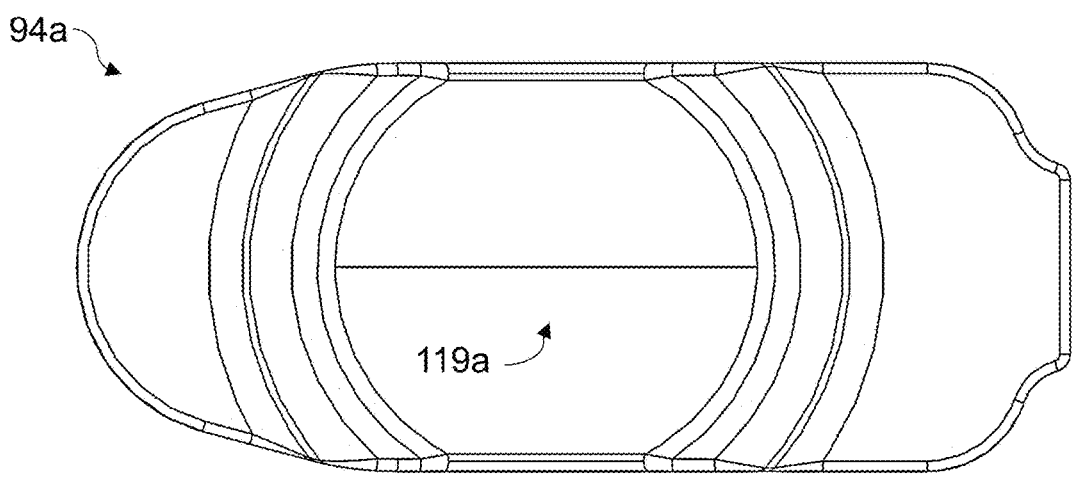
Figure 10E:
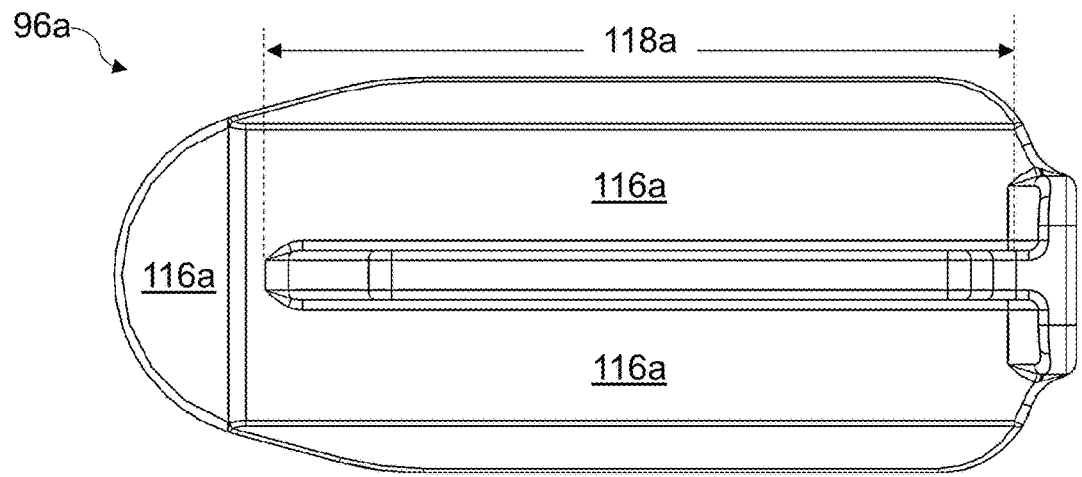
Figure 10F:
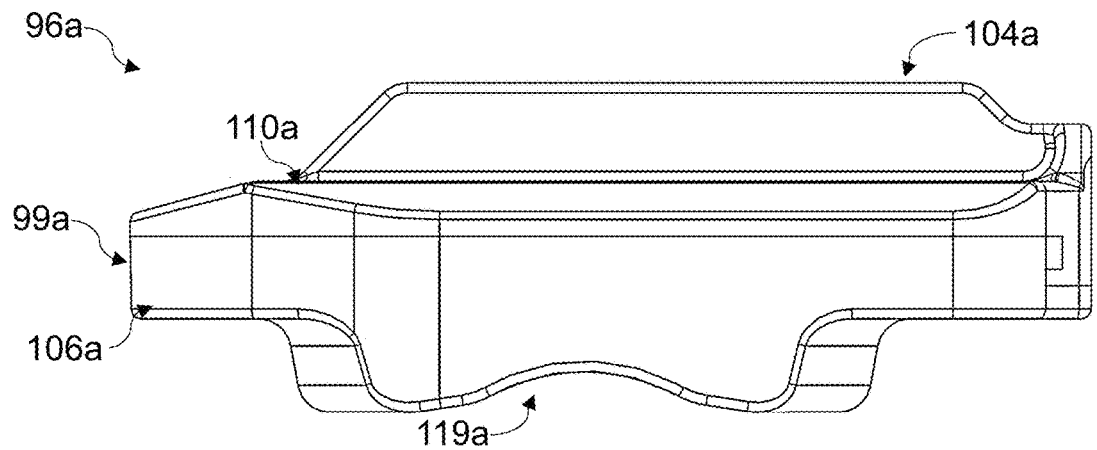
Figure 10G:
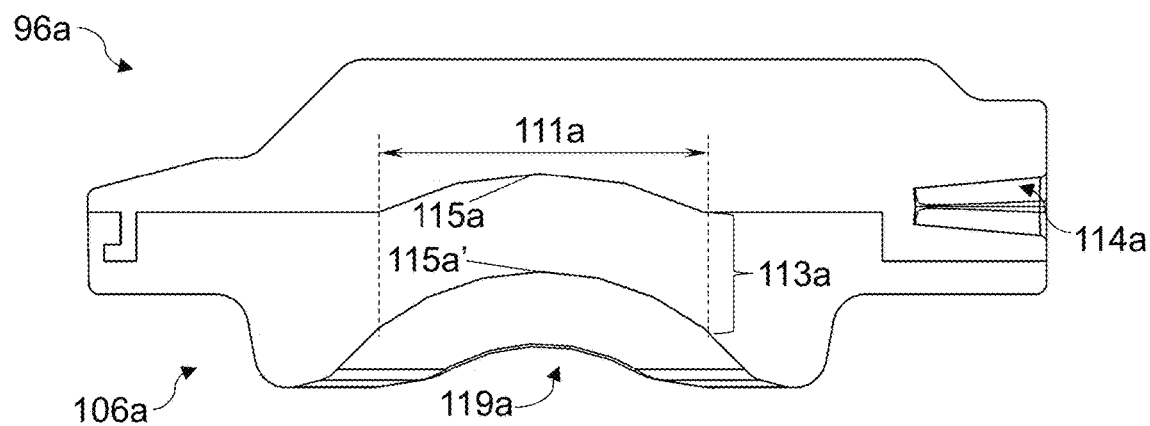
FIG. 10G depicts a side cross-sectional view of the superior element of FIGS. 10A-10F.
Figure 10H:
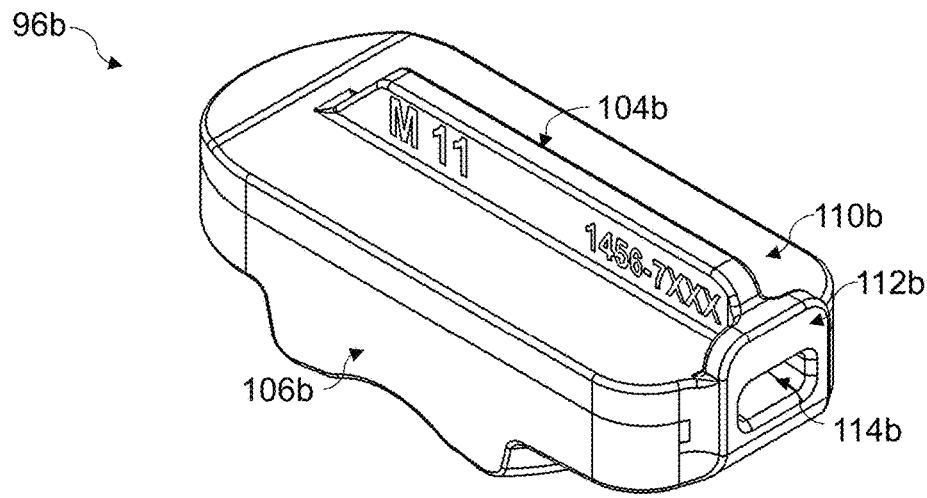
FIGS. 10H-10M depicts various plan views of an alternate embodiment of a superior element of the spinal implant of FIGS. 8A-8D.
Figure 10I:
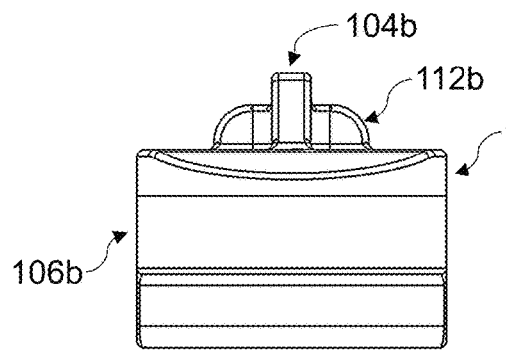
Figure 10J:
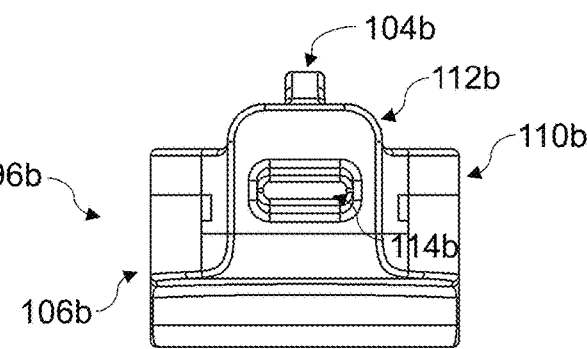
Figure 10K:
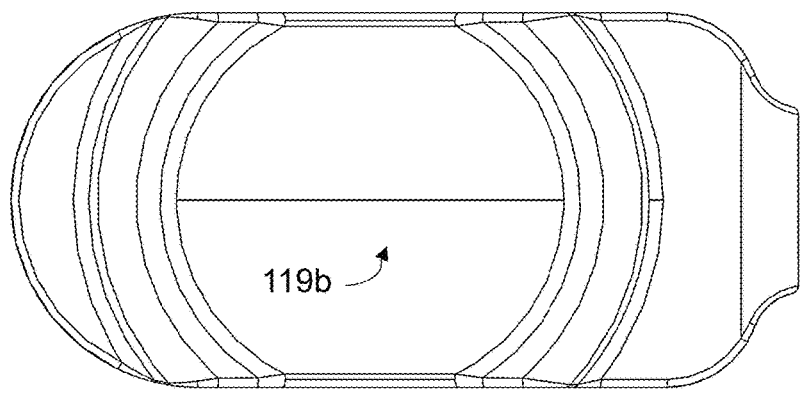
Figure 10L:
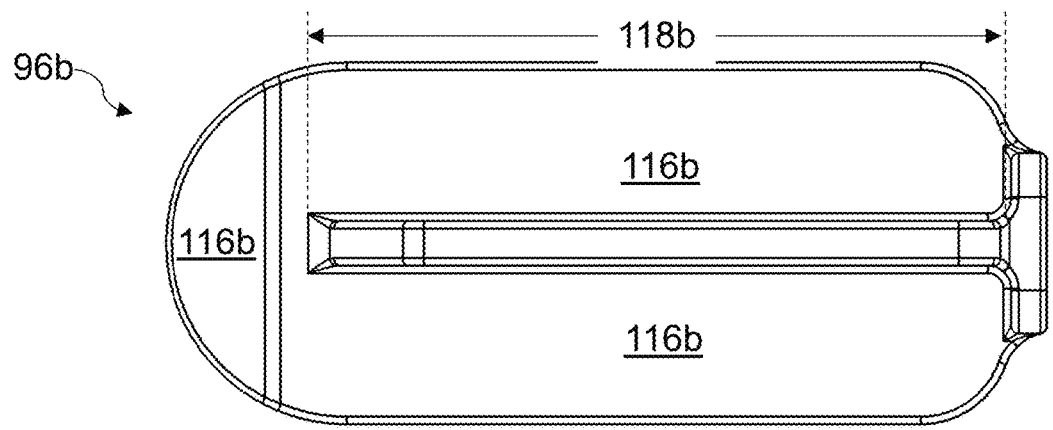
Figure 10M:
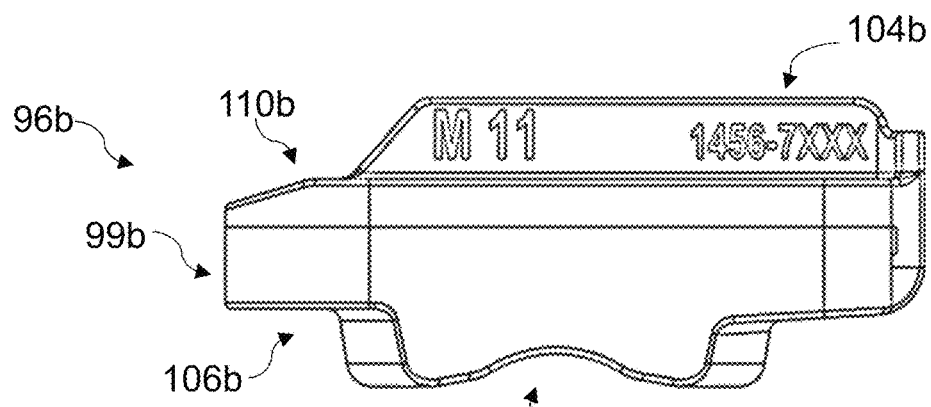
Figure 10N:
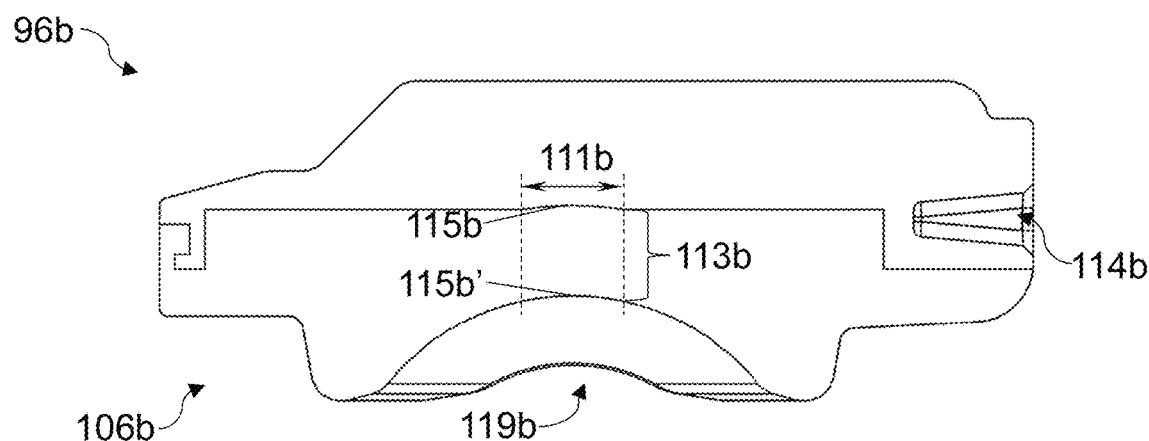
FIG. 10N depicts a side cross-sectional view of the superior element of FIGS. 10H-10M.
Figure 11A:
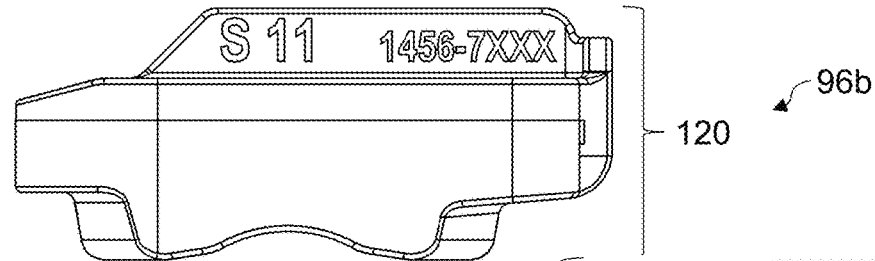
FIGS. 11A-11E depicts a side view of the superior element of FIGS. 10H-10N in different heights.
Figure 11B:
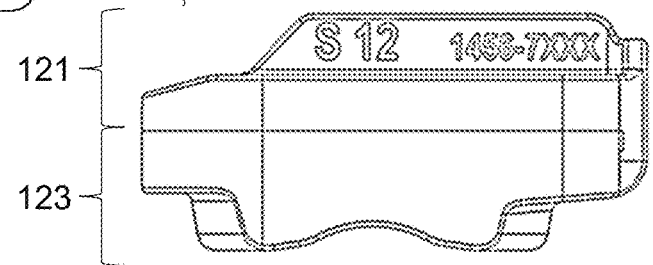
Figure 11C:
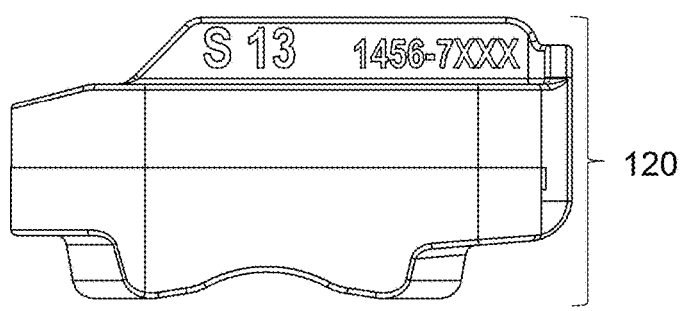
Figure 11D:
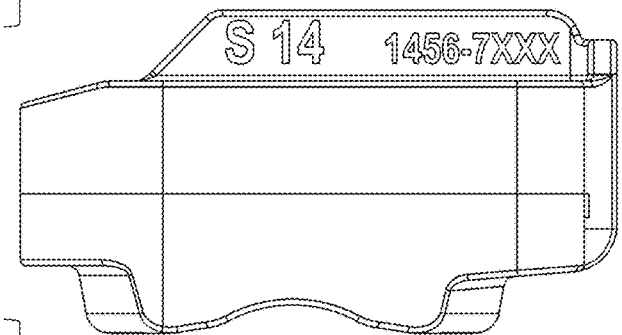
Figure 11E:
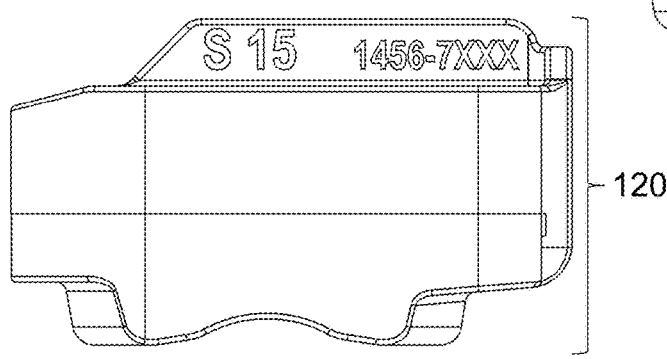

FIGS. 10G and 10N depict side cross-sectional views of the superior or upper element 96a, 96b of FIGS. 10A-10F and 10H-10M, respectively. The superior articulating component 106a, 106b comprises a socket 119a, 119b. The socket 119a, 119b comprises a articulating surface or socket surface 168a, 168b. The cross-sectional view illustrates the socket 119a, 119b and the shape of the socket or articulating surface 168a, 168b. The socket shape comprises a dome, arch, concave or hemispherical shape. The socket 119a, 119b further comprises a centroid curvature region 111a, 111b. The centroid curvature region 111a, 111b comprises a first surface distance radius 115a, 115b, a second surface distance radius 115a', 115b', and a centroid curvature region height 113a, 113b positioned between the first surface distance radius 115a, 115b and the second surface distance radius 115a', 115b'. In various embodiments, the centroid region height 113a, 113b desirably comprises at least 3 mm height or thickness, which in this embodiment desirably prevents excessive localized loading, premature material wear, material fatigue or material failure at or near the local or highest stress concentrations of the socket 119a, 119b during use or at rest. In addition, in this embodiment the centroid region height 113a, 113b desirably further comprises 3 mm or greater at any point within the centroid curvature region 111a, 111b. The centroid region height 113a, 113b comprises approximately or about 3 mm and/or at least 3 mm or greater at any point along the first surface distance radius 115a, 115b and the second surface distance radius 115*a*', 115*b*' within the centroid curvature region 111*a*, 111*b*. The centroid region height 113*a*, 113*b* allows the superior articulation component 106*a*, 106*b* to withstand maximum stress values in the centroid region 111*a*, 111*b* during compression and/or translational motion.

In some exemplary embodiments, the superior or upper element 96*a*, 96*b* may comprise a kit of different superior element implants 96*a*, 96*b* having a plurality of different total heights 120 such as shown in FIGS. 11A-11E, to accommodate different intervertebral spacings and/or other anatomical variations in one or more spinal regions, the spinal regions including cervical, thoracic and/or lumbar regions. The different superior element implant total heights 120 may include a range of 5 mm to 20 mm; the different total heights 120 may include a range of 5 mm to 15 mm; the different total heights 120 may include a range of 7 mm to 12 mm; the different total heights 120 may include a range of 11 mm to 15 mm; and/or the different heights may include a range of 15 mm to 20 mm. The superior element height 120 ranges may be incremental by 1 mm or by 0.5 mm. The implant total height 120 can include a base height 121 and an articulating component height 123.

The superior element base height 121 may change relative to the implant total height 120, if desired. In another embodiment, the superior articulating component height 123 may stay the same or substantially the same compared to the superior element implant total height 120 and/or the superior element base height 121. Alternatively, the superior element base height 121 can change relative to the articulating component height 123. The superior element base height 121 changes while the articulating component height 123 stays the same to accommodate the superior implant total height 120. By leaving the articulating component height 123 the same while the superior element base height 121 changes allow the mechanical and material function of the articulating component to be same and/or substantially the same across the different total heights 120 of the superior element 96*a*, 96*b*.

The superior articulating component 106*a*, 106*b* may comprise an articulating component height 123. The articulating component height 123 may stay the same as the total implant height 120 changes and/or the superior base height 121 changes. The superior articulating component height 123 may comprise a height of at least 4 mm; the superior articulating component height 123 may comprise a range of 4 mm to 8 mm; the superior articulating component height 123 may comprise a range of 4 mm to 6; and/or the superior articulating component height 123 may comprise a range of 5 mm to 6 mm. The superior articulating base height 121 may comprise a range of 4 mm to 10 mm; the superior articulating base height 121 may comprise a range of 4.5 mm to 8.5 mm.

Figure 12A:
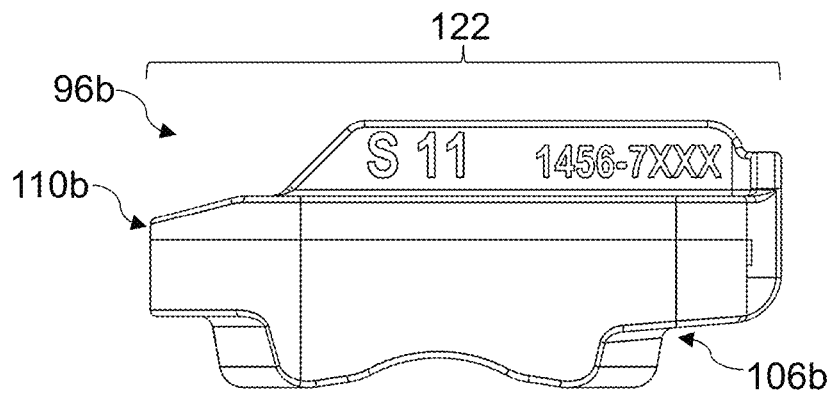
FIGS. 12A-12C depicts a side view of the superior element of FIGS. 10H-10N in different lengths.
Figure 12B:
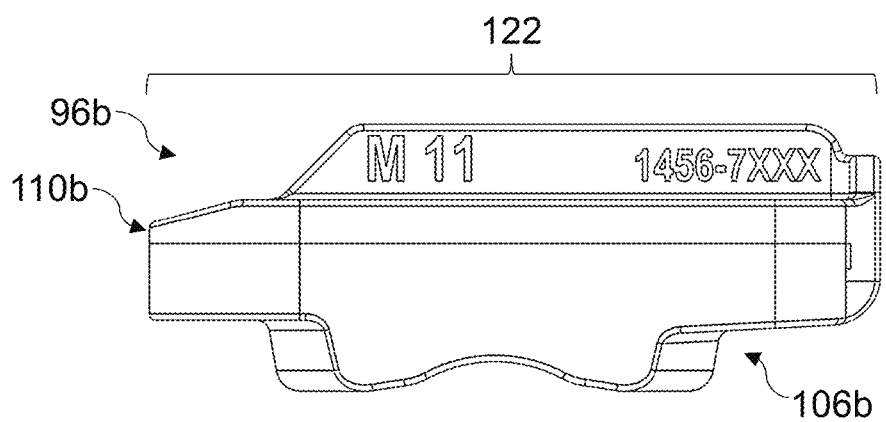
Figure 12C:
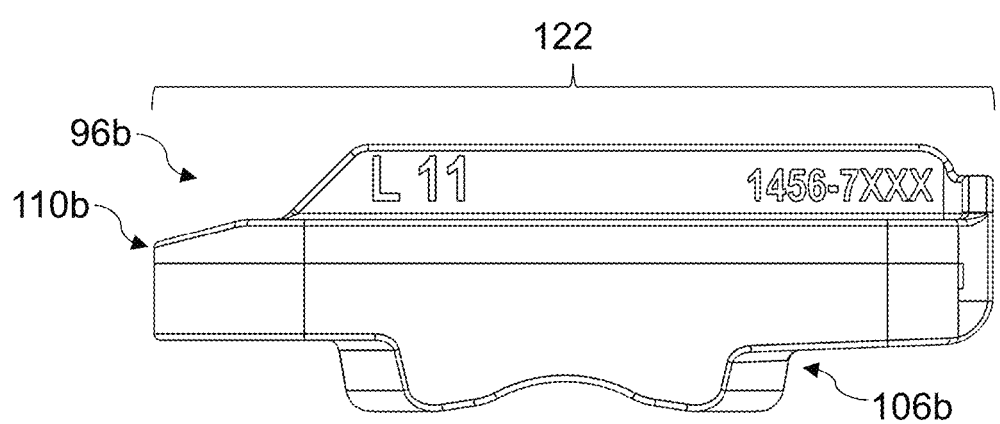
Figure 13E:
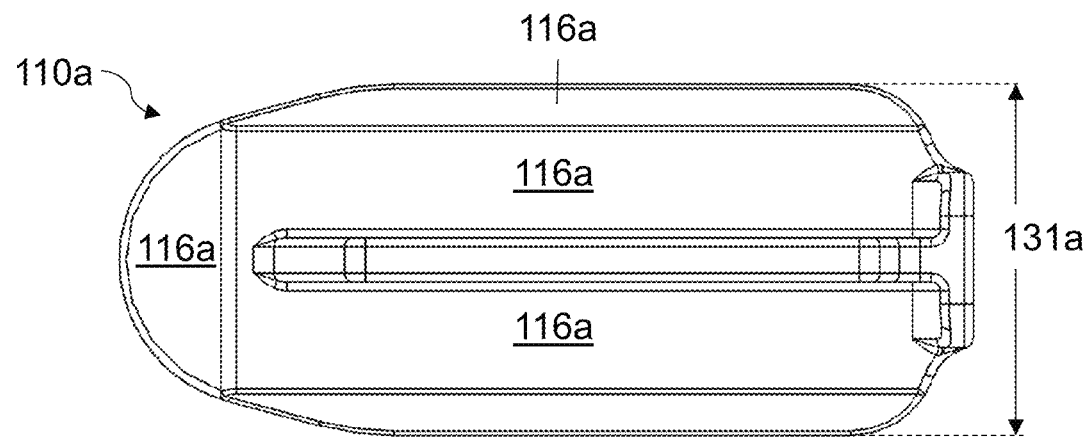
Figure 13F:
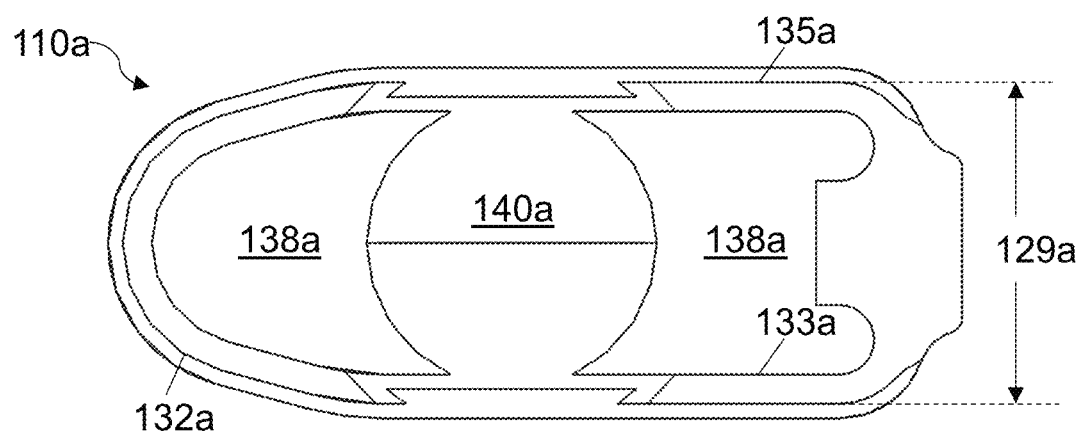
Figure 13G:
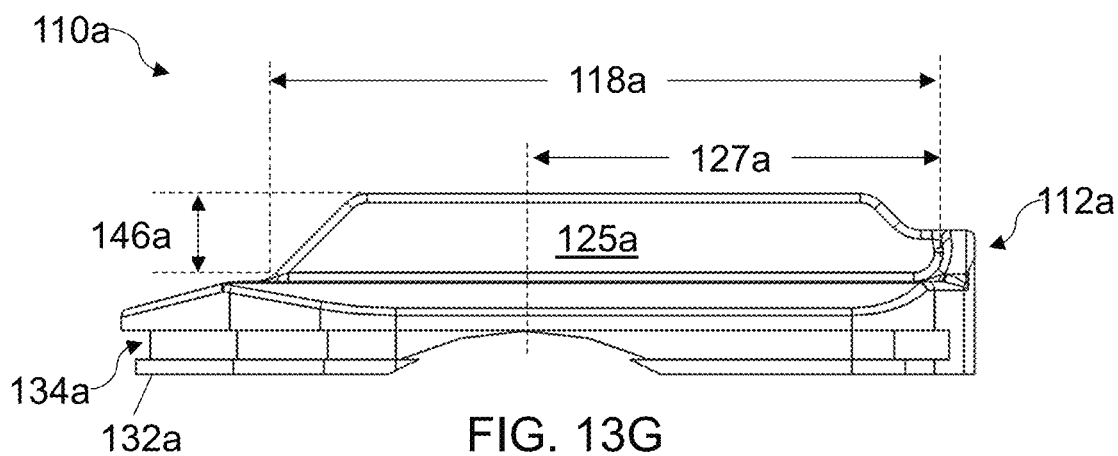

In another embodiment, the superior or upper element 96*a*, 96*b* may comprise a kit of implant components of different superior element implant lengths 122, such as shown in FIGS. 12A-12C, to accommodate different vertebral body sizes and/or other anatomical variations. The superior element implant lengths 122 may comprise generic lengths such as small, medium, large, and/or extra-large. Alternatively, the superior element lengths 122 may be offered in a range of 20 mm to 40 mm; the range of 25 mm to 35 mm; and/or the range of 30 to 40 mm. The superior element lengths 122 ranges may be incremental by 0.5 mm, 1 mm, 1.5 mm, 1.75 mm, 2 mm; the superior element lengths 122 ranges may be incremental by 0.5 mm or greater. In one embodiment, the kit may comprise a combination of at least 15 different superior element implant total lengths 122 and superior element implant total height 120.

With reference to FIGS. 7A-7H, 8A-8D, 9A-9B, 10A-10G, 10H-10N, 13A-13I, and 14A-14G the superior component may include a superior base 110*a*, 110*b* comprising a first end 124 or anterior end, a second end 126 or posterior end, a third end or medial end 128 and/or a fourth end or lateral end 130. The superior base 110*a*, 110*b* may further comprise a top surface 116*a*, 116*b*, a bottom surface 138*a*, 138*b* and/or a domed surface 140*a*, 140*b*. In another embodiment, the superior base 110*a*, 110*b* further may comprise a flange 132*a*, 132*b* and a posterior wall or posterior tab 112*a*, 112*b*.

In one embodiment, at least a portion of the top surface 116*a*, 116*b* may be flat or planar. In another embodiment, at least a portion of the top surface 116*a*, 116*b* may be angled, sloped or and/or not flat or planar. In another embodiment, at least a portion of the top surface 116*a*, 116*b* is flat or planar and another portion of the top surface is sloped or angled 138*a*, 138*b*. The angle or sloping may comprise a downward slope or angle. The slope or angle may comprise an angle of 10 degrees to 20 degrees; an angle of 12 degrees to 18 degrees; and/or an angle of 14 degrees to 16 degrees. The angled top surface portion may be positioned at the anterior end 124 of the superior base 110*a*, 110*b*. The angled top surface portion may be positioned at the medial 128 and/or the lateral ends 130. The angled top surface portion may be positioned at one or more locations, including at the anterior end 124, at the medial side 128 and/or the lateral side 130. At least a portion of the top surface 116*a*, 116*b* contacts the vertebra bone and/or at least a portion of the top surface 116*a*, 116*b* contacts the endplate of a vertebra and/or the endplate of the upper vertebra.

In one embodiment, the superior base 110*a*, 110*b* comprises a keel and/or an upper keel 104*a*, 104*b*. The upper keel 104*a*, 104*b* can include a height 146*a*, 146*b* and a length 118*a*, 118*b*. The upper keel 104*a*, 104*b* is disposed onto the superior base 110*a*, 110*b* and/or the upper keel 104*a*, 104*b* is disposed onto a portion of the top surface 116*a*, 116*b* of the superior base 110*a*, 110*b*. The upper keel 104*a*, 104*b* desirably extends upwardly from the superior base 110*a*, 110*b* and/or extends upwardly from a top surface 116*a*, 116*b* of the superior base 110*a*, 110*b*. The upper keel 104*a*, 104*b* may extend orthogonally or perpendicular to the superior base 110*a*, 110*b* and/or may extend orthogonal or perpendicular to a top surface 116*a*, 116*b* of the superior base 110*a*, 110*b*. At least a portion of at least one surface 125*a*, 125*b* of the upper keel 104*a*, 104*b* comprise flat or planar surfaces. At least a portion of the at least one surface 125*a*, 125*b* of the upper keel 104*a*, 104*b* desirably configured contacts the endplate of a vertebra and/or the endplate of the upper vertebra. At least a portion of the at least one surface 125*a*, 125*b* desirably contacts cancellous and/or cortical bone.

The upper keel 104*a*, 104*b* comprises a shape. The shape includes a shape substantially similar to a trapezoid, trapezium, rhombus, parallelogram and/or a sloped rectangle. The first end or anterior end of the upper keel 104*a*, 104*b* can optionally be sloped or angled to facilitate easier positioning and/or atraumatic insertion. The upper keel 104*a*, 104*b* slope or angle may comprise a range of 30 degrees to 60 degrees; may comprise a range of 40 degrees to 50 degrees; and/or may comprise a range of 43 degrees to 47 degrees.

The length 118*a*, 118*b* of the upper keel 104*a*, 104*b* extends from the posterior end or second end 126 towards the first end or anterior end 124. The length 118*a*, 118*b* of the upper keel 104*a* extends from the posterior end or second end 126 towards the first end or anterior end 124. The length 118*a*, 118*b* of the upper keel 104*a*, 104*b* extends between the posterior end or second end 126 and the first end or anterior end. The length 118*a*, 118*b* of the upper keel 104*a*, 104*b* may match or substantially match a length of the superior base 110*a*, 110*b* and/or the upper keel 104*a* may match or substantially match the length of a top surface 116*a* of the superior base 110*a*, 110*b*. The length 118*a*, 118*b* of the upper keel 104*a*, 104*b* aligns with and/or follows along the longitudinal axis of the superior base 110*a*, 110*b*.

In another embodiment, the upper keel 104*a*, 104*b* and/or the length 118*a*, 118*b* of the upper keel 104*a*, 104*b* may comprise or function as an additional structural support component to the superior base 110*a*, 110*b*, including acting similar to structures such as a truss, I-beam or H-beam. The upper keel 104*a*, 104*b* is coupled to and/or contacts a portion of the posterior wall or tab 112*a*, 112*b*. The upper keel 104*a*, 104*b* intersects perpendicularly and/or substantially perpendicular to the posterior wall or tab 112*a*, 112*b*. The upper keel 104*a*, 104*b* alone and/or in combination with the upper keel 104*a*, 104*b* to the posterior wall or tab 112*a*, 112*b* may be helpful in supporting the superior base 110*a*, 110*b* to provide a more rigid structure, resist bending and/or resist shear. Furthermore, such structural components may assist with supporting the superior base 110*a*, 110*b* to provide a more rigid structure within the centroid region 111*a*, 111*b* due to the thinner height 113*a*, 113*b* during motion, as well as resist bending and/or resist shear when coupled to the posterior wall or tab 112*a*, 112*b*.

In another embodiment, the superior base 110*a*, 110*b* further comprises a posterior wall or tab 112*a*, 112*b*. The posterior wall or tab 112*a*, 112*b* is positioned on the second end or posterior end 126 of the superior base 110*a*, 110*b*. The posterior wall 112*a*, 112*b* may include an anterior facing surface 142*a*, 142*b* and a posterior facing surface 144*a*, 144*b* that is flat or planar. The posterior wall or tab 112*a*, 112*b* may include an anterior facing surface 142*a*, 142*b* and a posterior facing wall 144*a*, 144*b* that is not flat or not planar. The posterior wall 112*a*, 112*b* extends upwardly to extend past or beyond the top surface 116*a*, 116*b* of the superior base 110*a*, 110*b*. The posterior end of the upper keel 104*a*, 104*b* intersects with the anterior facing surface 142*a*, 142*b* of the posterior wall or tab 112*a*, 112*b*. The posterior end of the upper keel 104*a*, 104*b* intersects orthogonally or perpendicularly with the anterior facing surface 142*a*, 142*b* of the posterior wall or tab 112*a*, 112*b*. At least a portion of the anterior facing surface 142*a*, 142*b* of the posterior wall or tab 112*a*, 112*b* contacts bone and/or at least a portion of the anterior facing surface 142*a*, 142*b* of the posterior wall or tab 112*a*, 112*b* contacts the posterior facing surface of the vertebra and/or the upper vertebra. At least a portion of the anterior facing surface 142*a*, 142*b* of the posterior wall or tab 112*a*, 112*b* contacts the apophyseal ring on the vertebra. The apophyseal ring is a secondary ossification center of the vertebral endplate connected to the intervertebral disc. It is firmly attached to disc fibrous annulus through Sharpey fibers.

The posterior wall or tab 112*a*, 112*b* can desirably function as a positive stop limiter or provide tactile feedback to surgeons for proper placement or positioning of the superior element 96*a*, 96*b* between the upper and lower vertebra and/or within the disc space. The proper positioning or placement may include the proper distance of the superior element 96*a*, 96*b* between the anterior end and the posterior end of the disc space. The proper positioning or placement may further include the center of rotation (COR) distance 127*a*, 127*b* to approximate the neutral or fixed center of rotation of a vertebral body. Desirably this structure may further prevent the superior element 96*a*, 96*b* from migrating anteriorly in an unwanted manner during placement, motion translation, and/or long-term use. Furthermore, the position of the posterior wall or tab 112*a*, 112*b* may be monitored with fluoroscopy or other visualization methods during surgery to determine the progress of the implantation and to confirm when the superior element 96*a*, 96*b* has been correctly implanted—such as by providing confirmation that the posterior wall or tab 112*a*, 112*b* contacts and/or is recessed against a posterior wall of the vertebral body or the upper vertebral body.

The superior base 110*a*, 110*b* further comprises a flange 132*a*, 132*b*. The flange 132*a*, 132*b* is disposed onto the anterior end 124 of the superior base 110*a*, 110*b* and the posterior end 126. The flange 132*a*, 132*b* is spaced apart from the superior base 110*a*, 110*b* to create a recessed channel 134*a*, 134*b* that is positioned in the anterior end 124 and the posterior end 126 of the superior base 110*a*, 110*b*. The recessed channel 134*a*, 134*b* is sized and configured to receive a portion of the superior articulating element 106*a*, 106*b*. The flange 132*a*, 132*b* comprises a flange width 129*a*, 129*b*, the flange width 129*a*, 129*b* is sized and configured to be disposed into a portion of the superior articulating element 106*a*, 106*b*. At least a portion of the flange 132*a*, 132*b* comprises a smaller width 129*a*, 129*b* than the superior base width 131*a*, 131*b* of superior base 110*a*, 110*b*. Alternatively, the first contacting surface 136*a*, 136*b* comprises a larger width than the flange width 129*a*, 129*b*. The first contacting surface 136*a*, 136*b* extends beyond the flange 132*a*, 132*b*. The flange 132*a*, 132*b* substantially surrounds the perimeter of the superior base 110*a*, 110*b* leaving an opening or recess in the center of the superior base 110*a*, 110*b*. The opening or recess extends through the medial 128 and/or the lateral ends 130 of the superior base 110*a*, 110*b*. The flange width 129*a*, 129*b* is sized and configured to be disposed into a gutter or channel 152*a*, 152*b* of the superior articulating element 106*a*, 106*b*. The flange width 129*a*, 129*b* is sized and configured to engage with the channel or gutter 152*a*, 152*b* of the superior articulating element or component 106*a*, 106*b*.

In another embodiment, the flange 132*a*, 132*b* comprises a first portion and a second portion. The first portion of the flange 132*a*, 132*b* is disposed on the anterior end 124 of the superior base 110*a*, 110*b* and the second portion of the flange 132*a*, 132*b* is disposed on the posterior end 126 of the superior base 110*a*, 110*b*. The first portion of the flange 132*a*, 132*b* does not connect to the second portion of the flange 132*a*, 132*b*. The third end or medial end 128 and/or a fourth end or lateral end 130 of the superior base 110*a*, 110*b* does not include a flange 132*a*, 132*b* leaving the center portion of the superior base 110*a*, 110*b* exposed or open. The flange 132*a*, 132*b* comprises a flange inside surface 133*a*, 133*b* and a flange outside surface 135*a*, 135*b*. The flange channel 134*a*, 134*b*, the flange inside surface 133*a*, 133*b*, and/or the flange outside surface 135*a*, 135*b* contact and/or engage with a portion of the superior articulation component 106*a*, 106*b*. The flange inside surface 133*a*, 133*b* provides a stop for the articulation component 106*a*, 106*b* from migrating or sliding anteriorly and/or posteriorly. The open or exposed center portion of the superior base 110*a*, 110*b* allows the superior element 96*a*, 96*b* to be axially rotated on the inferior articulation component 108*a*, 108*b* and allow further degrees of motion during flexion and/or extension.

In another embodiment, the superior base 110*a*, 110*b* may comprise an instrument opening 114*a*, 114*b*. The instrument opening 114*a*, 114*b* can be sized and configured to receive an instrument and/or at least a portion of an implantation instrument. The instrument opening 114a, 114b may be uniform or non-uniform. The instrument opening 114a, 114b may include a conical shape. Instruments that may be received include a driver, a deployment tool, and/or any tool that can be inserted within the instrument opening 114a, 114b to push and/or slide the superior element 96a, 96b to the proper positioning between the upper and lower vertebral bodies. As described in FIGS. 10G and 10N, the instrument opening 114a, 114b may be tapered and/or at least a portion of the instrument opening 114a, 114b may be tapered.

In another embodiment, the superior base 110a, 110b may comprise a second contacting surface or bottom surface 138a, 138b. The second contacting surface or bottom surface 138a, 138b is an inferior facing surface which is sized and configured to receive a portion of the top surface 154a, 154b of the upper articulating component 106a, 106b. The second contacting surface 138a, 138b of the superior base 110a, 110b is recessed from the flange 132a, 132b and/or the second contacting surface or bottom surface 138a, 138b of the superior base 110a, 110b is below the inferior facing surface of the flange 132a, 132b. In another embodiment, the superior base 110a, 110b comprises a third contacting surface and/or a domed surface 140a, 140b. The third contacting surface or domed surface 140a, 140b comprises a shape, the shape includes a hemispherical shape, a convex shape, arch shape, a dome shape and/or any combination thereof. The third contacting surface or domed surface 140a, 140b is sized and configured to receive the concave protrusion 152a, 152b of the superior articulating element 106a, 106b. The third contacting surface or domed surface 140a, 140b engaging with the concave protrusion 152a, 152b of the superior articulating element 106a, 16b allows the centroid curvature region 111a, 111b to maintain at least 3 mm of centroid curvature region height 113a, 113b and/or approximately 3 mm of centroid curvature region height 113a, 113b to prevent material fatigue, wear or stress locations during short and long-term translational motion.

In another embodiment, the superior base 110a, 110b comprises a material. The material may include metal, polymers or ceramic and/or any combination thereof. The metals may comprise titanium, titanium alloys, cobalt-chrome alloys, platinum, stainless steel and/or any combination thereof. More specifically, the metal includes titanium and/or cobalt-chrome molybdenum (CoCrMo). The polymers may include thermoplastic or thermoset polymers. The polymers may further include carbon fiber, polyether ether ketone (PEEK), polyethylene (PE), ultra-high molecular weight polyethylene (UHMWPE), polycarbonate (PC), polypropylene (PP) and/or any combination thereof. The ceramics may include alumina ceramics, Zirconia (ZrO2) ceramics, Calcium phosphate or hydroxyapatite (Ca10 (PO46(OH)2) ceramics, titanium dioxide (TiO2), silica (SiO2), Zinc Oxide (ZnO) and/or any combination thereof. The materials may be manufactured using traditional methods and/or using 3D printed techniques known in the art. Furthermore, the material may comprise a porous material, the porous material including (but not limited to) porous metal, porous polymer, porous ceramic and/or any combinations thereof.

In another embodiment, the material may be further antioxidant stabilized. The stabilized antioxidants may comprise Vitamin E or Vitamin C. The antioxidants may be incorporated into the material by blending the antioxidant into the material for subsequent cross-linking and/or diffusing the antioxidant into the material. The material may be further cross-linked before or after antioxidant stabilization.

Figure 14A:
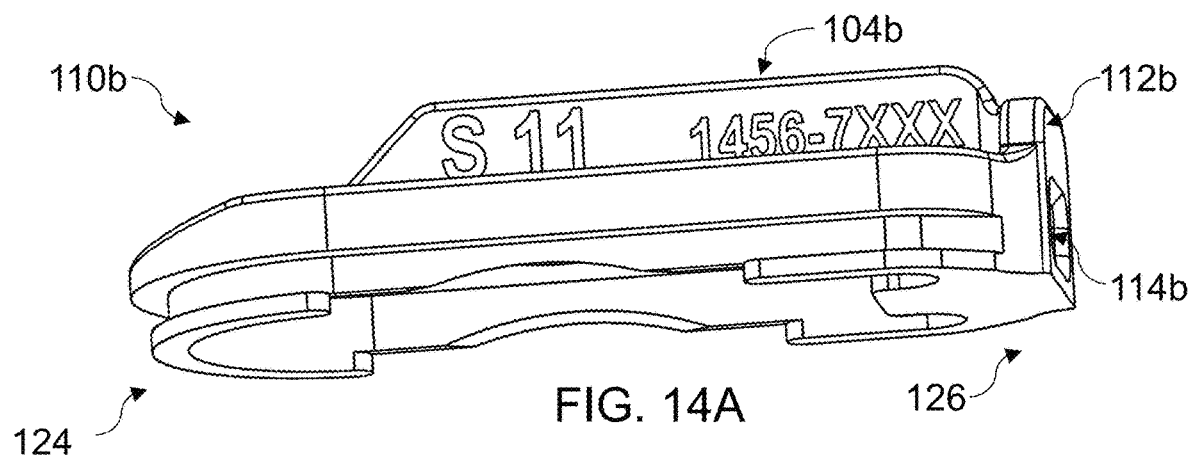
FIGS. 14A-14I depict various plan views of an alternate embodiment of a base of the superior element of FIGS. 10H-10M.
Figure 14B:
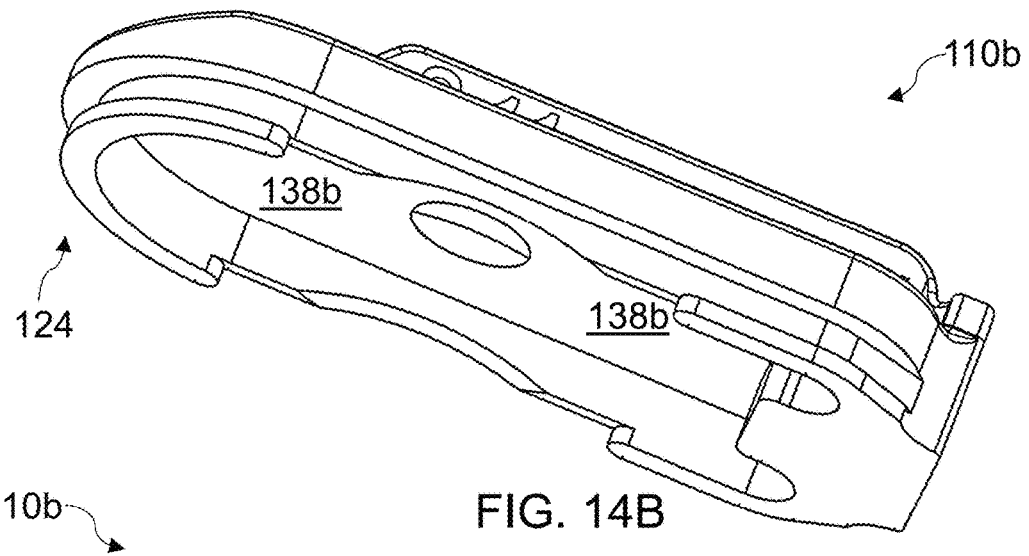
Figure 14C:
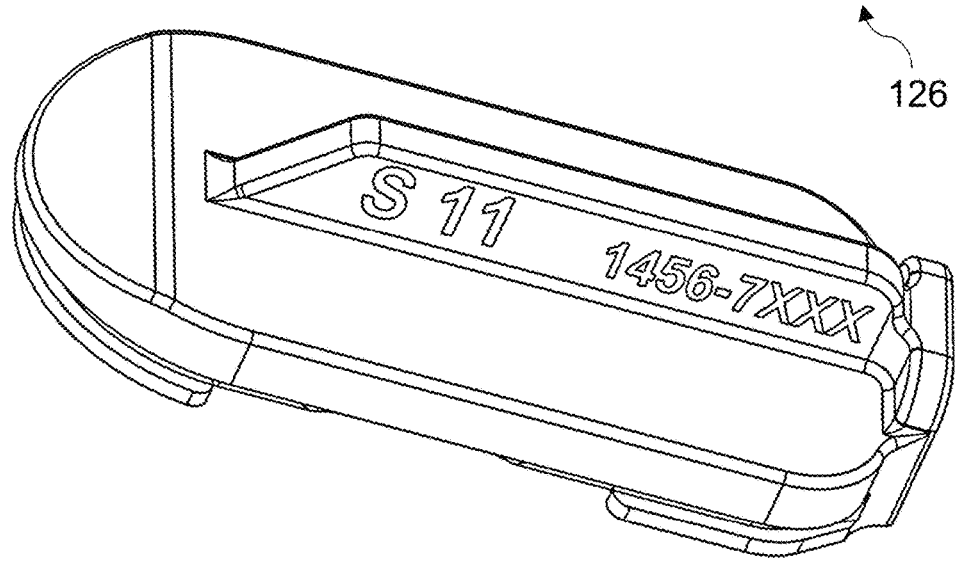
Figure 14D:
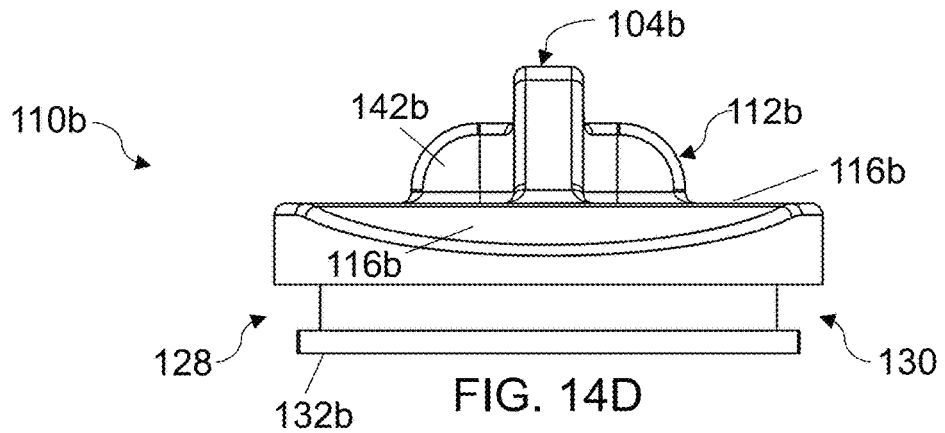
Figure 14E:
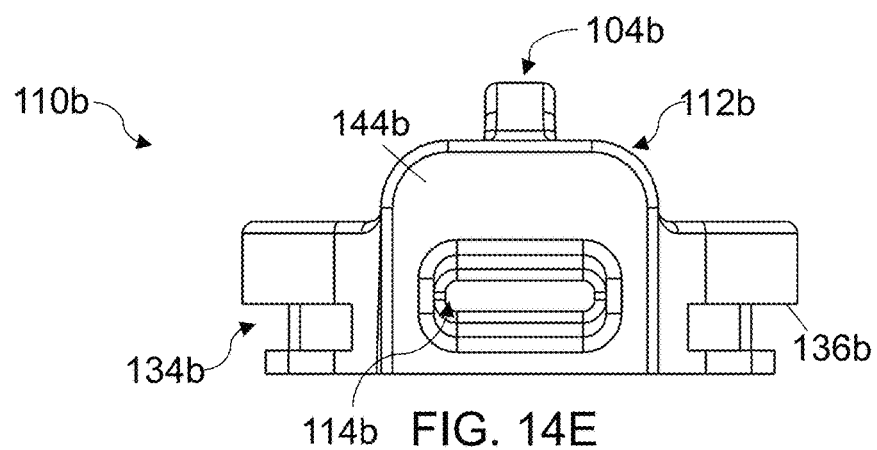
Figure 14F:
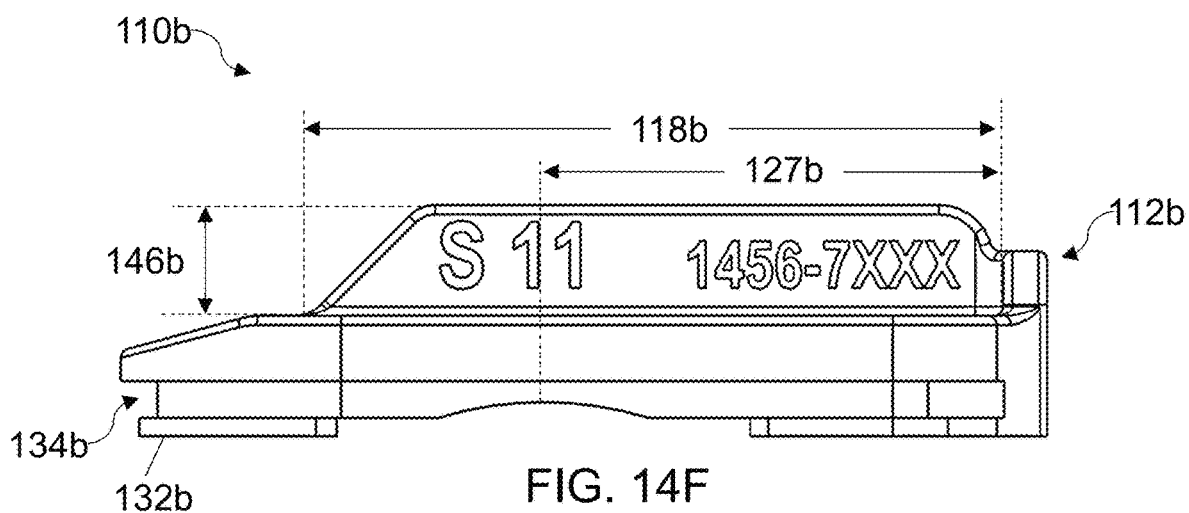
Figure 14G:
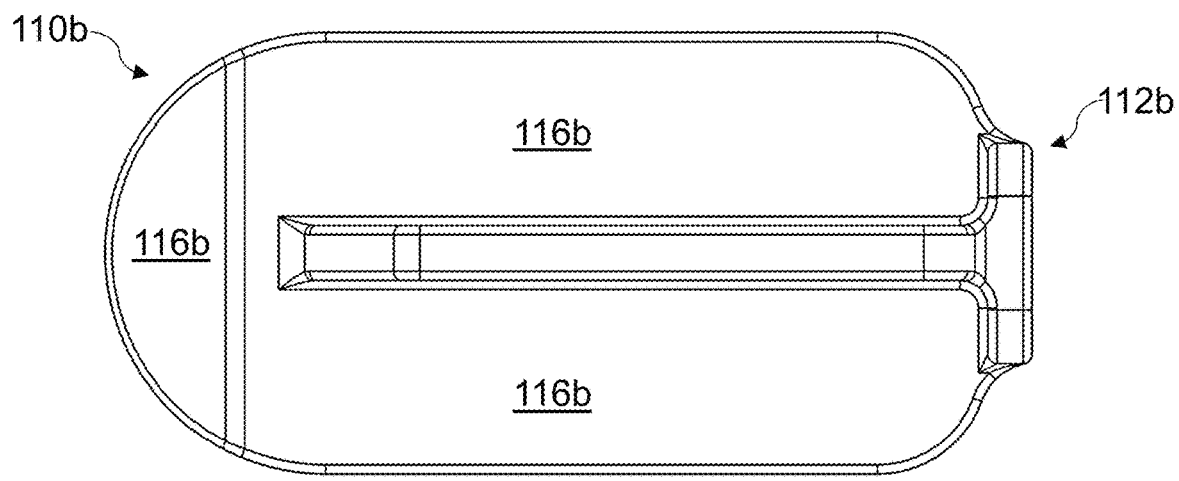
Figure 14H:
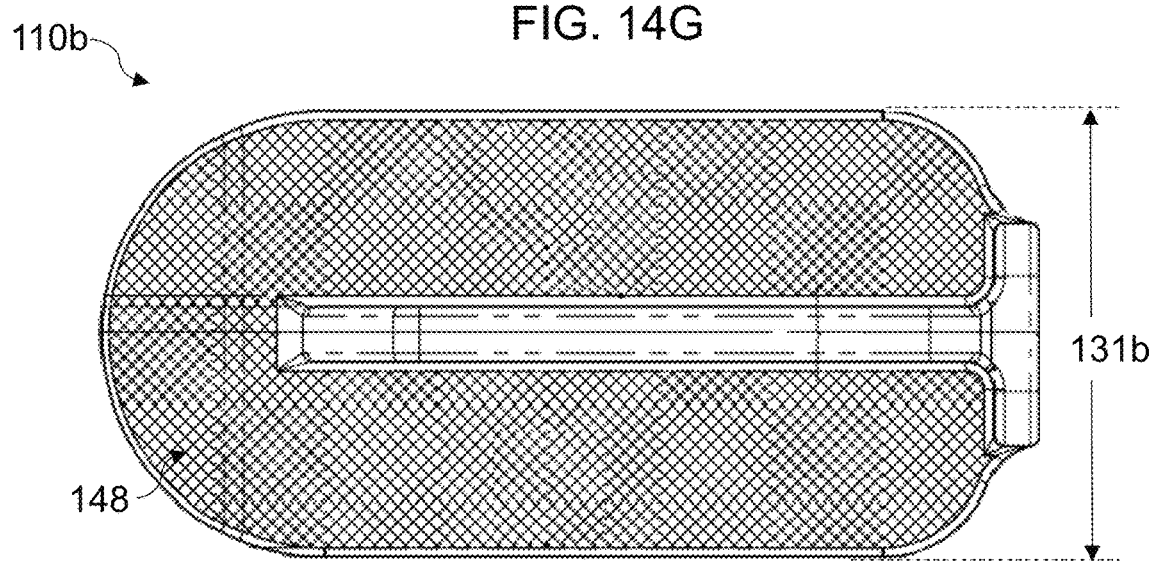
Figure 14I:
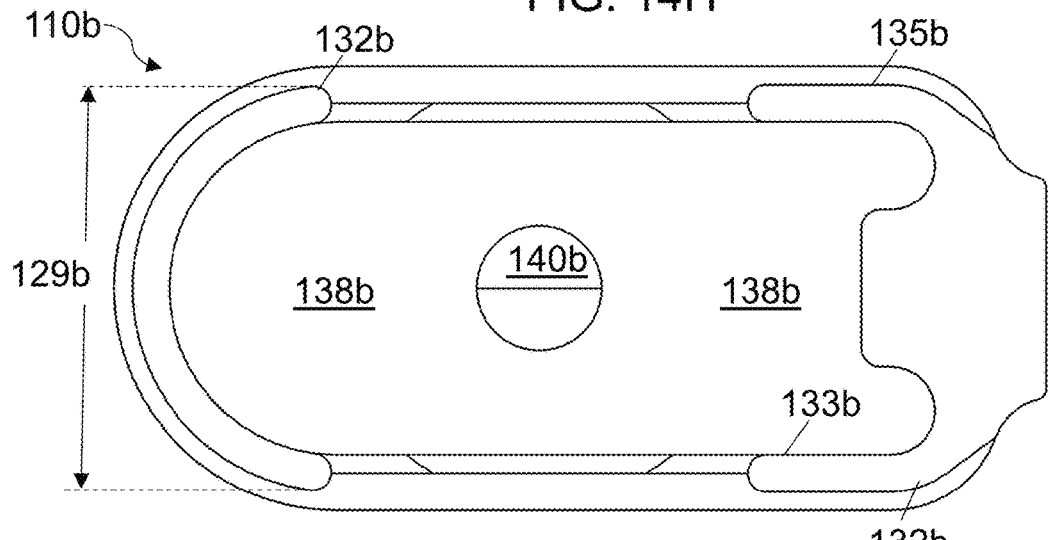
Figure 15A:
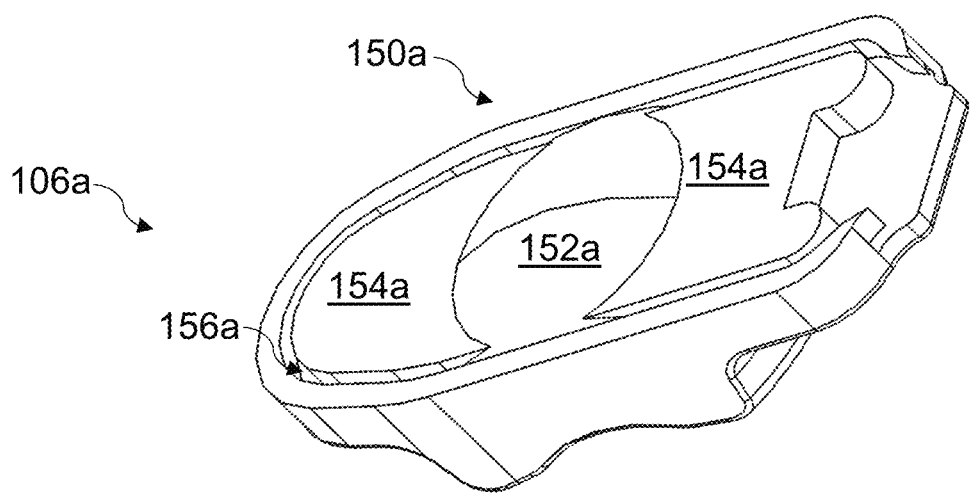
FIGS. 15A-15G depict various plan views of one embodiment of a superior articulating component.
Figure 15B:
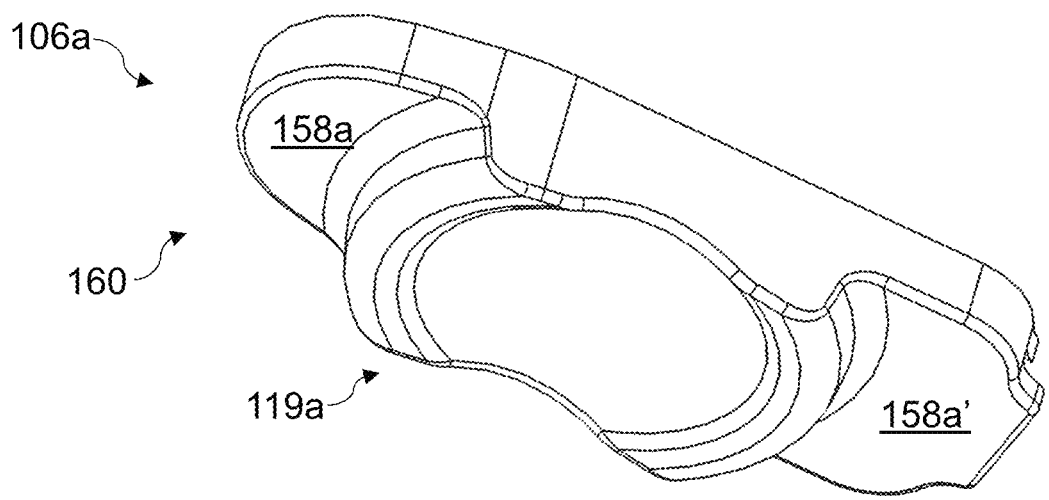
Figure 15C:
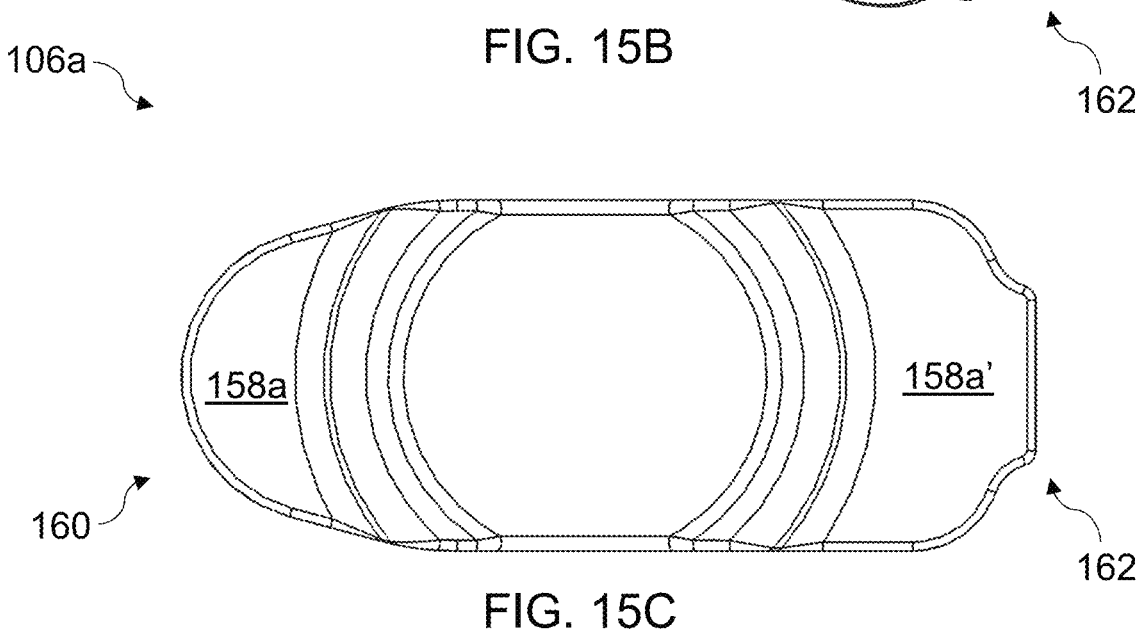
Figure 15D:
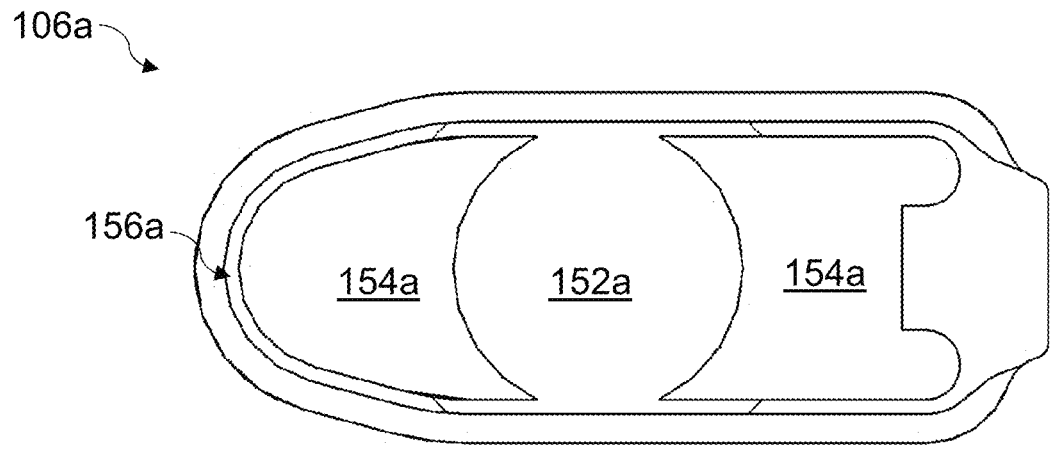
Figure 15E:
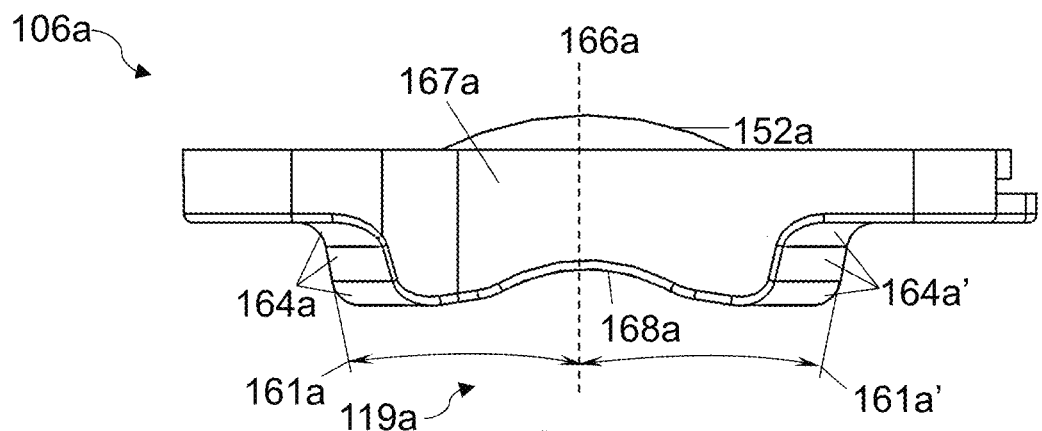
Figure 15F:
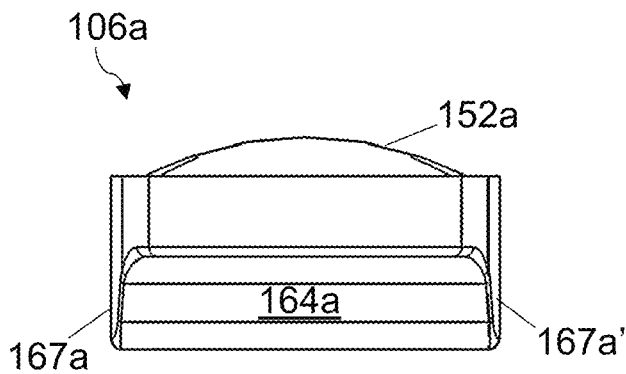
Figure 15G:
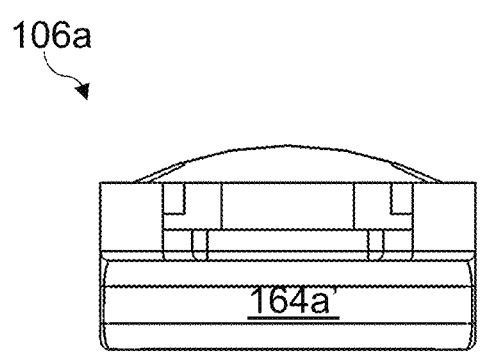
Figure 15H:
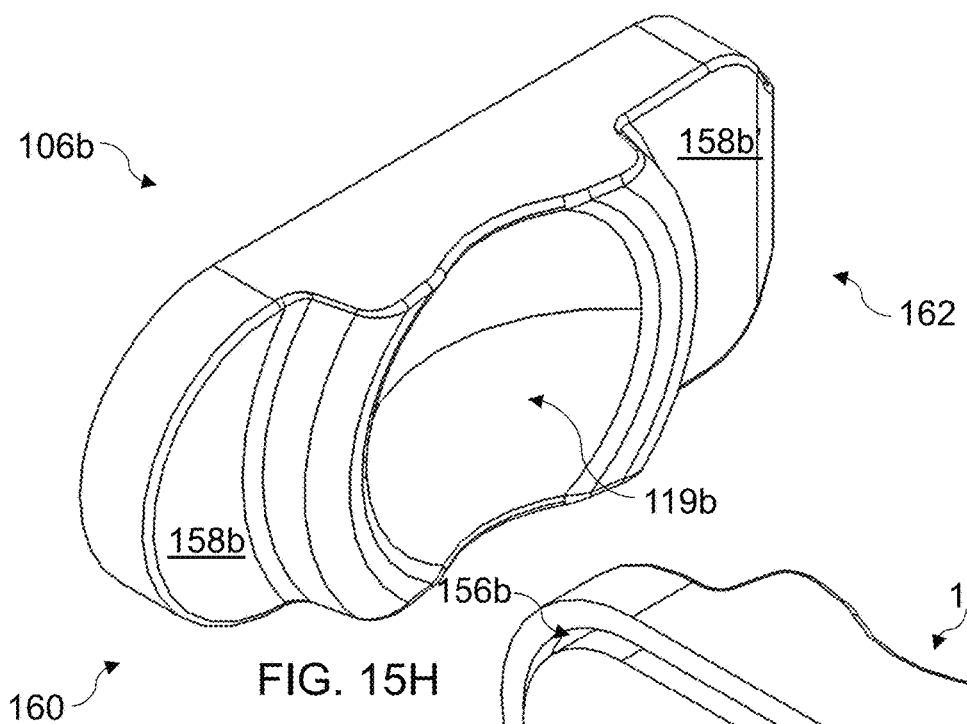
Figure 15I:
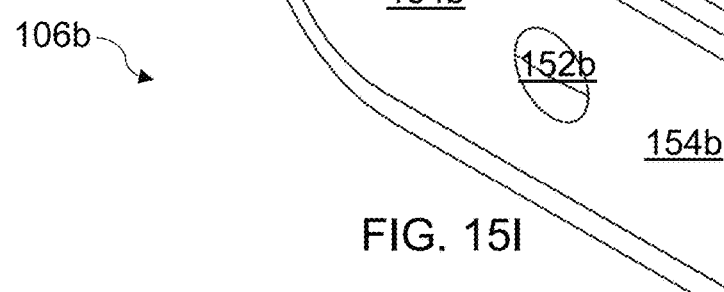
Figure 15J:
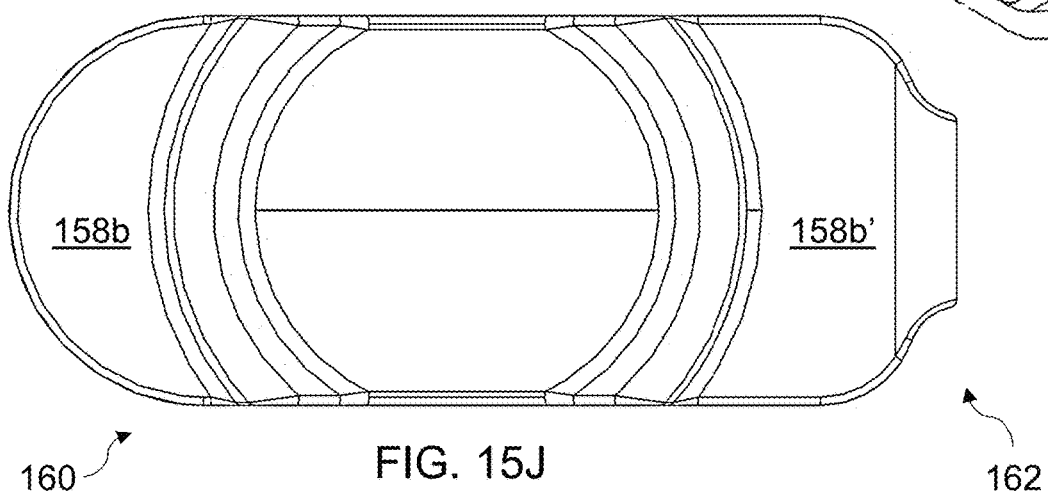

In another embodiment, at least one surface 116a, 116b, 138a, 138b, 140a, 140b of the superior base 110a, 110b may comprise a coating and/or surface texture 148 to desirably help facilitate healing or osseointegration, and/or to better accommodate loading forces and/or wear, such as shown in FIG. 14H. Alternatively, at least one or more surfaces 116a, 116b, 138a, 138b, 140a, 140b of the superior base 110a, 110b comprises a coating and/or surface texture 148a, 14b. At least a portion of the top surface 116a, 116b of the superior base 110a, 110b comprises a coating (not shown) and/or a surface texture or surface finish 148. At least a portion of the first contacting surface 136a, 136b comprises a coating and/or surface texture 148. At least a portion of the second contacting surface 138a, 138b comprises a coating and/or surface texture 148. At least a portion of the third contacting surface 140a, 140b comprises a coating and/or surface texture 148. Accordingly, the coating and/or surface texture 148 disposed onto each of the one or more top surfaces 116a, 116b, the first contacting surface 136a, 136b, the second contacting surface or bottom surface 138a, 138b, and/or the third contacting surface or domed surfaces 140a, 140b of the superior base 110a, 110b may be the same surface texture 148. the coating and/or surface texture 148 disposed onto each of the one or more top surfaces 116a, 116b, the first contacting surface 136a, 136b, the second contacting surface 138a, 138b, and/or the third contacting surfaces 140a, 140b of the superior base 110a, 110b may be different.

The surface textures or finishes 148 may comprise threads, flutes, grooves, and/or teeth that may include various shapes. The various shapes may include tapered, stepped, conical and/or paralleled, flat, pointed, and/or rounded. The surface textures or finishes 148 may further comprise roughened surfaces or porous surfaces, including turned, blasting, sand blasting, acid etching, chemical etching, dual acid etched, plasma sprayed, anodized surfaces, and/or any combination thereof. The surface textures or finishes 148 may further include a polish surface finish or texture. The polished surface may be accomplished using different techniques, mechanical polishing, chemical polishing, electrolytic polishing, and/or any combination thereof. Polished surfaces can be measured in "Ra" micrometers (μm) or microinches (μin.). The Ra may comprise a range of 0.025 to 1.60 μm; may comprise a range of 0.025 to 0.30 μm; may comprise a range of 0.025 to 0.20 μm; may comprise a range of 0.025 to 0.10 μm; and/or may comprise a range of 0.05 to 0.20 μm. Accordingly, the Ra may comprise at least 0.05 μm or higher; at least 0.10 μm or higher and/or at least 0.8 μm or higher. Surface structure is often closely related to the friction and wear properties of a surface. A surface with a large Ra value will usually have somewhat higher friction and wear quickly, and a surface with a lower Ra value will have a lower friction and enhanced part performance and/or prevent or reduce unwanted adhesion of molecules or components to surface(s) (e.g., surfaces are smooth, shiny and less porous). A polished surface has many further advantages, including improving cleanability, increases resistance to corrosion, reduces adhesive properties (for cells or other blood components to attach to), increases biocompatibility, increased light reflection for enhanced radiopacity, etc.

The coatings may include inorganic coatings or organic coatings. The coatings may further include a metal coating, a polymer coating, a composite coating (ceramic-ceramic, polymer-ceramic, metal-ceramic, metal-metal, polymer-metal, etc.), a ceramic coating, an anti-microbial coating, a growth factor coating, a protein coating, a peptide coating, an anti-coagulant coating, an antioxidant coating and/or any combination thereof. The antioxidant coatings may comprise naturally occurring or synthetic compounds. The natural occurring compounds comprises Vitamin E and Vitamin C (tocotrienols and tocopherols, in general), phenolic compounds and carotenoids. Synthetic antioxidant compounds include α-lipoic acid, N-acetyl cysteine, melatonin, gallic acid, captopril, taurine, catechin, and quercetin, and/or any combination thereof. The coatings can be impregnated, applied and/or deposited using a variety of coating techniques. These techniques include sintered coating, electrophoretic coating, electrochemical, plasma spray, laser deposition, flame spray, biomimetic deposition and wet methods such as sol-gel-based spin- and -dip or spray-coating deposition have been used most often for coating implants.

The metal coatings may comprise titanium, titanium alloys, cobalt-chrome alloys, platinum and stainless steel, and/or any combination thereof. More specifically, the metal coating includes titanium and/or cobalt-chrome molybdenum (CoCrMo). The polymer coatings may include thermoplastic or thermoset polymers. The polymers may further include carbon fiber, polyether ether ketone (PEEK), polyethylene (PE), ultra-high molecular weight polyethylene (UHMWPE), polycarbonate (PC), polypropylene (PP) and/or any combination thereof. The ceramic coatings may include alumina ceramics, Zirconia (ZrO2) ceramics, Calcium phosphate or hydroxyapatite (Ca10(PO46(OH)2) ceramics, titanium dioxide (TiO2), silica (SiO2), Zinc Oxide (ZnO) and/or any combination thereof.

With reference to FIGS. 7A-7H, 8A-8D, 9A-9B, 10A-10G, 10H-10N, 11A-11E, 12A-12C and 15A-15G, and 15H-15N, the superior element 96*a*, 96*b* comprises an articulating element or component 106*a*, 106*b*. The articulating element 106*a*, 106*b* comprises a body 150*a*, 150*b* and a socket 119*a*, 119*b*. The body or base 150*a*, 150*b* comprises a bottom surface 154*a*, 154*b*, a top surface 158*a*, 158*a'*, 158*b*, 158*b'*, an anterior end 160 and a posterior end 162. The bottom surface 154*a*, 154*b* of the body 150*a*, 150*b* is flat or planar and/or engages or contacts the second contacting surface or bottom surface 138*a*, 138*b* of the superior base 110*a*, 110*b*. The bottom surface 154*a*, 154*b* is a superior facing surface. The bottom surface 154*a*, 154*b* further comprises a protrusion 152*a*, 152*b* that extends away from the bottom surface 154*a*, 154*b* of the articulating component 106*a*, 106*b*. The protrusion 152*a*, 152*b* is normal to the plane of the bottom surface 154*a*, 154*b* or extends perpendicular to the plane of the bottom surface 154*a*, 154*b*. The protrusion 152*a*, 152*b* comprises a shape, the shape includes a dome shape, hemispherical shape, and/or a convex shape. The protrusion 152*a*, 152*b* is sized and configured to be disposed or engage with the third contacting surface or domed surface 140*a*, 140*b* of the base 110*a*, 110*b* of the superior element 96*a*, 96*b*.

The bottom surface 154*a*, 154*b* of the body 150*a*, 150*b* further comprises an articulation channel 156*a*, 156*b*. The articulation channel 156*a*, 156*b* surrounds and/or follows the perimeter of the bottom surface 154*a*, 154*b* and/or the body 150*a*, 150*b* of the articulating element 106*a*, 106*b*. The articulation channel 156*a*, 156*b* substantially surrounds and/or substantially follows the perimeter of the bottom surface 154*a*, 154*b* and/or the body 150*a*, 150*b* of the articulating element 106*a*, 106*b*. The channel 156*a*, 156*b* is sized and configured to receive the flange 132*a*, 132*b* of the base 110*a*, 110*b* of the superior element. The channel 156*a*, 156*b* may comprise a frictional fit and/or press fit with the flange 132*a*, 132*b* of the base 110*a*, 110*b* of the superior element 96*a*, 96*b* to prevent the migration of the base 110*a*, 110*b* relative to the articulating element 106*a*, 106*b* of the superior element 96*a*, 96*b*.

The body 150*a*, 150*b* comprises a top surface 158*a*, 158*a'*, 158*b*, 158*b'* and a longitudinal axis 166*a*, 166*b*. Alternatively, the body 150*a*, 150*b* comprises a first top surface 158*a*, 158*b*, and a second top surface 158*a'*, 158*b'*, and a longitudinal axis 166*a*, 166*b*. The top surface or the first top surface 158*a*, 158*b* is positioned proximate to the anterior end 160, and the top surface or the second top surface 158*a'*, 158*b'* is positioned proximate and/or adjacent to the posterior end 162. The socket 119*a*, 119*b* comprises a first anterior facing wall 164*a*, 164*b* and a second posterior facing wall 164*a'*, 164*b'*. The socket 119*a*, 119*b* may further comprise a side walls, including a medial wall 167*a*, 167*b* and a lateral wall 167*a'*, 167*b'*. The socket 119*a*, 119*b* may further comprise an articulation surface 168*a*, 168*b* that is positioned between a first anterior facing wall 164*a*, 164*b* and a second posterior facing wall 164*a'*, 164*b'*.

The socket 119*a*, 119*b* extends outwardly toward the inferior direction. The socket 119*a*, 119*b* is disposed between first top surface 158*a*, 158*b* positioned adjacent or proximate to the anterior end 160, and the second top surface 158*a'*, 158*b'* positioned adjacent or proximate to the posterior end 162. Alternatively, the socket 119*a*, 119*b* is positioned between the first top surface 158*a*, 158*b* of the base 150*a*, 150*b* and the second top surface 158*a'*, 158*b'* of the base 150*a*, 150*b*. The socket 119*a*, 119*b* aligns with the central axis 166*a*, 166*b* of the articulation component 106*a*, 106*b*.

The top surfaces 158*a*, 158*a'*, 158*b*, 158*b'* may comprise a flat or planar surface. The top surfaces 185*a*, 158*a'*, 158*b*, 158*b'* may comprise a curved, arched or convex surface. The top surfaces 185*a*, 158*a'*, 158*b*, 158*b'* may comprise an angled surface or angled orientation, the angled surface or orientation comprises an angle 163. The top surfaces 158*a*, 158*a'*, 158*b*, 158*b'* may comprise a flat and angled surface, the angled surface comprises an angle 163. The socket 119*a*, 119*b* extends away from the top surfaces 158*a*, 158*a'*, 158*b*, 158*b'* of the body or base 150*a*, 150*b*. The angle 163 may include a range of 0.25 degrees to 7 degrees; the range may include 1 degree to 5 degrees; and/or the range may include 3 degrees to 5 degrees. Alternatively, the angle 163 may include 7 degrees or less; the angle 163 may include 5 degrees or less; and/or the angle may include 5 degrees or more. The top surfaces In another embodiment, the body 150*a*, 150*b* comprises a first top surface 158*a*, 158*b* with a first top surface angle or orientation and a second top surface 158*a'*, 158*b'* with a second top surface angle orientation or surface type. The first surface orientation or angle may be the same orientation as the second surface orientation or angle. The first surface orientation or angle may be a different orientation than the second surface orientation or angle. The first surface orientation or angle may comprise flat, angled, curved and/or any combination thereof. The second surface orientation or angle may comprise flat, angled, curved and/or any combination thereof. In exemplary embodiment, the first surface orientation or angle may comprise a flat or planar surface and/or at a zero degrees angle, and the second surface orientation may comprise a flat/planar and an angled surface, the angled surface comprises an angle of at least 5 degrees.

The socket 119*a*, 119*b* comprises a plurality of walls 164*a*, 164*a'*, 164*b*, 164*b'*, 167*a*, 167*a'*, 167*b*, 167*b'*. Each of the plurality of walls 164*a*, 164*a'*, 164*b*, 164*b'*, 167*a*, 167*a'*, 167*b*, 167*b'* face a different direction and/or different orientation. The different directions include an anterior facing wall 164a, 164b, a posterior facing wall 164a', 164b', a medial facing wall 167a, 167b, and a lateral facing wall 167a', 167b'. At least two of the plurality of walls 164a, 164a', 164b, 164b' extend from the top surfaces 158a, 158a', 158b, 158b' at an angle and/or an oblique orientation 161a, 161a', 161b, 161b' from the longitudinal axis 166a, 166b. Each of the at least two of the plurality of walls 164a, 164a', 164b, 164b' comprise the same angle or a different angle.

In another embodiment, the anterior facing wall 164a, 164b comprises a first angle or an orientation 161a, 161b. The posterior facing wall 164a', 164b' comprises a second angle or orientation 161a', 161b'. The first angle or orientation 161a, 161b and the second angle or orientation 161a', 161b' are the same angle or orientation. The first angle or orientation 161a, 161b and the second angle or orientation 161a', 161b' are a different angle or orientation. In another embodiment, first wall 164a, 164b extends from the top surfaces 158a, 158b at a first angle and/or a first oblique orientation 161a, 161b and/or a second wall 164a', 164b' extends at a second angle or a second oblique orientation 161a', 161b'. The first angle 161a, 161b may be the same as the second angle 161a', 161b'. The first angle 161a, 161b may be different than the second angle 161a', 161b'. In one embodiment, at least a portion of the angle or orientation 161a, 161b of the anterior facing wall 164a, 164b of the socket 119a, 119b engages or contacts a portion of the posterior facing wall 184a, 184b of the first stop 180a, 180b during flexion.

The angle and/or the oblique orientation 161a, 161a', 161b, 161b' may comprise a range of 1 degree to 20 degrees; a range of 5 degrees to 15 degrees; a range of 10 degrees to 20 degrees; a range of 15 degrees to 20 degrees; and/or range of 5 degrees to 10 degrees. Accordingly, the angle and/or orientation 161 comprises at least 10 degrees or greater and/or 10 degrees or less. At least a portion of the walls 164a, 164a', 164b, 164b' contact at least one surface of the inferior element 98a, 98b.

Accordingly, at least two of the plurality of walls 167a, 167a', 167b, 167b' extend from the top surfaces 158a, 158a', 158b, 158b' perpendicular or normal to the planes of the top surfaces 158a, 158b of the body 150a, 150b. The plurality of side walls 167a, 167a', 167b, 167b' are flat or planar. The socket 119 further comprises an articulating surface 168a, 168b. The articulating surface 168a, 168b further comprises a shape and a size. The shape is sized and configured to receive the articulating component 108a, 108b of the inferior element 98a, 98b. The shape of the articulating surface 168a, 168b comprises a concave, an arch, a hemispherical shape. The size comprises a diameter of at least 10 mm to 20 mm; a diameter of 10 mm to 16 mm; a diameter of 15 mm to 20 mm; a diameter of 14 mm to 18 mm; a diameter of at least 15 mm or greater; a diameter of at least 16 mm or greater; a diameter of at least 16 mm or less and/or any combination thereof. The size of the superior articulating surface 168a, 168b of the superior articulation component 106a, 106b may match or substantially match the size of the inferior articulating surface 228a, 228b of the inferior articulation component 108a, 108b.

In various embodiments, the superior articulating component 106a, 106b of the superior element 96a, 96b comprises a material, which material may the same or different from the material of which the superior base 110a, 110b is comprised. The material may include metal, polymers or ceramic. The metals may comprise titanium, titanium alloys, cobalt-chrome alloys, platinum, stainless steel and/or any combination thereof. More specifically, the metal may include titanium and/or cobalt-chrome molybdenum (Co-CrMo). The polymers may include thermoplastic or thermoset polymers. The polymers may further include carbon fiber, polyether ether ketone (PEEK), polyethylene (PE), ultra-high molecular weight polyethylene (UHMWPE), polycarbonate (PC), polypropylene (PP) and/or any combination thereof. The polymers may further include cross-linking. The ceramics may include alumina ceramics, Zirconia (ZrO2) ceramics, Calcium phosphate or hydroxyapatite (Ca10(PO46(OH)2) ceramics, titanium dioxide (TiO2), silica (SiO2), Zinc Oxide (ZnO) and/or any combination thereof. The materials may be manufactured using traditional methods and/or using 3D printed techniques known in the art. Furthermore, the material may comprise a porous material, the porous material includes porous metal, porous polymer, porous ceramic and/or any combination thereof.

In another embodiment, the material may be further antioxidant stabilized. The stabilized antioxidants may comprise Vitamin E or Vitamin C. The antioxidants may be incorporated into the material by blending the antioxidant into the material for subsequent cross-linking and/or diffusing the antioxidant into the material. The material may be further cross-linked before or after antioxidant stabilization.

As previously noted, the material of the articulating component 106a, 106b of the superior element 96a, 96b may be the same as the material of the superior base 110a, 110b of the superior element. The material of the articulating component 106a, 106b of the superior element 96a, 96b may be different as the material of the base 110a, 110b of the superior element 96a, 96b.

In another embodiment, at least one surface 158a, 158a', 158b, 158b', 164a, 164a', 164b, 164b', 168a, 168b of the articulating component 106a, 106b comprises a coating and/or surface texture (not shown) to help facilitate healing, osseointegration, loading forces and/or wear. Alternatively, at least two or more surfaces 158a, 158a', 158b, 158b', 164a, 164a', 164b, 164b', 168a, 168b of the articulating component 106a, 106b comprises a coating and/or surface texture. At least a portion of the top surface 158a, 158b comprises a coating (not shown) and/or a surface texture or surface finish. At least a portion of one or more of the surfaces 158a, 158a', 158b, 158b', 164a, 164a', 164b, 164b', 168a, 168b comprises a coating and/or surface texture. The coating and/or surface finishes of the articulating component 106a, 106b of the superior element 96a, 96b may be the same as the coating of the base 110a, 110b of the superior element. The coating and/or surface finishes of the articulating component 106a, 106b of the superior element 96a, 96b may be different as the coating of the base 110a, 110b of the superior element 96a, 96b. Accordingly, the coating and/or surface finishes disposed on each of the surfaces 158a, 158a', 158b, 158b', 164a, 164a', 164b, 164b', 168a, 168b of the articulating component 106a, 106b may be the same or different.

The surface textures or finishes may comprise threads, flutes, grooves, and/or teeth that may include various shapes. The various shapes may include tapered, stepped, conical and/or paralleled, flat, pointed, and/or rounded. The surface textures or finishes may further comprise roughened surfaces or porous surfaces, including turned, blasting, sand blasting, acid etching, chemical etching, dual acid etched, plasma sprayed, anodized surfaces, and/or any combination thereof. The surface textures or finishes may further include a polish surface finish. The polished surface may be accomplished using different techniques, mechanical polishing, chemical polishing, electrolytic polishing, and/or any combination thereof. Polished surfaces can be measured in "Ra" micrometers (μm) or microinches (μin.). The Ra may comprise a range of 0.025 to 1.60 µm; may comprise a range of 0.025 to 0.30 µm; may comprise a range of 0.025 to 0.20 µm; may comprise a range of 0.025 to 0.10 µm; and/or may comprise a range of 0.05 to 0.20 µm. Accordingly, the Ra may comprise at least 0.05 µm or higher; at least 0.10 µm or higher and/or at least 0.8 µm or higher. Surface structure is often closely related to the friction and wear properties of a surface. A surface with a large Ra value will usually have somewhat higher friction and wear quickly, and a surface with a lower Ra value will have a lower friction and enhanced part performance and/or prevent or reduce unwanted adhesion of molecules or components to surface(s) (e.g., surfaces are smooth, shiny and less porous). A polished surface has many further advantages, including improving cleanability, increases resistance to corrosion, reduces adhesive properties (for cells or other blood components to attach to), increases biocompatibility, increased light reflection for enhanced radiopacity, etc.

The coatings may include inorganic coatings or organic coatings. The coatings may further include a metal coating, a polymer coating, a composite coating (ceramic-ceramic, polymer-ceramic, metal-ceramic, metal-metal, polymer-metal, etc.), a ceramic coating, an anti-microbial coating, a growth factor coating, a protein coating, a peptide coating, an anti-coagulant coating, an antioxidant coating and/or any combination thereof. The antioxidant coatings may comprise naturally occurring or synthetic compounds. The natural occurring compounds comprises Vitamin E and Vitamin C (tocotrienols and tocopherols, in general), phenolic compounds and carotenoids. Synthetic antioxidant compounds include α-lipoic acid, N-acetyl cysteine, melatonin, gallic acid, captopril, taurine, catechin, and quercetin, and/or any combination thereof. The coatings can be impregnated, applied and/or deposited using a variety of coating techniques. These techniques include sintered coating, electrophoretic coating, electrochemical, plasma spray, laser deposition, flame spray, biomimetic deposition and wet methods such as sol-gel-based spin- and -dip or spray-coating deposition have been used most often for coating implants.

With reference to FIGS. 7A-7H, 8A-8D, 9A-9B, 16A-16H and 17A-17F the lower or inferior element 98a, 98b comprises an articulating element 108a, 108b, a base or body and/or inferior base 216a, 216b, and a bridge 174a, 174b. The lower or inferior element 98a, 98b further comprises an anterior end 185, a posterior end 187, a medial end 191 and a lateral end 189. The lower inferior element 98a, 98b and/or the inferior base 216a, 216b comprises a first stop 180a, 180b and second stop 178a, 178b.

In another embodiment, the inferior element 98a, 98b comprises a base or a body 216a, 216b. The base 216a, 216b comprises a bottom surface 218a, 218b and a top surface 196a, 196b, 198a, 198b. At least a portion of the bottom surface 218a, 218b engages or contacts the inferior vertebral body. At least a portion of the bottom surface 218a, 218b engages or contacts the endplate of the inferior vertebral body. At least portion of the bottom surface 218a, 218b engages or contacts the cancellous bone and/or the cortical bone of the inferior vertebral body. Accordingly, at least a portion of the bottom surface 218a, 218b comprises a flat or planar surface. At least a portion of the bottom surface 218a, 218b may comprise a curved or angled surface. The at least a portion of the bottom surface 218a, 218b extends anteriorly at an angle 235a, 235b. The at least a portion of the bottom surface 218a, 218b extends anteriorly and upwardly towards the superior direction at an angle 235a, 235b. Alternatively, the entire bottom surface 218a, 218b comprises a flat or planar surface. The angle 235a, 235b of at least a portion of the body or base 216a, 216b and/or the bottom surface 218a, 218b comprises at 10 degrees or greater; an angle of 12 degrees or greater; an angle of 15 degrees or greater. Alternatively, the angle 235a, 235b of at least a portion of the body or base 216a, 216b and/or the bottom surface 218a, 218b comprises an angle of at least 20 degrees or less; an angle of 18 degrees or less; an angle of 15 degrees or less. The angle 235a, 235b of at least a portion of the body or base 216a, 216b and/or the bottom surface 218a, 218b comprises a range of 5 to 20 degrees; a range of 10 to 20 degrees; a range of 15 to 20 degrees; a range of 10 to 15 degrees; and/or a range of 13 to 18 degrees.

Figure 16A:
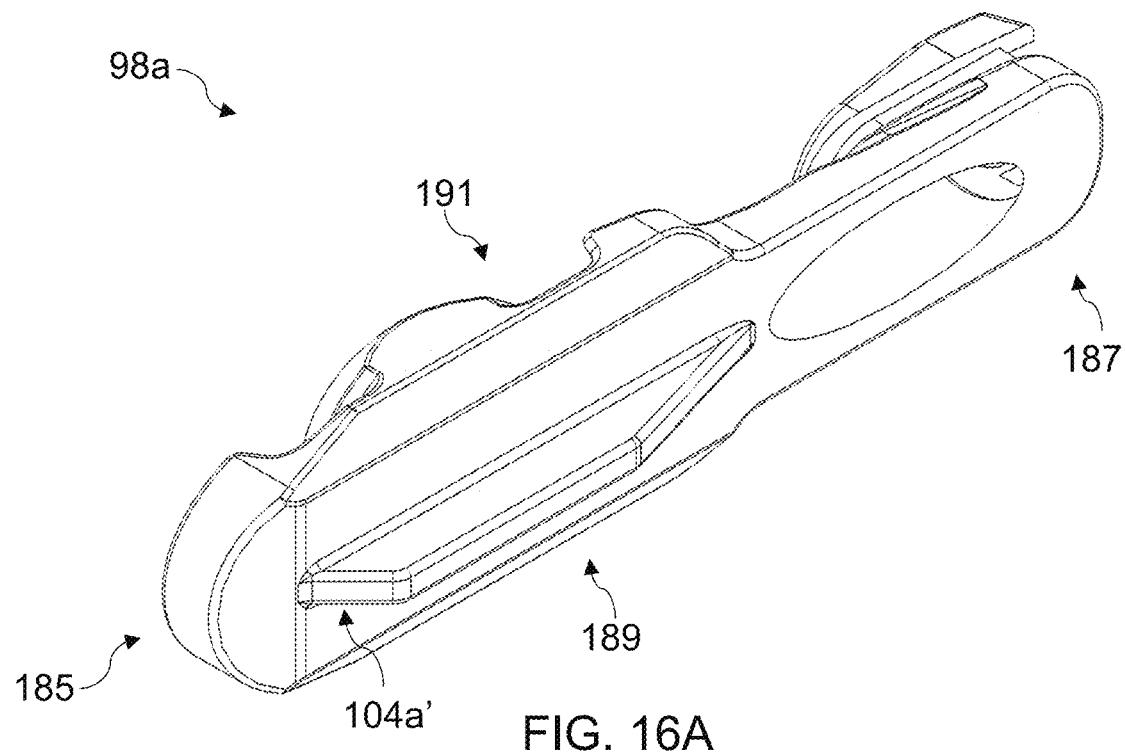
FIGS. 16A-16H depict various plan views of one embodiment of an inferior element of the spinal implant of FIGS. 7A-7H.
Figure 16B:
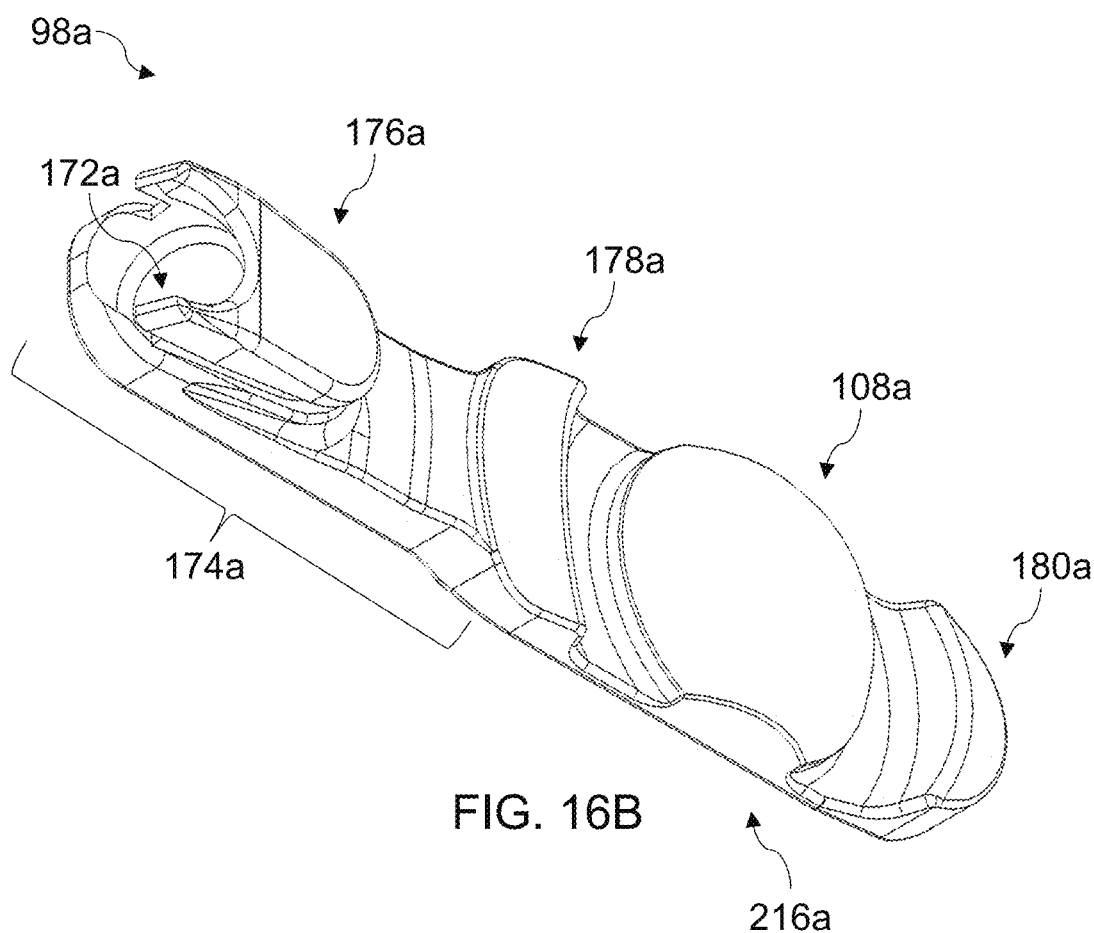
Figure 16C:
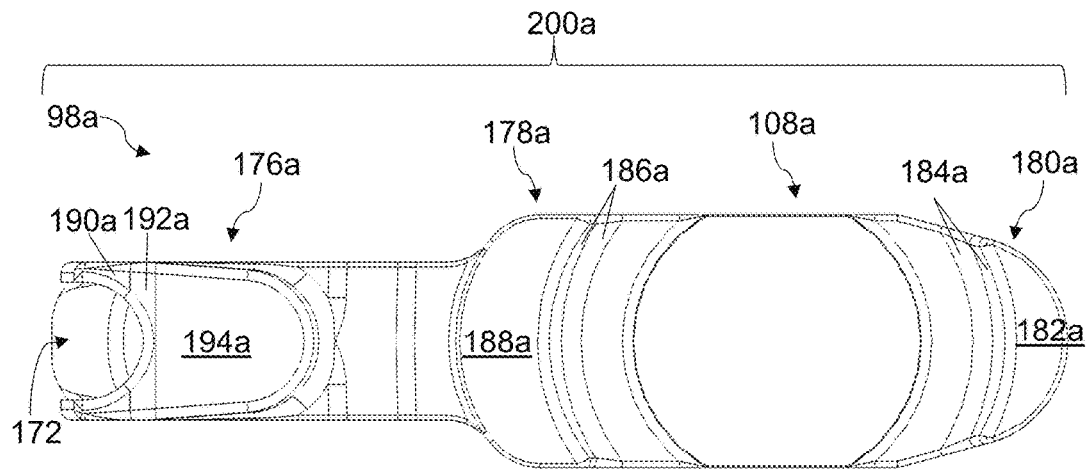
Figure 16D:
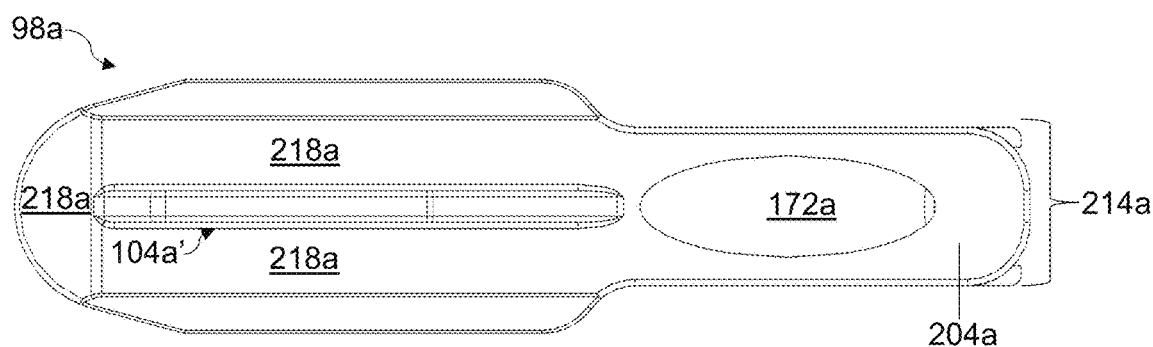
Figure 16E:
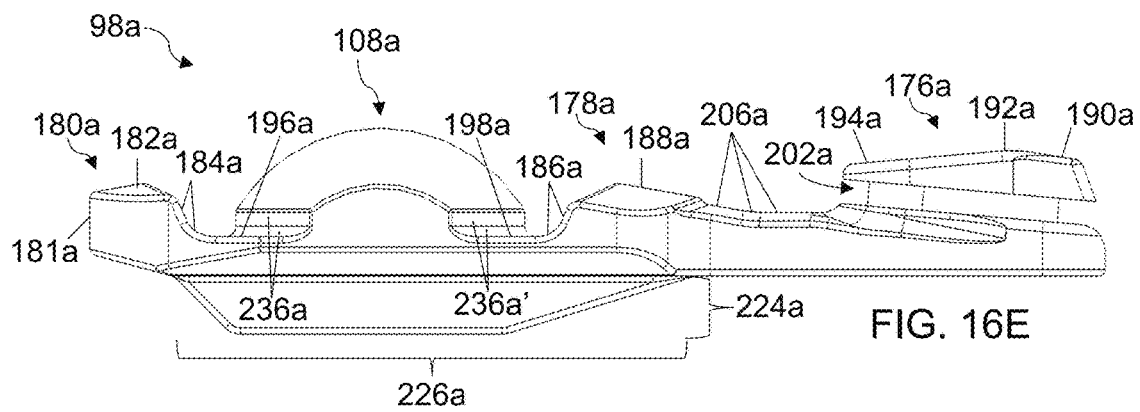
Figure 16F:
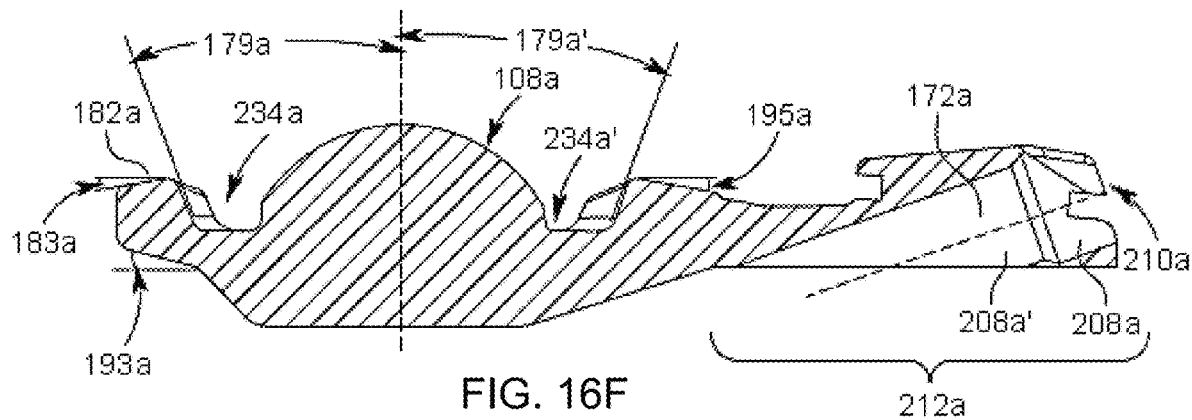
Figure 16G:
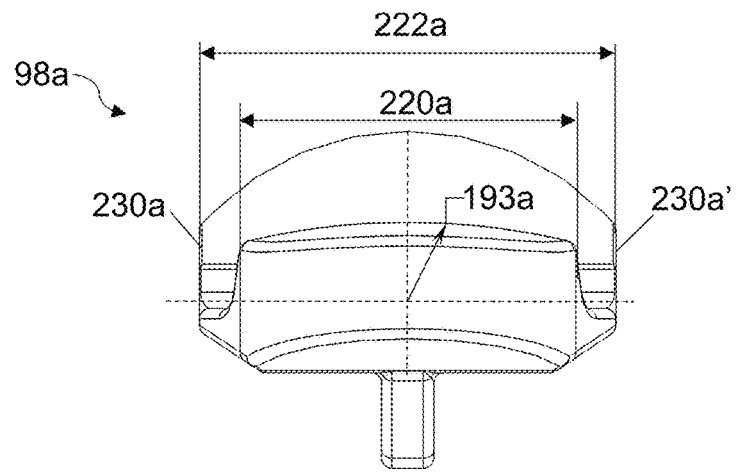
Figure 16H:
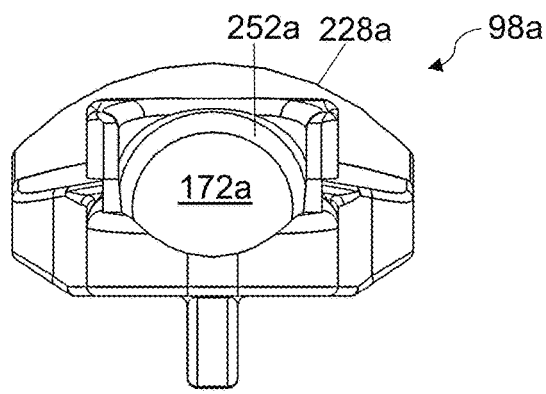
Figure 17A:
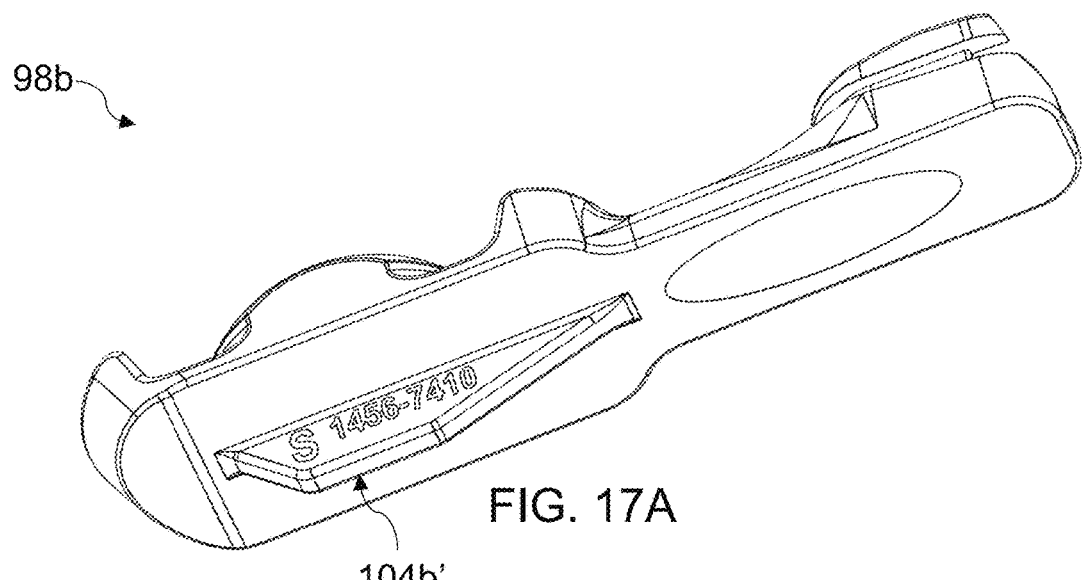
Figure 17B:
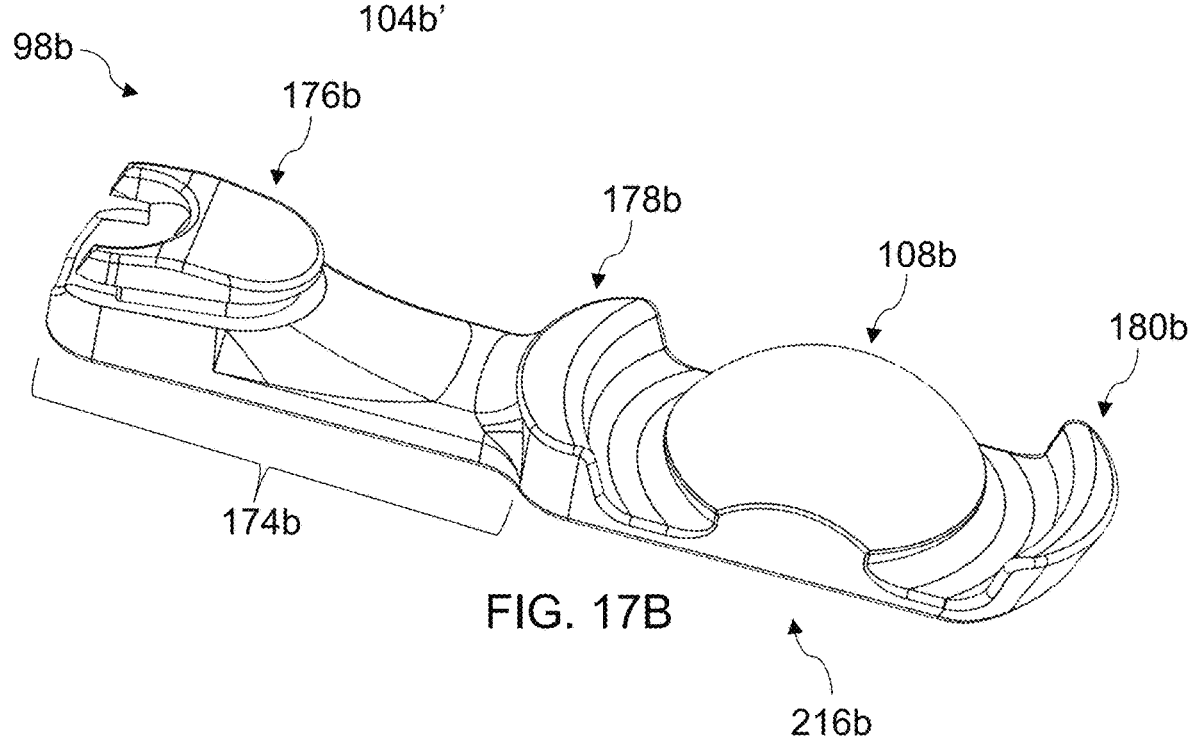

The inferior base 216a, 216b further comprises a plurality of base widths 220a, 220b, 222a, 222b as shown in FIGS. 16G and 17E. The plurality of base widths 220a, 220b, 222a, 222b may be uniform or non-uniform. The non-uniformity of the plurality of base widths 220a, 220b, 222a, 222b may include at least a portion that is tapered 222a. The tapered portion 222a, 222b includes a smaller width than the base width 220a, 220b. In another embodiment, the inferior base 216a, 216b comprises a first width 220a, 220b and a second width 222a, 222b. The second width 222a, 222b may be the same width as the first width 220a, 220b. The second width 222a, 222b may be a different width as the first width 220a, 220b. The first width 220a, 220b comprises a smaller width than the second width 222a, 22b. Alternatively, the second width 222a, 222b may comprise a larger width or a smaller width compared to the first width 220a, 220b. The first base width, the second base width, and/or plurality of base widths 220a, 220b, 222a, 222b may comprise a width of at least 10 mm or greater; a width of 12 mm or greater; a width of 15 mm or greater. Alternatively, the base width 220a, 220b, 222a, 222b may comprise a width of 10 mm to 20 mm; a width of 10 mm to 15 mm; a width of 12 mm to 15 mm; and/or any combination thereof.

The inferior base 216a, 216b further comprises a shape, the shape may include a uniform shape or a non-uniform shape. The shape may further include an oval, an ellipse, a rectangle, a rounded rectangle. At least one end of the inferior base 216a, 216b may be tapered. At least the anterior end 184 of the inferior base 216a, 216b may be tapered. The inferior base width 220a, 220b, 222a, 222b may be larger than the bridge width 214a, 214b. Each of the plurality of inferior base widths 220a, 220b, 222a, 222b may be larger than the bridge width 214a, 214b. Alternatively, at least a portion of the pluralities of base widths 220a, 220b, 222a, 222b comprises a larger width than the bridge width 214a, 214b. The second width 222a may comprise a larger width than the bridge width 214a, 214b. The inferior base width 220a, 220b, 222a, 222b may include at least 1.5 times larger than the bridge width 214a, 214b. The base width 220a, 220b, 222a, 222b may include at least 2 times larger than the bridge width 214a, 214b. The inferior base width 220a, 220b, 222a, 222b may include at least 1.5 to 1.7 times larger than the bridge width 214a, 214b.

The inferior element 98a, 98b and/or the inferior base 216a, 216b further comprises a first stop 180a, 180b and a second stop 180a, 180b. The first stop 180a, 180b extends upwardly from the base or inferior base 216a, 216b. The first stop 180a, 180b extends anteriorly and upwardly towards the superior direction from the base or inferior base 216a, 216b. Alternatively, the first stop 180a, 180b and the second stop 178a, 178b are disposed onto the inferior base 216a, 216b. The first stop 180a, 180b and the second stop 178a, 178b are disposed onto a top surface 196a, 196b, 198a, 198b of the inferior base 216a, 216b.

The first stop 180a, 180b is positioned adjacent or proximate to the anterior end 185 of the inferior element 98a, 98b. The first stop 180a, 180b comprises a first contact surface 182a, 182b, a first wall 184a, 184b, and a second wall 181a, 181b as shown in FIGS. 16C, 16E-16F, 16G and 17C-17F. The first contact surface 182a, 182b may comprise at least one of a flat or planar surface, an angle or angled surface 183a, 183b, a curved surface and/or any combination thereof. The curved surface may include a convex or concave shape. The curved surface may comprise a radius or diameter 193a, 193b. The curved surface may extend from a medial end 191 to the lateral end 189. The curved surface aligns perpendicular to the longitudinal axis of the inferior element 98a, 98b.

In one embodiment, the first contact surface 182a, 182b of the first stop 180a, 180b comprises an angled surface and a curved surface. The curved surface comprises a convex shape or semi-spherical shape, the curved surface comprising a radius 193a, 193b, the curved surface extending from a medial end 191 to the lateral end 189 of the inferior element or the curved surface aligns perpendicular to the longitudinal axis of the inferior element 98a, 98b. The angled surface slopes downwardly and anteriorly at a first contact surface angle 183a, 183b. The first contact surface angle 183a, 183b may comprise an angle of 5 degrees to 15 degrees; an angle of 7 degrees to 13 degrees; an angle of 9 degrees to 11 degrees; an angle of 10 degrees or greater; and/or an angle of 10 degrees or less.

The first wall 184a, 184b and/or a second wall 181a, 181b extends perpendicular or substantially perpendicular from the first contact surface 182a, 182b. Alternatively, the first wall 184a, 184b and/or the second wall 181a, 181b may extend at an orientation angle 179a, 179b from the first contact surface 182a, 182b. The second wall 181a, 181b may extend upwardly or superiorly from the bottom surface 218a, 218b of the base 216a, 216b. Alternatively, the second wall 181a, 181b may extend downwardly or inferiorly from the first contact surface 182a, 182b. The first wall 184a, 184b may further comprise a flat or planar surface and/or a curved surface, the curved surface may comprise a concave shape or a convex shape. The first wall curved surface comprises a first wall curved surface radius. The second wall 181a, 181b may be curved or arched in a convex shape. The first wall 184a, 184b may comprise a posterior facing wall. The second wall 181a, 181b may comprise an anterior facing wall.

Figure 7A:
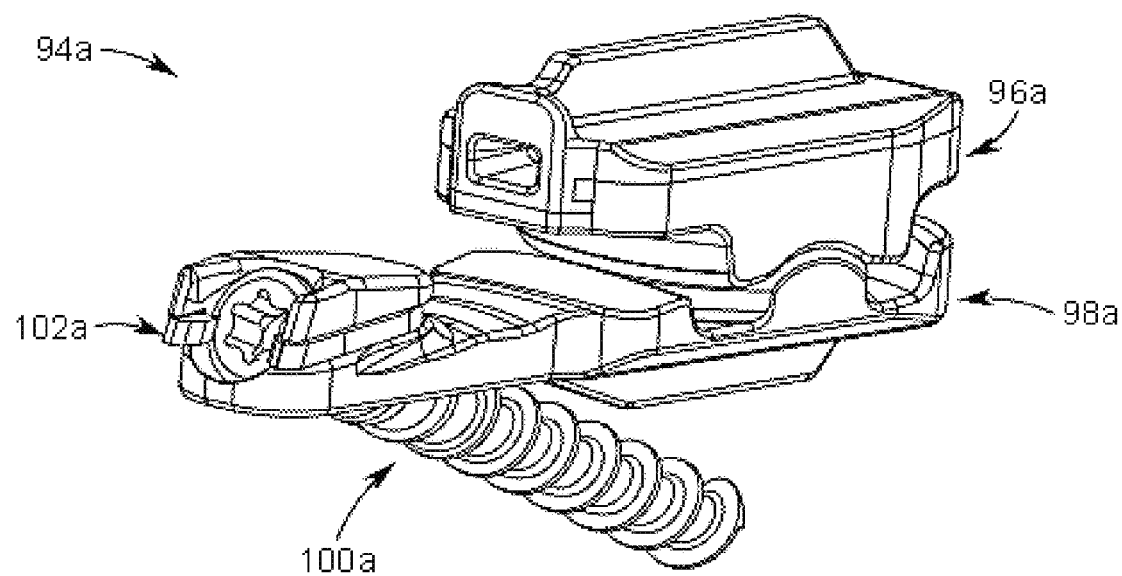
FIGS. 7A-7H depicts various plan views of one embodiment of a spinal implant.
Figure 7B:
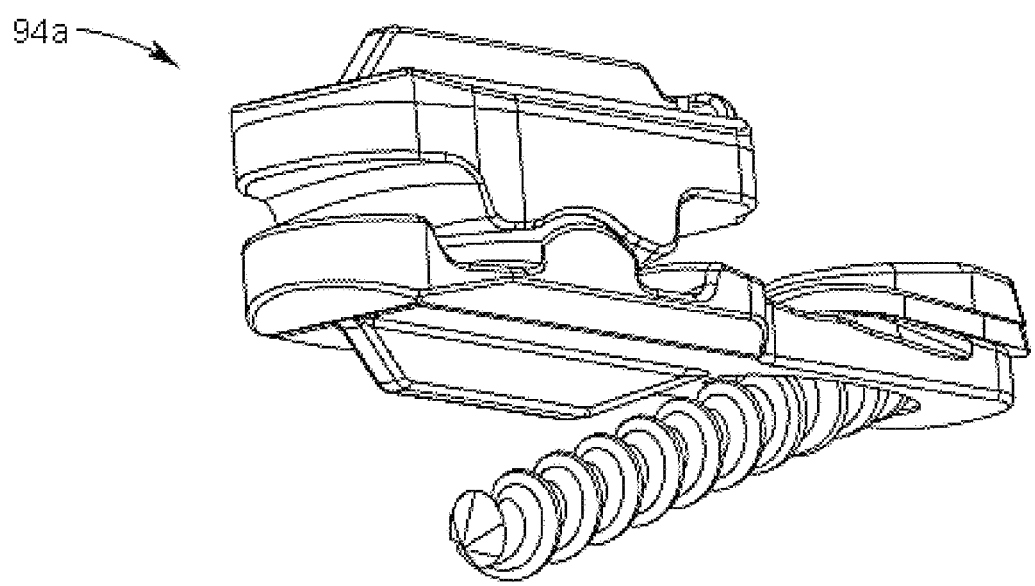
Figure 7C:
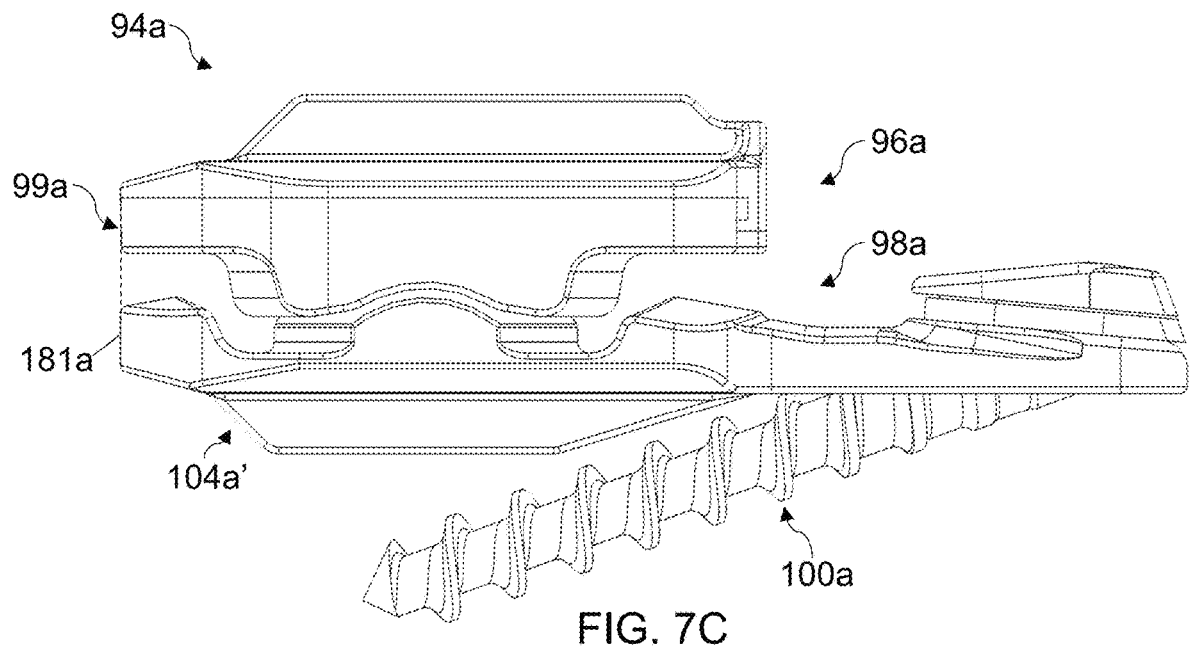
Figure 7D:
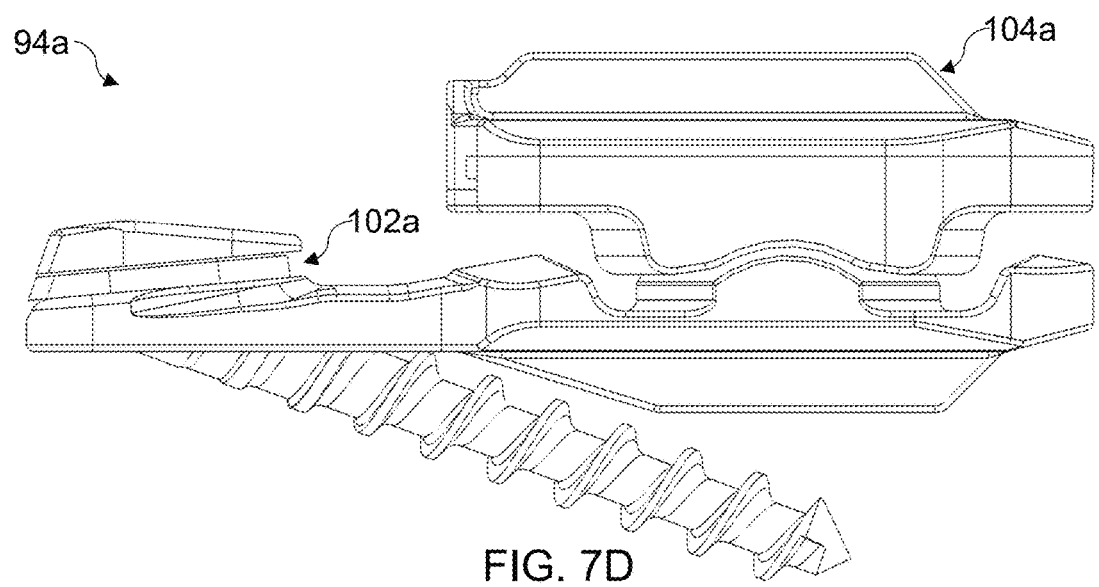
Figure 7E:
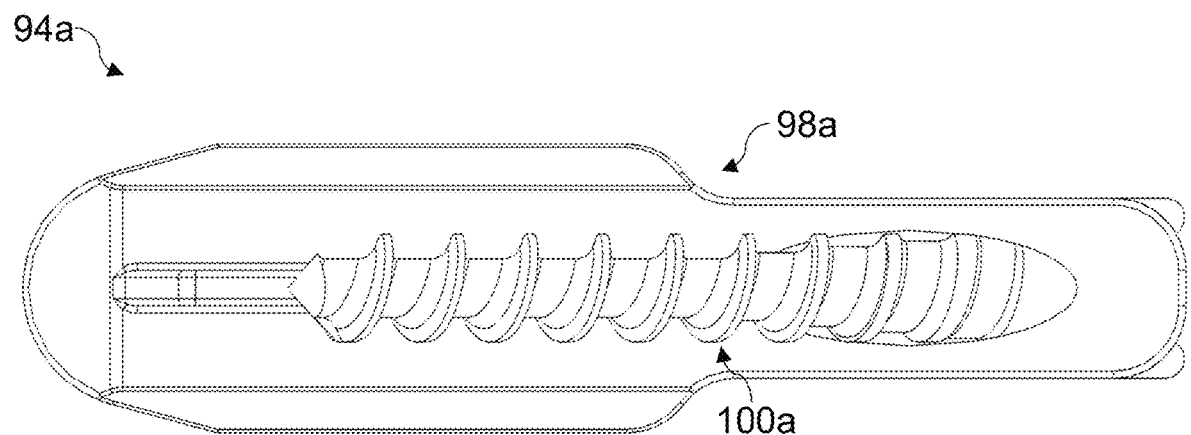
Figure 7F:
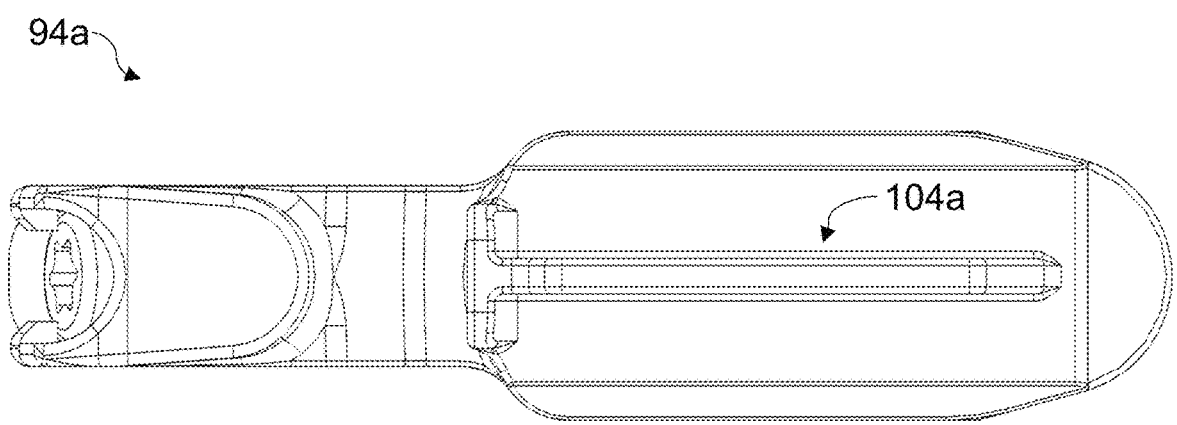
Figure 7G:
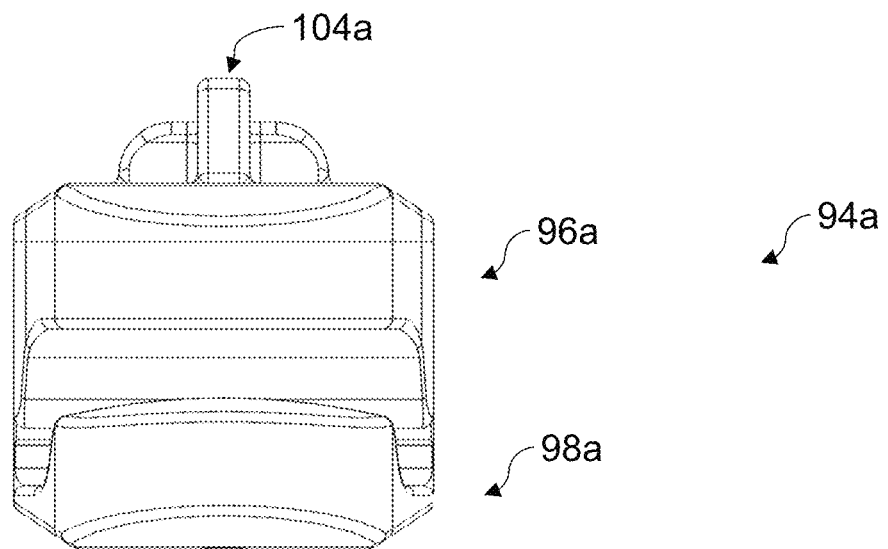
Figure 7H:
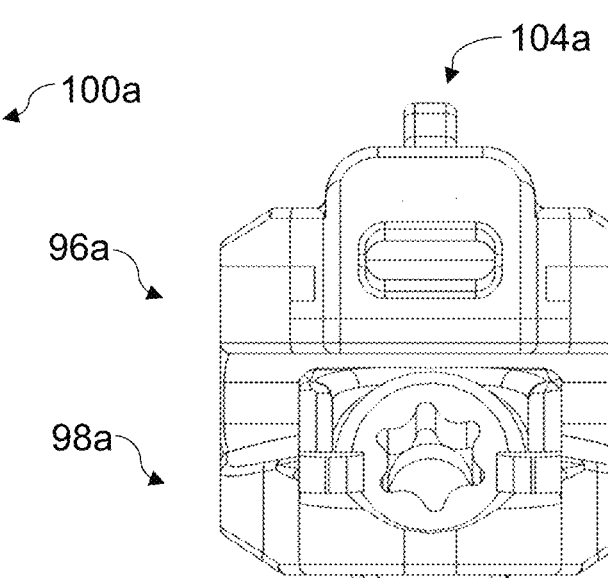
Figure 8A:
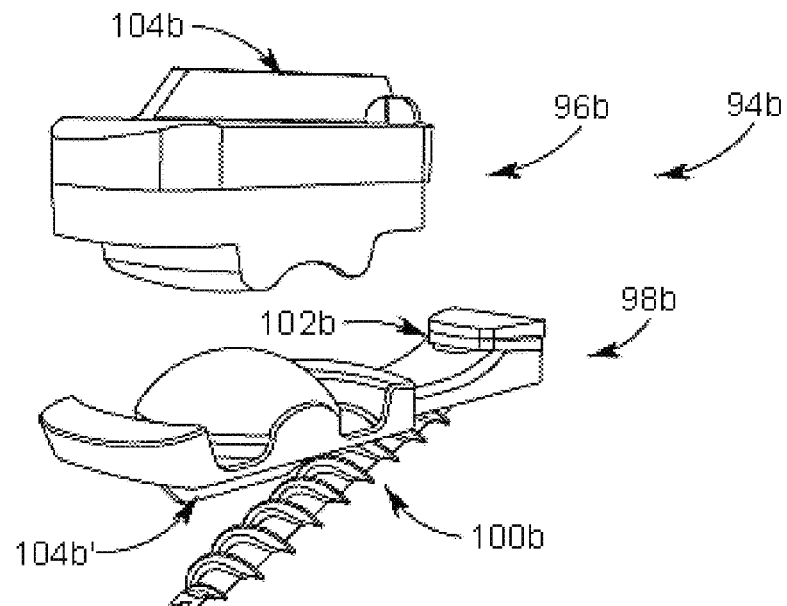
FIGS. 8A-8D depicts various plan views of an alternate embodiment of a spinal implant.
Figure 8B:
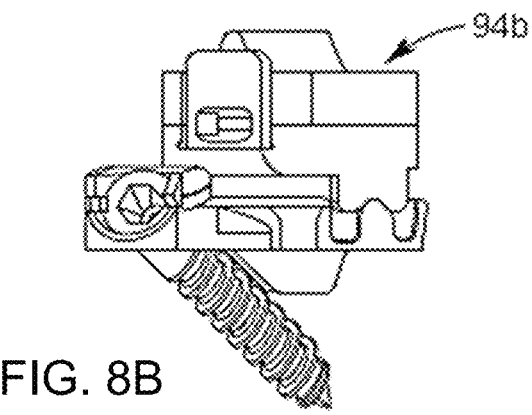
Figure 8C:
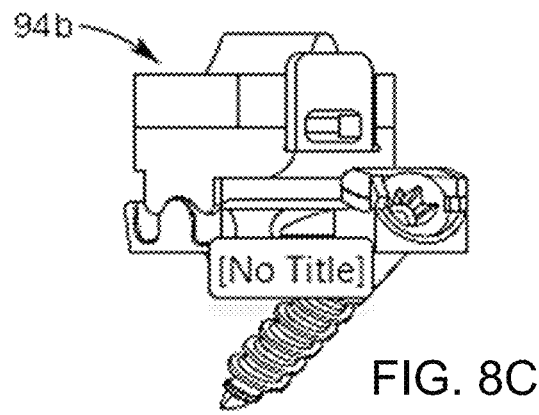
Figure 8D:
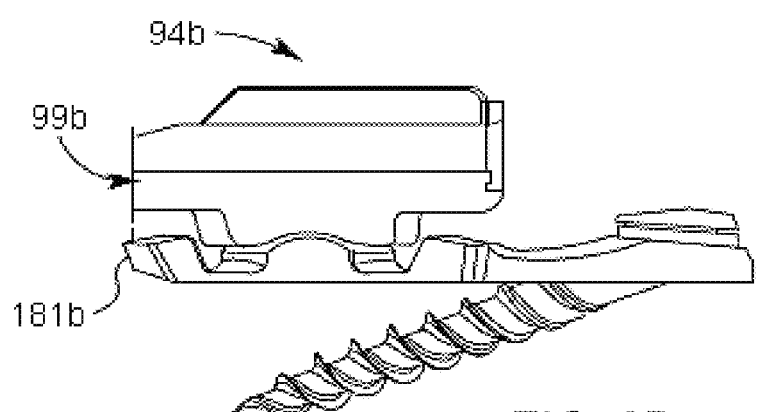
Figure 9A:
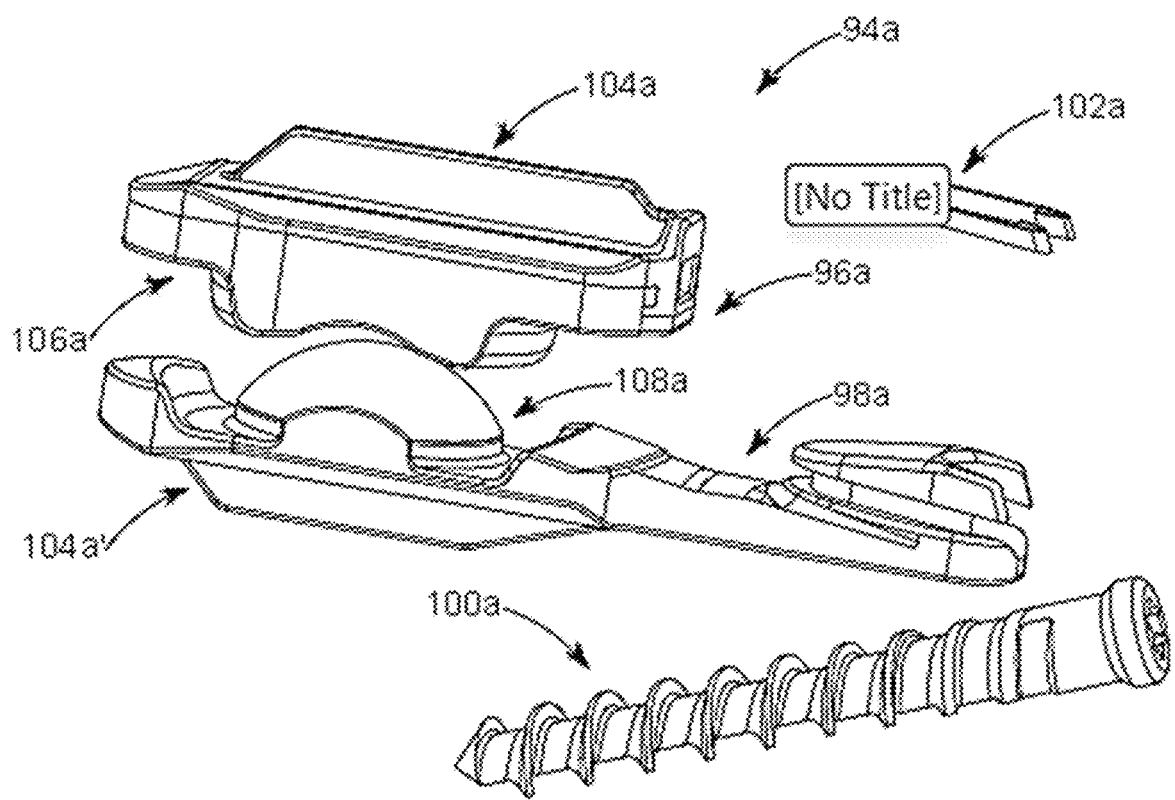
FIG. 9A depicts an exploded isometric view of one embodiment of the spinal implant of FIGS. 7A-7H.
Figure 9B:
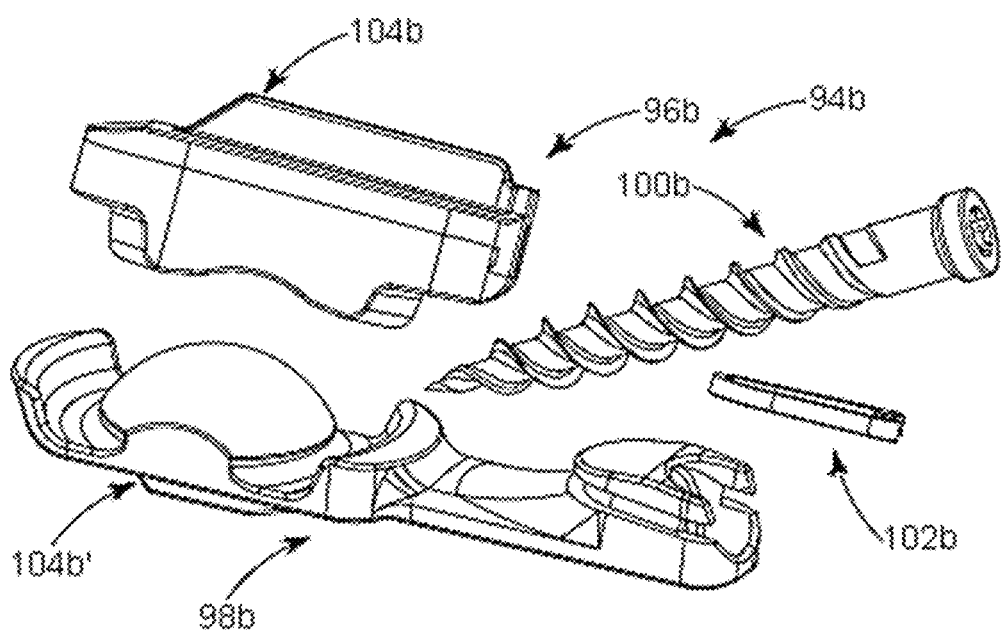
FIG. 9B depicts an exploded isometric view of the alternate embodiment of the spinal implant of FIGS. 8A-8D.

The first stop 180a, 180b of the inferior element 98a, 98b comprises a second wall 181a, 181b that faces in the anterior direction. At least a portion of the second wall 181a, 181b and at least a portion of the first contact surface 182a, 182b extends beyond at a distance from the anterior facing surface 99a, 99b of the superior element 96a, 96b as best shown in FIG. 8D. The distance on the first contact surface 182a, 182b allows additional sliding of the superior element 96a, 96b. Alternatively, the second wall 181a, 181b extends beyond the anterior facing surface 99a, 99b of the superior element 96a, 96b. In another embodiment, at least a portion of the second wall 181a, 181b of the first stop 180a, 180b is coaxial and/or aligns with the anterior facing surface 99a, 99b of the superior element 96a, 96b as best shown in FIG. 7C. The distance may comprise at least 3 mm or less.

The first stop 180a, 180b of the inferior element 98a, 98b further comprises the first contact surface 182a, 182b, the first contact surface 182a, 182b comprises a first contact surface area. The first contact surface area may comprise at least 0.002 mm² or greater. At least a portion of the first contact surface 182a, 182b contacts or engages with first top surface 158a, 158b of the superior articulation component 106a, 106b. At least a portion of the first contact surface area of the first contact surface 182a, 182b may match or substantially match the first top surface area of the first top surface 158a, 158b of the superior articulation component 106a, 106b. In another embodiment, the first surface area of the first contact surface 182a, 182b may be smaller than the articulating surface area of the first top surface 158a, 158b of the upper articulating component 106a, 106b of the superior element 96a, 96b. In another embodiment, the first surface area of the first contact surface 182a, 182b may be larger than the articulating surface area of the first top surface 158a, 158b of the upper articulating component 106a, 106b of the superior element 96a, 96b.

The second stop 178a, 178b is positioned towards the posterior end 187, and/or centrally located on the inferior element 98a, 98b between the bridge 174a, 174b and the first stop 180a, 180b. The second stop 178a, 178b comprises a second contact surface 188a, 188b and a third wall 186a, 186b as shown in FIGS. 16C, 16E-16F, 16G, and 17C-17F. The second contact surface 188a, 188b may comprise a flat or planar surface, it may comprise a slope, angle or angled surface 195a, 195b, it may comprise a curved surface, and/or any combination thereof. The curved surface may include a convex or concave shape, the curved surface comprising a radius, the curved surface extending from a medial end 191 to the lateral end 189 of the inferior element or the curved surface aligns perpendicular to the longitudinal axis of the inferior element 98a, 98b. The second contact surface angle 195a, 195b may comprise an angle of 5 degrees to 15 degrees; an angle of 7 degrees to 13 degrees; an angle of 9 degrees to 11 degrees; an angle of 10 degrees or greater; and/or an angle of 10 degrees or less. In one embodiment, the second contact surface 188a, 188b comprises an angled surface 195a, 195b and a curved surface.

The second contact surface angle 195a, 195b may comprise a same angle as the first contact surface angle 183a, 183b. The second contact surface angle 195a, 195b may comprise a different angle than the first contact surface angle 183a, 183b. In another embodiment, the first contact surface 182a, 182b and the second contact surface 188a, 188b comprises the same surface. The first contact surface 182a, 182b and the second contact surface 188a, 188b comprises a different surface. The surfaces include a flat or planar surface, an angled or sloped surface, a curved surface, and/or any combination thereof.

The first curved surface radius 193a, 193b of the first contact surface 182a, 182b comprises a same radius than the second curved surface radius of the second contact surface 188a, 188b. The first curved surface radius 193a, 193b of the first contact surface 182a, 182b comprises a same radius than the second curved surface radius of the second contact surface 188a, 188b. The radius may comprise a radius of 0.05 mm to 0.25 mm; a radius of 0.05 to 0.20 mm; a radius of 0.10 mm to 0.20 mm; and/or a radius of 0.15 mm to 0.20 mm. Alternatively, the curved surface of the first contact surface 182a, 182b and/or of the second contact surface 188a, 188b may comprise 0.15 mm or greater; it may comprise 0.20 mm or greater; it may comprise at least 0.20 mm or less and/or it may comprise at least 0.25 mm or less.

The second stop 178a, 178b of the inferior element 98a, 98b further comprises a second contact surface 188a, 188b, the second contact surface 188a, 188b comprises a second contact surface area. The second contact surface area may comprise at least 0.002 mm² or greater; may comprise at least 0.005 mm² or greater; may comprise 0.008 mm² or greater; and/or may comprise at least 0.010 mm² or greater.

At least a portion of the first contact surface 182a, 182b contacts or engages with first top surface 158a, 158b of the superior articulation component 106a, 106b. At least a portion of the second contact surface area of the second contact surface 188a, 188b may match or substantially match the second top surface area of the second top surface 158a', 158b' of the superior articulation component 106a, 106b. The second surface area of the second contact surface 188a, 188b may be smaller than the articulating surface area of the second top surface 158a', 158b' of the upper articulating component 106a, 106b of the superior element 96a, 96b. The second surface area of the second contacting surface 188a, 188b may be larger than the articulating surface area of the second top surface 158a', 158b' of the upper articulating component 106a, 106b of the superior element 96a, 96b. In one embodiment, the first contact surface area is smaller than the second contact surface area. In another embodiment, the second contact surface area is larger than the first contact surface area. Accordingly, the first contact surface area is equal to the second contact surface area.

The third wall 186a, 186b extends perpendicular or substantially perpendicular from the second contact surface 188a, 188b. Alternatively, the third wall 186a, 186b may extend at a wall orientation angle from the second contact surface 188a, 188b. The third wall 186a, 186b may comprise a flat or planar surface and/or a curved surface, the curved surface may comprise a concave shape. The third wall 186a, 186b may be curved or arched in a convex shape. The third wall curved surface comprises a third wall curved surface radius. The third wall 186a, 186b may comprise an anterior facing wall. A total range of motion (ROM) angle 179a, 179b, 179a', 179b' extends from a third wall 186a, 186b to the first wall 184a, 184b.

In another embodiment, the inferior component 98a, 98b may comprise a total ROM angle 179a, 179b, 179a', 179b'. The total ROM angle may comprise at least 25 degrees or greater; may comprise an angle of at least 30 degrees or greater; may comprise an angle of at least 35 degrees or greater; may comprise a range of 34 to 38 degrees. In another embodiment, the first wall 184a, 184b may comprise an first wall orientation angle 179a, 179b, and the third wall 186a, 186b may comprise a third wall orientation angle 179a', 179b'. The first wall orientation angle 179a, 179b and/or the third wall orientation angle 179a', 179b' may comprise an angle of at least 10 degrees or greater; may comprise an angle of at least 15 degrees or greater; may comprise an angle of at least 18 degrees or greater; and/or may comprise a range of 16 degrees to 20 degrees.

The first wall orientation angle 179a, 179b may comprise the same orientation angle as the third wall orientation angle 179a', 179b'. The first wall orientation angle 179a, 179b may comprise a different orientation angle as the third wall orientation angle 179a', 179b'. The first wall curved surface radius of the first stop 180a, 180b comprise a same radius than the third wall curved surface radius. The first wall curved surface radius of the first stop 180a, 180b comprise a different radius than the third wall curved surface radius. The first contact surface radius 193a, 193b of the first contact surface 182a, 182b comprises a same radius of the second contact surface radius of the second contact surface 188a, 188b. The first contact surface radius 193a, 193b of the first contact surface 182a, 182b comprises a same radius of the second contact surface radius of the second contact surface 188a, 188b.

In another embodiment, the first wall 184a, 184b may comprise the same or substantially the same orientation angle 179a, 179b than the anterior facing wall 164a, 164b of the upper articulating component 106a, 106b of the superior element 96a, 96b. Alternatively, the first wall 184a, 184b may comprise a different or substantially different orientation angle 179a, 179b than the anterior facing wall 164a, 164b of the upper articulating component 106a, 106b of the superior element 96a, 96b.

In another embodiment, the third wall 186a, 186b may comprise the same or substantially the same orientation angle 179a', 179b' of the posterior facing wall 164a', 164b' of the upper articulating component 106a, 106b of the superior element 96a, 96b. The third wall 186a, 186b may match or substantially match the orientation angle 179a', 179b' of the posterior facing wall 164a', 164b' of the upper articulating component 106a, 106b of the superior element 96a, 96b. Alternatively, the third wall 186a, 186b may comprise a different or substantially different orientation angle 179a', 179b' than the posterior facing wall 164a', 164b' of the upper articulating component 106a, 106b of the superior element 96a, 96b.

Accordingly, movement or translational motion of the upper component or element 96a, 96b relative to the lower component or element 98a, 96b is desirably controlled or regulated, at least in part, by the action of the first stop 180a, 180b and the second stop 178a, 178b. At least a portion of the first contact surface 182a, 182b contacts or engages with a portion of the first top surface 158a, 158b of the articulating component 106a, 106b of the superior element 96a, 96b during flexion to create a positive stop for movement. Furthermore, at least a portion of the first wall 184a, 184b also engages or contacts with at least a portion of the anterior facing wall 164a, 164b of the articulating component 106a, 106b of the superior element 96a, 96b during flexion to create a positive stop for movement.

In another embodiment, at least a portion of the second contact surface 188a, 188b contacts or engages with a portion of the second top surface 158a', 158b' of the articulating component 106a, 106b of the superior element 96a, 96b during extension to create a positive stop for movement. Furthermore, at least a portion of the third wall 186a, 186b also engages or contacts with at least a portion of the posterior facing wall 164a', 164b' of the articulating component 106a, 106b of the superior element 96a, 96b during extension to create a positive stop for movement.

The flexion and extension between the superior element 96a, 96b and the inferior element 98a, 98b will desirably comprise at least 10 degrees or greater of flexion and at least 10 degrees or greater of extension along the surfaces 182a, 182b, 188a, 188b of the first stop 180a, 180b and the second stop 178a, 178b and the walls 184a, 184b, 186a, 186b of the first stop 180a, 180b and the second stop 178a, 178b come into respective contact and serve as a positive stop. The flexion and extension between the superior element 96a, 96b and the inferior element 98a, 98b will desirably comprise at 10 degrees or greater of flexion and 10 degrees or greater of extension along the surfaces 182a, 182b, 188a, 188b of the first stop 180a, 180b and the second stop 178a, 178b and the walls 184a, 184b, 186a, 186b of the first stop 180a, 180b and the second stop 178a, 178b come into respective contact and serve as a positive stop. The flexion and extension between the superior element 96a, 96b and the inferior element 98a, 98b will desirably comprise at least 10 to 55 degrees of flexion and at least 10 to 30 degrees of extension along the surfaces 182a, 182b, 188a, 188b of the first stop 180a, 180b and the second stop 178a, 178b and the walls 184*a*, 184*b*, 186*a*, 186*b* of the first stop 180*a*, 180*b* and the second stop 178*a*, 178*b* come into respective contact and serve as a positive stop.

In another embodiment, the inferior base 216*a*, 216*b* comprises a keel and/or a lower keel 104*a*', 104*b*'. The lower keel 104*a*', 104*b*' includes a height 224*a*, 224*b* and a length 226*a*, 226*b*. At least a portion of the lower keel 104*a*', 104*b*' extends downwardly from the inferior base 216*a*, 216*b* and/or extends downwardly from a bottom surface 218*a*, 218*b* of the inferior base 216*a*, 216*b*. At least a portion of the lower keel 104*a*', 104*b*' may extend orthogonally or perpendicular to the inferior base 216*a*, 216*b* and/or may extend orthogonal or perpendicular to a bottom surface 218*a*, 218*b* of the inferior base 216*a*, 216*b*. At least a portion of the bottom surface 218*a*, 218*b* is flat or planar and/or curved.

The length 226*a*, 226*b* of the lower keel 104*a*', 104*b*' extends from the posterior end or second end 187 of the base or inferior base 216*a*, 216*b* towards the first end or anterior end 185 of the base 216*a*, 216*b*. The length 226*a*, 226*b* of the lower keel 104*b* extends from the posterior end or second end 187 of the base 216*a*, 216*b* towards the first end or anterior end 185 and extends downwardly away from the inferior base 216*a*, 216*b* and/or the top surface 218 of the inferior base 216*a*, 216*b*. Alternately, the length 226*a*, 226*b* of the lower keel 104*a*', 104*b*' extends from the second stop 178*a*, 178*b* towards the first stop 180*a*, 180*b*. The length 226*a*, 226*b* of the lower keel 104*a*, 104*b* extends substantially between or extends between the second stop 178*a*, 178*b* and the first stop 180*a*, 180*b*. The length 226*a*, 226*b* of the lower keel 104*a*', 104*b*' may match or substantially match a length of the inferior base 216*a*, 216*b* and/or the lower keel 104*a*', 104*b*' may match or substantially match the length of a bottom surface 218*a*, 218*b* of the inferior base 216*a*, 216*b*. At least one or more surfaces of the lower keel 104*a*', 104*b*' contacts the vertebra bone and/or at least one or more surfaces of the lower keel 104*a*', 104*b*' contacts the cancellous bone of the vertebra and/or the cortical bone of the lower vertebra.

The lower keel 104*a*', 104*b*' comprises a shape. The shape includes a shape substantially similar to a trapezoid, trapezium, rhombus, parallelogram and/or a sloped rectangle. The first end or anterior end 185 of the lower keel 104*a*', 104*b*' is sloped or at an angle to facilitate easier positioning and/or atraumatic insertion. The second end or posterior end 187 of the lower keel 104*a*', 104*b*' is sloped and/or at an angle to accommodate the placement of the fixation screw 100*a*, 100*b*. The angle of the second end of the lower keel 104*a*', 104*b*' may match or substantially match the transverse pedicle angles 82 and/or the bore axis 210*a*, 210*b*. The angle of the second end of the lower keel 104*a*', 104*b*' may be parallel or substantially parallel to the transverse pedicle angles 82 and/or the bore axis 210*a*, 210*b*. The length 226*a*, 226*b* of the lower keel 104*a*', 104*b*' may comprise a shorter or smaller length than the length 118*a*, 118*b* of the upper keel 104*a*, 104*b* of the superior base 110*a*, 110*b*.

In another embodiment, the inferior or lower element 98*a*, 98*b* and/or the inferior base 216*a*, 216*b* further comprises an inferior articulating component 108*a*, 108*b* as shown in FIGS. 8A-8D, 9A-9B, 16A-16H, 17A-17F, and 18A-18C. The inferior articulating component 108*a*, 108*b* can also be referred to as a ball or ball component or element. The ball component 108*a*, 108*b* comprises a radius or diameter and an lower articulation surface 228*a*, 228*b*. The diameter may include a diameter of; 10 mm or greater; 15 mm or greater; 20 mm or greater; and/or a range of; 10 mm to 20 mm; or 10 mm to 15 mm; or 15 mm to 20 mm; or 15 to 17 mm.

The ball or inferior articulating component 108*a*, 108*b* may comprise a uniform or non-uniform shape. The inferior articulating component and/or ball 108*a*, 108*b* comprises a uniform shape, the uniform shape includes a hemisphere or half sphere or dome shape. The non-uniform shape may include a truncated hemisphere, truncated half-sphere or truncated dome shape. The truncation is a portion of the ball 108*a*, 108*b* that is cut off by at least one plane or wall 230*a*, 230*b*, 230*a*', 230*b*'. The at least one plane or wall 230*a*, 230*b*, 230*a*', 230*b*' includes the left and right planes, wall or sides, the lateral or medial planes, wall or sides, and/or the sagittal planes, wall or sides. The truncation of the ball 108*a*, 108*b* helps limit the multi-axial movement of the superior element 96*a*, 96*b* relative to the inferior element 98*a*, 98*b*. More specifically, the truncation of the ball 108*a*, 108*b* helps limit the multi-axial movement or motion comprising axial rotation of the superior element 96 relative to the inferior element 98*a*, 98*b*. Axial rotation comprises an angle of rotation, the angle of rotation includes at least 1 degree or greater; at least 2 degrees or greater; at least 3 degrees or greater. In another embodiment, the angle of rotation includes 1 to 5 degrees; the angle of rotation includes 1 to 60 degrees; the angle of rotation includes 1 to 40 degrees; the angle of rotation includes 1 to 35 degrees; and/or any combination thereof. Accordingly, the ball or ball component or element 108*a*, 108*b* comprises a width 222*a*, 222*b*. The width 222*a*, 222*b* includes 8 mm or greater; 10 mm or greater; 12 mm or greater; and/or 15 mm or greater. The width may further include a range of 8 mm to 15 mm; 8 mm to 12 mm; 8 mm to 10 mm; and/or 10 mm to 15 mm; and/or 12 mm to 15 mm.

The inferior articulating component or ball 108*a*, 108*b* extends upwardly from the inferior base 216*a*, 216*b*. The inferior articulating component or ball 108*a*, 108*b* extends upwardly toward the superior direction. The inferior articulating component or ball 108*a*, 108*b* may be disposed onto the inferior base 216*a*, 216*b*. The inferior articulating component or ball 108*a*, 108*b* may be disposed onto a top surface 196*a*, 196*b*, 198*a*, 198*b* the inferior base 216*a*, 216*b*. The inferior articulating component or ball 108*a*, 108*b* extends normal to a plane of the inferior base 216*a*, 216*b* or extends perpendicular to the plane the base 216*a*, 216*b*.

The inferior articulating component or ball 108*a*, 108*b* is sized and configured to be disposed or engage with the socket 119*a*, 199*b* of the upper articulating component 106*a*, 106*b* of the superior element 96*a*, 96*b* to further allow movement or motion of the superior element 96 relative to the inferior element 98*a*, 98*b*. Accordingly, inferior articulating surface 228*a*, 228*b* of the inferior articulating component or ball 108*a*, 108*b* of the lower component 98*a*, 98*b* is sized and configured to be disposed or engage with superior articulating surface 168*a*, 168*b* of the socket 119*a*, 119*b* of the upper articulating component 106*a*, 106*b* of the superior element 96*a*, 96*b* to further allow movement or motion of the superior element 96 relative to the inferior element 98*a*, 98*b*. The motion may comprise flexion, extension, axial rotation, lateral flexion, contralateral flexion and/or any combination thereof.

The inferior articulating component or ball 108*a*, 108*b* is positioned between the first stop 180*a*, 180*b* and the second stop 178*a*, 178*b*. The inferior articulating component 108*a*, 108*b* is spaced apart from the first stop 180*a*, 180*b* and is spaced apart from the second stop 178 creating a plurality of gutters or channels 234*a*, 234*b*, 234*a*', 234*b*'. The plurality of gutters or channels 234*a*, 234*b*, 234*a*', 234*b*' are sized and configured to receive a portion of the plurality of walls 164*a*, 164*a*', 164*b*, 164*b*' to allow motion and/or limit motion of the superior element 96a, 96b relative to the inferior element 98a, 98b. Alternatively, the first top 180a, 180b and the second stop 178a, 178b are separated by the inferior articulating component or ball 108a, 108b.

The inferior articulating component 108a, 108b may be coupled to the inferior base 216a, 216b as a multi-piece implant or multi-piece assembly. Coupling may include adhesives, screws, quick release mechanisms, compression or friction coupling, ultrasonic welding, insert molding, compression molding and/or over molding. Alternatively, the inferior articulating component 108a, 108b may be fixed to the base 216a, 216b as a one-piece or single-piece component. Once the inferior articulating component 108a, 108b is coupled to the base 216a, 216b of the inferior element 98a, 98b, the perimeter edges or surfaces 167a, 167a', 167b, 167b' of the articulating component 106a, 106b should be flush with the perimeter edges and/or surfaces or truncated surfaces or surfaces 230a, 230a', 230b, 230b' of the base or inferior base 216a, 216b. Alternatively, the perimeter edges or surfaces 167a, 167a', 167b, 167b' of the articulating component 106a, 106b should not be flush with the perimeter edges and/or truncated surfaces or surfaces 230a, 230a', 230b, 230b' of the base or inferior base 216a, 216b.

With reference to FIGS. 16A-16F and 17A-17F, the inferior or lower element 98a, 98b comprises a bridge 174a, 174b. The bridge 174a, 174b comprises a bottom surface 204a, 204b, a top surface 206a, 206b, a bridge length 212a, 212b, and a bridge width 214a, 214b. The bottom surface 204a, 204b is flat or planar. At least a portion the bottom surface 204a, 204b of the bridge 174a, 174b contacts and/or is configured to contact the pedicle, the cancellous bone and/or the cortical bone, and/or any combination thereof. The top surface 206a, 206b of the bridge 174a, 174b comprises a plurality of faceted top surfaces. The plurality of faceted surfaces helps accommodate bone surfaces and/or other tissue. The top surface 206a, 206b comprises a concave shape to help accommodate bone surfaces and/or other tissue. The bottom surface 204a, 204b of the bridge 174a, 174b is co-planar with at least a portion of the bottom surface 218a, 218b of the base 216a, 216b. The bottom surface 204a, 204b of the bridge 174a, 174b is co-planar with the bottom surface 218a, 218b of the base 216a, 216b.

The bridge 174a, 174b helps eliminate or decrease implant subsidence and provides further support in the "posterior" column of the spine as shown in FIG. 6A-6B. At least a portion of the bridge 174a, 174b and/or the bottom surface 204a, 204b of the bridge 174a, 174b may contact and/or is configured to contact the cancellous bone (e.g., the spongy, porous bone), the cortical bone and/or the endplate. The bridge 174a, 174b and/or the bottom surface 204a, 204b of the bridge 174a, 174b is uniquely designed to help reduce or eliminate subsidence and provide additional support on the pedicle and/or below the pedicle surface due its material strength and a total surface area that contacts the cancellous or cortical bone.

The bottom surface 204a, 204b of the bridge 174a, 174b comprises a bridge surface area. This bridge bottom surface area, which the bridge surface area helps distribute the pressures exhibited by the movement of the superior element 96a, 96b relative to the inferior element 98a, 98b and helps keep the implant from "sinking" or subsiding. The bridge 174a, 174b and its bridge surface area provides further support in the "posterior" column of the spine.

The bridge 174a, 174b further comprises a bridge length 212a, 212b. The bridge length 212a, 212b may comprise at least 15 mm or greater, 20 mm or greater, and/or at least 25 mm or greater. The bridge length 212a, 212b may match or substantially match a pedicle length 73 at one segment level within one or both sides (right and left sides). The bridge length 212a, 212b may match or substantially match the pedicle length 73 at a plurality of segment levels. Alternatively, the bridge length 212a, 212b may the same at each segment level or different segment levels. Each of the bridge lengths 212a, 212b at each of the different segment levels may comprise the same bridge length 212a, 212b or it may be different.

The bridge 174a, 174b may further comprise a bridge width 214a, 214b. The bridge width 214a, 214b may comprise at least 5 mm or greater; at least 7 mm or greater; at least 10 mm or greater; and/or at least 10 mm or less. The bridge width 214a, 214b may match or substantially match the pedicle width 72 as referred to in FIG. 5B at one or a single segment level at one or both sides (right and left sides). Alternatively, the bridge width 214a, 214b may match or substantially match the pedicle width 72 at each different segment levels at one or both sides (right and left sides). Each of the bridge widths 214a, 214b at each of the different segment levels may comprise the same bridge width 214a, 214b and/or a different bridge width 214a, 214b.

In another embodiment, the inferior element 98a, 98b and/or the bridge 174a, 174b comprises a third stop 176a, 176b. The third stop 176a, 176b may also be referred to as a fixation housing. The third stop 176a, 176b comprises a plurality of top surfaces 190a, 190b, 192a, 192b, 194a, 194b. The plurality of top surfaces 190a, 190b, 192a, 192b, 194a, 194b may comprise a flat or planar surface and/or include an angled surface. Accordingly, the plurality of top surfaces 190a, 190b, 192a, 192b, 194a, 194b may comprise curved or arched in a convex shaped surface. The plurality of top surfaces 190a, 190b, 192a, 192b, 194a, 194b may be comprise a curved or convex shape and an angled orientation or an angle. Furthermore, each of the plurality of top surfaces 190a, 190b, 192a, 192b, 194a, 194b may comprise the same surface type and/or a different surface type. The surface type may include flat or planar, curved, angle and/or any combination thereof.

In another embodiment, the third stop 176a, 176b comprises a first surface 194a, 194b, a second surface 192a, 192b, and a third surface 190a, 190b. Alternatively, the third stop 176a, 176b comprises a first surface 194a, 194b and a second surface 192a, 192b. Each of the first surface first surface 194a, 194b, a second surface 192a, 192b and/or a third surface 190a, 190b comprises a same surface. Each of the first surface first surface 194a, 194b, a second surface 192a, 192b and/or a third surface 190a, 190b comprises a different surface. Alternatively, each of the first surface first surface 194a, 194b and/or a second surface 192a, 192b comprises a same surface. Each of the first surface first surface 194a, 194b and/or a second surface 192a, 192b comprises a different surface. The surfaces may include flat or planar, curved, angle and/or any combination thereof.

The angled or slope surface comprises an angle or slope and/or an angled orientation. The third stop angle or angled orientation may comprise a range of 1 degree to 20 degrees; a range of 1 degree to 10 degrees; a range of 1 to 5 degrees; a range of 5 degrees to 10 degrees; a range of 8-10 degrees; a range of 10 degrees to 15 degrees; and/or a range of 15 degrees to 20 degrees. Angled surfaces help facilitate deployment between the vertebrae.

The third stop 176a, 176b is spaced apart from the bridge 174a, 174b to form a recessed retention clip channel or recessed clip channel 202a, 202b. The third stop 176a, 176b is spaced apart from the top surface 206a, 206b of the bridge 174a, 174b to form a recessed retention clip channel or recessed clip channel 202a, 202b. Alternatively, the retention clip channel 202a, 202b is disposed between at least a portion of the bridge 174a, 174b and the third stop 176a, 176b. The retention clip channel 202a, 202b is disposed between the posterior end of the bridge 174a, 174b and the third stop 176a, 176b. The retention clip channel 202a, 202b is disposed between the posterior end of the top surface 206a, 206b of the bridge 174a, 174b and the third stop 176a, 176b.

The retention clip channel 202a, 202b is sized and configured to receive a retention clip 102a, 102b. The retention clip 102a, 102b is inserted into and/or disposed into the retention clip channel 202a, 202b until an audible sound is created or a "click" to ensure that the retention clip 102a, 102b is secured over the fixation screw 100a, 100b. At least one surface on the retention clip is flush or substantially flush to the third stop 176a, 176b.

In another embodiment, the bridge 174a, 174b further comprises a first end and a second end. The third stop 176a, 176b is positioned adjacent to the second end of the bridge 174a, 174b, and/or the third stop 176a, 176b is positioned adjacent to the second end 187 of the inferior component 98a, 98b. The first end of the bridge 174a, 174b is coupled to the inferior base 216a, 216b and/or coupled to the posterior facing end of the inferior base 216a, 216b.

The third stop 176a, 176b further comprising a shape, the shape includes an oval, an ellipse, a rectangle and/or a rounded rectangle. The shape may be uniform or non-uniform. At least one end of the third stop 176a, 176b is tapered. At least a portion of the third stop 176a, 176b. The taper angle is approximately a range from 8 degrees to 10 degrees and/or at least 8 degrees or greater. In another embodiment, the third stop 176a, 176b also is positioned at an angle or tilted at an angle. The third stop 176a, 176b angle is a range of 5 degrees to 10 degrees; a range of 5 degrees to 8 degrees; the third stop 176a, 176b angle is at least 5 degrees or greater.

At least a portion of the bridge 174a, 174b and/or the third stop 176a, 176b further comprises a bore 172a, 172b and a bore axis 210a, 210b. At least a portion of the bore 172a, 172b may further comprise a threaded bore. Alternatively, the bore 172a, 172b may comprise a first portion 208a, 208b and a second portion 208a', 208b'. The first portion 208a, 208b of the bore 172a, 172b may match or substantially match the head of a fixation screw 100a, 100b. The second portion 208a', 208b' of the bore 172a, 172b may match or substantially match the shaft and/or threads of the fixation screw 100a, 100b. The second portion 208a', 208b' of the bore 172a, 172b may comprise threads. In another embodiment, the first portion 208a, 208b comprises a first diameter and the second portion 208a', 208b' comprises a second diameter. The first diameter is larger than the first diameter.

The bore 172a, 172b and/or the bore axis 210a, 210b may be positioned at an angle and/or at an oblique angle. The angle may comprise at least 20 degrees from the opening central axis 210 or greater. The angle may be within a range of 15 degrees to 25 degrees; within a range of 15 degrees to 20 degrees; within a range of 20 degrees to 25 degrees. In another embodiment, the angle of the bore 172a, 172b and/or the bore axis 210a, 210b may match or substantially match the sagittal pedicle angle 82 as referred to in FIG. 5D at one segment level. Alternatively, the angle of the bore 172a, 172b and/or the bore axis 210a, 210b may match or substantially match the sagittal pedicle angle 82 at a plurality of segment levels. Accordingly, the angle of the bore 172a, 172b and/or the bore axis 210a, 210b may be different at a plurality of spine segment levels.

In another embodiment, the inferior element 98a, 98b, the inferior base 216a, 216b, the inferior or lower articulating component 108a, 108b and/or the bridge 174a, 174b further comprises one or more materials. The materials may include metal, polymers and/or ceramics. The metals may comprise titanium, titanium alloys, cobalt-chrome alloys, platinum, stainless steel and/or any combination thereof. More specifically, the metal may include titanium and/or cobalt-chrome molybdenum (CoCrMo). The polymers may include thermoplastic or thermoset polymers. The polymers may further include carbon fiber, polyether ether ketone (PEEK), polyethylene (PE), ultra-high molecular weight polyethylene (UHMWPE), polycarbonate (PC), polypropylene (PP) and/or any combination thereof. The ceramics may include alumina ceramics, Zirconia (ZrO2) ceramics, Calcium phosphate or hydroxyapatite (Ca10(PO46(OH)2) ceramics, titanium dioxide (TiO2), silica (SiO2), Zinc Oxide (ZnO) and/or any combination thereof. The materials may be manufactured using traditional methods and/or using 3D printed techniques known in the art. Furthermore, the material may comprise a porous material, the porous material includes porous metal, porous polymer, porous ceramic and/or any combination thereof.

In another embodiment, the material may be further antioxidant stabilized. The stabilized antioxidants may comprise Vitamin E or Vitamin C. The antioxidants may be incorporated, diffused or doped into the material by blending the antioxidant into the material for subsequent cross-linking and/or diffusing the antioxidant into the material. The material may be further cross-linked before or after stabilizing with an antioxidant.

In one embodiment, each of the materials for each of the inferior element 98a, 98b, the inferior base 216a, 216b, the bridge 174a, 174b, and/or inferior or lower articulating component 108a, 108b comprises a different material. Accordingly, each of the materials for each of the inferior element 98a, 98b, the inferior base 216a, 216b, the bridge 174a, 174b and/or the inferior or lower articulating component 108a, 108b comprises the same material.

In another embodiment, the bridge 174a, 174b and the inferior base 216a, 216b may comprise the same material or the material may be different. The bridge 174a, 174b and the inferior articulating component 108a, 108b may comprise the same material or the material may be different. The inferior base 216a, 216b and the inferior articulating component 108a, 108b may comprise the same material or the material may be different. The bridge 174a, 174b and the inferior base 216a, 216b may comprise the same material, but the inferior articulating component 108a, 108b comprises a different material than the bridge 174a, 174b and the inferior base 216a, 216b.

In another embodiment, at least one surface of the inferior element 98a, 98b, the inferior base 216a, 216b, the bridge 174a, 174b, the first stop 180a, 180b, the second stop 178a, 178b, the third stop 176a, 176b and/or the inferior or lower articulating component 108a, 108b comprises a coating (not shown) and/or surface texture (not shown) to help facilitate healing, osseointegration, loading forces and/or wear. Alternatively, at least two or more surfaces of the inferior element 98a, 98b, the inferior base 216a, 216b, the bridge 174a, 174b, second stop 178a, 178b, the third stop 176a, 176b and/or the inferior or lower articulating component 108a, 108b comprises a coating and/or surface texture.

In another embodiment, at least a portion of the inferior articulating surface 228a, 228b or the inferior articulating component 108a, 108b comprises a coating and/or surface texture. At least a portion of the bridge 174a, 174b, the bridge top surfaces 206a, 206b, and/or the bridge bottom surface 204a, 204b may comprise a coating and/or surface texture. Accordingly, the coating and/or surface texture disposed onto at least one of the surfaces the inferior element 98a, 98b, the inferior base 216a, 216b, the bridge 174a, 174b and the inferior or lower articulating component 108a, 108b may comprise the same coating and/or surface texture and/or comprise a different coating and/or surface texture.

The surface textures or finishes may comprise threads, flutes, grooves, and/or teeth that may include various shapes. The various shapes may include tapered, stepped, conical and/or paralleled, flat, pointed, and/or rounded. The surface textures or finishes may further comprise roughened surfaces or porous surfaces, including turned, blasting, sand blasting, acid etching, chemical etching, dual acid etched, plasma sprayed, anodized surfaces, and/or any combination thereof. The surface textures or finishes may further include a polish surface finish or texture. The polished surface may be accomplished via different techniques, mechanical polishing, chemical polishing, electrolytic polishing, and/or any combination thereof. Polished surfaces can be measured in "Ra" micrometers (µm) or microinches (µin.).

The "Ra" may comprise a range of 0.025 to 1.60 µm; may comprise a range of 0.025 to 0.30 µm; may comprise a range of 0.025 to 0.20 µm; may comprise a range of 0.025 to 0.10 µm; and/or may comprise a range of 0.05 to 0.20 µm. Accordingly, the Ra may comprise at least 0.05 µm or higher; at least 0.10 µm or higher and/or at least 0.8 µm or higher. Surface structure is often closely related to the friction and wear properties of a surface. A surface with a large Ra value will usually have somewhat higher friction and wear quickly, and a surface with a lower Ra value will have a lower friction and enhanced part performance and/or prevent or reduce unwanted adhesion of molecules or components to surface(s) (e.g., surfaces are smooth, shiny and less porous). Furthermore, a polished surface has many advantages, including improving cleanability, increases resistance to corrosion, reduces adhesive properties (for cells or other blood components to attach to), increases biocompatibility, increased light reflection for enhanced radiopacity, etc.

In one embodiment, the bridge 174a, 174b and the inferior base 216a, 216b comprise the same surface finish or texture, and the inferior articulating component 108a, 108b comprises a different surface finish or texture. The different surface texture or finish comprises a polished surface and the same surface texture or finish comprises a roughened surface texture. In another embodiment, the inferior base 216a, 216b comprises a first surface texture of finish, the bridge 174a, 174b comprises a second surface texture or finish, and the inferior articulating component 108a, 108b comprises a third surface texture or finish. The first surface texture and the second surface texture comprise the same surface texture. The third surface texture is different than the first and second surface texture.

In another embodiment, the top surfaces 206a, 206b of the bridge 174a, 174b comprise a first top surface texture and the bottom surface 204a, 204b of the bridge 174a, 174b comprises a first bottom surface texture. The bottom surface 218a, 218b of the inferior base 216a, 216b comprise a second bottom surface texture and the top surface 196a, 196b, 198a, 198b of the inferior base 216a, 216b comprise a second top surface texture. The first bottom surface texture is the same as the second bottom surface texture. The first top surface texture is the same as the second top surface texture. The first and second bottom surface texture is different than the first and second top surface texture. The first and second bottom surface texture comprises a roughened surface texture. The first and second top surface texture comprises a polish texture finish. The polish texture finish comprises at least an Ra of 0.8 µm or higher.

In another embodiment, at least a portion of the first contact surface 182a, 182b of the first stop 180a, 180b comprises a first surface texture, at least a portion of the second contact surface 188a, 188b of the second stop 178a, 178b comprises a second surface texture, and/or at least a portion of the inferior articulating component 108a, 108b comprises a third surface texture. The first and second surface texture may comprise the same surface texture or finish. The third surface texture or finish is different than the first and second surface texture or finish. The first surface texture or finish and the second texture or finish comprise polished surface finish. The third surface texture of finish comprises a polished surface finish. The polished surface finish of the third surface texture finish is higher or better than the polished surface finish of the first and second surface texture. Alternatively, the polished surface finish of the third surface texture finish is lower than the polished surface finish of the first and second surface texture. The polished surface finish of the third surface texture or finish comprises at least an Ra of 0.05 µm or higher. The polished surface finish of the first and second surface texture or finish comprises at least an Ra of 0.10 µm or higher.

The coatings may include inorganic coatings or organic coatings. The coatings may further include a metal coating, a polymer coating, a composite coating (ceramic-ceramic, polymer-ceramic, metal-ceramic, metal-metal, polymer-metal, etc.), a ceramic coating, an anti-microbial coating, a growth factor coating, a protein coating, a peptide coating, an anti-coagulant coating, an antioxidant coating and/or any combination thereof. The antioxidant coatings may comprise naturally occurring or synthetic compounds. The natural occurring compounds comprises Vitamin E and Vitamin C (tocotrienols and tocopherols, in general), phenolic compounds and carotenoids. Synthetic antioxidant compounds include α-lipoic acid, N-acetyl cysteine, melatonin, gallic acid, captopril, taurine, catechin, and quercetin, and/or any combination thereof. The coatings can be impregnated, applied and/or deposited using a variety of coating techniques. These techniques include sintered coating, electrophoretic coating, electrochemical, plasma spray, laser deposition, flame spray, biomimetic deposition and wet methods such as sol-gel-based spin- and -dip or spray-coating deposition have been used most often for coating implants.

The metal coatings may comprise titanium, titanium alloys, cobalt-chrome alloys, platinum and stainless steel, and/or any combination thereof. More specifically, the metal coating includes titanium and/or cobalt-chrome molybdenum (CoCrMo). The polymer coatings may include thermoplastic or thermoset polymers. The polymers may further include carbon fiber, polyether ether ketone (PEEK), polyethylene (PE), ultra-high molecular weight polyethylene (UHMWPE), polycarbonate (PC), polypropylene (PP) and/or any combination thereof. The ceramic coatings may include alumina ceramics, Zirconia (ZrO2) ceramics, Calcium phosphate or hydroxyapatite (Ca10(PO46(OH)2) ceramics, titanium dioxide (TiO2), silica (SiO2), Zinc Oxide (ZnO) and/or any combination thereof. The materials may be manufactured using traditional methods and/or using 3D printed techniques known in the art. Furthermore, the material may comprise a porous material, the porous material includes porous metal, porous polymer, porous ceramic and/or any combination thereof.

In one embodiment, the bridge 174a, 174b and the inferior base 216a, 216b comprise the same coating (not shown), and the inferior articulating component 108a, 108b comprises a different coating (not shown). In another embodiment, the bridge 174a, 174b, the inferior base 216a, 216b and the inferior articulating component 108a, 108b comprise the same coating. The same coating comprises a metal coating and the different coating comprises a polymer coating. In another embodiment, the inferior base 216a, 216b comprises a first coating, the bridge 174a, 174b comprises a second coating, and the inferior articulating component 108a, 108b comprises a third coating. The first coating and the second coating may comprise the same coating. The third coating may be different than the first and second coating. The first and second coatings may comprise a metal coating such as Titanium. The third coating may comprise a metal coating such as cobalt-chrome molybdenum (CoCrMo). In another embodiment, the top surfaces 206a, 206b of the bridge 174a, 174b may comprise a first coating and the bottom surface 204a, 204b of the bridge 188 may comprise a second coating. The first coating may be the same or different as the second coating.

In another embodiment, at least a portion of the first contact surface 182a, 182b of the first stop 180a, 180b comprises a first coating, at least a portion of the second contact surface 188a, 188b of the second stop 178a, 178b comprises a second coating, and/or at least a portion of the inferior articulating component 108a, 108b comprises a coating. The first and second coating may comprise the same coating. The third coating is different or the same as the first and second coating. The first coating and the second coating comprises a titanium coating. The third coating may optionally comprise no coating.

Figure 18A:
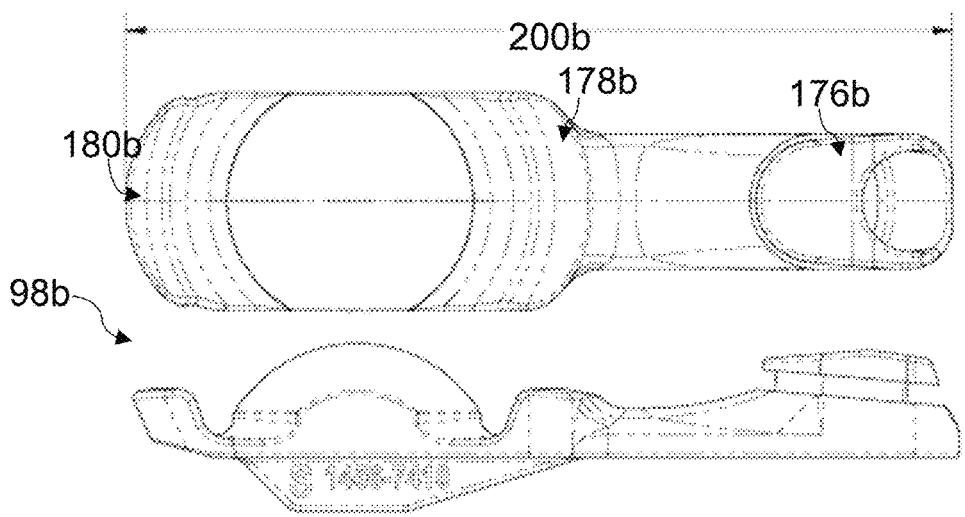
FIGS. 18A-18C depict top and side views of an inferior element of FIGS. 17A-17F in different lengths.
Figure 18B:
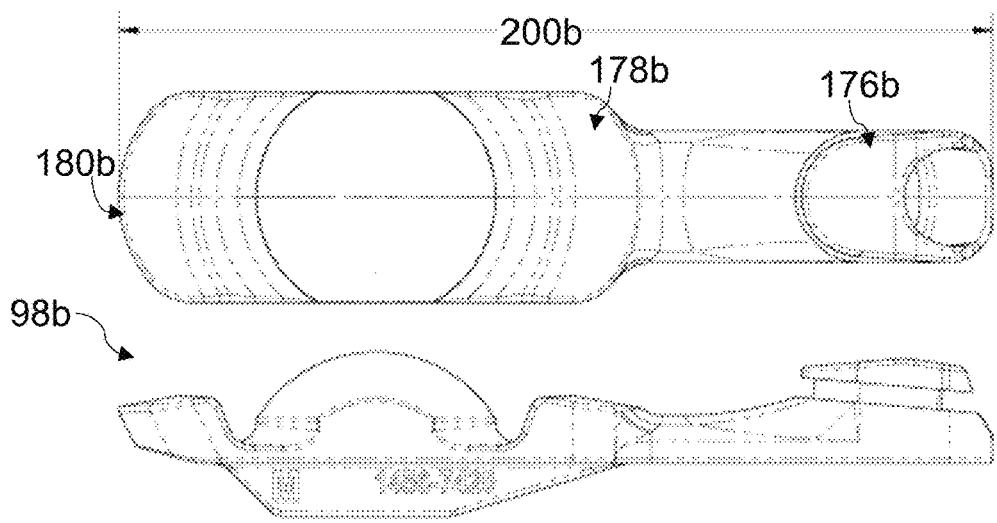
Figure 18C:
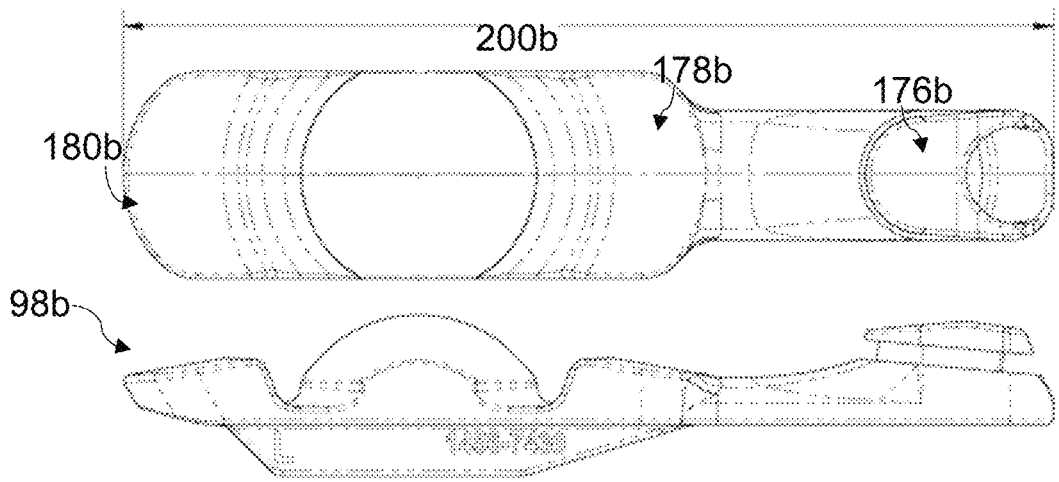
Figures 19A, 19B:
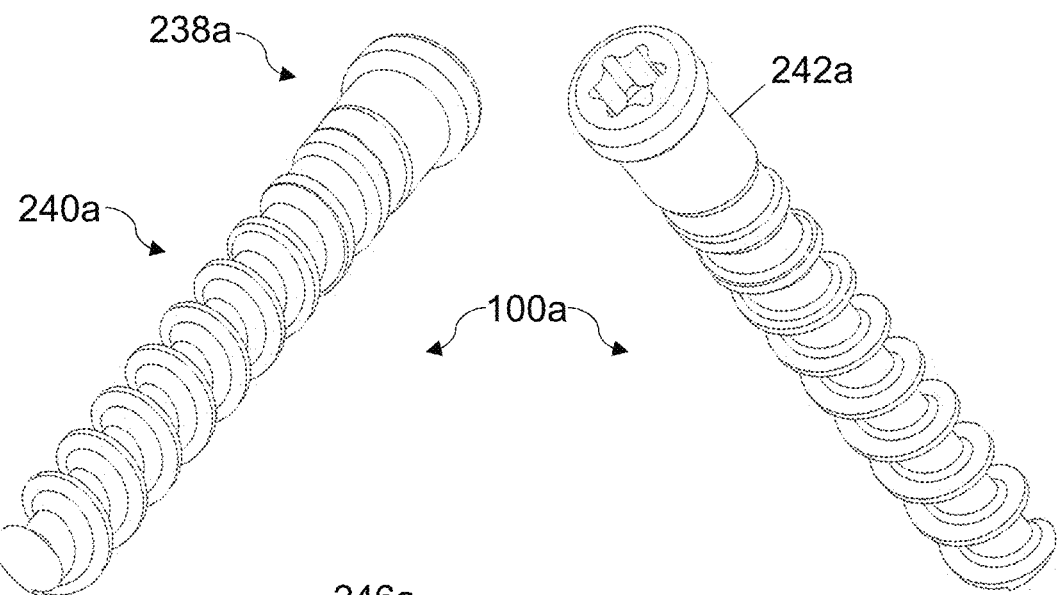
FIGS. 19A-19E depicts various plan views of one embodiment of a fixation screw.
Figure 19C:
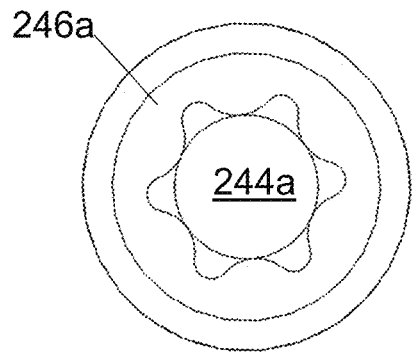
Figure 19D:
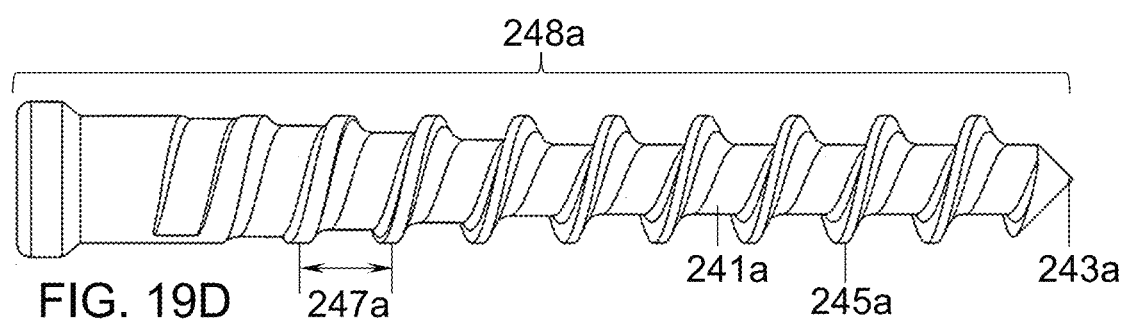
Figure 19E:
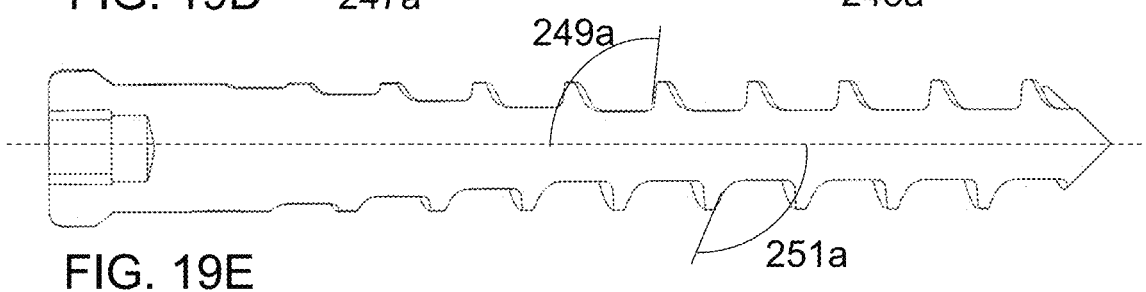
Figure 21E:
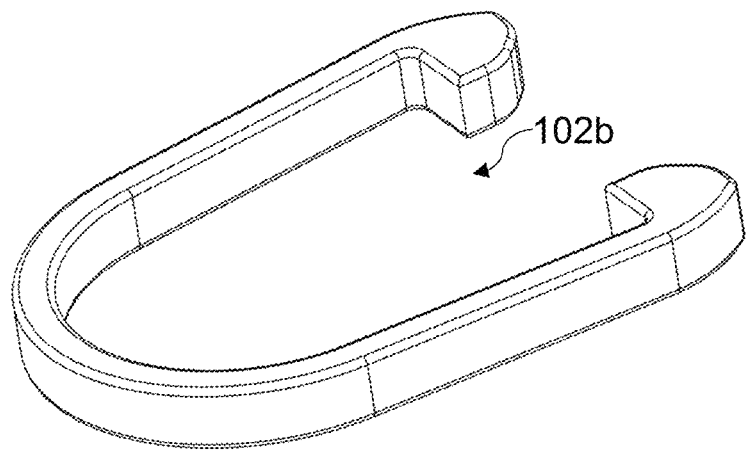
FIGS. 21E-21G depicts various plan views of an alternate embodiment of a retention clip.
Figure 21F:
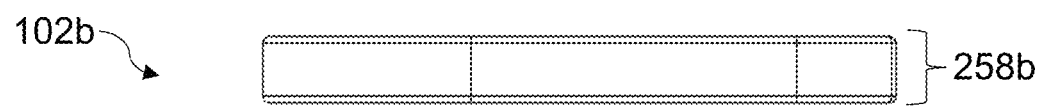
Figure 21G:
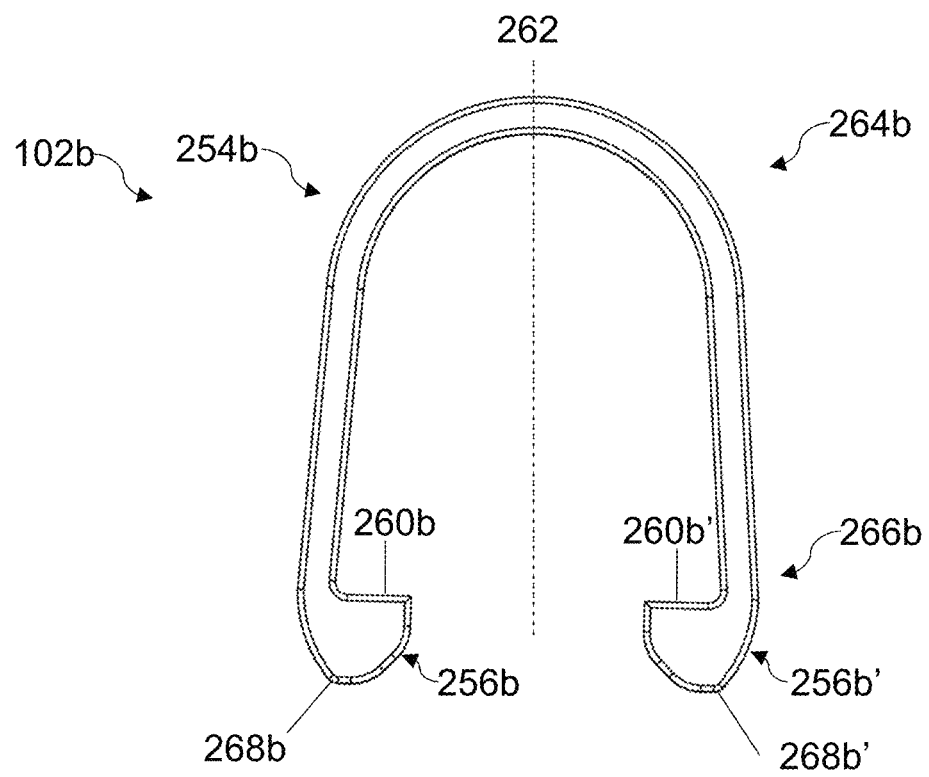
Figure 22A:
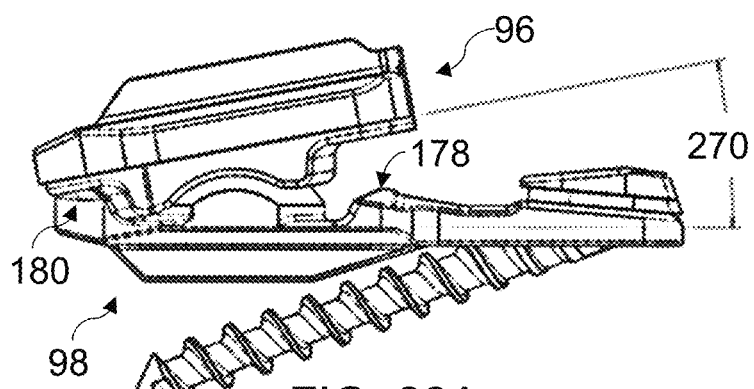
FIGS. 22A-22B depicts a side view of a spinal implant having flexion and extension motion.
Figure 22B:
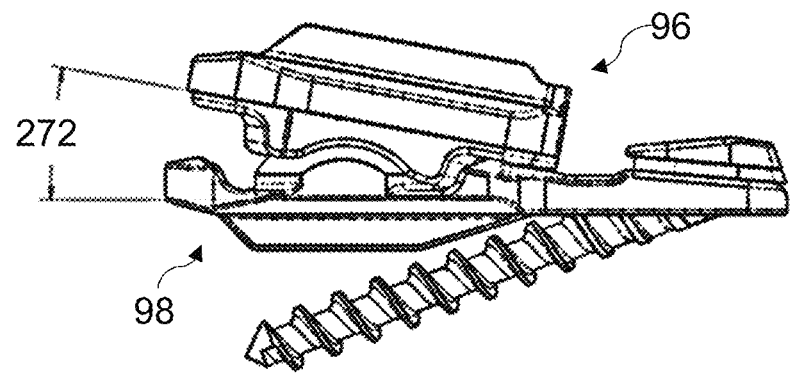
Figures 23A, 23B:
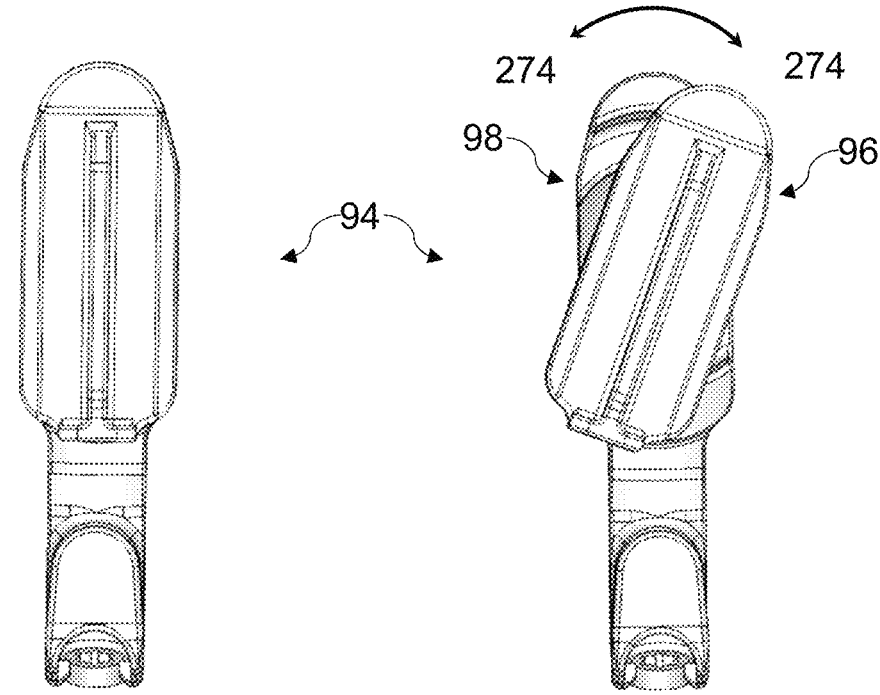
FIGS. 23A-23B depicts a top view of a spinal implant having right to left axial rotation.

With reference to FIGS. 18A-18C, the inferior or lower element 98a, 98b may comprise different total inferior element lengths 200a, 200b to accommodate different vertebral body sizes. The total inferior element lengths 200a, 200b may comprise generic lengths such as small, medium, large, extra-large. Alternatively, the total inferior element lengths 200a, 200b may be offered in a range of 20 mm to 60 mm; a range of 20 mm to 40 mm; a range of 40 to 60 mm; and/or a range of 45 mm to 55 mm. The total inferior element lengths 200a, 200b ranges may be incremental by 1 mm, 2 mm, 3 mm, 4 mm, or 5 mm; the inferior element lengths 200a, 200b ranges may be incremental by 3 mm or greater. The inferior or lower element 98a, 98b is solid.

With reference to FIGS. 7A-7H, 8A-8D, 9A-9B, 19A-19D and 20A-20E, the total joint or dynamic spinal implant 94a, 94b may further comprise a fixation screw 100a, 100b. The fixation screw 100a, 100b comprises a head 238a, 238b, a shaft 242a, 242b, threads 240a, 240b, a tip 243a, 243b and a screw total length 248a, 248b. The shaft 242a, 242b comprises a minor diameter or shaft diameter 241a, 241b. The threads 240a, 240b comprises a major diameter or thread diameter 245a and a pitch 247a, 247b. At least a portion of the screw 100a, 100b is designed and configured to be disposed into the bore 172a, 172b of the inferior element 98a, 98b. Alternatively, the screw 100a, 100b is designed and configured to be disposed into the bore 172a, 172b. The fixation screw shaft 242a, 242b and threads 240a, 240b are solid. Alternatively, the fixation screw shaft 242a, 242b and threads 240a, 240b may be hollow to allow guidewires or cannulas through the cannula opening (not shown).

In one embodiment, the head 238a, 238b is sized and configured to fit or be disposed within the first portion 208a, 208b of the bore 172a, 172a of the inferior element 98a, 98b. The shaft 242a, 242b and the threads 240a, 240b is sized and configured to be disposed within the second portion 208a', 208b' of the bore 172a, 172b. The head 238a, 238b comprises a top surface 246a, 246b and a driving style or drive recess 244a, 244b. The head 238a, 238b comprises at least one selected from a hex head, a pan head, a flat head, a round head, an oval head, a truss head, a socket head, a button head, a fillister head, an indented head, and/or any combination thereof. The drive recess 244a, 244b may comprise a Phillips, a Frearson, a Posidrive, a Slotted, a Combo, a Hex Socket, a Square, a Torx, a Supadriv, a Spanner, hexalobular and/or any combination thereof. The drive recess 244a, 244b extends from the top surface towards the shaft 242a, 242b. The drive recess 244a, 244b is sized and configured to receive a driving tool (not shown).

At least a portion of the top surface 246a, 246a of the head 238a, 238b contacts a portion of the retainer clip 102a, 102b. At least a portion of the top surface 246a, 246b contacts a portion of the flanges 256a, 256b of the retainer clip 102a, 102b. Alternatively, at least a portion of the top surface 246a, 246b contacts a flange surface 260a, 260b of the flanges 256a, 256b of the retainer clip 102a, 102b. Furthermore, at least a portion of the top surface 246a, 246b of the head 238a, 238b sits or positioned equal to the contact surface 252a, 252b of the bore 172a, 172b of the inferior element 98a, 98b. At least a portion of the top surface 246a, 246b sits or is positioned below the contact surface 252a, 252b of the opening 172a, 172b of the inferior element 98a, 98b.

The fixation screw 100a, 100b comprises a total screw length 248a, 248b. The total screw length 248a, 248b may match or substantially match pedicle length 73 as shown in FIG. 5B. The total screw length 248a, 248b may comprise a range of 30 mm to 60 mm; a range of 30 mm to 50 mm; a range of 30 mm to 40 mm; a range of 35 mm to 45 mm; and/or any combination thereof. The total screw length 248a, 248b may be sufficient to engage with cortical bone, cancellous bone, and/or cortical and cancellous bone.

The fixation screw 100a, 100b further comprises threads 240a, 240b. The threads 240a, 240b may comprise a single lead or multiple lead or multi-start threads. In one embodiment, the threads 240a, 240b may comprise a double-lead, a triple-lead and/or a quad-lead threads. The threads 240a, 240b may further comprise a pitch 247a, 247b. The pitch 247a, 247b may comprise a fine or coarse pitch. In one embodiment, the pitch 247a, 247b comprises a coarse pitch. The coarse pitch is designed to anchor into the softer, spongy bone. The fine pitch is designed cortical bone because the bone is denser, and the torque may be high. In one embodiment, the pitch 247a, 247b may comprise a range of 2 mm to 5 mm; may comprise a range of 3 mm to 5 mm; may comprise a range of 3 mm to 4 mm; and/or may comprise a range of 3 mm to 3.5 mm. Alternatively, the pitch may comprise at least 2.5 mm or greater; may comprise at least 3.0 mm or greater; may comprise at least 3.20 mm or greater; it may comprise at least 3.5 mm or greater; it may comprise at least 4 mm or greater. The threads 240a, 240b may comprise a clockwise or counterclockwise rotation.

In one embodiment, the threads 240a, 240b may comprise a thread diameter or major diameter 245a, 245b. The thread diameter 245a, 245b may comprise a small, medium or large diameter. Large diameter threads and higher or coarser pitch offers a greater surface area for the purchase of the threads 240a, 240b on the cancellous bone. Furthermore, large diameter threads increase the pull-out strength or pull-out resistance—the large diameter threads form companion or complementary threads in the bone by compression as well as by deforming the bone trabeculae. The spring or elastic reaction occurs as the cancellous bone is deformed during the thread forming procedure resulting in the compressed companion threads of the cancellous bone to contact the larger surface area of the threads 240a, 240b. Alternatively, smaller diameter threads and finer or lower pitch also increases holding power or pull-out strength of the fixation screw. More turns may be completed to engage to a given depth into the bone—the more threads engage, the greater the pull-out resistance. The smaller diameter threads cut into bone while it is inserted cause an elastic reaction of the bone to grip the bone surfaces together—causing elastic deformation of the bone. The bone deforms and offers an elastic binding force.

In another embodiment, the thread diameter 245a, 245b may comprise a range of 3 mm to 10 mm; may comprise a range of 3 mm to 8 mm; may comprise a range of 3 mm to 6 mm; and/or may comprise a range of 4 mm to 5 mm. Accordingly, the thread diameter 245a, 245b may comprise at least 3.5 mm or greater; may comprise at least 4 mm or greater; may comprise at least 4.5 mm or greater; and/or may comprise at least 5 mm or greater. Alternatively, the thread diameter 245a, 245b and/or the threads 240a, 240b may match or substantially match the pedicle width 80 as shown in FIG. 5D.

In another embodiment, the threads 240a, 240b of the fixation screw 100a, 100b may comprise different thread forms. The thread forms may comprise V-thread, buttress, unified, metric, square, ACME, helical and/or any combination thereof. The helical threads allow the user to transform smaller radial movement into large axial movement. In one embodiment, the thread form of the threads comprises a helical thread form. In another embodiment, the fixation screw 100a, 100b may comprise different screw tips or points to properly cut and affix to different bone types. More specifically, the threads 240a, 240b may include threads known in the art that can properly cut and affix to cancellous and/or cortical bone.

In another embodiment, the threads 240a, 240b may comprise one or more thread angles 249a, 249b, 251a, 251b. Each of the one or more thread angles 249a, 249b, 251a, 251b may comprise the same angles. Each of the one or more thread angles 249a, 249b, 251a, 251b may comprise different angles. Alternatively, the threads 240a, 240b may comprise a first thread angle 249a, 249b and a second thread angle 251a, 251b. The first thread angle 249a, 249b and the second thread angle 251a, 251b may comprise the same angle. The first thread angle 249a, 249b and the second thread angle 251a, 251b may comprise a different angle. The thread angles 249a, 249b, 251a, 251b may comprise a range of 60 degrees to 120 degrees; may comprise a range of 70 degrees to 120 degrees; may comprise a range of 80 degrees to 120 degrees; and/or may comprise a range of 85 degrees to 120 degrees. Accordingly, the first thread angle 249a, 249b may comprise at least 75 degrees or greater; may comprise at least 80 degrees or greater; and/or may comprise at least 85 degrees or greater. The second thread angle 251a, 251b may comprise at least 105 degrees or greater; it may comprise at least 110 degrees or greater; and/or it may comprise at least 115 degrees or greater.

In another embodiment, the fixation screw shaft 242a comprises a minor diameter 241a, 241b. The minor diameter 241a, 241b may be uniform or non-uniform. The minor diameter 241a, 241b may be tapered. The minor diameter 241a, 241b may be tapered along the screw length 248a, 248b. The minor diameter 241a, 241b may be tapered along a portion of the screw length 248a, 248b. Alternatively, at least a portion of the minor diameter 241a, 241b may be tapered along a portion of the screw length 248a, 248b. The tapering comprises a taper angle, the taper angle may comprise at least 5 degrees to 10 degrees; may comprise at least 7 degrees to 10 degrees; may comprise at least 8 degrees to 10 degrees; and/or may comprise at least 8 degrees to 9 degrees. Accordingly, the taper angle may be at least 5 degrees or greater; the taper angle may be at least 7 degrees or greater; the taper angle may be at least 8 degrees or greater; the taper angle may be at least 8.5 degrees or greater; and/or the taper angle may be at least 10 degrees or greater or 10 degrees or less. In another embodiment, the minor diameter 241a, 241b may comprise a diameter of 1.5 mm or greater; it may comprise a diameter of 2.0 mm or greater; it may comprise a diameter of 2.25 mm or greater; and/or it may comprise a diameter of 2.5 mm or greater and/or 2.5 mm or less.

In another embodiment, the fixation screw 100a, 100b comprises a tip 243a, 243b. The screw points or tips 243a, 243b may comprise self-drilling, self-piercing, self-tapping, and/or a combination thereof. The long, sharp screw points or tips would desirably help eliminate hole preparation (no punching, pre-drilling or tapping required) and/or help penetrate the bone quicker or quickly and/or capture bone chips or bone debris for increasing local bone density and/or increase the bone's ability to withstand "back out" pressure (e.g., less loosening or migration).

The fixation screw 100a, 100b comprises a material, which may include metal, polymers or ceramic. The metals may comprise titanium, titanium alloys, cobalt-chrome alloys, platinum, stainless steel and/or any combination thereof. More specifically, the metal may include titanium and/or cobalt-chrome molybdenum (CoCrMo). The polymers may include thermoplastic or thermoset polymers. The polymers may further include carbon fiber, polyether ether ketone (PEEK), polyethylene (PE), ultra-high molecular weight polyethylene (UHMWPE), polycarbonate (PC), polypropylene (PP) and/or any combination thereof. The ceramics may include alumina ceramics, Zirconia (ZrO2) ceramics, Calcium phosphate or hydroxyapatite (Ca10(PO46(OH)2) ceramics, titanium dioxide (TiO2), silica (SiO2), Zinc Oxide (ZnO) and/or any combination thereof. The materials may be manufactured using traditional methods and/or using 3D printed techniques known in the art. Furthermore, the material may comprise a porous material, the porous material includes porous metal, porous polymer, porous ceramic and/or any combination thereof. The fixation screw 100a, 100b is solid and/or the fixation screw 100a, 100b is hollow.

With reference to FIGS. 7A-7H, 8A-8D, 9A-9B and 21A-21D, the total joint or dynamic spinal implant 94a, 94b further comprises a retainer clip 102a, 102b. The retainer clip 102a, 102b may be disposed into to the recessed clip channel 202a, 202b to help prevent migration of the fixation screw 100a, 100b after deployment and/or securement to the bone. At least a portion of the retainer clip 102a, 102b is movable from a first position to a second position, the first position being moved axially away from the central axis 262 while the fixation screw 102a, 102b is being secured to the bone, and the second position that allows the retainer clip to return to rest once the head 238a, 238b of the fixation screw 102a, 102b is below the at least one flange 256a, 256b.

The retainer clip 102a, 102b comprises a body 254a, 254b and at least one flange 256a, 256a', 256b, 256b'. The body 254a, 254b of the retainer clip 102a, 102b comprises a shape, the shape includes a "U" shape. Alternatively, the body 254a, 254b comprises a first arm and a second arm. The body 254a, 254b comprises a first end 264a, 264b and a second end 266a, 266b. The at least one flange 256a, 256a', 256b, 256b' are disposed at the second end 266a, 266b of the body 254a, 254b of the retainer clip 102a, 102b. The at least one flange 256a, 256a', 256b, 256b' extends away from the second end 266a, 266b of the body 254a, 254b of the retainer clip 102a, 102b. Alternatively, the at least one flange 256a, 256a', 256b, 256b' extends inwardly towards a central axis 262 of the retainer clip 102a, 102b. The at least one flange 256a, 256a', 256b, 256b' extends perpendicularly from the second end 266a, 266b of the body 254a, 266b of the retainer clip. The at least one flange 256a, 256a', 256b, 256b' extends from the second end 266a, 266b of the body perpendicularly toward the central axis 262.

In another embodiment, the retainer clip 102a, 102b comprises a body 254a, 254b, a first flange 256a, 256b and a second flange 256a', 256b'. The body 254a, 254b comprises a first arm and a second arm. The body 254a, 254b and/or each of the first arm and second arm of the body 254a, 254b comprises a first end 264a, 264b and a second end 266a, 266b. The first flange 256a, 256b is disposed at the second end of the first arm of the body 254a, 254b. The second flange 256a', 256b' is disposed at the second end 266a, 266b of the second arm of the body 254a, 254b. The first flange 256a, 256b extends away from the second end 266a, 266b the first arm of the body 254a, 254b of the retainer clip 102a, 102b. The second flange 256a', 256b' extends away from the second end 266a, 266b the second arm of the body 254a, 254b of the retainer clip 102a, 102b. Alternatively, the first flange 256a, 256b and the second flange 256a', 256b' extends inwardly towards the central axis 262 of the retainer clip 102a, 102b. The first flange 256a, 256b extends perpendicularly from the second end 266a, 266b of the first arm of the body 254a, 254b of the retainer clip 102a, 102b. The second flange 256a', 256b' extends perpendicularly from the second end 266a, 266b of the second arm of the body 254a, 254b of the retainer clip 102a, 102b. The first flange 256a, 256b extends from the second end 266a, 266b of the first arm of the body 254a, 254b perpendicularly toward the central axis 262.

The body 254a, 254b is sized and configured to be disposed and/or positioned into the recessed clip channel 202a, 202b. The body 254a, 254b comprises a clip width 258a, 258b, the clip width 258a, 258b may match or substantially match a width of the recessed clip channel 202a, 202b. The at least one flange 256a, 256a', 256b, 256b', the first flange 256a, 256b, and/or the second flange 256a', 256b' extend into the opening 172a, 172b of the inferior element 98a, 98b. Alternatively, at least a portion of the at least one flange 256a, 256a', 256b, 256b' extend into a portion of the opening 172a, 172b of the inferior element 98a, 98b. The at least one flange 256a, 256a', 256b, 256b' comprises a flange surface 260a, 260a', 260b, 260b'. Alternatively, the first flange 256a, 256b comprises a first flange surface 260a, 260b. The second flange 256a', 256b' comprises a second flange surface 260a', 260b'. The flange surface 260a, 260a', 260b, 260b', the first flange surface 260a, 260b and/or the second flange surface 260a', 260b' faces towards the top head surface 246a, 246b of the fixation screw 100a, 100b. At least a portion of the top head surface 246a, 246b contacts a portion of the at least one flange surface 260a, 260a', 260b, 260b', the first flange surface 260a, 260b, and/or the second flange surface 260a', 260b' of the flanges 256a, 256a', 256b, 256b' of the retainer clip 102a, 102b. The at least one flange 256a, 256a', 256b, 256b', the first flange 256a, 256b and/or the second flange 256a', 256b' further comprises rounded or radiused edges 268a, 268a', 268b, 268b' to facilitate easier insertion of the fixation screw 102a, 102b. Accordingly, at least a portion of the body 254a, 254b may comprise filleted or beveled edges and/or at least a portion of the body 254a, 254b may comprise filleted or beveled edges surrounding the perimeter.

The retainer clip 102a, 102b comprises a material including metal, polymers or ceramic. The metals may comprise titanium, titanium alloys, cobalt-chrome alloys, platinum, stainless steel and/or any combination thereof. More specifically, the metal may include titanium and/or cobalt-chrome molybdenum (CoCrMo). The polymers may include thermoplastic or thermoset polymers. The polymers may further include carbon fiber, polyether ether ketone (PEEK), polyethylene (PE), ultra-high molecular weight polyethylene (UHMWPE), polycarbonate (PC), polypropylene (PP) and/or any combination thereof. The ceramics may include alumina ceramics, Zirconia (ZrO2) ceramics, Calcium phosphate or hydroxyapatite (Ca10(PO46(OH)2) ceramics, titanium dioxide (TiO2), silica (SiO2), Zinc Oxide (ZnO) and/or any combination thereof. The retainer clip 102a, 102b may be solid and/or the retainer clip 102a, 102b may be hollow. The materials may be manufactured using traditional methods and/or using 3D printed techniques known in the art. Furthermore, the material may comprise a porous material, the porous material includes porous metal, porous polymer, porous ceramic and/or any combination thereof.

Exemplary Implantation Procedure

With reference to FIGS. 3A-3C, 4, 28A-28B, 29A-29D, 30A-30D, 31 and 32A-32D, the disclosed surgical procedure and the spinal implant 94a, 94b may be desirably used as a total joint replacement resulting in sagittal and/or coronal alignment by creating more lordosis and/or more kyphosis during the surgical procedure. As shown in FIGS. 3A-3C and 4, all patients or people typically have a natural lumbar lordotic angular variance across various spinal levels within the different spine regions. The spine's natural lordotic and kyphotic curvatures and its angular variance are designed for even distribution of weight and flexibility of movement. These natural curves work in harmony to keep the body's center of gravity aligned over the hips and pelvis—i.e., keeps our head over our pelvis and hips. However, degenerated discs 42 and/or facets can adversely affect the structural integrity of the spine and contribute to scoliosis 38 (FIG. 3A) and/or lordosis or kyphosis 40 (FIG. 3B) as well as other curvature disorders such as scoliosis. Any exaggeration or abnormalities of the curves in the sagittal plane or coronal plane, results in sagittal imbalance or coronal imbalance. Thus, maintaining a mechanical balance within the sagittal plane and coronal plane would help facilitate equilibrium of the spine and body with minimum energy expenditure or reduction of stresses to other regions of the spine. It is desirable to restore the spine to adequate or optimal coronal and/or sagittal alignment as a primary surgical strategy to prevent adjacent segment disease and/or changes of load on different structures within the spine.

One or more spinal implants 94a, 94b can be deployed utilizing different surgical spinal stabilization approaches into one or more spinal functional units or spinal segments in one or more spinal regions. The one or more dynamic spinal implants 94a, 94b can be deployed using a posterior approach. The one or more dynamic spinal implants can be deployed using an anterior approach and/or a transverse approach. Furthermore, a discectomy, laminectomy and/or other procedures may be necessary. Traditional methods may be used to access the one or more spinal segments. However, the use of robotics and/or computer guided surgical platforms (and/or computer-aided navigation) are contemplated herein, including in the planning and/or execution stages of the surgery.

FIGS. 28A-28B, 29A-29D, 30A-30D depicts a side view or sagittal view of one exemplary spinal motion unit that is undergoing a surgical procedure in accordance with one exemplary embodiment of the spinal implant 94a, 94b. In this embodiment, preoperative image data of the spinal motion unit has been obtained, and a preoperative surgical plan to alter the coronal and/or sagittal alignment of the spinal motion is proposed.

During the preoperative surgical planning, a proposed implant size, orientation (toe-in angle and/or coronal angle) and/or a proposed amount of correction for the spinal implant 94a, 94b to correct coronal and/or sagittal deformities may be presented. In some embodiments, the proposed amount of correction or proposed orientation of the spinal implant 94a, 94b may comprise a new alignment path or resection plane 284 that may be different than the anatomical or endplate plane 282 currently in the patient. The new or revised alignment path or resection plane 284 may require the surgical removal of at least a portion of the intervertebral disc and/or bony material from the lower vertebral body 18 in a right side, a left side, and/or right and left sides at one or both pedicles, which is represented within FIGS. 29A-29D and 30A-30D (involving removal of bony material at or below the anatomical alignment line or anatomical plane 282 up to the revised alignment line, plane or resected plane 284. In various embodiments, this surgical procedure might allow some and/or all of at least a portion of the pedicles to be preserved during such removal, such that the remaining portions of the pedicle remain attached to the vertebral body and are capable of providing additional support and stability to portions of the spinal implant 94a, 94b.

The revised alignment line, plane or resected plane 284 may be flat, planar, or comprise no angle. The revised alignment line, plane or resection plane 284 may be at and/or below the anatomical plane 282. The revised alignment line, plane or resected plane 284 may comprise an angle, the angle being oriented relative to the anatomical line or plane 282. The revised alignment line, plane or resection plane 284 will desirably define the new orientation of the dynamic spinal implant 94a, 94b with respect to the upper vertebra 12 and the lower vertebra 18. If desired, the revised alignment line or resected plane 284 may be symmetrical on right and/or left sides of the vertebral body, or the resection may be asymmetrical in some fashion (i.e., differing depths, endplate angulations, toe in angles, etc.).

Different sizes of the spinal implant 94a, 94b may be contemplated as described within FIGS. 11A-11E, 12A-12C, 18A-18C and FIG. 25. The desired size of the spinal implant 94a, 94b may depend on several factors including surgical approach, intended spinal segment region (e.g., thoracic or lumbar), patient anatomy, degree of degeneration, and amount of alignment or correction required. As described herein and within FIG. 25, the total joint or dynamic spinal implant 94a, 94b may include different lengths and different heights. The different lengths may include short, medium, and/or long. The specific lengths may be available in 11 mm to 15 mm, with 1 mm increment change in length. Furthermore, the dynamic spinal implant 94a, 94b may be available in different heights 120. The height 120 of the dynamic spinal implant may include at least 5 mm to 15 mm; the height 120 may include at least 5 mm to 12 mm; and/or the height 120 may include at least 7 mm to 12 mm. Alternatively, the height 120 may include at least 7.5 mm. Each of the heights are available for each of the lengths to produce approximately 15 or greater different combinations.

Spinal Implant Placement

After the one or more spinal segments within each spinal region are prepared and/or resected to create the revised alignment line or resection plane 284 for implantation of one or more spinal implants 94a, 94b, the one or more dynamic spinal implants 94a, 94b may be deployed into the one or more prepared and/or resected spinal segments or spinal functional unit in one or more sides of the patient (right, left and/or right and left sides). Once the desired length and height of the one or more dynamic spinal implants 94a, 94b has been selected, the one or more spinal implants 94a, 94b can be positioned within at least one spinal functional unit or spinal segment 276a between an upper vertebra 12 and a lower vertebra 18 in one or more spinal regions between one or more upper vertebra 12 and a lower vertebra 18 on one or more sides of the patient as shown in FIG. 24A-24B, 26A-26D.

Figure 24A:
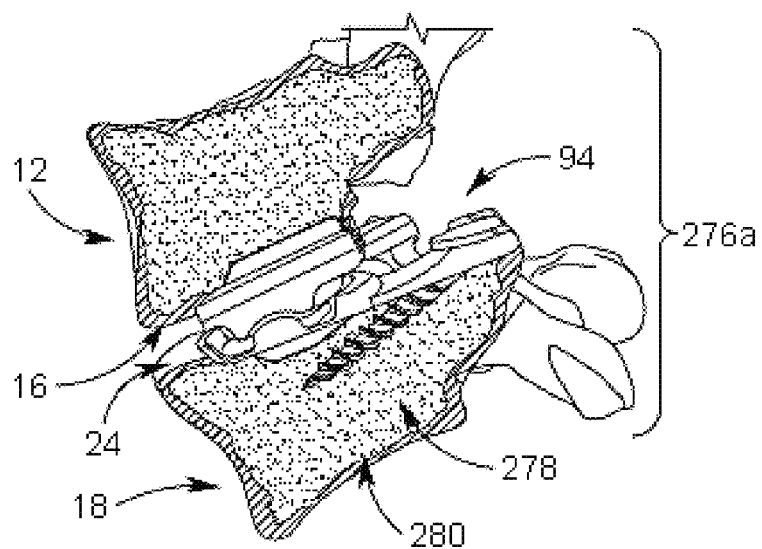
FIG. 24A depicts a sagittal cross-sectional view of a spinal implant disposed between at least one spinal segment or level.
Figure 24B:
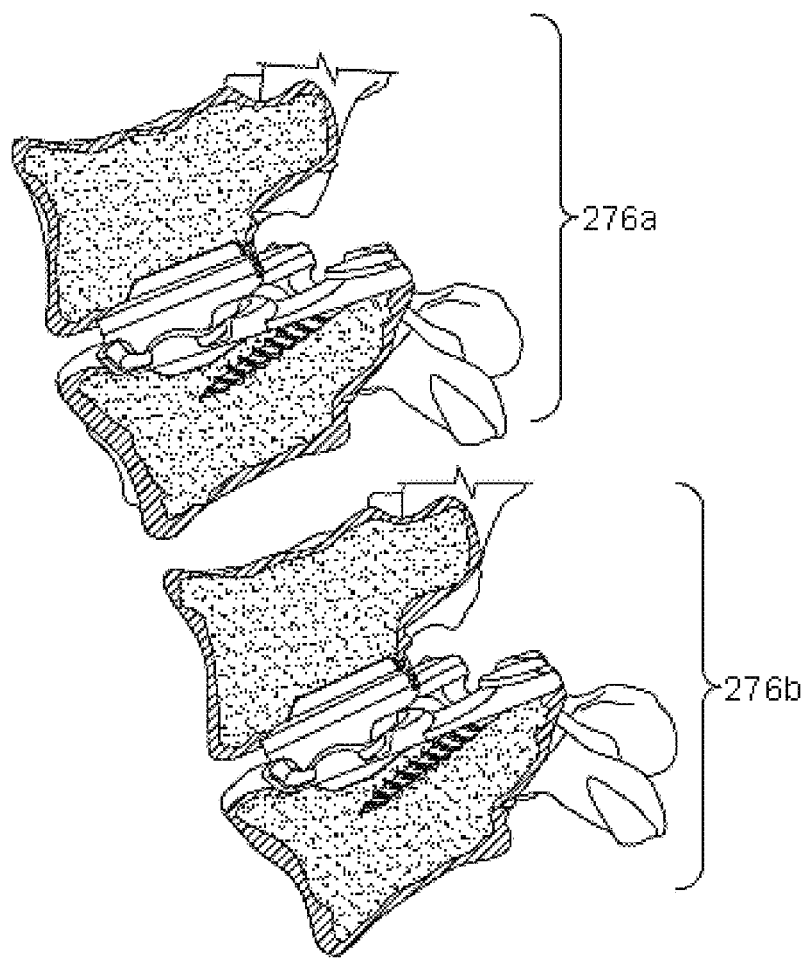
FIG. 24B depicts a sagittal cross-sectional view of a spinal implant disposed between at multiple spinal segment or levels.
Figure 25:
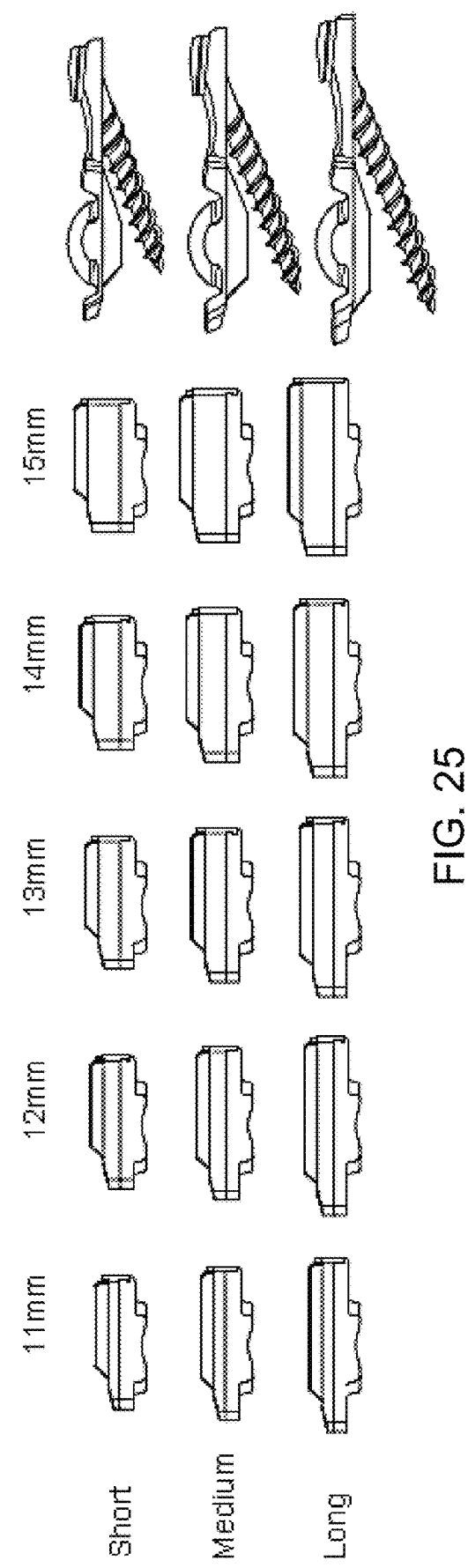
FIG. 25 depicts a side view of the different heights and widths of a spinal implant.

With further reference to FIGS. 24A-24B, one or more spinal implants 94a, 94b may be used to treat a single vertebral level or single vertebral segment 276a, between a single upper 12 and lower vertebra 18 in a right or left side of a patient. Alternatively, a single spinal implant 94a, 94b may be used to treat multiple vertebral levels or segments 276a, 276b, between multiple upper and lower vertebras in a right or left side of a patient. Furthermore, two or more spinal implants 94a, 94b may be used to treat a single vertebral level or single vertebral segment 276a, between a single upper 12 and lower vertebra 18 for the right and left sides. Alternatively, two or more spinal implants 94a, 94b may be used to treat multiple vertebral levels or segments 276a, 276b, between multiple upper and lower vertebras in the right and left sides. The one or more dynamic spinal implants 94a, 94b may be deployed into a single spine segment 276a in a spinal region, and or multiple spinal segments 276a, 276b in one or more spinal regions. The spinal regions may comprise cervical, thoracic and lumbar regions. Accordingly, the one or more spinal implants 94a, 94b, may be deployed into different orientations for sagittal or coronal correction, the orientations comprise toe-in angles, coronal angles (or scoliotic angles), sagittal angles (or lordotic angles), and/or any combinations thereof.

The spinal implant 94a, 94b generally includes an upper or superior element 96a, 96b, a lower or inferior element 98a, 98b, and a fixation screw 100a, 100b. The superior element 96a, 96b comprises a superior articulating component 106a, 106b and the inferior articulating component 108a, 108b. When the superior articulating component 106a, 106b contacts and engages the inferior articulating component 108a, 108b, it allows the superior articulating component 106a, 106b to move relative to the inferior articulating component 108a, 108b. Such movement mimics or substantially mimics the behavior of a normal functional spinal segment and/or unit. The motion includes at least one or more of flexion 270, extension 272, axial rotational motion 274 and/or lateral bending (not shown). The spinal region may include cervical, thoracic, lumbar, and/or any combination thereof.

Figure 26A:
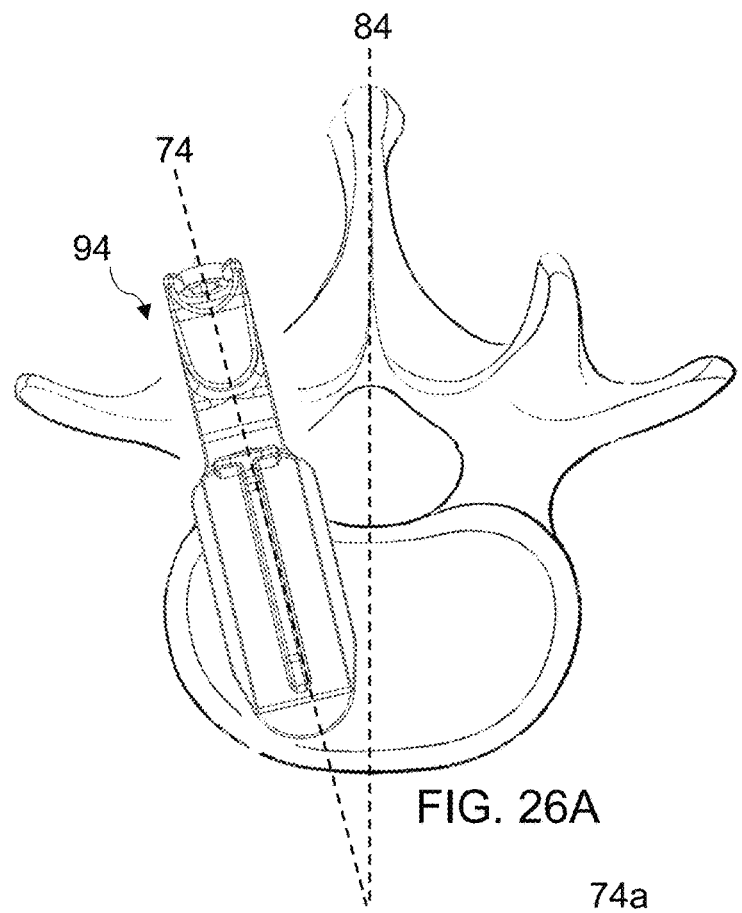
FIGS. 26A-26D depicts a top or superior views of a spinal implant disposed onto a vertebral body in various toe-in orientations.
Figure 26B:
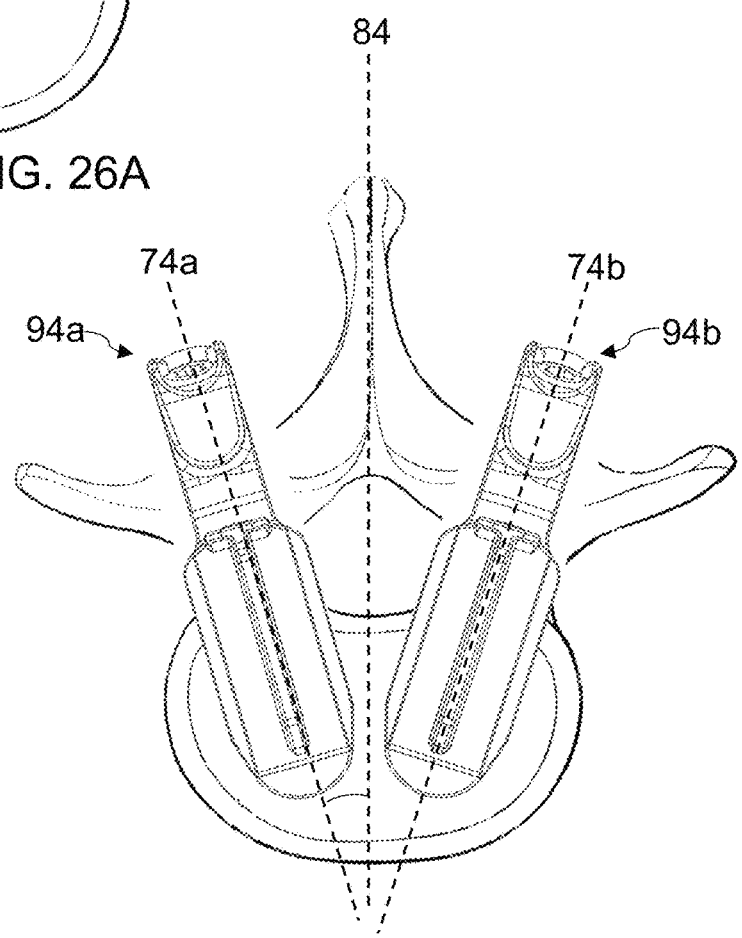
Figure 26C:
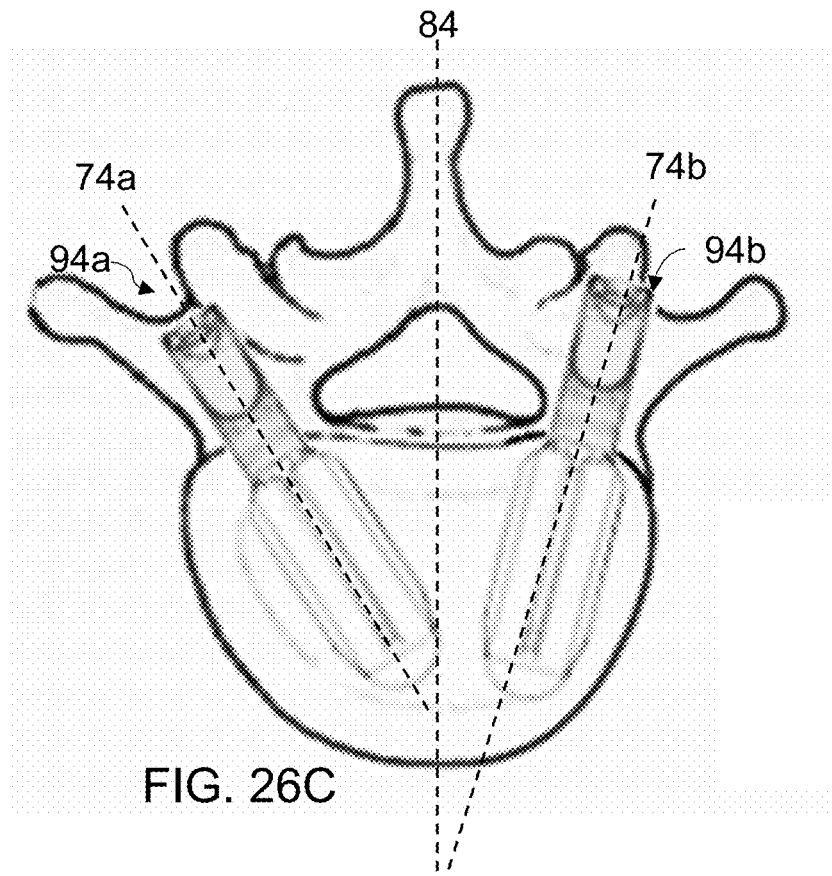
Figure 26D:
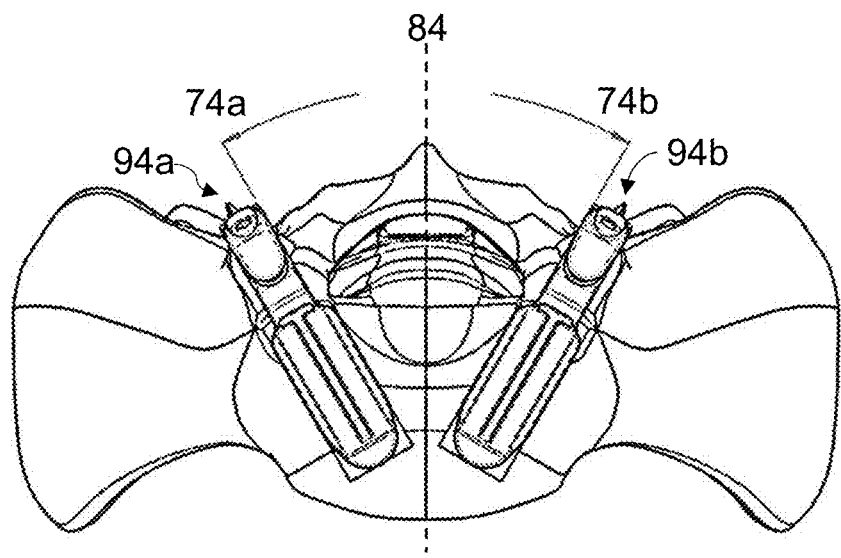
Figure 27:
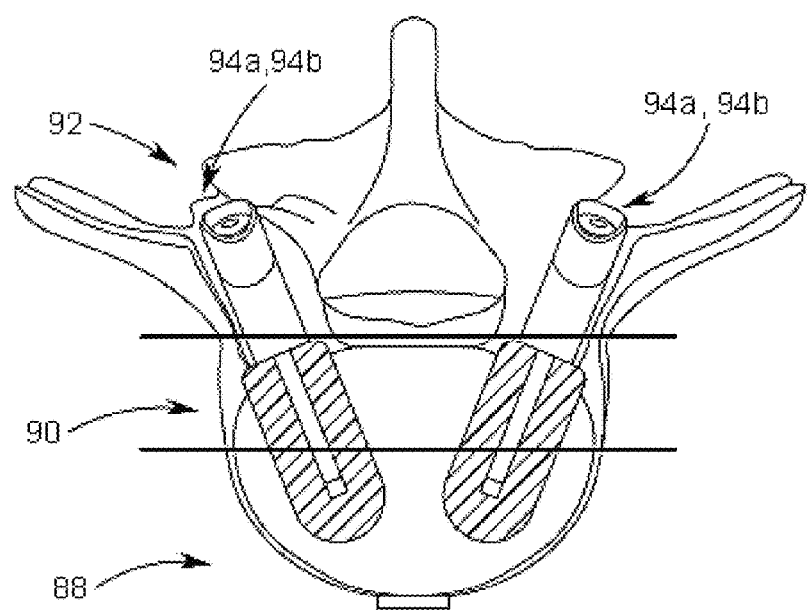
FIG. 27 depicts a top or superior view of a spinal implant disposed onto and supporting the three columns of a vertebral body.
Figure 28A:
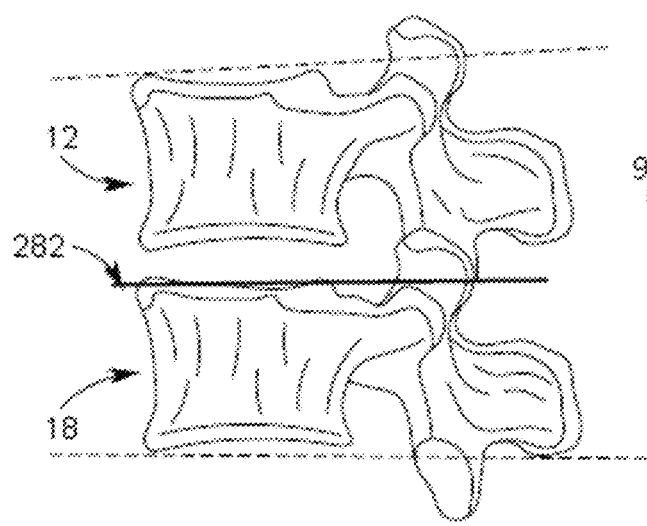
FIGS. 28A-28B illustrates a sagittal view of a spinal implant disposed between an upper and lower vertebral body in a parallel plane to the endplate.
Figure 28B:
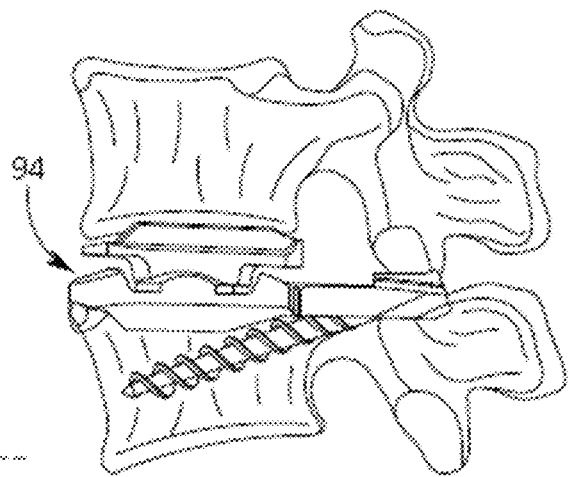
Figure 29A:
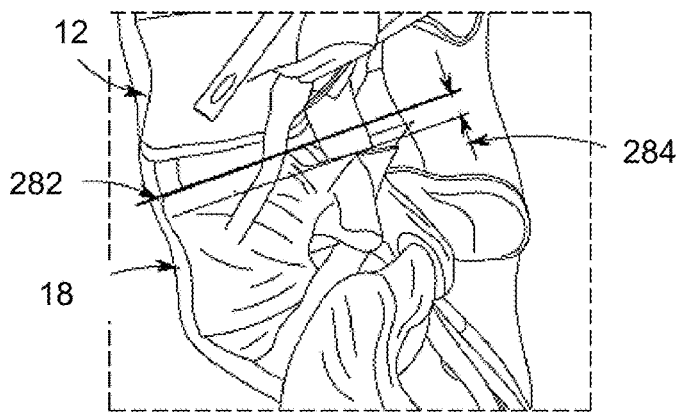
FIGS. 29A-29D illustrates a sagittal view and cross-sectional view of one embodiment of the parallel orientation angles or orientation planes cut into the vertebral body.
Figure 29B:
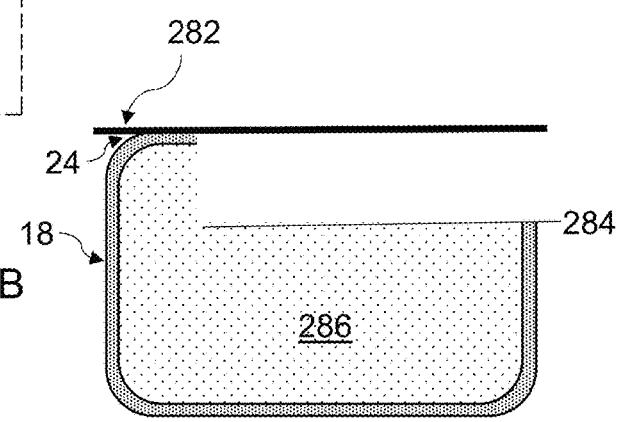
Figure 29C:
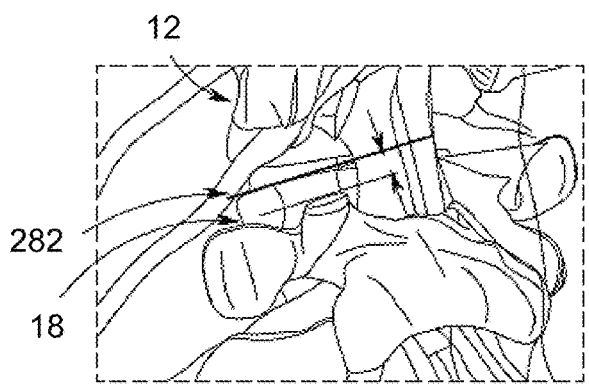
Figure 29D:
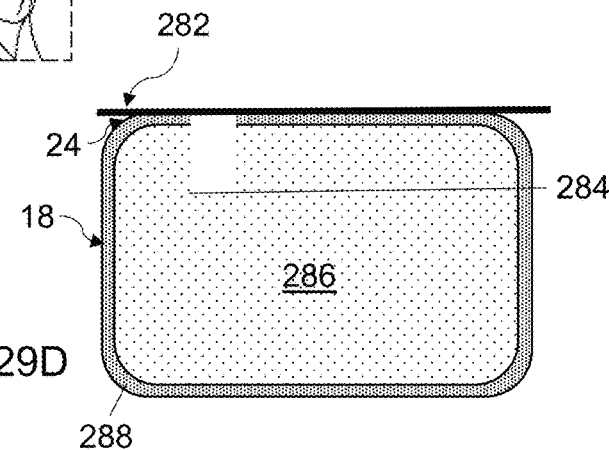
Figure 31:
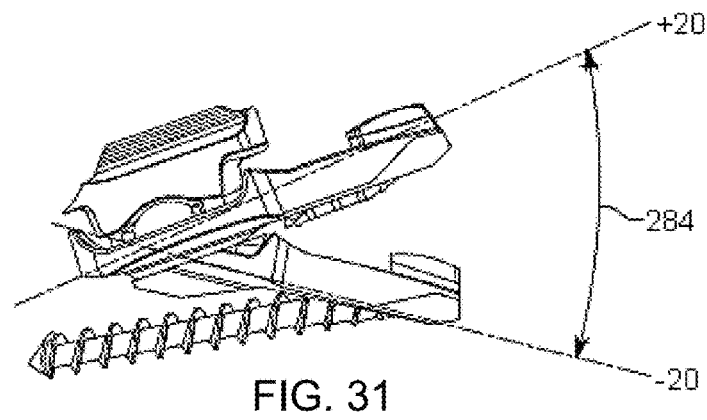
FIG. 31 depicts a side view or sagittal view of the spinal implant in different non-parallel sagittal orientation planes.
Figure 32A:
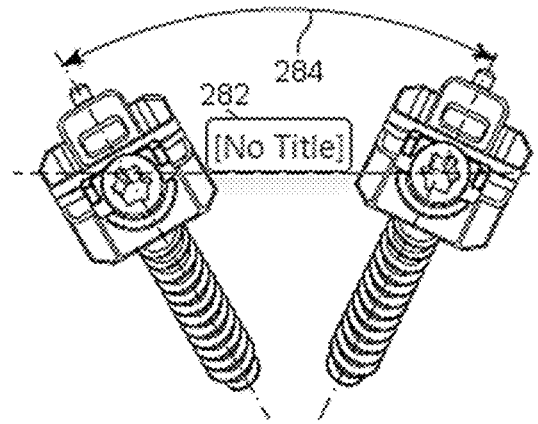
FIGS. 32A-32D depicts a coronal views and sagittal cross-sectional view of one embodiment of the non-parallel orientation angles or orientation planes in the coronal view cut into the vertebral body to create additional scoliosis for correcting coronal imbalance.
Figure 32B:
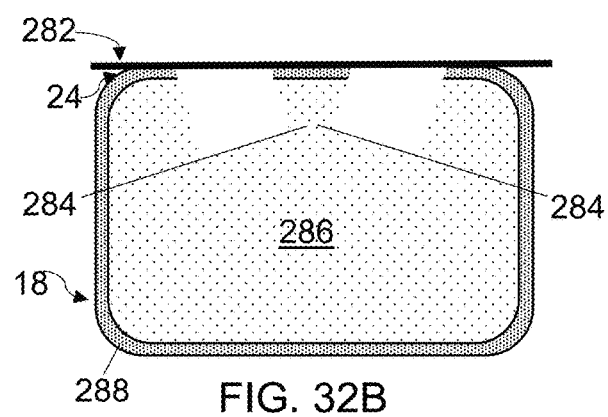
Figure 32C:
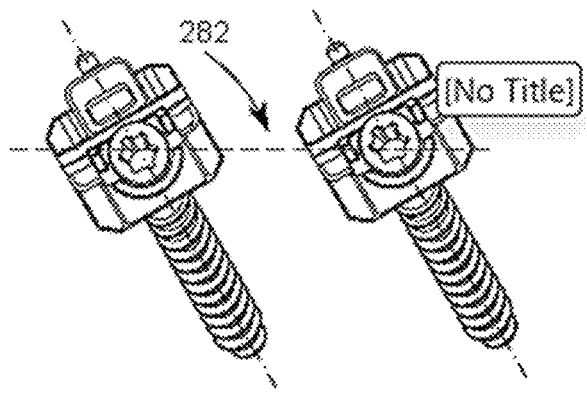
Figure 32D:
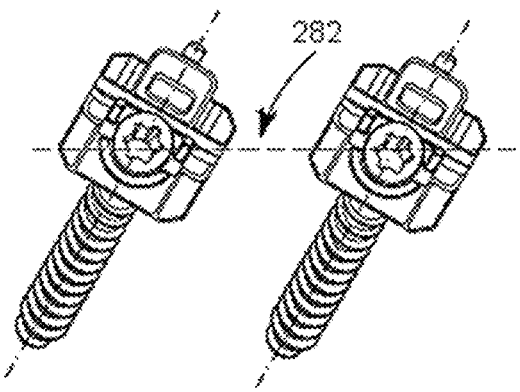

In another embodiment, the at least one total joint or dynamic spinal implant 94a, 94b can be positioned at a toe-in angle 74 within at least one spinal functional unit or spinal segment 276a between an upper vertebra 12 and a lower vertebra 18 on a first side of the patient as shown in FIG. 26A. A spinal implant 94a, 94b comprising: an inferior element 96 and a superior element 98a, 98b; the superior element 96 comprises a socket 119; the inferior element 98a, 98b comprises a articulation or ball component 108a, 108b with a ball articulation surface 226a, 226b, the ball articulation surface 226a, 226b of the ball component 108a, 108b of the inferior component 98a, 98b engages with the socket 119a, 119b of the superior element 96a, 96b to allow the superior element 96a, 96b to move relative to the inferior element 98a, 98b; the spinal implant 94a, 94b positioned at a toe-in angle 74 between an upper vertebra 12 and a lower vertebra 18 in a spinal region. The motion includes at least one or more of flexion 270, extension 272, axial rotational motion 274 and/or lateral bending (not shown). The spinal region may include cervical, thoracic, lumbar, and/or any combination thereof. The toe-in angle may include a range of 0 degrees to 40 degrees; a range of 10 degrees to 30 degrees; a range of 10 degrees to 20 degrees; a range of 20 degrees to 40 degrees, and/or any combination thereof. Alternatively, the toe-in angle may match or substantially match the transverse pedicle angle 74, 76, 78 as shown in FIGS. 5A-5D and 26A-26D.

In another embodiment, the at least two spinal implants 94a, 94b can be positioned at a plurality of toe-in angles 74a, 74b within at least one spinal functional unit or spinal segment 276a between an upper vertebra 12 and a lower vertebra 18 on a both sides (e.g., first side and second side) of the patient as shown in FIG. 26A-26D and 27. A spinal implant 94a, 94b comprising: a first spinal implant 94a, 94b, the first spinal implant 94a, 94b comprises a first inferior element 98a, 98b and a first superior element 96a, 96b; the first superior element 96a, 96b comprises a socket 119a, 119b; the first inferior element 98a, 98b comprises a ball component 108a, 108b, the ball component 108a, 108b of the first inferior component 98a, 98b engages with the socket component 119a, 119b of the first superior component 96a, 96b to allow the first superior element 96a, 96b to move relative to the first inferior element 98a, 98b; and a second spinal implant system 94a, 94b, the second spinal implant 94a, 94b comprises a second inferior element 98a, 98b and a second superior element 96a, 96b; the second superior element 96a, 96b comprises a socket 119a, 119b; the second inferior element 98a, 98b comprises a ball component 108a, 108b, the ball component 108a, 108b of the second inferior component 98a, 98b engages with the socket 119a, 119b of the second superior component 96a, 96b to allow the second superior element 96a, 96b to move relative to the second inferior element 98a, 98b; the first spinal implant 94a, 94b positioned at a first toe-in angle 74a between an upper vertebra 12 and a lower vertebra 18 in a spinal region; the second spinal implant 94a, 94b positioned at a second toe-in angle 74b between the upper vertebra 12 and lower vertebra 18 in the spinal region. The motion includes at least one or more of flexion 270, extension 272, axial rotational motion 274 and/or lateral bending flexion (not shown). The spinal region may include cervical, thoracic, lumbar, and/or any combination thereof. The toe-in angle may include a range of 0 degrees to 40 degrees; a range of 10 degrees to 30 degrees; a range of 10 degrees to 20 degrees; a range of 20 degrees to 40 degrees, and/or any combination thereof. The first toe-in angle 74a may be the same as the second toe-in angle 74b. The first toe-in-angle 74a may be different compared to the second toe-in angle 74b. The first toe-in angle 74a may match or substantially match the transverse pedicle angle on a first side as shown in FIGS. 5A-5D and 26A-26D. The second toe-in angle 74a may match or substantially match the transverse pedicle angle on the second side. The first toe-in angle may match or substantially match the first transverse pedicle angle 74, 76, 78 and the second toe-in angle may match or substantially match the second transverse pedicle angle 74, 76, 78.

In another embodiment, at least two spinal implants 94a, 94b can be positioned at a plurality of toe-in angles 74a, 74b within two or more spinal functional units or spinal segments 276a between a plurality of upper vertebras and a plurality of lower vertebras on a plurality of two sides (e.g., first and second sides) of the patient. However, when deploying implants in different spinal segments in different regions, the toe-in angles 74a, 74b change or affect the motion of the spinal implants 94a, 94b. As described in FIG. 4B, 5A-5D and 26A-26D, each spinal segment within different spinal regions comprises different transverse pedicle angles and/or different toe-in angles for spinal implant deployment within the first or second sides. Furthermore, each spinal segment within the same spinal regions comprises different transverse pedicle angles and/or different toe-in angles for spinal implant deployment within the first or second sides. Accordingly, even a single spinal segment, the first and second sides can comprise different transverse pedicle angles and/or toe-in angles 74a, 74b.

In one exemplary embodiment, shown in Table 1 below, the dynamic implant 94a, 94b can alter or change the motion when deployed in a variety of toe-in angulations 274, 274a, 274b in a single spinal segment 276a or multiple spinal segments 276a, 276b within one or more spinal regions. Alternatively, the dynamic implant 94a, 94b can alter or change the flexion and extension when deployed in a variety of toe-in angulations 274, 274a, 274b in a single spinal segment or multiple spinal segments. In this manner, the various dynamic spinal implants described herein can provide a desired range of motion for a treated spinal level within any spinal region, regardless of implant alignment and/or natural anatomical variation.

TABLE 1

Change in Flexion/Extension Relative to Toe-In Angle

| Toe-In Angle | Flexion angle | Extension Angle | Total Range of Motion (ROM) |
|---|---|---|---|
| 0° | 10° | 8°-10° | 18°-20° |
| 15° | 10°-10.5° | 8°-10.5° | 18°-21° |
| 20° | 10°-11° | 8°-11° | 18°-22° |
| 30° | 10°-11.5° | 7°-11.5° | 17°-23° |
| 45° | 10°-14° | 7°-14° | 17°-24° |

Figure 33:
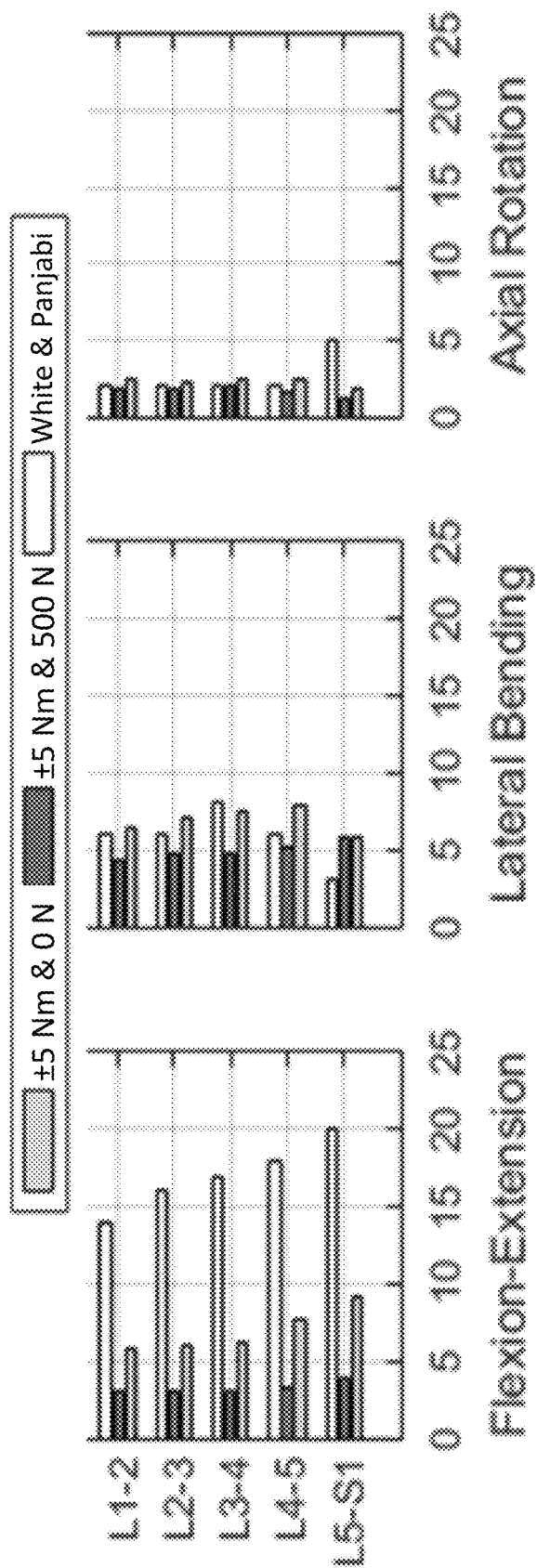
FIG. 33 depicts a portion of an illustration of lumbar total ranges of motion degrees calculated from fixed-effect models for flexion-extension, lateral bending, and axial rotation.

In another embodiment, the spinal implant 94a, 94b may match or substantially match the natural or original translational motion of a patient. Accordingly, the spinal implant 94a, 94b may match or substantially match natural or original translational motion of a patient at each spine segment or level within a spine region. The spine regions may comprise cervical, thoracic, and/or lumbar regions. The spine segments may include cervical (C0-C7), thoracic (T1-T12), and lumbar (L1-L5). The spine's natural or original translation of motion comprises flexion, extension, lateral bending, axial rotation. FIG. 33 only highlights a portion of the illustration of lumbar total ranges of motion (°) calculated from fixed-effect models for flexion-extension, lateral bending, and axial rotation, by level, with applied moments of ±5 Nm and compressive loads of 0 and 500 N compared to data reported by White and Panjabi (1978) as evidenced in the article by Zhang et al., *Moment-Rotation Behavior of Intervertebral Joints in Flexion-Extension, Lateral Bending, and Axial Rotation at all levels of the Human Spine: A Structured Review and Meta-Regres-*

*sion Analysis*, J. Biomech (Feb. 13, 2020), which is herein incorporated by reference in its entirety. The remaining regions, cervical and thoracic, can be referenced within the article.

In another embodiment, a spinal implant 94a, 94b comprising: a first plurality of spinal implants 94a, 94b, each of the first plurality spinal implants 94a, 94b comprises a first inferior element 98a, 98b and a first superior element 96a, 96b; the first superior element 96a, 96b comprises a socket 119a, 119b; the first inferior element 98a, 98b comprises a ball component 108a, 108b, the ball component 108a, 108b of the first inferior component 98a, 98b engages with the socket of the first superior component 96a, 96b to allow the first superior element 96a, 96b to move relative to the first inferior element 98a, 98b; and a second plurality of spinal implant systems 94a, 94b, each of the second plurality of spinal implants 94a, 94b comprises a second inferior element 98a, 98b and a second superior element 96a, 96b; the second superior element comprises a socket 119a, 119b; the second inferior element 98a, 98b comprises a ball component 108a, 108b, the ball component 108a, 108b of the second inferior component 98a, 98b engages with the socket 119a, 119b of the second superior component 96a, 96b to allow the second superior element 96a, 96b to move relative to the second inferior element 98a, 98b; the first plurality of spinal implants 94a, 94b positioned at a first plurality of toe-in angles 274, 274a, 274b between a first spinal segment, the spinal segment includes an first upper vertebra and a first lower vertebra in a first spinal region; the second plurality of spinal implants 94a, 94b positioned at a second plurality of toe-in angles 274, 274a, 274b between a second spinal segment, the second spinal segment includes a second upper vertebra and second lower vertebra in a second spinal region. The first and second motions may include at least one or more of flexion 270, extension 272, axial rotational motion 274 and/or lateral bending (not shown). The spinal region may include cervical, thoracic, lumbar, and/or any combination thereof. The first spinal region may be the same as the second spinal region. The first spinal region may be different than the second spinal region.

The first plurality and second plurality of toe-in angles 274, 274a, 274b and/or each of the first plurality and each of the second plurality of toe-in angles 274, 274a, 274b may include a range of 0 degrees to 40 degrees; a range of 10 degrees to 30 degrees; a range of 10 degrees to 20 degrees; a range of 20 degrees to 40 degrees, and/or any combination thereof. The first plurality of toe-in angle may be the same as the second plurality of toe-in angles 274, 274a, 274b. The first plurality of toe-in-angles 274, 274a, 274b may be different as the second plurality of toe-in angles 274, 274a, 274b. Each of the first plurality of toe-in angles 274, 274a, 274b may be the same or different. Each of the second plurality of toe-in angles 274, 274a, 274b may be the same or different. The first plurality of toe-in angles 274, 274a, 274b or each of the first plurality of toe-in angles 274, 274a, 274b may match or substantially match the transverse pedicle angles of the first and/or second sides in the first spinal segment. The second plurality of toe-in angles 274, 274a, 274b and/or each of the second plurality of toe-in angles 274, 274a, 274b may match or substantially match the second transverse pedicle angle of the first and/or second sides in the second spinal segment. The first spinal segment may be the same as the second spinal segment. The first spinal segment may be different than the second spinal segment. The first motion of the first plurality of spinal implants may be the same as the motion of the second spinal implant. The first motion of the first plurality of spinal implants may be different as the second motion of the second plurality of spinal implants.

With reference to FIGS. 28A-28B, 30A-30D, 31, 32A-32D, the change in orientation plane 284 of the spinal implant 94a, 94b results in and/or correlates to a lordosis correction or correction of sagittal imbalance. For example, a spinal implant 94a, 94b positioned below the endplate plate plane 282 and having a lordotic or sagittal orientation angle or orientation plane 284 that is not parallel to the endplate plane 282 creates and/or correlates to a lordotic correction. More specifically, a spinal implant 94a, 94b positioned below the endplate plate and having a lordotic or sagittal orientation angle or orientation plane of 4 degrees that is not parallel to the endplate plane creates and/or correlates to a lordotic correction of 14 degrees.

Because of various anatomical differences between spinal levels or segments, some spinal segments will typically require and/or accommodate a greater degree of osteotomy correction than others. For example, at the L1/L2 level, an osteotomy angle $\alpha$ of up to 10 degrees (i.e., a correction of from zero to 10 degrees) might be accomplished on one or both sides of a treated lower vertebral body, while retaining sufficient pedicular structure underneath the implant to maintain adequate implant support. At the L2/L3 level, an osteotomy angle $\alpha$ of up to 15 degrees (i.e., a correction of from zero to 15 degrees) might be accomplished on one or both sides of a treated lower vertebral body, while retaining sufficient pedicular structure underneath the implant to maintain adequate implant support. At the L3/L4 level, an osteotomy angle $\alpha$ of up to 20 degrees (i.e., a correction of from zero to 20 degrees) might be accomplished on one or both sides of a treated lower vertebral body, while retaining sufficient pedicular structure underneath the implant to maintain adequate implant support. At the L4/L5 level, an osteotomy angle $\alpha$ of up to 25 degrees (i.e., a correction of from zero to 25 degrees) might be accomplished on one or both sides of a treated lower vertebral body, while retaining sufficient pedicular structure underneath the implant to maintain adequate implant support. At the L5/S1 level, an osteotomy angle $\alpha$ of up to 30 degrees (i.e., a correction of from zero to 30 degrees) might be accomplished on one or both sides of a treated lower vertebral body, while retaining sufficient pedicular structure underneath the implant to maintain adequate implant support. Such a significant degree of surgical correction in a procedure utilizing a motion preserving implant is heretofore unheard of in spinal surgery, and such dramatic corrections are even infrequent using fusion implants and/or during other corrective surgeries.

In another embodiment, the at least two spinal implants 94a, 94b can be positioned at a plurality of toe-in angles 74a, 74b and a plurality of resected planes, plurality of orientations and/or orientation planes 284 within at least one spinal functional unit or spinal segment 276a between an upper vertebra 12 and a lower vertebra 18 on both sides (e.g., first side and second side) of the patient in one or more spinal regions. A spinal implant system comprising: a first spinal implant 94a, 94b, the first spinal implant 94a, 94b comprises a first inferior element 98a, 98b and a first superior element 96a, 96b; the first superior element 98a, 98b comprises a socket 119a, 119b; the first inferior element 98a, 98b comprises a ball component 108a, 108b, the ball component 108a, 108b of the first inferior component 98a, 98b engages with the socket 119a, 119b of the first superior component 98a, 98b to allow the first superior element 96a, 96b to move relative to the first inferior element 98a, 98b; and a second spinal implant 94*a*, 94*b*, the second spinal implant 94*a*, 94*b* comprises a second inferior element 98*a*, 98*b* and a second superior element 98*a*, 98*b*; the second superior element 98*a*, 98*b* comprises a socket 119*a*, 119*b*; the second inferior element 98*a*, 98*b* comprises a ball component 108*a*, 108*b*, the ball component 108*a*, 108*b* of the second inferior element 98*a*, 98*b* engages with the socket 119*a*, 119*b* of the second superior element 98*a*, 98*b* to allow the second superior element 98*a*, 98*b* to include a second motion relative to the second inferior element 98*a*, 98*b*; the first spinal implant 94*a* positioned at a first toe-in angle 74*a* and an first orientation plane or resected plane 284 in a spinal segment on a first side, the spinal segment between an upper vertebra 12 and a lower vertebra 18 in a spinal region; the second spinal implant 94*a*, 94*b* positioned at a second toe-in angle 74*b* and second orientation plane or resected plane 284 between the upper vertebra 12 and lower vertebra 18 in the spinal region on a second side.

The first and second side comprise a right and left side. The motion includes at least one or more of flexion 270, extension 272, axial rotational motion 274 and/or lateral bending (not shown). The spinal region may include cervical, thoracic, lumbar, and/or any combination thereof. The first toe-in angle 74*a* may be the same as the second toe-in angle 74*b*. The first toe-in-angle 74*a* may be different compared to the second toe-in angle 74*b*. The first toe-in angle 74*a* may match or substantially match the transverse pedicle angle on a first side. The second toe-in angle 74*a* may match or substantially match the transverse pedicle angle on the second side. The first toe-in angle may match or substantially match the first transverse pedicle angle and the second toe-in angle may match or substantially match the second transverse pedicle angle. The toe-in angle 74*a*, 74*b* may include a range of 0 degrees to 40 degrees; a range of 10 degrees to 30 degrees; a range of 10 degrees to 20 degrees; a range of 20 degrees to 40 degrees, and/or any combination thereof.

The first orientation plane or resected plane may be the same as the second orientation plane or resected plane. The first orientation or resected plane may be different than the second orientation or resected plane. The first and/or second orientation or resected plane 284 be parallel to the endplate or anatomical plane 282. The first and/or the second orientation or resected plane 284 may be below the endplate or anatomical plane 282. The first and/or the second orientation or resected plane 284 may be below and parallel to the endplate or anatomical plane 282. The first and/or the second orientation or resected plane 284 may be below and parallel to the endplate or anatomical plane 282, which a portion of the inferior element 98*a*, 98*b* contacts cancellous 286 and/or cortical bone 288. The first and/or second orientation or resected plane is at 0 degrees; the orientation or resected plane may comprise a range of −20 degrees to 20 degrees; the orientation or resected plane may comprise a range of −10 degrees to 10 degrees; the orientation or resected plane may comprise a range of −5 degrees to 5 degrees. The orientation or resected plane may match or substantially match a lordotic angle and/or sagittal angle. The orientation or resected plane may match or substantially match a scoliosis angle and/or a coronal angle.

In one embodiment, the dynamic spinal implant 94*a*, 94*b* may be deployed within at least one spinal functional unit or spinal segment 276*a* between an upper vertebra 12 and a lower vertebra 18 on a first side of the patient in revised resected plane or implant orientation angle 284 parallel to the anatomical line or plane 282 as shown in FIGS. 26A-26B and 27A-27D. The resected plane or orientation angle 284 may be at the same plane as the endplate or anatomical plane 282. The resected plane 284 may be at a plane below the endplate or anatomical plane 284 as shown in the generalized sagittal cross-sectional view in FIG. 27B and the generalized posterior cross-sectional view in FIG. 27D. Alternatively, the spinal implant 94*a*, 94*b* may be deployed within at least one spinal functional unit or spinal segment 276*a* between an upper vertebra 12 and a lower vertebra 18 on a first side of the patient in deployment resected plane or implant orientation angle 284 that is not parallel and/or is oblique to the endplate or anatomical plane 282 as shown in FIGS. 26A-26B and 27A-27D. The resected plane or orientation angle 284 may be not parallel and/or oblique to the endplate or anatomical plane 282. The resected plane 284 may be at a plane below the endplate or anatomical plane 284 as shown in the generalized sagittal cross-sectional view in FIG. 28C. The resected plane 284 may be at a plane below the endplate or anatomical plane 284 and not parallel or oblique to the endplate or anatomical plane 282 as shown in the generalized sagittal cross-sectional view in FIG. 28C.

In one embodiment, the spinal implant 94*a*, 94*b* comprising: an inferior element 98*a*, 98*b* and a superior element 96*a*, 96*b*; the superior element 96*a*, 96*b* comprises a socket 119*a*, 119*b*; the inferior element 98*a*, 98*b* comprises a ball component 108*a*, 108*b*, the ball component 108*a*, 108*b* of the inferior component 98*a*, 98*b* engages with the socket 119*a*, 119*b* of the superior element 96*a*, 96*b* to allow the superior element 96*a*, 96*b* to include a motion relative to the inferior element 98*a*, 98*b*; the spinal implant 94*a*, 94*b* positioned at a toe-in angle 274 and at an orientation or resected plane 284 between an a single spinal segment of an upper vertebra 12 and a lower vertebra 18 in a spinal region.

The motion includes at least one or more of flexion 270, extension 272, axial rotational motion 274 and/or lateral bending (not shown). The spinal region may include cervical, thoracic, lumbar, and/or any combination thereof. The toe-in angle 274 may include a range of 0 degrees to 40 degrees; a range of 10 degrees to 30 degrees; a range of 10 degrees to 20 degrees; a range of 20 degrees to 40 degrees, and/or any combination thereof. Alternatively, the toe-in angle 274 may match or substantially match the transverse pedicle angle.

The orientation or resected plane 284 be parallel or not parallel to the endplate or anatomical plane 282. The orientation or resected plane 284 may be below the endplate or anatomical plane 282. The orientation or resected plane 284 may be below and parallel to the endplate or anatomical plane 282. The orientation or resected plane 284 may be below and not parallel and/or oblique to the endplate or anatomical plane 282. The orientation or resected plane 284 may be below and parallel to the endplate or anatomical plane 282, which a portion of the inferior element 98*a*, 98*b* contacts cancellous 286 and/or cortical bone 288. The orientation or resected plane 284 may be below and not parallel to the endplate or anatomical plane 282, which a portion of the inferior element 98*a*, 98*b* contacts cancellous 286 and/or cortical bone 288. The orientation plane or orientation angle is at 0 degrees; the orientation plane or orientation angle may comprise a range of −20 degrees to 20 degrees; the orientation plane or orientation angle may comprise a range of −10 degrees to 10 degrees; the orientation plane or orientation angle may comprise a range of −5 degrees to 5 degrees. The orientation plane or orientation angle may match or substantially match a lordotic angle and/or sagittal angle. The orientation plane or orientation angle may match or substantially match a scoliosis angle and/or a coronal angle.

With reference to 6A-6B and 27, the spinal implant 94*a*, 94*b* can support three (3) columns of each one or more spine segments. In one embodiment, a spinal implant system comprising: a first spinal implant 94*a*, 94*b*, the first spinal implant 94*a*, 94*b* comprises a first implant length, a first inferior element 98*a*, 98*b* and a first superior element 96*a*, 96*b*; the first superior element 96*a*, 96*b* comprises a socket 119*a*, 119*b*; the first inferior element 98*a*, 98*b* comprises a ball component 108*a*, 108*b*, the ball component 108*a*, 108*b* of the first inferior component 98*a*, 98*b* engages with the socket 119*a*, 119*b* of the first superior component 96*a*, 96*b* to allow the first superior element 96*a*, 96*b* to move relative to the first inferior element 98*a*, 98*b*; and a second spinal implant 94*a*, 94*b*, the second spinal implant 94*b* comprises a second implant length, a second inferior element 98*a*, 98*b* and a second superior element 96*a*, 96*b*; the second superior element 96*a*, 96*b* comprises a socket 119*a*, 119*b*; the second inferior element 98*a*, 98*b* comprises a ball component 108*a*, 108*b*, the ball component 108*a*, 108*b* of the second inferior component 98*a*, 98*b* engages with the socket 119*a*, 119*b* of the second superior element 96*a*, 96*b* to allow the second superior element 96*a*, 96*b* to move or have motion relative to the second inferior element 98*a*, 98*b*; the first spinal implant system 94*a*, 94*b* disposed between a spinal segment and/or a first vertebra and a second vertebra at a first orientation in a spinal region, at least a portion of the first spinal implant 94*a*, 94*b* is disposed, extends or contacts within each of the three columns 88, 90, 92 of the spinal segment; the second spinal implant 94*a*, 94*b* disposed between the spinal segment and/or a first vertebra and the second vertebra at a second orientation within a spinal region, at least a portion of the second spinal implant 94*b* extends or contacts within each of the three columns 88, 90, 92 of the spinal segment.

The first and second motion or movements may include at least one or more of flexion 270, extension 272, axial rotational motion 274 and/or lateral bending (not shown). The spinal region may include cervical, thoracic, lumbar, and/or any combination thereof. The three columns of the spine comprise an anterior column 88, a middle column 90, and a posterior column 92. The first orientation may be the same as the second orientation. The first orientation may be different than the first orientation. The first and/or second orientation may comprise a toe-in angle, a sagittal angle, a coronal angle and/or any combination thereof. The first toe-in angle 74*a* may be the same as the second toe-in angle 74*b*. The first toe-in-angle 74*a* may be different than the second toe-in angle 74*b*. The first toe-in angle 74*a* may match or substantially match the transverse pedicle angle on a first side as shown in FIGS. 5A-5D. The second toe-in angle 74*a* may match or substantially match the transverse pedicle angle on the second side. The first toe-in angle may match or substantially match the first transverse pedicle angle and the second toe-in angle may match or substantially match the second transverse pedicle angle.

Once the spinal implant 94*a*, 94*b* is deployed into the one or more spinal segments within one or more spinal regions, the dynamic spinal implant 94*a*, 94*b* may replace or supplement a normal, damaged, degenerated and/or removed facet joint and intervertebral disc. Alternatively, the spinal implant 94*a*, 94*b* may replace or supplement a portion of a normal, damaged, degenerated and/or removed facet joint and intervertebral disc. The spinal implant 94*a*, 94*b* can facilitate replacement of the intervertebral disc by having the superior articulating component 106*a*, 106*b* contacting and engaging the inferior articulating component 108*a*, 108*b* to allow the superior articulating component 106*a*, 106*b* to move relative to the inferior articulating component 108*a*, 108*b*.

With reference to FIGS. 22A-22B and 23A-23B, the spinal implant 94*a*, 94*b* allows for replacement of at least one facet and the intervertebral disc. The facet joints comprise the inferior and superior articular processes, which are bony protuberances that arise vertically from the junction of pedicles and laminae behind the transverse processes. Furthermore, the facet joint has a capsule. The capsule consists of an outer layer made of densely packed parallel bundles of collagen fibers and an inner layer of irregularly oriented wavy elastic fibers that act like "rubber band" to coordinate movements within a spinal segment of a spinal region. The facet and the facet joints help guide and stabilize each spine segment, as well as help the spine to bend, twist, and extend in different directions. Although these joints enable movement, they also restrict excessive movement such as hyperextension and hyperflexion (i.e. whiplash).

Traditionally, during flexion 270 of the spine, the superior vertebral body may slide slightly anteriorly, tilting forward and compressing the anterior portions of the intervertebral discs. This simultaneously causes the inferior articular surface of the superior vertebra to move superiorly and anteriorly relative to the superior articular surface of the inferior vertebra, similar to a seesaw movement. The result is a posterior widening of the facet joint causing tension of the joint capsule of the facet joint to limit flexion 270. Since some or all of the facet joint is likely to be removed by the surgical procedure associated with the present spinal implant 94*a*, 94*b*, this traditional restraint obtained by the facet joint capsule and related structures will be reduced and/or missing and will be replaced by with one or more spinal implants 94*a*, 94*b*.

In a similar manner, during extension of the spine, opposite actions typically occur. The superior vertebral body slides posteriorly, tilts backwards and compresses the posterior portion of the intervertebral discs. The inferior articular surface moves posteriorly and inferiorly, widening the anterior part of the facet joint. Extension is limited by tension of the anterior longitudinal ligament (ALL), impaction of the posterior vertebral processes and tone of the anterior neck (cervical spine only) and anterior abdominal muscles (thoracic spine only). As described above, some or all of the facet joint capsule and/or related facet structures are likely to be removed during the implantation procedure, and thus the traditional motion restraints provided by the facet joint would be reduced or not available.

The intervertebral discs are flat, round "cushions" that act as shock absorbers between each vertebra in your spine in all spine regions. Each disc has a strong outer ring of fibers called the annulus, and a soft, jelly-like center called the nucleus pulposus. The annulus is the disc's outer layer and the strongest area of the disc. It also helps keep the disc's center intact. The annulus is a strong ligament that connects each vertebra together. The mushy nucleus of the disc serves as the main shock absorber.

In one embodiment, a spinal implant system that replaces the intervertebral disc and/or the facets comprises: The spinal implant 94*a*, 94*b* can include an upper or superior element 96*a*, 96*b* and a lower or inferior element 98*a*, 98*b*. The upper or superior element 96*a*, 96*b* desirably includes a posterior wall or posterior tab 112*a*, 112*b*, an upper keel 104*a*, 104*b*, and an superior articulation component 106*a*, 106*b* that includes an superior articulation surface 168*a*, 168*b* and a superior articulation component material, which may be smooth, concave, and/or generally spherical in shape. The lower or inferior element 98*a*, 98*b* can include lower keel 104*a*', 104*b*', a first stop 180*a*, 180*b*, a second stop 178*a*, 178*b*, a bridge 174*a*, 174, an inferior articulation component 108*a*, 108*b* that includes an inferior articulation component material an inferior an articulation surface 228*a*, 228*b*, which may be smooth, convex, and/or generally spherical in shape.

In one embodiment, the spinal implant 94*a*, 94*b* may behave the same or substantially the same as the intravertebral disc by having substantially similar mechanical properties. The inferior articulation component material comprises a metal, the superior articulation component comprises a polymer. The metal comprises Cobalt Chrome (CoCr) and/or Titanium. The polymer may comprise ultrahigh weight molecular polyethylene (UHWMPE). The polymer may comprise an antioxidant. The antioxidant includes Vitamin E. The vitamin E and the polymer has a low frictional resistance and improves or enhances fatigue, wear and impact resistance, making it to be an ideal bearing surface for implants. As assembled, the superior articulation component articulation surface 168*a*, 168*b* of the superior element 96*a*, 96*b* may engage the articulation surface 168*a*, 168*b* of the inferior element 98*a*, 98*b* to produce a ball-and-socket style articulation joint that allows shock absorption and motion or movement of the superior element 96*a*, 96*b* relative to the inferior element 98*a*, 98*b*. The superior articulation component comprising a polymer and Vitamin E contacts and/or engages with the inferior articulation component comprising a metal for the superior articulation component to behave like a shock absorber and/or shock vibration absorber during the movement or motion of the spine. The polymer may also allow some deformation and elasticity acting or behaving like the nucleus and the annulus.

In another embodiment, the spinal implant 94*a*, 94*b* comprises two different materials for the superior element 96*a*, 96*b* and the inferior element 98*a*, 98*b*. The superior element 96*a*, 96*b* comprises a superior articulation component 106*a*, 106*b* that comprises a first material, and the inferior element 96*a*, 96*b* comprises an inferior articulation component 108*a*, 108*b* that further comprises a second material. The first material of the superior articulation component 106*a*, 106*b* may be different than the second material of the inferior articulation component. The first material of the superior articulation component 106*a*, 106*b* may be the same than the second material of the inferior articulation component.

In one embodiment, the spinal implant 94*a*, 94*b* may behave the same or substantially the same as the facet joint by limiting or restricting anterior migration or sliding. The posterior wall or posterior tab 112*a*, 112*b* of the superior element 96*a*, 96*b* during the movement or motion helps restrict unnecessary motion. At least a portion of the posterior wall or posterior tab 112*a*, 112*b* contacts a posterior surface of the superior vertebra to prevent or restrict anterior migration or sliding. Accordingly, at least a portion of the anterior facing surface of the posterior wall or posterior tab 112*a*, 112*b* contacts the apophyseal ring of the superior vertebra to prevent anterior migration or sliding.

In another embodiment, the spinal implant 94*a*, 94*b* may behave the same or substantially the same as the facet joint by limiting or restricting shear loading. The upper keel 104*a*, 104*b* and the lower keel 104*a*', 104*b*' are inserted into keel channels within the upper and lower vertebra to allow the top surface of the superior element 96*a*, 96*b* and the bottom surface of the inferior element 98*a*, 98*b* to contact cancellous or cortical bone. This prevents and/or restricts the superior element 96*a*, 96*b* and the inferior element 98*a*, 98*b* from being damaged by any shear loading on the spine. The upper keel 104*a*, 104*b* and the lower keel 104*a*', 104*b*' may also help limit or restrict axial rotation.

In another embodiment, the spinal implant 94*a*, 94*b* may behave the same or substantially the same as the facet joint and/or the ALL by limiting or restricting flexion and extension. The first stop 180*a*, 180*b* and the second stop 178*a*, 178*b* also help guide or restrict motion or movement in flexion or extension and/or axial rotation. The first stop 180*a*, 180*b* is configured to behave the same or substantially the same as the facet joint capsule, and the second stop is configured to behave the same or substantially the same as the anterior longitudinal ligament and/or the facet joint capsule. As the superior articulation component articulation surface 168*a*, 168*b* of the superior element 96*a*, 96*b* may engage the articulation surface 168*a*, 168*b* of the inferior element 98*a*, 98*b*, the superior element 96*a*, 96*b* moves or has motion relative to the inferior element 98*a*, 98*b*, which the first stop 180*a*, 180 restricts the flexion motion, and the second stop 178*a*, 178*b* restricts the extension motion from over exertion and potential damage to the implant and/or the spine.

At least a portion of the superior element 96*a*, 96*b* may come into respective contact with a portion of the first stop 180*a*, 180*b* and the second stop 178*a*, 178*b* to serve as a positive stop or motion limiter. Alternatively, the flexion 270 and extension 272 between the superior element 96*a*, 96*b* and the inferior element 98*a*, 98*b* will desirably provide at least 10 degrees or greater of flexion and at least 10 degrees or greater of extension when contacting the first stop 180*a*, 180*b* and the second stop 178*a*, 278*b*. In another embodiment, at least a portion of the articulation component 106*a*, 106*b* on the anterior or posterior ends contacts a portion of the first stop 180*a*, 180*b* during flexion 270 and contacts at least a portion of the second stop 178*a*, 178*b* during extension 272. In another embodiment, at least a portion of the articulation component 106*a*, 106*b* on the anterior end contacts a portion of the first stop 180*a*, 180*b* during flexion 270 and at least a portion of the anterior component contacts the second stop 178*a*, 178*b* during extension 272.

In another embodiment, the spinal implant 94*a*, 94*b* may behave the same or substantially the same as the facet joint and/or the intervertebral disc by limiting or restricting axial rotation 274. The axial rotation occurs when the superior element rotates towards the medial and/or lateral direction in the flexion 270 motion and/or in the extension 272 motion. Traditionally, during axial rotation, the inferior process of the superior vertebra slides laterally and externally relative to the superior process of the inferior vertebra. This causes the vertebral bodies to rotate relative to one another around a shared axis. The intervening intervertebral disc is simultaneously twisted, an action that pulls the vertebra closer together, which may also engage the facet joint capsule. The facet joint capsule will be stretched or twisted in a direction parallel to the rotation causing or limiting rotation because the elasticity of facet joint capsule wants to return to original unloaded or neutral position (pulling or returning rotation to neutral).

The spinal implant 94*a*, 94*b* may also restrict axial rotation the first stop 180*a*, 180*b*, the second stop 178*a*, 178*b*, and/or truncated surfaces or surfaces 230*a*, 230*a*', 230*b*, 230*b*' of the inferior element 98*a*, 98*b*, as well as the first anterior facing wall 164*a*, 164*b* and a second posterior facing wall 164*a*', 164*b*' of the socket 119*a*, 119*b*. As the superior element 96*a*, 96*b* axially rotates relative to the inferior element 98*a*, 98*b*, the superior element first top surface 158*a*, 158*b* of the superior articulation component 106a, 106b contacts or engages with a portion of the first stop 180a, 180b of the inferior element 98a, 98b, at least a portion the superior element first anterior facing wall 164a, 164b contacts and engages the first wall 184a, 184b of the first stop 180a, 180b and at least a portion of the superior element second posterior facing wall 164a', 164b' contacts and engages the third wall 186a, 186b of the second stop 180a, 180b.

The axial rotation 274 may include an angle range of 0 degrees to 50 degrees; the angle may include 0 to 40 degrees; the range may include 0 to 25 degrees; the range may comprise 0 degrees to 5 degrees; the range may comprise 5 degrees to 10 degrees. Alternatively, the axial rotation may include an angle of at least 1 degree or greater; the angle of at least 3 degrees or greater; and/or the angle of at least 5 degrees or greater. The degree of axial rotation 274 may be different in each region of the spine, the regions are lumbar, thoracic and cervical. The axial rotation within the lumbar region may comprise 0 to 5 degrees; the axial rotation within the thoracic region may comprise 0 to 40 degrees; the axial rotation within the cervical region may comprise 0 to 60 degrees.

In another embodiment, the spinal implant 94a, 94b may behave the same or substantially the same as the facet joint to restrict lateral or bilateral flexion. The bilateral flexion comprises right lateral flexion and left lateral flexion. Traditionally, when the vertebral column is flexed laterally to the right, the right sided (ipsilateral) articular processes extend, while the left sided (contralateral) articular processes flex at the facet joints. The right inferior articular process of the superior vertebra glides inferiorly and posteriorly relative to the superior articular process of the inferior vertebra. Simultaneously, the right side of the intervertebral disc is compressed, while the left side is stretched. Then, during contralateral flexion of the vertebral column to the left, the opposite occurs; the left facet joints extend and the right one's flex. More specifically, the bilateral flexion is limited by the joint capsule of the facet joints, compression of the intervertebral discs, impaction of the articular processes and tension of other muscles and ligaments.

As described above, the facet joint is likely to be removed by the procedure of the spinal dynamic implant 94a, 94b, the traditional restraint obtained by the facet joint would not be available. However, the first stop 180a, 180b, the second stop 178a, 178b and/or truncated surfaces or surfaces 230a, 230a', 230b, 230b' of the inferior element 98a, 98b serves as the bilateral flexion limiter or restraint in place or substituting the facet joint. Bilateral flexion comprises an angle, the bilateral flexion angle includes 0 degrees to 60 degrees; the bilateral flexion angle includes 0 degrees to 30 degrees; the bilateral flexion angle includes 0 to 45 degrees. The degree of bilateral flexion may be different in each region of the spine, the regions are lumbar, thoracic and cervical. The bilateral flexion within the lumbar region may comprise 0 to 30 degrees; the bilateral flexion within the thoracic region may comprise 0 to 30 degrees; the bilateral flexion within the cervical region may comprise 0 to 45 degrees.

Equivalents

The invention may be embodied in other specific forms without departing from the spirit or essential characteristics thereof. The foregoing embodiments are therefore to be considered in all respects illustrative rather than limiting on the invention described herein. Scope of the invention is thus intended to include all changes that come within the meaning and range of equivalency of the descriptions provided herein.

Many of the aspects and advantages of the present invention may be more clearly understood and appreciated by reference to the accompanying drawings. The accompanying drawings are incorporated herein and form a part of the specification, illustrating embodiments of the present invention and together with the description, disclose the principles of the invention.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the disclosure herein. What have been described above are examples of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications and variations that fall within the spirit and scope of the appended claims.

Exemplary Embodiments

Claim 1. A motion preserving spinal implant system comprising: an upper element; the upper element comprises a base and a first articulating component, the base including a material, at least a portion of the first articulating component coupled to the base, the first articulating component comprising a material, a top surface and a bottom surface, the bottom surface including a socket, the socket is centrally positioned or located, the socket extending above or away from the bottom surface of the first articulating component, a length of the socket is less than a length of the bottom surface; the lower element, the lower element comprises a base, a second articulating component, and a bridge, the base comprising a first stop and a second stop, the second articulating component is disposed between the first stop and the second stop, the second articulating component comprises a ball joint, the ball joint is sized and configured to be disposed within the socket of the first articulating component of the upper element, the bridge extends away from a posterior surface of the base, the base comprising a screw housing, the screw housing including a third stop and a base, the third stop is spaced apart from the base creating a channel; the screw housing including a threaded through hole, the through-hole positioned in an oblique orientation; the ball joint of the second articulating component reciprocally engages with the socket of the first articulating component to allow motion of the upper element relative to the lower element; a fixation screw, the fixation screw comprising a screw body and a screw head, the fixation screw disposed within the threaded through-hole of the lower element, the screw head is positioned below or equal to a posterior surface of the screw housing, a clip; the clip comprising a body, a first flange and a second flange, the first and second flange extend perpendicular to the body, the clip disposed within the channel of the screw housing, at least a portion of the first and second flange extend into the threaded through-hole, at least a portion of the first and second flange contact a portion of the screw head to prevent migration of the fixation screw.

Claim 2. A motion preserving spinal implant system comprising: an upper element; the upper element comprises a base and a first articulating component, the base including a material, a superior surface, an inferior surface, and anterior surface, and a posterior surface, the inferior surface of the base comprises a recess, the recess is sized and configured to receive a portion of the first articulating component, at least a portion of the posterior surface extends upwardly to extend beyond the superior surface, at least a portion of the posterior surface includes a cavity extending towards the anterior surface, the first articulating component including a material, a top surface and a bottom surface, at least a portion of the articulating component being coupled within the recess of the base, at least a portion of the bottom surface of the articulating component comprising a concave cup, the concave cup extending below the bottom surface of the articulating component and/or the concave cup extending above or away from the bottom surface of the articulating component to create at least one rim edge (and/or a first rim edge and a second rim edge; a lower element; the lower element comprises a base, a bridge and a second articulating component, the base including a material, a superior surface, an inferior surface, and anterior surface, and a posterior surface, the base further including a first stop and a second stop, the first stop and the second stop are spaced apart, the superior surface of the base comprising a recess, the recess disposed between the first stop and the second stop, the first stop comprising a first contact surface and the second top comprising a second contact surface, the first and second contact surface including a sloped surface; the second articulating component comprising a convex hemispherical ball, at least a portion the second articulating component coupled or disposed within the recess, centrally located between the first stop and the second stop, the second articulating component is spaced apart from the first stop and the second stop creating a first channel and a second channel, the second articulating component of the lower element is sized and configured to be disposed within the first articulating component of the upper element; at least a portion of a top surface of the second articulating element engages with the portion of the concave cup to allow motion of the upper element relative to the lower element; a fixation screw, the fixation screw comprising a screw body and a screw head, the fixation screw disposed within the threaded through-hole, the screw head is positioned below or equal to a posterior surface of the screw housing; and a clip; the clip comprising a body, a first flange and a second flange, the first and second flange extend perpendicular to the body, the clip disposed within the channel of the screw housing, at least a portion of the first and second flange extend into the threaded through-hole, at least a portion of the first and second flange contact a portion of the screw head to prevent migration of the fixation screw.

Claim 3. The motion preserving spinal implant system of claim 1 or 2, wherein the material of the base of the upper element and the lower element comprises a metal.

Claim 4. The motion preserving spinal implant system of claim 3, wherein the metal comprises titanium or chrome-cobalt-molybdenum (CoCrMo).

Claim 5. The motion preserving spinal implant system of claim 1 or 2, wherein the material of the articulating component of the upper element comprises a plastic.

Claim 6. The motion preserving spinal implant system of claim 5, wherein the plastic is ultra-high molecular weight polyethylene (UHMWPE).

Claim 7. The motion preserving spinal implant system of 5, wherein the plastic comprises Vitamin E.

Claim 8. The motion preserving implant of claim 1 and 2, wherein the motion comprises flexion and extension.

Claim 9. The motion preserving implant of claim 1 and 2, wherein the motion comprises rotation.

Claim 10. The motion preserving implant of claim 1 and 2, wherein the motion comprises rotation, flexion and extension.

Claim 11. The motion preserving implant of claim 8 and 10, wherein flexion comprise 0 degrees to 20 degrees and extension comprises 0 degrees to 20 degrees.

Claim 12. The motion preserving implant of claim 1 or 2, wherein base of the upper element or the lower element comprises a keel.

Claim 13. The motion preserving implant of claim 1 or 2, wherein the base of the lower element and the upper element comprises a keel.

Claim 14. The motion preserving implant of claim 1 or 2, wherein at least one surface of the base of the upper element comprises a coating or texture.

Claim 15. The motion preserving implant of claim 1 or 2, wherein at least one surface of the base of the lower element comprises a coating or texture.

Claim 16. The motion preserving implant of claim 14 or 15, wherein the coating comprises metal coating, the metal coating comprises a Titanium coating.

Claim 17. The motion preserving implant of claim 14 or 15, wherein the texture comprises a roughened surface texture.

Claim 18. The motion preserving implant of claim 14 or 15, wherein the texture comprises a polish finish texture.

Claim 19. The motion preserving implant of claim 1 or 2, wherein at least one surface of the base of the upper element comprises a coating and a texture.

Claim 20. The motion preserving implant of claim 1 or 2, wherein the oblique orientation of the through-hole matches or substantially matches the sagittal pedicle angle.

Claim 21. A dynamic spinal implant system comprising: a first spinal implant system; and a second spinal implant system; each of the first and second spinal implant systems comprises a superior element, an inferior element, a clip and a fixation screw, the superior element comprises a base and a first articulating element, the first articulating element includes a top surface and a bottom surface, the bottom surface comprises a socket, the socket extends away from the bottom surface; the inferior element comprises a base, a bridge and a second articulating element; the second articulating element comprises a ball component, the bridge extends axially or longitudinally towards the posterior direction and/or in same plane, the bridge includes a screw housing, the screw housing includes a first portion and a second portion, the first portion is spaced apart from the second portion to create a channel, the channel is sized and configured to receive a clip; the screw housing further includes a threaded through-hole; the fixation screw comprising a screw body and a screw head, the fixation screw disposed within the threaded through-hole, the screw head is positioned below or equal to a posterior surface of the mount housing, the ball component is sized and configured to engage with the socket of the first articulating element making the superior element movable relative to the inferior element in a multi-axial range of motion; the first spinal implant system disposed between a first vertebra and a second vertebra at a first orientation, the second spinal implant system disposed between the first vertebra and the second vertebra at a second orientation, the fixation screw being secured to the first or second vertebra.

Claim 22. A dynamic spinal implant system comprising: a first spinal implant system; and a second spinal implant system; each of the first and second spinal implant systems comprises a superior element, an inferior element, a clip and a fixation screw, the superior element comprises a base and a first articulating component, the first articulating element includes a socket, the first articulating element coupled to the base, the inferior element comprises a base, a bridge and a second articulating component; the second articulating component comprises a ball component, the bridge extends from the base axially or longitudinally towards the posterior direction, the bridge includes a first end, a second end, and a mount housing, the mount housing includes a threaded through-hole; the fixation screw comprising a screw body and a screw head, the fixation screw disposed within the threaded through-hole, the ball component of the articulating component of the inferior element engages with the socket of the first articulating element of the superior element making the superior element movable relative to the inferior element, the first spinal implant system disposed between a first vertebra and a second vertebra at a first orientation, the second spinal implant system disposed between the first vertebra and the second vertebra at a second orientation, the fixation screw being secured to the first or second vertebra.

Claim 23. The dynamic spinal implant of claim 21 or 22, wherein the first orientation and the second orientation are the same orientations.

Claim 24. The dynamic spinal implant of claim 21 or 22, wherein the first orientation and the second orientation are different orientations.

Claim 25. The dynamic spinal implant of claim 21 or 22, wherein the first and second orientation comprises a toe-in angle or toe-out angle.

Claim 26. The dynamic spinal implant of claim 25, wherein the toe-in angles are matching or substantially matching the transverse plane pedicle angle.

Claim 27. The dynamic spinal implant of claim 21 or 22, wherein the first and second orientation comprises a coronal angle.

Claim 28. The dynamic spinal implant of claim 27, wherein the coronal angle match or substantially matches coronal realignment or balance of the segment of the spine.

Claim 29. The dynamic spinal implant of claim 21 or 22, where in the first and second orientation comprises a sagittal angle.

Claim 30. The dynamic spinal implant of claim 29, wherein the sagittal angle matches or substantially matches the sagittal realignment or balance of the segment of the spine.

Claim 31. The dynamic spinal implant of claim 21 or 22, wherein the first and second orientation comprises a toe-in angle and a coronal angle.

Claim 32. The dynamic spinal implant of claim 21 or 22, wherein the first and second orientation comprises a toe-in angle, a coronal angle and a sagittal angle.

Claim 33. The dynamic spinal implant of claim 21 or 22, wherein the bridge comprises a bridge length, the bridge length matches or substantially matches a pedicle length.

Claim 34. The dynamic spinal implant of claim 21 or 22, wherein the bridge comprises a bridge width, the bridge width matches or substantially matches a pedicle width.

Claim 35. The dynamic spinal implant of claim 21 or 22, wherein the first spinal implant system is spaced apart from the second spinal implant in the transverse plane.

Claim 36. The dynamic spinal implant of claim 25, 31 and 32, wherein the toe-in angle comprises a range between 0 to 40 degrees.

Claim 37. The dynamic spinal implant of claim 27, 31 and 32, wherein the coronal angle comprises a range between 0 and 20 degrees.

Claim 38. The dynamic spinal implant of claim 29, 31 and 32, wherein the sagittal angle comprises a range between 0 to 30 degrees.

Claim 39. The dynamic spinal implant of claim 21 or 22, wherein the base of the inferior element and the superior element comprises a keel.

Claim 40. The dynamic spinal implant of claim 21 or 22, wherein the superior element is movable relative to the inferior element comprises flexion and extension.

Claim 41. The dynamic spinal implant of claim 21 or 22, wherein the superior element is movable relative to the inferior element comprises axial rotation.

Claim 42. The dynamic spinal implant of claim 21 or 22, wherein the superior element is movable relative to the inferior element comprises flexion, extension and axial rotation.

Claim 43. The dynamic spinal implant of claim 21 or 22, wherein the first articulating component of the superior element comprises a material and the base of the superior element comprises a material, the material of the base and the material of the first articulating component are different.

Claim 44. The dynamic spinal implant of claim 43, wherein the material of the first articulating component is a plastic and the material for the base is metal.

Claim 45. The dynamic spinal implant of claim 44, wherein the plastic is UHDWMPE and the metal is CrCoMo.

Claim 46. The dynamic spinal implant of claim 21 or 22, wherein at least one surface of the base of the inferior element or at least one surface of the base of the superior element comprises a texture.

Claim 47. The dynamic spinal implant of claim 21 or 22, wherein at least one surface of the base of the inferior element and at least one surface of the base of the superior element comprises a texture.

Claim 48. The dynamic spinal implant of claim 21 or 22, wherein the first articulating component of the superior element comprises a coating, the coating includes Vitamin E.

Claim 49. A dynamic spinal implant system comprising (3 columns): a first spinal implant; and a second spinal implant; each of the first and second spinal implant comprises a superior element, an inferior element, and a fixation screw; the superior element comprises a base and a first articulating element, the first articulating element is coupled to the base, the first articulating element comprises a socket; the inferior element comprises a base, a bridge and a second articulating element; the second articulating element comprises a ball component, the second articulating element disposed onto the base, the bridge comprises a first end and a second end, the first end is attached to the base and extends from the base axially or longitudinally towards the posterior direction, the second end of the bridge includes a mounted housing, the mounted housing extends upwardly from the bridge towards the superior direction and the mounted housing includes a threaded through-hole; the fixation screw comprising a screw body and a screw head, the fixation screw disposed within the threaded through-hole, the screw head is positioned below or equal to a posterior surface of the mounted housing, the ball component is sized and configured to engage with the socket of the first articulating element making the superior element movable relative to the inferior element in a multi-axial range of motion; the first spinal implant disposed between a first vertebra and a second vertebra at a first orientation in a spinal region, the second spinal implant system disposed between the first vertebra and the second vertebra at a second orientation in the spinal region, at least a portion of the first spinal implant and at least a portion of the second spinal implant extending or contacting in each of three columns of the spine, the three columns of the spine comprise the anterior column region, the middle column region and the posterior column region.

Claim 50. A dynamic spinal implant system comprising (3 columns): a first spinal implant, the first spinal implant comprises a first length, a first inferior element and a first superior element; the first superior element comprises a socket; the first inferior element comprises a ball component, the ball component of the first inferior component engages with the socket component of the first superior component to allow the first superior element to be movable relative to the first inferior element; and a second spinal implant, the second spinal implant comprises a second length, a second inferior element and a second superior element; the second superior element comprises a socket; the second inferior element comprises a ball component, the ball component of the second inferior component engages with the socket component of the second superior component to allow the second superior element to be movable relative to the second inferior element; the first spinal implant disposed between a first vertebra and a second vertebra at a first orientation in a spinal region, at least a portion of the first spinal implant is disposed, extends or contacts within each of the three columns of the spine, the second spinal implant disposed between the first vertebra and the second vertebra at a second orientation in the spinal region, at least a portion of the second spinal implant extends or contacts within each of the three columns of the spine.

Claim 51. A multi-level dynamic spinal implant system comprising: a first spinal implant, the first spinal implant comprises a first length, a first inferior element and a first superior element; the first superior element comprises a socket; the first inferior element comprises a ball component, the ball component of the first inferior component engages with the socket component of the first superior component to allow the first superior element to have a first motion relative to the first inferior element; and a second spinal implant, the second spinal implant comprises a second length, a second inferior element and a second superior element; the second superior element comprises a socket; the second inferior element comprises a ball component, the ball component of the second inferior component engages with the socket component of the second superior component to allow the second superior element to have a second motion relative to the second inferior element; the first spinal implant positioned into a first spinal segment or unit and a first toe-in angle in a first spinal region; the second spinal implant positioned into a second spinal segment and a second toe-in angle in a second spinal region.

Claim 52. The multi-level dynamic spinal implant system of claim 51, wherein the first toe-in angle of the first spinal implant is different than the second toe-in angle of the second spinal implant.

Claim 53. The multi-level dynamic spinal implant system of claim 51, wherein the first toe-in angle or the second toe-in angle matches or substantially matches the transverse pedicle angle.

Claim 54. The multi-level dynamic spinal implant system of claim 51, wherein the first motion of the first spinal implant is different than the second motion of the second spinal implant.

Claim 55. The multi-level dynamic spinal implant system of claim 51, wherein the first vertebral level is immediately adjacent to the second vertebral level.

Claim 56. The multi-level dynamic spinal implant system of claim 51, wherein the first vertebral level is not immediate adjacent to the second vertebral level (there is an intermediate vertebral level).

Claim 57. The multi-level dynamic spinal implant system of claim 52, wherein the first toe-in angle being different than the second-toe in angle causes the first motion to be different than the second motion.

Claim 58. The multi-level dynamic spinal implant system of claim 52, wherein the first toe-in angle being different than the second-toe in angle causes the first motion to be larger than the second motion.

Claim 59. The multi-level dynamic spinal implant system of claim 52, wherein the first toe-in angle being different than the second-toe in angle causes the first motion to be smaller than the second motion.

Claim 60. The multi-level dynamic spinal implant system of claim 51, wherein the first motion or a second motion comprises flexion and extension.

Claim 61. The multi-level dynamic spinal implant system of claim 51, wherein the first motion or second motion comprises rotation.

Claim 62. The multi-level dynamic spinal implant system of claim 51, wherein the first motion or the second motion comprises flexion, extension, lateral bending and rotation.

Claim 63. The multi-level dynamic spinal implant system of claim 60 and 62, wherein the flexion comprises a range of 0 to 20 degrees and the extension comprises a range of 0 to 20 degrees.

Claim 64. A total joint spinal implant system comprising: an upper element, the upper element comprises an upper base and an upper articulation component, the upper base comprising a first material, at least a portion of the superior articulation component coupled to the upper base, the upper articulation component comprising socket and a second material, the upper articulation surface includes a concave shape; and a lower element, the lower element comprises an lower base, an lower articulation component and a bridge, the lower base comprising a third material, a first stop and a second stop, the lower articulation component comprising ball and a fourth material, the lower articulation component disposed onto the base and between the first stop and the second stop, the bridge extends from a posterior end of the lower base; the socket of upper articulation component of the upper element engages with the ball of the lower articulation component of the lower element to allow movement.

Claim 65. The total joint spinal implant system of claim 64, wherein the first material of the upper base comprises a different material compared to the second material of the upper articulation component.

Claim 66. The total joint spinal implant system of claim 64, wherein the first material of the upper base comprises a same material compared to the second material of the upper articulation component.

Claim 67. The total joint spinal implant system of claim 64, wherein the first material of the upper base comprises a metal and the second material of the upper articulation component comprises a polymer material.

Claim 68. The total joint spinal implant system of claim 67, wherein the metal comprises Cobalt Chrome Molybdenum (CoCrMo) and the polymer comprises ultra-high molecular weight polyethylene (UHMWPE).

Claim 69. The total joint spinal implant system of claim 68, wherein the UHMWPE comprises cross-linked UHMWPE.

Claim 70. The total joint spinal implant system of claim 68, wherein the UHMWPE comprises double cross-linked UHMWPE.

Claim 71. The total joint spinal implant system of claim 69 and 70, wherein the cross-linked UHMWPE or the double cross-linked UHMWPE comprises a vitamin E.

Claim 72. The total joint spinal implant system of claim 64, wherein the lower base of the lower element further comprises a coating, the coating includes a metal coating.

Claim 73. The total joint spinal implant system of claim 72, wherein the metal coating comprises titanium (Ti).

Claim 74. The total joint spinal implant system of claim 64, wherein the third material of the lower base and the fourth material of the lower articulation component comprises a same material.

Claim 75. The total joint spinal implant system of claim 64, wherein the third material of the lower base and the fourth material of the lower articulation component comprises a different material.

Claim 76. The total joint spinal implant system of claim 74, wherein the same material comprises a metal.

Claim 77. The total joint spinal implant system of claim 76, wherein the metal comprises cobalt chrome molybdenum (CoCrMo).

Claim 78. The total joint spinal implant system of claim 64, wherein the lower base of the lower element or the lower articulation component further comprises a coating, the coating includes a metal coating.

Claim 79. The total joint spinal implant system of claim 64, wherein the lower base of the lower element and the lower articulation component further comprises a coating, the coating includes a metal coating.

Claim 80. The total joint spinal implant system of claim 78 or 79, wherein the metal coating comprises Titanium (Ti).

Claim 81. The total joint spinal implant system of claim 64, wherein the upper base comprises a superior facing surface, at least a portion of the superior facing surface contacting a portion of the superior vertebral body and the lower base comprises an inferior facing surface, at least a portion of the inferior facing surface contacts a portion of the inferior vertebral body, the superior facing surface of the upper base or the inferior facing surface of the lower base comprises a surface texture.

Claim 82. The total joint spinal implant system of claim 64, wherein the upper base comprises a superior facing surface, at least a portion of the superior facing surface contacting a portion of the superior vertebral body and the lower base comprises an inferior facing surface, at least a portion of the inferior facing surface contacts a portion of the inferior vertebral body, the superior facing surface of the upper base or the inferior facing surface of the lower base comprises a surface texture.

Claim 83. The total joint spinal implant system of claim 72, 78 or 79, wherein the upper base comprises a superior facing surface, at least a portion of the superior facing surface contacting a portion of the superior vertebral body and the lower base comprises an inferior facing surface, at least a portion of the inferior facing surface contacts a portion of the inferior vertebral body, the superior facing surface of the upper base or the inferior facing surface of the lower base comprises a surface texture.

Claim 84. The total joint spinal implant system of claim 64, wherein the upper base comprises a superior facing surface, at least a portion of the superior facing surface contacting a portion of the superior vertebral body and the lower base comprises an inferior facing surface, at least a portion of the inferior facing surface contacts a portion of the inferior vertebral body, the superior facing surface of the upper base and the inferior facing surface of the lower base comprises a surface texture.

Claim 85. The total joint spinal implant system of claim 64, wherein the upper base comprises a superior facing surface, at least a portion of the superior facing surface contacting a portion of the superior vertebral body and the lower base comprises an inferior facing surface, at least a portion of the inferior facing surface contacts a portion of the inferior vertebral body, the superior facing surface of the upper base and the inferior facing surface of the lower base comprises a surface texture.

Claim 86. The total joint spinal implant system of claim 72, 78 or 79, wherein the upper base comprises a superior facing surface, at least a portion of the superior facing surface contacting a portion of the superior vertebral body and the lower base comprises an inferior facing surface, at least a portion of the inferior facing surface contacts a portion of the inferior vertebral body, the superior facing surface of the upper base and the inferior facing surface of the lower base comprises a surface texture.

Claim 87. The total joint spinal implant system of claim 81-86, wherein the surface texture comprises a roughened surface, the roughened surface includes a grit blasted surface.

Claim 88. The total joint spinal implant system of claim 64, wherein the ball of the lower articulation component comprises a lower articulation surface, the lower articulation surface includes a concave shape, and the socket of the upper articulation component comprises an upper articulation surface, the upper articulation surface includes a convex shape.

Claim 89. The total joint spinal implant system of claim 64, wherein the first stop comprises a first contact surface and the second stop comprises a second contact surface.

Claim 90. The total joint spinal implant system of claim 88 and 89, wherein the lower articulation surface of the lower element further comprises a lower articulation surface texture, the first contact surface of the first stop comprises a first surface texture, and the second contact surface of the second stop comprises a second surface texture.

Claim 91. The total joint spinal implant system of claim 90, wherein the lower articulation surface texture, the first surface texture, and the second surface texture comprise the same surface texture.

Claim 92. The total joint spinal implant system of claim 90, wherein each of the lower articulation surface texture, the first surface texture, and the second surface texture comprise a different surface texture.

Claim 93. The total joint spinal implant system of claim 90, wherein the first surface texture and the second surface texture comprise the same surface texture and the lower articulation surface texture comprises a different surface texture than the first and second surface texture.

Claim 94. The total joint spinal implant system of claim 91 or 93, wherein the same surface texture comprises a polished surface.

Claim 95. The total joint spinal implant system of claim 90, wherein each of the lower articulation surface texture, the first surface texture, and the second surface texture comprise a polished surface.

Claim 96. The total joint spinal implant system of claim 94 or 95, wherein the polished surface comprises a surface finish of at least Ra 0.10 μm or better.

Claim 97. The total joint spinal implant system of claim 94 or 95, wherein the polished surface comprises a surface finish of at least Ra 0.05 μm or better.

Claim 98. The total joint spinal implant system of claim 90, wherein the lower articulation surface texture comprises a lower polished surface, the first surface texture comprises a first polished surface and the second surface texture comprises a second polished surface, the lower polished surface texture comprises a surface finish of at least Ra 0.05 μm or better, and the first and second polished surface comprises a surface finish of at least Ra 0.10 μm or better.

Claim 99. The total joint spinal implant system of claim 89, wherein the first contact surface of the first stop comprises a first curved surface shape and the second contact surface of the second stop comprises a second curved surface shape.

Claim 100. The total joint spinal implant system of claim 99, wherein the first curved surface shape and the second curved surface shape comprises a convex shape.

Claim 101. The total joint spinal implant system of claim 99 or 100, wherein the first contact surface and the second contact surface are positioned at an angled orientation.

Claim 102. The total joint spinal implant system of claim 101, wherein the angled orientation comprises at least 10 degrees.

Claim 103. The total joint spinal implant system of claim 99, wherein the first curved surface shape and the second curved surface shape comprises the same curved surface shape.

Claim 104. The total joint spinal implant system of claim 99, wherein the first curved surface shape and the second curved surface shape comprises a different curved surface shape.

Claim 105. The total joint spinal implant system of claim 89, wherein the first contact surface of the first stop comprises a first curved surface shape, the first contact surface positioned at a first angled orientation and the second contact surface of the second stop comprises a second curved surface shape, the second contact surface positioned at a second angled orientation.

Claim 106. The total joint spinal implant system of claim 105, the first angled orientation and the second angled orientation comprises a same angle.

Claim 107. The total joint spinal implant system of claim 105, the first angled orientation and the second angled orientation comprises a different angle.

Claim 108. The total joint spinal implant system of claim 106, wherein the same angle comprises an angle of at least 10 degrees.

Claim 109. The total joint spinal implant system of claim 65, wherein the upper articulation component of the upper element further comprises an upper first contact surface and an upper second contact surface, the socket positioned between the upper first contact surface and the upper second contact surface.

Claim 110. The total joint spinal implant system of claim 65, wherein the upper first contact surface of the upper articulation component is positioned at an anterior end of the upper element, and the upper second contact surface is positioned at the posterior end of the upper element.

Claim 111. The total joint spinal implant system of claim 89, 109 and/or 110, wherein the upper first contact surface of the upper articulation component contacts a portion of the first contact surface of the first stop to create a limit for flexion motion, and the upper second contact surface of the upper articulation component contacts a portion of the second contact surface of the second stop to create a limit for extension motion.

Claim 112. The total joint spinal implant system of claim 89, 109, 110, and/or 111, wherein each of the upper first contact surface of the upper articulation component and the second upper contact surface comprises a planar surface orientation.

Claim 113. The total joint spinal implant system of claim 89, 109, 110, and/or 111, wherein each of the upper first contact surface of the upper articulation component and the second upper contact surface comprises an angled surface orientation.

Claim 114. The total joint spinal implant system of claim 89, 109, 110, 111, wherein the upper first contact surface of the upper articulation component comprises a planar surface orientation and the upper second contact surface of the upper articulation component comprises an angled surface orientation.

Claim 115. The total joint spinal implant system of claim 113 or 114, wherein the angled surface orientation comprises at least 5 degrees or greater.

Claim 116. The total joint spinal implant system of claim 89, 109, and/or 110, wherein the upper first contact surface of the upper articulation component contacts a portion of the first contact surface of the first stop to create a first interface surface area and a first contact pressure, and the upper second contact surface of the upper articulation component contacts a portion of the second contact surface of the second stop to create a second interface or impingement surface area and a second interface or impingement pressure.

Claim 117. The total joint spinal implant system of claim 116, wherein the first interface or impingement pressure and the second interface or impingement pressure comprise a same impingement or interface pressure.

Claim 118. The total joint spinal implant system of claim 116, wherein the first interface or impingement pressure and the second interface or impingement pressure comprise a different impingement or interface pressure.

Claim 119. The total joint spinal implant of claim 117, wherein the same interface or impingement pressures comprise a pressure of 35 MPa or less.

Claim 120. The total joint spinal implant system of claim 116, wherein the first contact surface area and the second contact surface area comprise a same surface area.

Claim 121. The total joint spinal implant system of claim 116, wherein the first contact surface area and the second contact surface area comprise a different surface area.

Claim 122. The total joint spinal implant system of claim 116, wherein the first contact surface area and the second contact surface area comprise at least 50% contact.

Claim 123. The total joint spinal implant system of claim 64, wherein the dynamic spinal implant further comprises a fixation screw.

Claim 124. The total joint spinal implant system of claim 64, wherein the dynamic spinal implant further comprises a fixation screw and a retainer clip.

Claim 125. The total joint spinal implant system of claim 64, wherein the bridge further comprises a third stop or a screw housing, the screw housing comprises a screw bore and a channel, the channel surrounds a portion of a perimeter of the screw housing.

Claim 126. The total joint spinal implant system of claim 124 and 125, wherein the channel is sized and configured to receive a portion of the retainer clip.

Claim 127. The total joint spinal implant system of claim 123, 124, and/or 125, wherein the screw bore comprises a screw bore axis, the screw bore axis includes an angled orientation.

Claim 128. The total joint spinal implant system of claim 127, wherein the angled orientation matches or substantially matches a sagittal pedicle angle.

Claim 129. The total joint spinal implant system of claim 127, wherein the angled orientation comprises at least 20 degrees.

Claim 130. The total joint spinal implant system of claim 124, wherein the fixation screw comprises a thread diameter, the thread diameter matches or substantially matches the pedicle width.

Claim 131. The total joint spinal implant system of claim 124, wherein the fixation screw comprises a self-tapping, self-piercing and self-drilling screw.

Claim 132. The total joint spinal implant system of claim 64, wherein the bridge further comprises an inferior facing or bone contacting surface, the inferior facing surface comprises a surface texture.

Claim 133. The total joint spinal implant system of claim 132, wherein the surface texture is a roughened surface.

Claim 144. The total joint spinal implant system of claim 133, wherein the roughened surface comprises a grit blasted surface.

Claim 145. The dynamic spinal implant system of claim 132, wherein surface texture of the inferior facing surface of the bridge matches or substantially matches the surface texture of the inferior facing surface of the lower base of the lower element.

We claim:

1. A spinal implant system comprising:
   a superior element having a first superior stop, a second superior stop and a superior articulation surface positioned between the first and second superior stops;
   an inferior element having an inferior base and a bridge portion coupled to a posterior portion of the inferior base, the inferior base including a first inferior stop, a second inferior stop and an inferior articulation component positioned between the first and second inferior stops, the inferior articulation component having an inferior articulation surface which engages with the superior articulation surface to allow articulation of the superior element relative to the inferior element between a first relative position where the first superior stop contacts the first inferior stop and a second relative position where the second superior stop contacts the second inferior stop, the first relative position being different than the second relative position;
   the inferior articulation surface having an inferior articulation surface finish and a first stop surface having a first stop surface finish, wherein the inferior articulation surface finish is a smoother surface finish than the first stop surface finish.

2. The spinal implant system of claim 1, wherein the inferior articulation surface finish comprises a surface finish of Ra 0.05 μm (2.0 μIn) or less, and the first stop surface finish is at least Ra 0.10 μm (4.0 μIn) or greater.

3. The spinal implant system of claim 2, wherein the inferior element comprises a metallic material.

4. The spinal implant system of claim 3, wherein the metallic material comprises cobalt chrome molybdenum (CoCrMo).

5. The spinal implant system of claim 2, wherein the superior element comprises a metallic base with a polymer insert.

6. The spinal implant system of claim 5, wherein the first superior stop and the superior articulation surface each comprise an ultra-high weight molecular polyethylene (UHWMPE).

7. The spinal implant system of claim 5, wherein the polymer insert is pressure molded into a depression in the metallic base.

8. A spinal implant system comprising:
   a superior element having a first superior stop, a second superior stop and a superior articulation surface positioned between the first and second superior stops;
   an inferior element having an inferior base and a bridge portion coupled to a posterior portion of the inferior base, the inferior base including a first inferior stop, a second inferior stop and an inferior articulation component positioned between the first and second inferior stops, the inferior articulation component having an inferior articulation surface which engages with the superior articulation surface to allow articulation of the superior element relative to the inferior element between a first relative position where the first superior stop contacts the first inferior stop and a second relative position where the second superior stop contacts the second inferior stop, the first relative position being different than the second relative position;
   the inferior articulation surface having an inferior articulation surface finish and a second stop surface having a second stop surface finish, wherein the inferior articulation surface finish is a smoother surface finish than the second stop surface finish.

9. The spinal implant system of claim 8, wherein the inferior articulation surface finish comprises a surface finish of Ra 0.05 μm (2.0 μIn) or less, and the second stop surface finish is at least Ra 0.10 μm (4.0 μIn) or greater.

10. The spinal implant system of claim 9, wherein the inferior element comprises a metallic material.

11. The spinal implant system of claim 10, wherein the metallic material comprises cobalt chrome molybdenum (CoCrMo).

12. The spinal implant system of claim 9, wherein the superior element comprises a metallic base with a polymer insert.

13. The spinal implant system of claim 12, wherein the second superior stop and the superior articulation surface each comprise an ultra-high weight molecular polyethylene (UHWMPE).

14. The spinal implant system of claim 12, wherein the polymer insert is pressure molded into a depression in the metallic base.

15. A spinal implant system comprising:
   a superior element having a first superior stop, a second superior stop and a superior articulation surface positioned between the first and second superior stops;
   an inferior element having an inferior base and a bridge portion coupled to a posterior portion of the inferior base, the inferior base including a first inferior stop, a second inferior stop and an inferior articulation component positioned between the first and second inferior stops, the inferior articulation component having an inferior articulation surface which engages with the superior articulation surface to allow articulation of the superior element relative to the inferior element between a first relative position where the first superior stop contacts the first inferior stop and a second relative position where the second superior stop contacts the second inferior stop, the first relative position being different than the second relative position;

the inferior articulation surface having an inferior articulation surface finish, the first inferior stop having a first stop surface finish and the second inferior stop having a second stop surface finish, wherein the inferior articulation surface finish is a smoother surface finish than both of the first stop surface finish and the second stop surface finish.

16. The spinal implant system of claim 15, wherein the inferior articulation surface finish comprises a surface finish of Ra 0.05 μm (2.0 μIn) or less, the first stop surface finish is at least Ra 0.10 μm (4.0 μIn) or greater and the second stop surface finish is at least Ra 0.10 μm (4.0 μIn) or greater.

17. The spinal implant system of claim 16, wherein the inferior element comprises a metallic material.

18. The spinal implant system of claim 17, wherein the metallic material comprises cobalt chrome molybdenum (CoCrMo).

19. The spinal implant system of claim 16, wherein the superior element comprises a metallic base with a polymer insert.

20. The spinal implant system of claim 19, wherein the first superior stop, the second superior stop and the superior articulation surface each comprise an ultra-high weight molecular polyethylene (UHWMPE).

* * * * *